US011813337B2

(12) United States Patent
O'Shea et al.

(10) Patent No.: US 11,813,337 B2
(45) Date of Patent: Nov. 14, 2023

(54) TUMOR-TARGETING SYNTHETIC ADENOVIRUSES AND USES THEREOF

(71) Applicant: Salk Institute for Biological Studies, La Jolla, CA (US)

(72) Inventors: Clodagh O'Shea, San Diego, CA (US); Colin Powers, San Diego, CA (US); Lei Zhang, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 806 days.

(21) Appl. No.: 16/434,714

(22) Filed: Jun. 7, 2019

(65) Prior Publication Data

US 2019/0314523 A1 Oct. 17, 2019

Related U.S. Application Data

(63) Continuation of application No. PCT/US2017/065604, filed on Dec. 11, 2017.

(60) Provisional application No. 62/433,140, filed on Dec. 12, 2016.

(51) Int. Cl.

| | |
|---|---|
| ***A61K 48/00*** | (2006.01) |
| ***A61P 35/00*** | (2006.01) |
| ***C12N 7/00*** | (2006.01) |
| ***C12Q 1/66*** | (2006.01) |

(52) U.S. Cl.

CPC ............ *A61K 48/005* (2013.01); *A61P 35/00* (2018.01); *C12N 7/00* (2013.01); *C12Q 1/66* (2013.01); *C12N 2799/022* (2013.01); *C12Y 113/12007* (2013.01); *G01N 2800/7028* (2013.01)

(58) Field of Classification Search

None

See application file for complete search history.

(56) References Cited

U.S. PATENT DOCUMENTS

| | | | |
|---|---|---|---|
| 5,559,099 | A | 9/1996 | Wickham et al. |
| 5,670,488 | A | 9/1997 | Gregory et al. |
| 5,677,178 | A | 10/1997 | McCormick |
| 5,731,190 | A | 3/1998 | Wickham et al. |
| 5,801,029 | A | 9/1998 | McCormick |
| 5,846,782 | A | 12/1998 | Wickham et al. |
| 5,846,945 | A | 12/1998 | McCormick |
| 5,856,181 | A | 1/1999 | McCormick |
| 5,922,315 | A | 7/1999 | Roy |
| 5,945,335 | A | 8/1999 | Colosi |
| 5,962,311 | A | 10/1999 | Wickham et al. |
| 5,965,541 | A | 10/1999 | Wickham et al. |
| 5,972,706 | A | 10/1999 | McCormick |
| 6,020,172 | A | 2/2000 | Both |
| 6,069,134 | A | 5/2000 | Roth et al. |
| 6,127,525 | A | 10/2000 | Crystal et al. |
| 6,133,243 | A | 10/2000 | Kirn |
| 6,153,435 | A | 11/2000 | Crystal et al. |
| 6,296,845 | B1 | 10/2001 | Sampson et al. |
| 6,329,190 | B1 | 12/2001 | Wickham et al. |
| 6,410,010 | B1 | 6/2002 | Zhang et al. |
| 6,455,314 | B1 | 9/2002 | Wickham et al. |
| 6,465,253 | B1 | 10/2002 | Wickham et al. |
| 6,475,480 | B1 | 11/2002 | Mehtali et al. |
| 6,506,379 | B1 | 1/2003 | Clackson et al. |
| 6,506,602 | B1 | 1/2003 | Stemmer |
| 6,569,677 | B1 | 5/2003 | Legrand et al. |
| 6,596,268 | B1 | 7/2003 | Coffey et al. |
| 6,635,466 | B2 | 10/2003 | Davidson et al. |
| 6,635,476 | B1 | 10/2003 | Murphy |
| 6,649,157 | B2 | 11/2003 | Coffey et al. |
| 6,737,234 | B1 | 5/2004 | Freimuth |
| 6,740,525 | B2 | 5/2004 | Roelvink et al. |
| 6,797,702 | B1 | 9/2004 | Roth et al. |
| 6,811,774 | B2 | 11/2004 | Haddada et al. |
| 6,824,771 | B1 | 11/2004 | Curiel et al. |
| 6,838,285 | B2 | 1/2005 | Farmer et al. |
| 6,841,540 | B1 | 1/2005 | Curiel et al. |
| 6,849,446 | B2 | 2/2005 | Tikoo et al. |
| 6,867,022 | B1 | 3/2005 | Imperiale |
| 6,869,936 | B1 | 3/2005 | Vogels et al. |
| 6,878,549 | B1 | 4/2005 | Vogels et al. |
| 6,905,678 | B2 | 6/2005 | Havenga et al. |
| 6,911,199 | B2 | 6/2005 | Vigne et al. |
| 6,911,200 | B2 | 6/2005 | Yu et al. |

(Continued)

FOREIGN PATENT DOCUMENTS

| | | | |
|---|---|---|---|
| CN | 1330715 | A | 1/2002 |
| CN | 1380420 | A | 11/2002 |

(Continued)

OTHER PUBLICATIONS

Fukazawa et al. Adenovirus-mediated Cancer Gene Therapy and Virotherapy (Review). International Journal of Molecular Medicine , 2010. 25:3-10.*

Shimizu et al., "Development of a Novel Adenovirus Vector Exhibiting MicroRNA-mediated Suppression of the Leaky Expression of Adenovirus Genes," Yakugaku Zasshi, vol. 132:1407-1412, 2012 (in Japanese) (English abstract).

Suzuki et al., "miR-122A-Regulated Expression of a Suicide Gene Prevents Hepatotoxicity Without Altering Antitumor Effects in Suicide Gene Therapy," *Mol. Ther.*, vol. 16:1719-1726, 2008.

Bremnes et al., "The Role of Tumor Stroma in Cancer Progression and Prognosis," *J. Thorac. Oncol.*, vol. 6:209-217, 2011.

(Continued)

*Primary Examiner* — Christopher M Babic

*Assistant Examiner* — Kimberly A Aron

(74) *Attorney, Agent, or Firm* — KLARQUIST SPARKMAN, LLP

(57) ABSTRACT

Synthetic adenoviruses with liver detargeting mutations and expressing an adenovirus type 34 (Ad34) fiber protein, or a chimeric fiber protein with an Ad34 knob domain, are described. The synthetic adenoviruses traffic to sites of tumors. Use of the synthetic adenoviruses for delivering diagnostic or therapeutic transgenes to tumors are also described.

24 Claims, 10 Drawing Sheets

Specification includes a Sequence Listing.

(56) References Cited

U.S. PATENT DOCUMENTS

| | | | |
|---|---|---|---|
| 6,913,922 | B1 | 7/2005 | Bout et al. |
| 6,929,946 | B1 | 8/2005 | Vogels et al. |
| 6,951,755 | B2 | 10/2005 | Wickham et al. |
| 6,984,635 | B1 | 1/2006 | Schreiber et al. |
| 7,001,596 | B1 | 2/2006 | Johnson et al. |
| 7,045,347 | B2 | 5/2006 | Graham et al. |
| 7,094,398 | B1 | 8/2006 | Lieber et al. |
| 7,094,399 | B2 | 8/2006 | Otto |
| 7,109,179 | B2 | 9/2006 | Roth et al. |
| 7,157,266 | B2 | 1/2007 | Freimuth et al. |
| 7,232,899 | B2 | 6/2007 | Von Seggern et al. |
| 7,235,233 | B2 | 6/2007 | Havenga et al. |
| 7,247,472 | B2 | 7/2007 | Wilson et al. |
| 7,252,817 | B2 | 8/2007 | Coffey et al. |
| 7,252,989 | B1 | 8/2007 | Zhang et al. |
| 7,256,036 | B2 | 8/2007 | Legrand et al. |
| 7,291,498 | B2 | 11/2007 | Roy et al. |
| 7,297,542 | B2 | 11/2007 | Curiel et al. |
| 7,306,793 | B2 | 12/2007 | Haddada et al. |
| 7,332,337 | B2 | 2/2008 | van Es et al. |
| 7,344,711 | B2 | 3/2008 | Bonastre et al. |
| 7,344,872 | B2 | 3/2008 | Gao et al. |
| 7,364,727 | B2 | 4/2008 | Li et al. |
| 7,410,954 | B2 | 8/2008 | Davidson et al. |
| 7,456,008 | B2 | 11/2008 | Lindholm et al. |
| 7,473,418 | B2 | 1/2009 | Yu et al. |
| 7,482,156 | B2 | 1/2009 | Arroyo et al. |
| 7,491,508 | B2 | 2/2009 | Roy et al. |
| 7,510,868 | B2 | 3/2009 | Harden et al. |
| 7,589,069 | B1 | 9/2009 | Wold et al. |
| 7,611,868 | B2 | 11/2009 | Monaci et al. |
| 7,741,099 | B2 | 6/2010 | Havenga et al. |
| 7,749,493 | B2 | 7/2010 | Havenga et al. |
| 7,754,201 | B2 | 7/2010 | Wang et al. |
| 7,906,113 | B2 | 3/2011 | Bout et al. |
| 7,943,373 | B2 | 5/2011 | Fujiwara et al. |
| 7,951,585 | B2 | 5/2011 | Ke |
| 7,968,333 | B2 | 6/2011 | Yu et al. |
| 8,105,574 | B2 | 1/2012 | Wilson et al. |
| 8,168,168 | B2 | 5/2012 | Fueyo et al. |
| 8,231,880 | B2 | 7/2012 | Roy et al. |
| 8,470,310 | B2 | 6/2013 | Roy et al. |
| 8,524,219 | B2 | 9/2013 | Roy et al. |
| 8,603,459 | B2 | 12/2013 | Wilson et al. |
| 8,685,387 | B2 | 4/2014 | Roy et al. |
| 8,715,642 | B2 | 5/2014 | Kochanek et al. |
| 8,765,146 | B2 | 7/2014 | Bruder et al. |
| 8,765,463 | B2 | 7/2014 | Harden et al. |
| 8,808,986 | B2 | 8/2014 | Jacobson et al. |
| 8,815,563 | B2 | 8/2014 | Davis et al. |
| 8,834,863 | B2 | 9/2014 | Roy et al. |
| 8,846,031 | B2 | 9/2014 | Roy et al. |
| 8,865,182 | B2 | 10/2014 | Mayall et al. |
| 8,920,813 | B2 | 12/2014 | Bruder et al. |
| 8,940,290 | B2 | 1/2015 | Roy et al. |
| 8,974,777 | B2 | 3/2015 | Cascallo et al. |
| 9,017,672 | B2 | 4/2015 | Yu et al. |
| 9,018,182 | B2 | 4/2015 | Koh et al. |
| 9,056,090 | B2 | 6/2015 | Colloca et al. |
| 9,061,055 | B2 | 6/2015 | Fueyo et al. |
| 9,133,483 | B2 | 9/2015 | Wilson et al. |
| 9,163,261 | B2 | 10/2015 | Kollipara et al. |
| 9,187,733 | B2 | 11/2015 | O'Shea et al. |
| 9,200,041 | B2 | 12/2015 | Lieber et al. |
| 9,206,238 | B2 | 12/2015 | Roy et al. |
| 9,217,159 | B2 | 12/2015 | Roy et al. |
| 9,217,160 | B2 | 12/2015 | O'Shea et al. |
| 9,267,153 | B2 | 2/2016 | Curiel |
| 9,315,827 | B2 | 4/2016 | Wang et al. |
| 9,359,618 | B2 | 6/2016 | Roy et al. |
| 9,382,551 | B2 | 7/2016 | Roy et al. |
| 9,410,129 | B2 | 8/2016 | Ranki et al. |
| 9,476,061 | B2 | 10/2016 | Baker et al. |
| 9,493,745 | B2 | 11/2016 | Lee et al. |
| 9,555,089 | B2 | 1/2017 | Shiratsuchi et al. |
| 9,593,346 | B2 | 3/2017 | Roy et al. |
| 9,597,363 | B2 | 3/2017 | Roy et al. |
| 9,682,133 | B2 | 6/2017 | Crystal et al. |
| 9,688,727 | B2 | 6/2017 | Lieber et al. |
| 9,714,435 | B2 | 7/2017 | Dicks et al. |
| 9,718,863 | B2 | 8/2017 | Colloca et al. |
| 9,790,519 | B2 | 10/2017 | Wei et al. |
| 9,885,090 | B2 | 2/2018 | O'Shea et al. |
| 9,913,866 | B2 | 3/2018 | O'Shea et al. |
| 10,016,470 | B2 | 7/2018 | Bonastre et al. |
| 10,034,905 | B2 | 7/2018 | Seymour et al. |
| 10,046,067 | B2 | 8/2018 | Yun et al. |
| 10,066,215 | B2 | 9/2018 | Lee et al. |
| 10,071,126 | B2 | 9/2018 | Kumon et al. |
| 10,077,430 | B2 | 9/2018 | Lee et al. |
| 10,080,774 | B2 | 9/2018 | Fueyo et al. |
| 10,113,182 | B2 | 10/2018 | Roy et al. |
| 10,149,873 | B2 | 12/2018 | Roy et al. |
| 10,150,798 | B2 | 12/2018 | Lieber et al. |
| 10,155,930 | B2 | 12/2018 | Holm |
| 10,232,053 | B2 | 3/2019 | Hicklin et al. |
| 10,272,162 | B2 | 4/2019 | McVey et al. |
| 10,294,493 | B2 | 5/2019 | Wang et al. |
| 10,316,065 | B2 | 6/2019 | Carrióet al. |
| 10,376,549 | B2 | 8/2019 | Shayakhmetov et al. |
| 10,391,183 | B2 | 8/2019 | Fueyo-Margareto et al. |
| 10,501,757 | B2 | 12/2019 | Roy et al. |
| 10,538,744 | B2 | 1/2020 | Holm |
| 10,544,192 | B2 | 1/2020 | Colloca et al. |
| 10,604,549 | B2 | 3/2020 | Alemany Bonastre et al. |
| 10,611,803 | B2 | 4/2020 | Lieber et al. |
| 10,617,729 | B2 | 4/2020 | Dobbins |
| 10,738,325 | B2 | 8/2020 | O'Shea et al. |
| 2001/0039046 | A1 | 11/2001 | Yeh et al. |
| 2002/0037274 | A1 | 3/2002 | Williams et al. |
| 2002/0086411 | A1 | 7/2002 | Holm et al. |
| 2002/0106382 | A1 | 8/2002 | Young et al. |
| 2002/0142989 | A1 | 10/2002 | Alemany et al. |
| 2002/0151069 | A1 | 10/2002 | Korokhov |
| 2002/0168343 | A1 | 11/2002 | Curiel et al. |
| 2002/0187128 | A1 | 12/2002 | Imperiale |
| 2002/0193327 | A1 | 12/2002 | Nemerow |
| 2002/0193328 | A1 | 12/2002 | Ketner |
| 2003/0017138 | A1 | 1/2003 | Havenga et al. |
| 2003/0021768 | A1 | 1/2003 | Shen |
| 2003/0027338 | A1 | 2/2003 | Freimuth |
| 2003/0073072 | A1 | 4/2003 | Havenga et al. |
| 2003/0082146 | A1 | 5/2003 | van Es |
| 2003/0082150 | A1 | 5/2003 | Falleur et al. |
| 2003/0082811 | A1 | 5/2003 | Orlando et al. |
| 2003/0092162 | A1 | 5/2003 | Shankara et al. |
| 2003/0095989 | A1 | 5/2003 | Irving et al. |
| 2003/0099615 | A1 | 5/2003 | Tikoo |
| 2003/0099619 | A1 | 5/2003 | Wickham et al. |
| 2003/0104625 | A1 | 6/2003 | Cheng et al. |
| 2003/0138405 | A1 | 7/2003 | Fueyo et al. |
| 2003/0143730 | A1 | 7/2003 | Blanche et al. |
| 2003/0166286 | A1 | 9/2003 | Wickham et al. |
| 2003/0170899 | A1 | 9/2003 | McVey et al. |
| 2003/0175244 | A1 | 9/2003 | Curiel et al. |
| 2003/0175245 | A1 | 9/2003 | Brough et al. |
| 2003/0215948 | A1 | 11/2003 | Kaleko et al. |
| 2003/0219899 | A1 | 11/2003 | Korokhov |
| 2003/0220284 | A1 | 11/2003 | Yotnda et al. |
| 2004/0002060 | A1 | 1/2004 | Kaleko et al. |
| 2004/0038205 | A1 | 2/2004 | Van Raaij et al. |
| 2004/0091456 | A1 | 5/2004 | Nakai et al. |
| 2004/0102382 | A1 | 5/2004 | Schughart et al. |
| 2004/0146489 | A1 | 7/2004 | Yu et al. |
| 2004/0175362 | A1 | 9/2004 | Curiel et al. |
| 2004/0185555 | A1 | 9/2004 | Emini et al. |
| 2004/0191222 | A1 | 9/2004 | Emini et al. |
| 2004/0191761 | A1 | 9/2004 | Routes |
| 2004/0213764 | A1 | 10/2004 | Wold et al. |
| 2004/0219516 | A1 | 11/2004 | Bennett et al. |
| 2004/0219543 | A1 | 11/2004 | Wirtz |
| 2004/0265277 | A1 | 12/2004 | Holm |
| 2005/0032045 | A1 | 2/2005 | Tikoo et al. |
| 2005/0036989 | A1 | 2/2005 | Shen et al. |

(56) References Cited

U.S. PATENT DOCUMENTS

| | | | |
|---|---|---|---|
| 2005/0079158 | A1 | 4/2005 | Zhou et al. |
| 2005/0095231 | A1 | 5/2005 | Curiel et al. |
| 2005/0095705 | A1 | 5/2005 | Kadan et al. |
| 2005/0169891 | A1 | 8/2005 | Vogels et al. |
| 2005/0181507 | A1 | 8/2005 | Havenga et al. |
| 2005/0186178 | A1 | 8/2005 | Ennist |
| 2005/0201936 | A1 | 9/2005 | Wold et al. |
| 2005/0201978 | A1 | 9/2005 | Lipton |
| 2005/0232900 | A1 | 10/2005 | Vogels et al. |
| 2005/0238622 | A1 | 10/2005 | Axelrod et al. |
| 2005/0260162 | A1 | 11/2005 | Fueyo et al. |
| 2005/0271622 | A1 | 12/2005 | Zhou et al. |
| 2005/0277193 | A1 | 12/2005 | Wickham et al. |
| 2005/0287120 | A1 | 12/2005 | Fisher et al. |
| 2006/0002893 | A1 | 1/2006 | Vigne et al. |
| 2006/0034804 | A1 | 2/2006 | Gregory et al. |
| 2006/0099178 | A1 | 5/2006 | Holm |
| 2006/0104953 | A1 | 5/2006 | Havenga et al. |
| 2006/0140910 | A1 | 6/2006 | Gregory et al. |
| 2006/0147420 | A1 | 7/2006 | Fueyo et al. |
| 2006/0182718 | A1 | 8/2006 | Roth et al. |
| 2006/0211115 | A1 | 9/2006 | Roy et al. |
| 2006/0228334 | A1 | 10/2006 | Calatrava et al. |
| 2006/0257370 | A1 | 11/2006 | Hermiston et al. |
| 2006/0281090 | A1 | 12/2006 | Lieber et al. |
| 2006/0286121 | A1 | 12/2006 | Gall et al. |
| 2006/0292122 | A1 | 12/2006 | Hermiston et al. |
| 2006/0292682 | A1 | 12/2006 | Hawkins et al. |
| 2007/0003923 | A1 | 1/2007 | Nemerow |
| 2007/0110719 | A1 | 5/2007 | Holm |
| 2007/0122817 | A1 | 5/2007 | Church et al. |
| 2007/0202080 | A1 | 8/2007 | Yun et al. |
| 2007/0202524 | A1 | 8/2007 | Murphy |
| 2007/0253932 | A1 | 11/2007 | Gregory et al. |
| 2007/0254357 | A1 | 11/2007 | Gregory et al. |
| 2007/0292396 | A1 | 12/2007 | Fueyo et al. |
| 2007/0292954 | A1 | 12/2007 | Elledge |
| 2008/0069836 | A1 | 3/2008 | Nabel et al. |
| 2008/0089864 | A1 | 4/2008 | Bonastre et al. |
| 2008/0108129 | A1 | 5/2008 | Pitcovski et al. |
| 2008/0112929 | A1 | 5/2008 | Kovesdi et al. |
| 2008/0118470 | A1 | 5/2008 | Ennist et al. |
| 2008/0124360 | A1 | 5/2008 | Seggern |
| 2008/0213220 | A1 | 9/2008 | Fisher et al. |
| 2008/0242608 | A1 | 10/2008 | Bonni et al. |
| 2008/0247996 | A1 | 10/2008 | Yu et al. |
| 2008/0254059 | A1 | 10/2008 | Bett et al. |
| 2009/0074810 | A1 | 3/2009 | Roy et al. |
| 2009/0111144 | A1 | 4/2009 | Bebbington |
| 2009/0202565 | A1 | 8/2009 | Labow et al. |
| 2009/0232800 | A1 | 9/2009 | Holm |
| 2009/0280089 | A1 | 11/2009 | Benihoud et al. |
| 2009/0311219 | A1 | 12/2009 | Bonastre et al. |
| 2010/0008977 | A1 | 1/2010 | Boulikas et al. |
| 2010/0034774 | A1 | 2/2010 | Vogels et al. |
| 2010/0047208 | A1 | 2/2010 | Ke |
| 2010/0075951 | A1 | 3/2010 | Cardin et al. |
| 2010/0075998 | A1 | 3/2010 | Vanotti et al. |
| 2010/0098668 | A1 | 4/2010 | Seth |
| 2010/0151576 | A1 | 6/2010 | Li et al. |
| 2010/0233125 | A1 | 9/2010 | Tagawa |
| 2010/0272753 | A1 | 10/2010 | Ketner et al. |
| 2010/0292166 | A1 | 11/2010 | Lee et al. |
| 2010/0310554 | A1 | 12/2010 | Holm |
| 2010/0311145 | A1 | 12/2010 | Holm |
| 2011/0053249 | A1 | 3/2011 | Bonastre et al. |
| 2011/0059135 | A1 | 3/2011 | Kovesdi et al. |
| 2011/0086063 | A1 | 4/2011 | Crystal et al. |
| 2011/0104788 | A1 | 5/2011 | Baker et al. |
| 2011/0189234 | A1 | 8/2011 | Van Beusechem et al. |
| 2011/0256524 | A1 | 10/2011 | Lee et al. |
| 2011/0275093 | A1 | 11/2011 | Holm |
| 2011/0286999 | A1 | 11/2011 | Holm |
| 2012/0020924 | A1 | 1/2012 | Nakai et al. |
| 2012/0039877 | A1 | 2/2012 | Holm |
| 2012/0207711 | A1 | 8/2012 | Fueyo et al. |
| 2013/0058897 | A1 | 3/2013 | Lee et al. |
| 2013/0101557 | A1 | 4/2013 | Yun et al. |
| 2013/0130292 | A1 | 5/2013 | Szalay et al. |
| 2013/0231267 | A1 | 9/2013 | O'Shea et al. |
| 2013/0243729 | A1 | 9/2013 | O'Shea et al. |
| 2013/0243731 | A1 | 9/2013 | Dias et al. |
| 2013/0323205 | A1 | 12/2013 | Diaconu et al. |
| 2013/0345295 | A1 | 12/2013 | Wang et al. |
| 2014/0023619 | A1 | 1/2014 | Kosai et al. |
| 2014/0199688 | A1 | 7/2014 | Mizuguchi et al. |
| 2014/0294890 | A1 | 10/2014 | Ketner et al. |
| 2014/0341857 | A1 | 11/2014 | Bressy et al. |
| 2014/0348791 | A1 | 11/2014 | Barouch et al. |
| 2014/0377294 | A1 | 12/2014 | Fueyo-Margareto et al. |
| 2014/0377295 | A1 | 12/2014 | Ertl et al. |
| 2015/0005397 | A1 | 1/2015 | O'Shea et al. |
| 2015/0017127 | A1 | 3/2015 | O'Shea et al. |
| 2015/0071881 | A1 | 3/2015 | Bonastre et al. |
| 2015/0086579 | A1 | 3/2015 | Mayall et al. |
| 2015/0202324 | A1 | 7/2015 | Hemminki et al. |
| 2015/0232880 | A1 | 8/2015 | Hemminki et al. |
| 2015/0246949 | A1 | 9/2015 | Lieber et al. |
| 2015/0352203 | A1 | 12/2015 | Wilson et al. |
| 2015/0374766 | A1 | 12/2015 | O'Shea et al. |
| 2016/0017294 | A1 | 1/2016 | Reid et al. |
| 2016/0051603 | A1 | 2/2016 | Roy et al. |
| 2016/0053235 | A1 | 2/2016 | O'Shea et al. |
| 2016/0082100 | A1 | 3/2016 | Ranki et al. |
| 2016/0090574 | A1 | 3/2016 | Fisher et al. |
| 2016/0102295 | A1 | 4/2016 | Roy et al. |
| 2016/0143967 | A1 | 5/2016 | Fueyo-Margareto et al. |
| 2016/0208287 | A1 | 7/2016 | Hemminki et al. |
| 2016/0244783 | A1 | 8/2016 | Roy et al. |
| 2016/0289645 | A1 | 10/2016 | Tufaro et al. |
| 2017/0035818 | A1 | 2/2017 | Seymour et al. |
| 2017/0073647 | A1 | 3/2017 | Fisher et al. |
| 2017/0080069 | A1 | 3/2017 | Cerullo et al. |
| 2017/0096646 | A1 | 4/2017 | Roy et al. |
| 2017/0137786 | A1 | 5/2017 | Hemminki et al. |
| 2017/0183636 | A1 | 6/2017 | Roy et al. |
| 2017/0190752 | A1 | 7/2017 | Holm |
| 2017/0202893 | A1 | 7/2017 | O'Shea et al. |
| 2017/0252443 | A1 | 9/2017 | Holm |
| 2017/0314044 | A1 | 11/2017 | Davydova et al. |
| 2017/0348405 | A1 | 12/2017 | Shiratsuchi et al. |
| 2018/0000966 | A1 | 1/2018 | Dicks et al. |
| 2018/0051301 | A1 | 2/2018 | Rentschler et al. |
| 2018/0072809 | A1 | 3/2018 | Hemminki et al. |
| 2018/0100164 | A1 | 4/2018 | Wei et al. |
| 2018/0104288 | A1 | 4/2018 | Galili et al. |
| 2018/0163190 | A1 | 6/2018 | Gerardy-Schahn et al. |
| 2018/0216081 | A1 | 8/2018 | Colloca et al. |
| 2018/0221423 | A1 | 8/2018 | O'Shea et al. |
| 2018/0318365 | A1 | 11/2018 | Yeung et al. |
| 2018/0346929 | A1 | 12/2018 | Kosai et al. |
| 2018/0355374 | A1 | 12/2018 | O'Shea et al. |
| 2018/0355379 | A1 | 12/2018 | O'Shea et al. |
| 2018/0369417 | A1 | 12/2018 | Yun et al. |
| 2019/0055522 | A1 | 2/2019 | Holm |
| 2019/0062395 | A1 | 2/2019 | Merchant et al. |
| 2019/0070233 | A1 | 3/2019 | Yeung et al. |
| 2019/0093085 | A1 | 3/2019 | Tufaro et al. |
| 2019/0136204 | A1 | 5/2019 | Reid et al. |
| 2019/0142967 | A1 | 5/2019 | Hicklin et al. |
| 2019/0175716 | A1 | 6/2019 | Gilbert et al. |
| 2019/0183946 | A1 | 6/2019 | Bonastre et al. |
| 2019/0201462 | A1 | 7/2019 | Tufaro et al. |
| 2019/0201551 | A1 | 7/2019 | Curiel |
| 2019/0233845 | A1 | 8/2019 | Maloveste et al. |
| 2019/0247452 | A1 | 8/2019 | Lan et al. |
| 2019/0269794 | A1 | 9/2019 | McVey et al. |
| 2019/0275092 | A1 | 9/2019 | Tufaro et al. |
| 2019/0275093 | A1 | 9/2019 | Aboody et al. |
| 2019/0300905 | A1 | 10/2019 | Ammendola et al. |
| 2019/0314523 | A1 | 10/2019 | O'Shea et al. |
| 2019/0314525 | A1 | 10/2019 | O'Shea et al. |
| 2019/0345204 | A1 | 11/2019 | Carrióet al. |
| 2019/0350992 | A1 | 11/2019 | Cascallo Piqueras et al. |

(56) References Cited

U.S. PATENT DOCUMENTS

| | | | |
|---|---|---|---|
| 2019/0352616 | A1 | 11/2019 | Reid et al. |
| 2019/0352669 | A1 | 11/2019 | Reid et al. |
| 2019/0374589 | A1 | 12/2019 | Suzuki et al. |
| 2019/0388487 | A1 | 12/2019 | Shayakhmetov et al. |
| 2020/0014798 | A1 | 1/2020 | Hicklin et al. |
| 2020/0032223 | A1 | 1/2020 | Reid et al. |
| 2020/0078415 | A1 | 3/2020 | Reid et al. |
| 2020/0095560 | A1 | 3/2020 | Holm |
| 2020/0102352 | A1 | 4/2020 | Colloca et al. |

FOREIGN PATENT DOCUMENTS

| | | |
|---|---|---|
| CN | 102191245 A | 9/2011 |
| EP | 0689447 | 4/1999 |
| EP | 0931830 | 3/2001 |
| EP | 0760675 | 8/2001 |
| EP | 1167533 | 1/2002 |
| EP | 1284294 | 2/2003 |
| EP | 1413586 | 4/2004 |
| EP | 1196616 | 12/2004 |
| EP | 1185279 | 1/2005 |
| EP | 0851769 | 2/2005 |
| EP | 0861329 | 3/2005 |
| EP | 1181382 | 3/2005 |
| EP | 1121137 | 7/2005 |
| EP | 0991763 | 9/2005 |
| EP | 1294918 | 10/2005 |
| EP | 0889969 | 11/2005 |
| EP | 1498129 | 11/2005 |
| EP | 1593742 | 11/2005 |
| EP | 0920524 | 12/2005 |
| EP | 1307573 | 1/2006 |
| EP | 0978566 | 5/2006 |
| EP | 0778889 | 7/2006 |
| EP | 1070118 | 10/2006 |
| EP | 1214098 | 11/2006 |
| EP | 1230378 | 6/2007 |
| EP | 1550722 | 6/2007 |
| EP | 1187919 | 11/2007 |
| EP | 0863987 | 1/2008 |
| EP | 0920514 | 1/2008 |
| EP | 1159438 | 7/2008 |
| EP | 1266022 | 10/2008 |
| EP | 1678193 | 12/2008 |
| EP | 1054064 | 12/2009 |
| EP | 2012822 | 1/2010 |
| EP | 1816204 | 10/2010 |
| EP | 1749098 | 12/2010 |
| EP | 1799836 | 12/2010 |
| EP | 1816205 | 8/2011 |
| EP | 1818408 | 8/2011 |
| EP | 1409748 | 10/2011 |
| EP | 1180932 | 1/2012 |
| EP | 1466001 | 4/2012 |
| EP | 1743041 | 6/2012 |
| EP | 1446479 | 8/2012 |
| EP | 1649028 | 8/2012 |
| EP | 1990418 | 8/2012 |
| EP | 2311499 | 8/2012 |
| EP | 1636370 | 4/2014 |
| EP | 1767642 | 4/2014 |
| EP | 1689445 | 2/2015 |
| EP | 2350269 | 9/2015 |
| EP | 2403951 | 9/2015 |
| EP | 2643465 | 5/2016 |
| EP | 2428229 | 8/2016 |
| EP | 2459716 | 8/2016 |
| EP | 2220241 | 9/2016 |
| EP | 2325298 | 10/2016 |
| EP | 2379586 | 11/2016 |
| EP | 2220242 | 12/2016 |
| EP | 2774985 | 12/2016 |
| EP | 2163260 | 3/2017 |
| EP | 2580234 | 3/2017 |
| EP | 2798069 | 3/2017 |
| EP | 2855685 | 3/2017 |
| EP | 2900818 | 6/2017 |
| EP | 2301582 | 7/2017 |
| EP | 3049520 | 7/2017 |
| EP | 1453543 | 8/2017 |
| EP | 2463362 | 11/2017 |
| EP | 2558481 | 12/2017 |
| EP | 2682459 | 12/2017 |
| EP | 2714916 | 1/2018 |
| EP | 2391638 | 6/2018 |
| EP | 2563919 | 6/2018 |
| EP | 2971008 | 7/2018 |
| EP | 2606137 | 8/2018 |
| EP | 2855669 | 10/2018 |
| EP | 2986311 | 11/2018 |
| EP | 3145537 | 12/2018 |
| EP | 2654786 | 2/2019 |
| EP | 3280798 | 6/2019 |
| EP | 3029144 | 7/2019 |
| EP | 3150706 | 7/2019 |
| EP | 2809788 | 9/2019 |
| EP | 3071697 | 10/2019 |
| EP | 3274363 | 10/2019 |
| EP | 3460052 | 10/2019 |
| JP | 2005-525779 | 9/2005 |
| JP | 2008-517627 | 5/2008 |
| JP | 2010-527324 | 8/2010 |
| JP | 2011-524904 | 9/2011 |
| WO | WO 96/18418 | 6/1996 |
| WO | WO 98/54346 | 12/1998 |
| WO | WO 98/55641 | 12/1998 |
| WO | WO 99/44423 | 9/1999 |
| WO | WO 00/03029 | 1/2000 |
| WO | WO 00/22137 | 4/2000 |
| WO | WO 00/42208 | 7/2000 |
| WO | WO 01/02431 | 1/2001 |
| WO | WO 01/004282 | 1/2001 |
| WO | WO 01/21217 | 3/2001 |
| WO | WO 01/23004 | 4/2001 |
| WO | WO 01/90392 | 11/2001 |
| WO | WO 01/98513 | 12/2001 |
| WO | WO 02/46372 | 6/2002 |
| WO | WO 03/064666 | 8/2003 |
| WO | WO 03/076605 | 9/2003 |
| WO | WO 2003/092579 | 11/2003 |
| WO | WO 03/104467 | 12/2003 |
| WO | WO 2004/018627 | 3/2004 |
| WO | WO 2004/031357 | 4/2004 |
| WO | WO 2005/001103 | 1/2005 |
| WO | WO 2005/023848 | 3/2005 |
| WO | WO 2005/030261 | 4/2005 |
| WO | WO 2005/065348 | 7/2005 |
| WO | WO 2005/075506 | 8/2005 |
| WO | WO 2005/107474 | 11/2005 |
| WO | WO 2005/113781 | 12/2005 |
| WO | WO 2005/117993 | 12/2005 |
| WO | WO 2006/086357 | 8/2006 |
| WO | WO 2006/119449 | 11/2006 |
| WO | WO 2007/124065 | 11/2007 |
| WO | WO 2008/095168 | 8/2008 |
| WO | WO 2008/150496 | 12/2008 |
| WO | WO 2009/065800 | 5/2009 |
| WO | WO 2010/024483 | 3/2010 |
| WO | WO 2010/037027 | 4/2010 |
| WO | WO 2011/133040 | 10/2011 |
| WO | WO 2012/003287 | 1/2012 |
| WO | WO 2012/022496 | 2/2012 |
| WO | WO 2012/024350 | 2/2012 |
| WO | WO 2012/024351 | 2/2012 |
| WO | WO 2012/038606 | 3/2012 |
| WO | WO 2012/083297 | 6/2012 |
| WO | WO 2013/036791 | 3/2013 |
| WO | WO 2013/135615 | 9/2013 |
| WO | WO 2013/138505 | 9/2013 |
| WO | WO 2014/000026 | 1/2014 |
| WO | WO 2014/153204 | 9/2014 |
| WO | WO 2014/170389 | 10/2014 |
| WO | WO 2015/155370 | 10/2015 |
| WO | WO 2016/049201 | 3/2016 |

(56) References Cited

FOREIGN PATENT DOCUMENTS

| | | |
|---|---|---|
| WO | WO 2017/062511 | 4/2017 |
| WO | WO 2017/147265 | 8/2017 |
| WO | WO 2017/147269 | 8/2017 |
| WO | WO 2018/078220 | 5/2018 |
| WO | WO 2018/083257 | 5/2018 |
| WO | WO 2018/083258 | 5/2018 |
| WO | WO 2018/083259 | 5/2018 |
| WO | WO 2018/104919 | 6/2018 |
| WO | WO 2018/201017 | 11/2018 |
| WO | WO 2018/204677 | 11/2018 |
| WO | WO 2018/218083 | 11/2018 |
| WO | WO 2019/016756 | 1/2019 |
| WO | WO 2019/057745 | 3/2019 |
| WO | WO 2019/073059 | 4/2019 |
| WO | WO 2019/086450 | 5/2019 |
| WO | WO 2019/086456 | 5/2019 |
| WO | WO 2019/086461 | 5/2019 |
| WO | WO 2019/086466 | 5/2019 |
| WO | WO 2019/158914 | 8/2019 |
| WO | WO 2019/179977 | 9/2019 |
| WO | WO 2019/179979 | 9/2019 |
| WO | WO 2019/191494 | 10/2019 |
| WO | WO 2019/199859 | 10/2019 |
| WO | WO 2019/202118 | 10/2019 |
| WO | WO 2019/239311 | 12/2019 |
| WO | WO 2020/014539 | 1/2020 |
| WO | WO 2020/046130 | 3/2020 |
| WO | WO 2020/076820 | 4/2020 |

OTHER PUBLICATIONS

Yaghoubi et al., "Positron Emission Tomography Reporter Genes and Reporter Probes: Gene and Cell Therapy Applications," *Theranostics*, vol. 2:374-391, 2012.

Alba et al., "Gutless adenovirus: last-generation adenovirus for gene therapy," Gene Ther 12:S18-S27, 2005.

Alba et al., "Identification of coagulation factor (F)X binding sites on the adenovirus serotype 5 hexon: effect of mutagenesis on FX interactions and gene transfer," Blood 114(5): 965-971, 2009.

Alonso et al., "Combination of the oncolytic adenovirus ICOVIR-5 with chemotherapy provides enhanced anti-glioma effect in vivo," Cancer Gene Ther 14:756-761, 2007.

Barton, et al., "Second-Generation Replication-Competent Oncolytic Adenovirus Armed with Improved Suicide Genes and ADP Gene Demonstrates Greater Efficacy without Increased Toxicity", Molecular Therapy, 2006, 13(2):347-356.

Batzer et al., "Enhanced evolutionary PCR using oligonucleotides with inosine at the 3'-terminus", Nucleic Acid Research, 1991, 19(18):5081.

Bauerschmitz et al., "Tissue-Specific Promoters Active in CD44+ CD24-llow Breast Cancer Cells," Cancer Res 68(14):5533-5539, 2008.

Bayle et al., "Rapamycin Analogs with Differential Binding Specificity Permit Orthogonal Control of Protein Activity," Chem Biol 13:99-107, 2006.

Behar et al., "Llama Single-Domain Antibodies Directed against Nonconventional Epitopes of Tumor-Associated Carcinoembryonic Antigen Absent from Nonspecific Cross-Reacting Antigen," FEBS J., vol. 276:3881-3893, 2009.

Belousova et al., "Modulation of Adenovirus Vector Tropism via Incorporation of Polypeptide Ligands into the Fiber Protein," J Virol 76(17):8621-8631, 2002.

Berge et al., "Pharmaceutical Salts", Journal of Pharmaceutical Science, 1977, 66: 1-19.

Bett et al., "DNA sequence of the deletion/insertion in early region 3 of Ad5 d1309," Virus Res 39: 75-82, 1995.

Binkowski et al., "Ligand-Regulated Peptides: A General Approach for Modulating Protein-Peptide Interactions with Small Molecules," *Chem. Biol.*, vol. 12: 847-855, 2005.

Bradshaw et al., "Biodistribution and inflammatory profiles of novel pen ton and hexon double-mutant serotype 5 adenoviruses," J Control Release 164(3): 394-402, 2012.

Card et al., "MicroRNA silencing improves the tumor specificity of adenoviral transgene expression," Cancer Gene Ther 19: 451-459, 2012.

Chen et al., "Identification of an 11-kDa FKBP12-rapamycin-binding domain within the 289-kDa FKBP12-rapamycin-associated protein and characterization of a critical serine residue," Proc Natl Acad Sci USA 92:4947-4951, 1995.

Cheo et al., "Concerted Assembly and Cloning of Multiple DNA Segments Using In Vitro Site-Specific Recombination: Functional Analysis of Multi-Segment Expression Clones," Genome Res 14:2111-2120, 2004.

Chong et al., "A System for Small-Molecule Control of Conditionally Replication-Competent Adenoviral Vectors," Mal Ther 5(2): 195-203, 2002.

Chopra, "Recombinant Adenovirus with Enhanced Green Fluorescent Protein," Molecular Imaging and Contrast Agent Database (MICAD), Bethesda, MD: National Center for Biotechnology Information (US) (2004-2013): (Dec. 9, 2007, updated Jan. 2, 2008), 5 pp.

Doronin et al., "Overexpression of ADP (E3-11.6K) Protein Increases Cell Lysis and Spread of Adenovirus," Virology 305: 378-387, 2003.

Doronin et al., "Tumor-Specific, Replication-Competent Adenovirus Vectors Overexpressing the Adenovirus Death Protein," J. Viral., vol. 74:6147-6155, 2000.

Evans et al., "Relocalization of the Mre11-Rad50-Nbs1 Complex by the Adenovirus E4 ORF3 Protein is Required for Viral Replication", Journal of Virology, 2005, 79(10):6207-6215.

Extended European Search Report dated Dec. 11, 2013 for European Application No. 11818698.0, 10 pages.

Extended European Search Report for European Application No. 13760821.2, dated Sep. 30, 2015.

Fang et al., "An Antibody Delivery System for Regulated Expression of Therapeutic Levels of Monoclonal Antibodies In Vivo," Mal. Ther., vol. 15:1153-1159, 2007.

Finke et al., "Tracking Fluorescence-Labeled Rabies Virus: Enhanced Green Fluorescent Protein-Tagged Phosphoprotein P Supports Virus Gene Expression and Formation of Infectious Particles," J. Viral., vol. 78(22): 12333-12343, 2004.

Frese et al., "Selective PDZ protein-dependent stimulation of phosphatidylinositol 3-kinase by the adenovirus E4-ORF1 oncoprotein," Oncogene 22: 710-721, 2003.

Fuerer et al., "Adenoviruses with Tcf binding sites in multiple early promoters show enhanced selectivity for tumour cells with constitutive activation of the wnt signalling pathway," Gene Ther 9:270-281, 2002.

Funston et al., "Expression of heterologous genes in oncol ytic adenoviruses using picornaviral 2A sequences that trigger ribosome skipping," J Gen Viral 89:389-396, 2008.

Gall et al., "Construction and Characterization of Hexon-Chimeric Adenoviruses: Specification of Adenovirus Serotype," J Virol 72(12): 10260-10264, 1998.

Gibson et al., "Enzymatic Assembly of DNA Molecules up to Several Hundred Kilobases," Nature Meth., vol. 6:343-360, 2009.

Glasgow et al., "A Strategy for Adenovirus Vector Targeting with a Secreted Single Chain Antibody," PLoS One, vol. 4:e8355, 2009.

Havenga et al., "Novel Replication-Incompetent Adenoviral B-group Vectors: High Vector Stability and Yield in PER.C6 Cells," J. Gen. Viral., vol. 87:2135-2143, 2006.

Hawkins et al., "Gene delivery from the E3 region of replicating human adenovirus: evaluation of the E3B region," Gene Therapy 8, 1142-1148, 2001.

Heise et al., "An Adenovirus EIA Mutant that Demonstrates Potent and Selective Systemic Anti-Tumoral Efficacy," Nat Med. 6: 1134-1139, 2000.

Helin et al., "Heterodimerization of the Transcription Factors E2F-1 and DP-1 is required for Binding to the Adenovirus E4 (ORF6/7) Protein," J Virol 68: 5027-5035, 1994.

Henikoff et al., "Amino acid substitution matrices from protein blocks", Proc. Natl. Acad. Sci. USA , 1992, 89:10915-10919.

(56) References Cited

OTHER PUBLICATIONS

Hernandez-Aya et al. "Targeting the Phosphatidylinositol 3-Kinase Signaling Pathway in Breast Cancer", The Oncologist, 16, pp. 404-414, 2011.
Holm et al., "Multidrug-resistance Cancer Cells Facilitate El-independent Adenovirus Replication: Impact for Cancer Gene Therapy," Cancer Res 64:322-328, 2004.
International Preliminary Report on Patentability and Written Opinion dated Feb. 19, 2013 for International Application No. PCT/US2011/048005, 5 pages.
International Search Report dated Mar. 23, 2012 for International Application No. PCT/US2011 /048005, 6 pages.
International Search Report and Written Opinion for PCT/US2019/026626, dated Jun. 24, 2019 (12 pages).
Javier, "Cell polarity proteins: common targets for tumorigenic human viruses," Oncogene 27:7031-7046, 2008.
Johnson et al., "Selectively replicating adenoviruses targeting deregulated E2F activity are potent, systemic antitumor agents," Cancer Cell 1:325-337, 2012.
Ketzer et al., "Synthetic riboswitches for external regulation of genes transferred by replication-deficient and oncolytic adenoviruses," Nucleic Acids Res 40(21):e167 (10 pages), 2012.
Kim et al., "High Cleavage Efficiency of a 2A Peptide Derived from Porcine Teschovirus-1 in Human Cell Lines, Zebrafish and Mice," PLoS ONE, vol. 64:e18556, 2011.
Kirn, "Clinical research results with d11520 (Onyx-015, a replication-selective adenovirus for the treatment of cancer: what have we learned?", Gene Therapy, 2001, 8(2):89-98.
Kovesdi et al., "Role of an Adenovirus E2 Promoter Binding Factor in E1A Mediated Coordinate Gene Control," Proc Nat Acad Sci USA 84: 2180-2184, 1987.
Leicher et al., "Coexpression of the KCNA3B Gene Product with Kv1 .5 Leads to a Novel A-type Potassium Channel*", The Journal of Biological Chemistry, 1998, 273(52):35095-35101.
Leppard et al., "Adenovirus type 5 E4 Orf3 protein targets promyelocytic leukaemia (PML) protein nuclear domains for disruption via a sequence in PML isoform II that is predicted as protein as a protein interaction site of bioinformatics anaylsis", Journal of General Virology 2009, 90(1):95-104.
Li et al., "Harnessing homologous recombination in vitro to generate recombinant DNA via SLIC," Nat Methods 4(3):251-256, 2007.
Liu et al., "Oncolytic Adenoviral Vector Carrying the Cytosine Deaminase Gene for Melanoma Gene Therapy," Cancer Gene Ther., vol. 13:845-855, 2006.
Lopez et al., "A Tumor-stroma Targeted Oncolytic Adenovirus Replicated in Human Ovary Cancer Samples and Inhibited Growth of Disseminated Solid Tumors in Mice," Mal Ther 20(12):2222-2233, 2012.
McCormick, "Cancer Gene Therapy: Fringe or Cutting Edge?," Nature Rev. Cancer, vol. 1:130-141, 2001.
Minskaia et al., "Protein Coexpression Using FMDV 2A: Effect of "Linker" Residues," BioMed Research International, vol. 2013, 12 pp.
Mohr, "To replicate or not to replicate: achieving selective oncolytic virus replication in cancer cells through translational control," Oncogene, vol. 24:7697-7709, 2005.
Murakami et al., "Chimeric Adenoviral Vectors Incorporating a Fiber of Human Adenovims 3 Efficiently Mediate Gene Transfer into Prostrate Cancer Cells," The Prostate, vol. 70:362-376, 2009.
NCBI Accession No. CV1 10986, Jan. 11, 2011, 3 pages.
Nevels et al., "The Adenovirus E4orf6 can Promote E1A/E1B-induced Focus Formation by Interfering with p53 Tumor Suppressor Function," Proc. Natl. Acad. Sci. USA, vol. 94:1206-1211, 1997.
Office Action and Search Report from China Application No. 2013 80014047.7, dated Aug. 5, 2015 (English translation).
Ono et al., "Noninvasive Visualization of Adenovirus Replication with a Fluorescent Reporter in the E3 Region," Cancer Res., vol. 65: 10154-10158, 2005.
O'Shea et al., "Adenoviral Proteins Mimic Nutrient/Growth Signals to Activate the mTOR Pathway for Viral Replication," EMBO J., vol. 24:1211-1221, 2005.
O'Shea et al., "Adenovirus Overrides Cellular Checkpoints for Protein Translation," Cell Cycle 4(7):883-888, 2005.
O'Shea et al., "DNA Tumor Viruses—the Spies who Lyse Us," Curr. Opin. Genet. Dev., vol. 15:18-26, 2005.
O'Shea et al., "Viruses—seeking and destroying the tumor program," Oncogene 24: 7640-7655, 2005.
Pearson et al., "Improved tools for biological sequence comparison", Proc. Nat'/. Acad. Sci. USA , 1988, 85:2444-2448.
Pelka et al., "Adenovirus EIA Directly Targets the E2F/DP-1 Complex," J Viral 85(17):8841-8851, 2011.
Rossolini et al., "Use of deoxyinosine-containing primers vs degenerate primers for polymerase chain reaction based on ambiguous sequence information", Mo/. Cell. Probes, 1994, 8:91-98.
Roy et al., "Rescue of chimeric adenoviral vectors to expand the serotype repertoire," J Viral Methods 14:41-21, 2007.
Shapiro et al., "Recombinant Adenoviral Vectors Can Induce Expression of p73 via the E4-orf6/7 Protein," J Viral 80(11):5349-5360, 2006.
Shepard et al., "E4orf13 is Necessary for Enhanced S-Phase Replication of Cell Cycle-Restricted Subgroup C Adenoviruses," J Virol 77(15):8593-8595, 2003.
Smith et al., "Comparison of Biosequences", Advances in Applied Mathematics, 1981, 2:482-489.
Soria et al., "Heterochromatin silencing of p53 target genes by a small viral protein", Nature, 2010, 466(7310):1076-1083.
Stanton et al. "Re-engineering adenovirus vector systems to enable high-throughput analyses of gene function" Bio Techniques 45: 659-668 (Dec. 2008).
Szymczak et al., "Correction of Multi-Gene Deficiency in vivo using a Single 'selfcleaving' 2A Peptide-Based Retroviral Vector," Nature Biotech., vol. 22:589-594, 2004.
Tan et al., "Coexpression of double or triple the rabies virus glycoprotein gene using a 'self-cleaving' 2A peptide-based replication-defective human adenovirus serotype 5 vector," Biologicals, vol. 38:586-593, 2010.
Ullman et al., "Adenovirus E4 ORF3 Protein Inhibits the Interferon-Mediated Antiviral Response", Journal of Virology, 2007, 81(9):47 44-4752.
Verheije et al., "Retargeting of Viruses to Generate Oncolytic Agents," Adv. Viral., vol. 2012:1-15, 2012.
Volk et al., "Enhanced Adenovirus Infection of Melanoma Cells by Fiber-Modification," Cancer Biol Ther 2(5): 511-515, 2003.
Waehler et al., "Engineering targeted viral vectors for gene therapy," Nat Rev Genet 8(8):573-587, 2007.
Wang et al., "Identification of Specific Adenovirus E1A-N-Terminal Residues Critical to the Binding of Cellular Proteins and to the Control of Cell Growth," J. Viral., vol. 67:476-488, 1993.
Warram et al., "A Genetic Strategy for Combined Screening and Localized Imaging of Breast Cancer," Mal Imaging Biol 13:452-461, 2011.
Whyte et al., "Association between an Oncogene and an Anti-Oncogene: the Adenovirus E1A Proteins Bind to the Retinoblastoma Gene Product," Nature 334:124-129, 1988.
Yount et al., "Strategy for Systematic Assembly of Large RNA and DNA Genomes: Transmissible Gastroenteritis Virus Model," J. Viral., vol. 74: 10600-10611, 2000.
Fueyo et al., "A mutant Oncolytic Adenovirus Targeting the Rb Pathway Produces Anti-Glioma Effect In Vivo," *Oncogene*, vol. 19:2-12, 2000.
Ji et al., "Oncolytic Adenoviruses Delivering Herpes Simplex Virus Thymidine Kinase Suicide Gene Reduces the Growth of Human Retinoblastoma in an in vivo Mouse Model," *Experimental Eye Res.*, vol. 89:193-199, 2009.
Kubo et al., "Complete Regression of Human Malignant Mesothelioma Xenografts Following Local Injection of Midkine Promoter-Driven Oncolytic Adenovirus," *J. Gene Med.*, vol. 12:681-692, 2010.
Li, "Self-Cleaving Fusion Tags for Recombinant Protein Production," *Biotechnol. Lett.*, vol. 33:869-881, 2011 .
Loskog, "Immunostimulatory Gene Therapy Using Oncolytic Viruses as Vehicles," *Viruses*, vol. 7:5780-5791. 2015.

(56) References Cited

OTHER PUBLICATIONS

Wu et al., "The Application of Intein in the Research of Membrane Protein," *Chemistry of Life*, vol. 35:200-205, 2015 (with English language abstract).
Hibma et al., "Increased apoptosis and reduced replication efficiency of the E3 region-modified dl309 adenovirus in cancer cells," *Virus Res* 145:112-120, 2009.
Dias et al., "Targeted cancer immunotherapy with oncolytic adenovirus coding for a fully human monoclonal antibody specific for CTLA-4," *Gene Therapy*, vol. 19:988-998, 2012.
Kurihara et al., "Selectivity of a replication-competent adenovirus for human breast carcinoma cells expressing the MUCI antigen," *J. Clin. Invest.*, vol. 106:763-771, 2000.

* cited by examiner

Kras; p53/+; Cre
(2 month old)

FIG. 8A
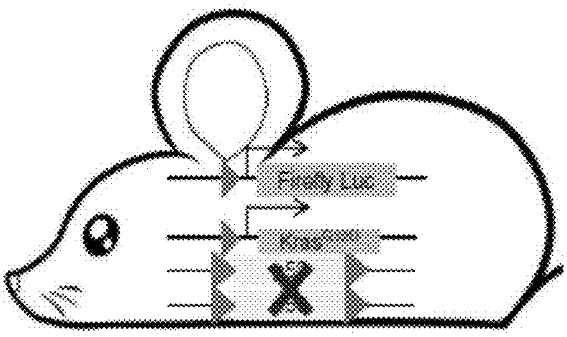
FIG. 8B
| Treatment | Ave. Survival (days) |
|---|---|
| No treatment | 37.5 |
| AdSyn-CO989 i.v. + GCV i.p. | 42 |
| AdSyn-CO987 i.v. + saline i.p. | 42 |
| Only GCV i.p. | 46.5 |
| Only GCV i.v. | 48 |
| AdSyn-CO987 i.v. + GCV i.p. | 55 |
| AdSyn-CO987 i.v. + GCV i.v. | 54 |
FIG. 8C
6 days after the viruses injection
9 days after the viruses injection
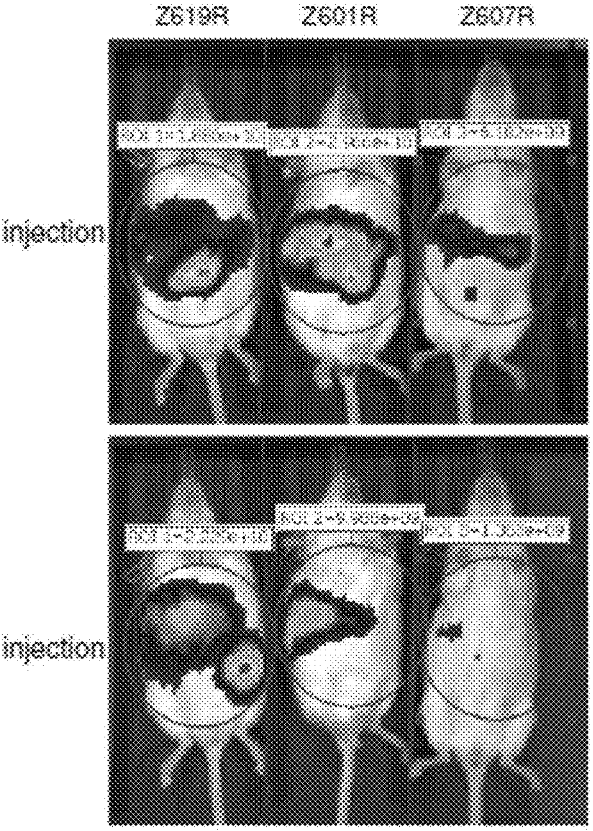

TUMOR-TARGETING SYNTHETIC ADENOVIRUSES AND USES THEREOF

CROSS REFERENCE TO RELATED APPLICATIONS

This application a continuation of International Application No. PCT/US2017/065604, filed Dec. 11, 2017, published in English under PCT Articles 21(2), which claims the benefit of U.S. Provisional Application No. 62/433,140, filed Dec. 12, 2016, which are both herein incorporated by reference in their entireties.

FIELD

This disclosure concerns synthetic adenoviruses having chimeric fiber proteins and liver detargeting mutations that traffic to sites of tumors. This disclosure further concerns use of the synthetic adenoviruses to express diagnostic or therapeutic transgenes in tumors.

BACKGROUND

Adenovirus (Ad) is a natural multi-gene expression vehicle. Certain coding regions of the virus, such as the E1, E3 and E4 regions, are either not necessary for replication in culture or can be complemented with available cell lines. Therefore, each of these regions can be replaced with non-viral genes to drive the expression of multiple transgenes from a single virus. There are 68 different human adenovirus serotypes, each of which has different properties. Ad5 has been the predominant Ad vector used in basic research, gene therapy and oncolytic virus therapy. However, Ad5 has a limited tropism and only infects epithelial cells that have the coxsackie adenovirus receptor (CAR) receptor for viral uptake. Furthermore, when injected intravenously, Ad5 binds to blood factors that cause it to be sequestered in the liver where it can trigger potentially limiting inflammation and toxicity. Thus, a need remains for modified adenovirus vectors capable of infecting specific cell types following intravenous administration.

SUMMARY

Described herein is the finding that a liver-detargeted synthetic adenovirus expressing a fiber protein with an adenovirus type 34 (Ad34) knob domain is capable of homing to sites of tumors. The synthetic adenoviruses can be used to deliver and express diagnostic or therapeutic transgenes in tumor cells, including tumor stromal cells.

Provided herein is a method of expressing a transgene in tumor cells of a subject. In some embodiments, the method includes administering to the subject a synthetic adenovirus that includes the transgene, a native or modified capsid that detargets the synthetic adenovirus from the liver, and an Ad34 fiber protein or a chimeric fiber protein comprising an adenovirus type 5 (Ad5) shaft domain and an Ad34 knob domain. The transgene can be, for example, a diagnostic transgene or a therapeutic transgene.

Also provided herein is a method of diagnosing a subject as having a tumor. In some embodiments, the method includes administering to the subject a synthetic adenovirus that includes a diagnostic transgene, a native or modified capsid that detargets the synthetic adenovirus from the liver, and an Ad34 fiber protein or a chimeric fiber protein comprising an Ad5 shaft domain and an Ad34 knob domain. In some examples, the diagnostic transgene is a positron emission tomography (PET) reporter gene. In other examples, the diagnostic transgene encodes a fluorescent protein or an enzyme.

Further provided herein is a method of treating a tumor in a subject. In some embodiments, the method includes administering to the subject a synthetic adenovirus that includes a therapeutic transgene, a native or modified capsid that detargets the synthetic adenovirus from the liver, and an Ad34 fiber protein or a chimeric fiber protein comprising an Ad5 shaft domain and an Ad34 knob domain. In some examples, the therapeutic transgene encodes an anti-cancer agent or an agent that disrupts or kills tumor stromal cells.

Synthetic adenovirus genomes having at least 95% sequence identity to SEQ ID NO: 2 or SEQ ID NO: 5 are also provided by the present disclosure.

The foregoing and other objects and features of the disclosure will become more apparent from the following detailed description, which proceeds with reference to the accompanying figures.

BRIEF DESCRIPTION OF THE DRAWINGS

(FIG. 1A) Cre-LoxP Kras$^{G12D}$/p53 pancreatic tumor model overview. Mice designated as "Kras; p53/p53" encode the Kras$^{G12D}$ oncogene downstream of the sequence encoding LoxP-stop codon-LoxP. The stop codon blocks the expression of Kras$^{G12D}$ in the absence of Cre recombinase. However, in the presence of Cre recombinase, the stop codon is removed and allows for expression of the Kras$^{G12D}$ oncogene. In these same mice, both alleles of the p53 gene are flanked by LoxP sites (LoxP-p53-LoxP). Mice designated "p53/p53; Cre" have both alleles of the p53 gene flanked by LoxP sites (LoxP-p53-LoxP) and also express the Cre recombinase transgene driven by the pancreatic and duodenal homeobox 1 (Pdx1) promoter. Pdx1 is a gene that is expressed specifically in the pancreatic cells, and thus both copies of p53 are deleted in the pancreatic cells. Breeding between the strains gives rise to offspring in which the Pdx1 promoter-driven Cre mediates the deletion of both alleles of the tumor suppressor p53 and activation of the mutant Kras$^{G12D}$ in pancreatic cells. Homozygous mice designated "Kras; p53/p53; Cre" develop pancreatic tumors in 5-7 weeks. (FIG. 1B) AdSyn-CO176, a synthetic virus with a chimeric fiber protein comprising the Ad34 knob domain, was injected intravenously into Kras; p53/p53 and Kras; p53/p53; Cre mice. Seventy-two hours after the injection of virus, tissues were collected, incubated for 5 minutes with luciferin, and then scanned for 5 minutes using the IVIS™ imaging system. The Kras; p53/p53 mouse had a normal pancreas, and the luciferase signal was mainly from the spleen. The Kras; p53/p53; Cre mouse had pancreatic tumors, and the signal was mainly from the pancreatic tumor.

(FIG. 2A) Kras; p53/p53 mice are as described for FIG. 1A. Mice designated as "p53/+; Cre" mice have one wild type p53 allele and one p53 allele flanked by LoxP sites (LoxP-p53-LoxP). Breeding between these two strains gives rise to offspring in which the Pdx1 promoter-driven Cre recombinase mediates the deletion of a single allele of the tumor suppressor p53 and activation of the mutant Kras$^{G12D}$ in pancreatic cells. These heterozygous mice, designated "Kras; p53/+; Cre," develop tumors later in life (at 4-9 months of age) due to the fact that they have one wild type allele of p53. This wild type allele must be lost or mutated in order for pancreatic tumors to develop. (FIG. 2B) AdSyn-CO176 was injected intravenously into p53/+; Cre and Kras; p53/+; Cre mice (4 months old). Seventy-two hours after the injection of virus, tissues were collected, incubated with luciferin for 5 minutes, and then scanned for 1 minute using the IVIS™ imaging system. The p53/+; Cre mouse had a normal pancreas, and the signal was mainly from spleen. The Kras; p53/+; Cre mouse at 4 months of age had a pancreatic tumor, and the signal was mainly from the tumor and liver.

(FIG. 3A) AdSyn-CO176 was injected intravenously into Kras; p53/+; Cre mice at 2 months of age. Seventy-two hours after the injection of virus, tissues were collected, incubated with luciferin for 5 minutes, and scanned for 4 minutes using the IVIS™ imaging system. The pancreas of Kras; p53/+; Cre mouse at 2 months old looked normal but luciferase signal was found in this tissue. (FIG. 3B) H&E staining showing the typical histology of normal pancreas (a) and pancreatic tumor (b). (FIG. 3C) H&E staining of the pancreas from a Kras; p53/+; Cre mouse at 2 months of age showing that a small part of the pancreas was developing the tumor (as shown in the polygon). Most of the pancreas appeared normal. This result indicates that AdSyn-CO176 can infect pancreatic tumors at a very early stage.

(FIG. 4A) IHC staining of a pancreatic tumor infected with AdSyn-CO176. CK19 is a marker of tumor cells while smooth muscle actin (SMA) is a marker of stromal cells. The staining of GFP, which was expressed from AdSyn-CO176 overlapped with SMA staining, indicating that AdSyn-CO176 targets stromal cells. (FIG. 4B) IF staining of the pancreatic tumor infected by AdSyn-CO176. GFP staining overlapped with SMA staining, confirming AdSyn-CO176 infection of stromal cells.

(FIG. 5A) Schematic of a Cre-mediated genetic manipulation glioblastoma model. Lentiviruses were injected directly into the brain of GFAP-Cre mice. Glial fibrillary acidic protein (GFAP) promoter-driven Cre recombinase cleaves out RFP from the lentivirus-encoded gene and induces the expression of $HRas^{V12}$ and GFP primarily in astrocytes. Expression of lentivirus-encoded U6-p53 shRNA knocks down the expression of p53 in the brain cells that take up the virus. The expression of $HRas^{V12}$ and the knock down of p53 induces tumorigenesis in the brain from 1 week after the injection. GFP signal is used to indicate the formation of glioblastoma. (FIG. 5B) Saline, AdSyn-CO171, or AdSyn-CO176 were injected via intravenous (IV) administration into GFAP-Cre mice that had received the tumor-inducing lentiviruses 4 weeks earlier. Forty-eight hours after the injection of virus, mice were scanned for 1 minute using the IVIS™ imaging system 5 minutes after the intraperitoneal injection of luciferin. The luciferase signal was detected in AdSyn-CO176-infected mice (arrow), while no signal was detected in saline-treated or AdSyn-CO171-injected mice. (FIG. 5C) Wild type mice (normal brain) and GFAP-Cre mice with the injection of lentiviruses (develop brain tumors) were injected with AdSyn-CO171 or AdSyn-CO176. Brain tissues were collected 72 hours after the injection of synthetic adenoviruses, incubated with luciferin for 5 minutes, and scanned for 5 minutes using the IVIS™ imaging system. Only the GFAP-Cre mouse injected with the tumor-inducing lentiviruses showed a luciferase signal from AdSyn-CO176. This demonstrates that AdSyn-CO176 will traffic to the brain tissue only when a tumor is present. (FIG. 5D) Brain tissues were also scanned for the GFP signal. The GFP signal is used to identify the glioblastoma. Both of the GFAP-Cre mice that received the tumor-inducing lentiviruses had the GFP signal in the brain, while no GFP was detected in mice that did not receive lentivirus. The GFP signal overlapped with the luciferase signal perfectly in the GFAP-Cre mouse that received the tumor-inducing lentiviruses and AdSyn-CO176.

(FIG. 6A) GFAP-Cre mice were injected with either Hanks' balanced salt solution (HBSS) or tumor-inducing lentiviruses. After 4 weeks, AdSyn-CO171 was injected intravenously. There was no luciferase signal from AdSyn-CO171 in the brain in either group of mice. (FIG. 6B) GFAP-Cre mice were injected with HBSS or tumor-inducing lentiviruses, or received no injection. After 4 weeks, mice were injected intravenously with AdSyn-CO176. The luciferase signal was detected only in the brain of the mouse that received the tumor-inducing lentiviruses, while the mouse that received HBSS or no injection produced no signal. These results demonstrate that the specificity of AdSyn-CO176 is driven by the tumor and not the injection site injury.

(FIG. 7A) Schematic of the human glioblastoma xenograft model. Human glioblastoma U87 cells that expresses the tdTomato fluorescent protein (U87-tdTomato) were injected intracranially into NOD scid gamma (NSG) mice to generate glioblastoma tumors. (FIG. 7B) AdSyn-CO171 and AdSyn-CO176 were injected intravenously into NSG mice by tail vein injection 4 weeks after they received the intracranial injection of U87-tdTomato. Forty-eight hours after the injection of viruses, the tissues indicated in the panel were collected, incubated with luciferin for five minutes and then scanned for 1 minute using the IVIS™ imaging system. Only the AdSyn-CO176 injected mice showed luciferase signal in the brain, and this signal completely overlapped with tdTomato expression.

FIGS. 8A-8C. Administration of a synthetic adenovirus with a therapeutic transgene. (FIG. 8A) Schematic of the KPCL ($Kras^{G12D}$; p53 knockout; Pdx1-Cre; firefly Luciferase) mouse model. KPCL mice are similar to homozygous "Kras; p53/p53; Cre" mice, which specifically express $Kras^{G12D}$ in the pancreas and have the p53 gene knocked out only in the pancreas. However, KPCL mice also specifically express firefly luciferase in the pancreas. The development of tumors in KPCL mice is also similar to the "Kras; p53/p53; Cre" mice. (FIG. 8B) Table showing average survival of KPCL mice for each treatment (at least 4 mice per treatment group). AdSyn-CO987 is a synthetic adenovirus based upon AdSyn-CO176. The herpes simplex virus-1 thymidine kinase (TK)/ganciclovir (GCV) suicide gene was cloned into AdSyn-CO176 to replace the firefly luciferase/GFP gene. A Renilla luciferase was also inserted just after TK in the genome of AdSyn-CO176. Control virus AdSyn-CO989 was generated by cloning TK-P2A-renilla luciferase into AdSyn-CO171 to replace the original firefly luciferase/GFP gene. KPCL mice were injected intravenously via the tail vein with $1\times10^6$ plaque forming units (PFU) of the indicated viruses at 5-6 weeks of age. Two days later, the mice were injected intraperitoneally (i.p.) or intravenously (i.v.) with GCV. Three control groups were used: AdSyn-CO989+GCV; AdSyn-CO987 followed with saline injection (AdSyn-CO987+saline); and GCV injection only (i.p. or i.v.). Treatment with AdSyn-CO987+GCV extended mouse survival compared with controls. (FIG. 8C) Images of representative mice showing firefly luciferase signal. The firefly luciferase signal (expressed by tumors) was analyzed during treatment to monitor tumor growth. The treatment for mouse Z619R was AdSyn-CO987+saline, which served as the control. Mice Z601R and Z607R were treated with AdSyn-CO987+GCV (i.p.). While the strength of the firefly luciferase signal increased in the control mouse Z619R (indicating an increase in tumor size), the signal decreased in mice Z601R and Z607R (indicating a reduction in tumor size).

(FIG. 9A) Images of H&E staining of pancreatic tumors. Mice Z655, 1806, Z619 and Z621 were all control mice. Mouse Z655 was treated with i.p. injected GCV only; mouse 1806 was treated with i.v. injected GCV only; mouse Z619 was treated with AdSyn-CO987+saline; and mouse Z621 received no treatment. Mouse Z656 received treatment with AdSyn-CO987+GCV i.v. Compared to the controls, the tumor from Z656 had more regions of necrosis (as indicated by the arrowheads). (FIG. 9B) Representative regions of necrosis in the tumor of Z656 with magnification. The regions are also indicated in FIG. 9A.

SEQUENCE LISTING

Figure 1A:
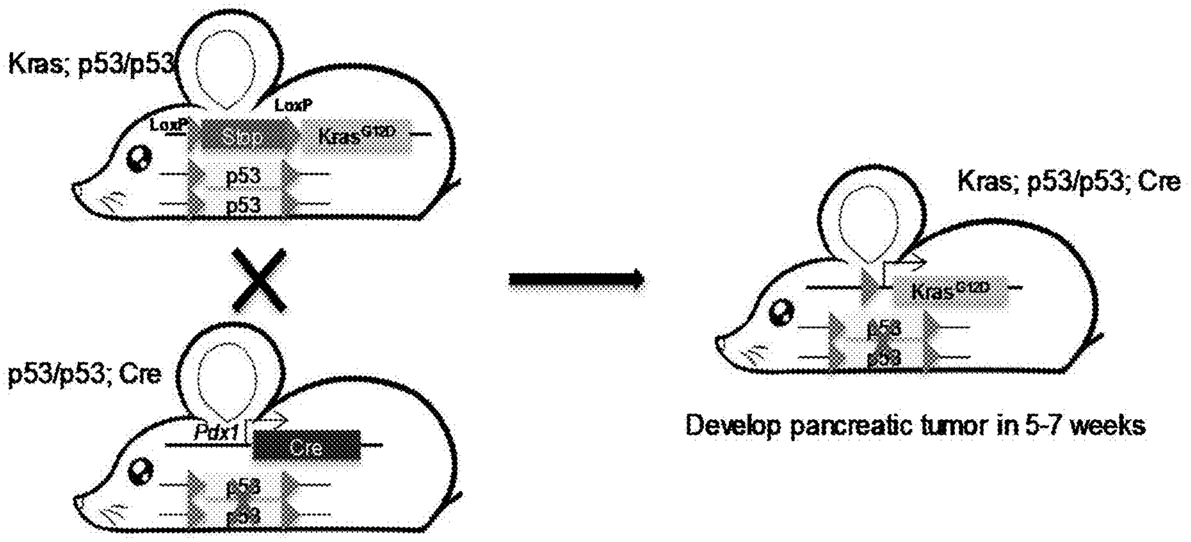
FIGS. 1A-1B. AdSyn-CO176 homes to pancreatic tumors.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jun. 3, 2019, 215 KB, which is incorporated by reference herein. In the accompanying sequence listing:

SEQ ID NO: 1 is the nucleotide sequence of synthetic adenovirus AdSyn-CO171.

SEQ ID NO: 2 is the nucleotide sequence of synthetic adenovirus AdSyn-CO176.

SEQ ID NO: 3 is the amino acid sequence of Ad5 hexon.

SEQ ID NO: 4 is the amino acid sequence of Ad5 hexon E451Q.

SEQ ID NO: 5 is the nucleotide sequence of synthetic adenovirus AdSyn-CO987.

SEQ ID NO: 6 is the nucleotide sequence of synthetic adenovirus AdSyn-CO989.

DETAILED DESCRIPTION

I. Abbreviations

Ad adenovirus
CAR coxsackie adenovirus receptor
CEA carcinoembryonic antigen
EGF epidermal growth factor
EGFR epidermal growth factor receptor
FLT3 Fms-related tyrosine kinase 3
GCV ganciclovir
GFAP glial fibrillary acidic protein
GFP green fluorescent protein
GM-CSF granulocyte macrophage colony stimulating factor
H&E hematoxylin and eosin
HSV herpes simplex virus
ICAM intercellular adhesion molecule
IF immunofluorescence
IHC immunohistochemistry
IL interleukin
IRES internal ribosomal entry site
i.p. intraperitoneal
i.v. intravenous
KPCL $Kras^{G12D}$; p53 knockout; Pdx1-Cre; firefly Luciferase
LFA lymphocyte function-associated antigen
miR microRNA
MUC1 mucin 1
NOD non-obese diabetic
NSG NOD scid gamma
PD-1 programmed cell death protein 1
PDGF platelet derived growth factor
PET positron emission tomography
PFU plaque forming unit
shRNA short hairpin RNA
SMA smooth muscle actin
TGF transforming growth factor
TK thymidine kinase
TNF tumor necrosis factor
UTR untranslated region
VEGF vascular endothelial growth factor
WT wild-type

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adenovirus: A non-enveloped virus with a linear, double-stranded DNA genome and an icosahedral capsid. There are currently 68 known serotypes of human adenovirus, which are divided into seven species (species A, B, C, D, E, F and G). Different serotypes of adenovirus are associated with different types of disease, with some serotypes causing respiratory disease (primarily species B and C), conjunctivitis (species B and D) and/or gastroenteritis (species F and G).

Administration: To provide or give a subject an agent, such as a therapeutic agent (e.g. a recombinant virus), by any effective route. Exemplary routes of administration include, but are not limited to, injection (such as subcutaneous, intramuscular, intradermal, intraperitoneal, intratumoral and intravenous), oral, intraductal, sublingual, rectal, transdermal, intranasal, vaginal and inhalation routes.

Chimeric: Composed of at least two parts having different origins. In the context of the present disclosure, a “chimeric adenovirus” is an adenovirus having genetic material and/or proteins derived from at least two different serotypes (such as from Ad5 and a second serotype of adenovirus). In this context, a “capsid-swapped” adenovirus refers to a chimeric adenovirus in which the capsid proteins are derived from one serotype of adenovirus and the remaining proteins are derived from another adenovirus serotype. Similarly, a “chimeric fiber” is a fiber protein having amino acid sequence derived from at least two different serotypes of adenovirus. For example, a chimeric fiber can be composed of a fiber shaft from Ad5 and a fiber knob from a second serotype of adenovirus.

Contacting: Placement in direct physical association; includes both in solid and liquid form.

Degenerate variant: In the context of the present disclosure, a “degenerate variant” refers to a polynucleotide encoding a peptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detargeted: In the context of the present disclosure, a “detargeted” adenovirus is a recombinant or synthetic adenovirus comprising one or more modifications that alter tropism of the virus such that is no longer infects, or no longer substantially infects, a particular cell or tissue type. In some embodiments, the recombinant or synthetic adenovirus comprises a capsid mutation, such as a mutation in the hexon protein (for example, E451Q). In some embodiments, the recombinant or synthetic adenovirus comprises a native capsid from an adenovirus that naturally does not infect, or does not substantially infect, a particular cell or tissue type. In some embodiments herein, the recombinant or synthetic adenovirus is liver detargeted and/or spleen detargeted.

E1A: The adenovirus early region 1A (E1A) gene and polypeptides expressed from the gene. The E1A protein plays a role in viral genome replication by driving cells into the cell cycle. As used herein, the term “E1A protein” refers to the proteins expressed from the E1A gene and the term includes E1A proteins produced by any adenovirus serotype.

Fiber: The adenovirus fiber protein is a trimeric protein that mediates binding to cell surface receptors. The fiber protein is comprised of a long N-terminal shaft and globular C-terminal knob.

Fusion protein: A protein containing amino acid sequence from at least two different (heterologous) proteins or peptides. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Glioblastoma: A fast-growing type of central nervous system tumor that forms from glial tissue of the brain and spinal cord. Glioblastoma usually occurs in adults and affects the brain more often than the spinal cord. Glioblastoma is the most common and most aggressive cancer that initiates in the brain. Glioblastoma is also known as glioblastoma multiforme (GBM) and grade IV astrocytoma.

Heterologous: A heterologous protein or gene refers to a protein or gene derived from a different source or species.

Hexon: A major adenovirus capsid protein. An exemplary hexon sequence from Ad5 is set forth herein as SEQ ID NO: 3. A mutant hexon sequence comprising an E451Q substitution is set forth herein as SEQ ID NO: 4.

Isolated: An “isolated” biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been “isolated” include those purified by standard purification methods. The term also embraces nucleic acid molecules and proteins prepared by recombinant expression in a host cell as well as chemically synthesized nucleic acid molecules and proteins.

MicroRNA (miRNA or miR): A single-stranded RNA molecule that regulates gene expression in plants, animals and viruses. A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs). MicroRNAs modulate gene expression by promoting cleavage of target mRNAs or by blocking translation of the cellular transcript. In the context of the present disclosure, a “liver-specific microRNA” is a microRNA that is preferentially expressed in the liver, such as a microRNA that is expressed only in the liver, or a microRNA that is expressed significantly more in the liver as compared to other organs or tissue types. In some embodiments, the microRNA is miR-122. In the context of the present disclosure, a “spleen-specific microRNA” is a microRNA that is preferentially expressed in the spleen, such as a microRNA that is expressed only in the spleen, or a microRNA that is expressed significantly more in the spleen as compared to other organs or tissue types. In some embodiments, the microRNA is miR-142-3p.

Modification: A change in the sequence of a nucleic acid or protein sequence. For example, amino acid sequence modifications include, for example, substitutions, insertions and deletions, or combinations thereof. Insertions include amino and/or carboxyl terminal fusions as well as intrasequence insertions of single or multiple amino acid residues. Deletions are characterized by the removal of one or more amino acid residues from the protein sequence. In some embodiments herein, the modification (such as a substitution, insertion or deletion) results in a change in function, such as a reduction or enhancement of a particular activity of a protein. As used herein, “Δ” or “delta” refer to a deletion. Substitutional modifications are those in which at least one residue has been removed and a different residue inserted in its place. Amino acid substitutions are typically of single residues, but can occur at a number of different locations at once. Substitutions, deletions, insertions or any combination thereof may be combined to arrive at a final mutant sequence. These modifications can be prepared by modification of nucleotides in the DNA encoding the protein, thereby producing DNA encoding the modification. Techniques for making insertion, deletion and substitution mutations at predetermined sites in DNA having a known sequence are well known in the art. A "modified" protein, nucleic acid or virus is one that has one or more modifications as outlined above.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pancreatic cancer: Cancer that begins in the tissues of the pancreas. Pancreatic cancer typically spreads rapidly and is seldom detected at early stages, leading to a poor prognosis for most diagnosed patients. The most common type of pancreatic cancer is pancreatic adenocarcinoma, which accounts for approximately 85% of pancreatic cancer cases.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents (e.g. a synthetic virus disclosed herein).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide, peptide or protein: A polymer in which the monomers are amino acid residues which are joined together through amide bonds. When the amino acids are alpha-amino acids, either the L-optical isomer or the D-optical isomer can be used. The terms "polypeptide," "peptide" and "protein" are used interchangeably herein. These terms apply to amino acid polymers in which one or more amino acid residue is an artificial chemical mimetic of a corresponding naturally occurring amino acid, as well as to naturally occurring amino acid polymers and non-naturally occurring amino acid polymers. The term "residue" or "amino acid residue" includes reference to an amino acid that is incorporated into a protein, polypeptide, or peptide.

A conservative substitution in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Positron emission tomography (PET): An imaging technique that is used to observe metabolic processes in the body. PET detects pairs of gamma rays emitted indirectly by a positron-emitting radionuclide, which is introduced into the body on a biologically active molecule. PET reporter genes encode molecules (such as receptors or enzymes) that provide a target for PET probes, which can then be detected by imaging. PET reporter genes are generally classified into three different groups: (1) reporter genes encoding enzymes that phosphorylate specific PET reporter probes, leading to their intracellular entrapment; (2) reporter genes encoding protein receptors that can be bound by specific PET reporter probes; and (3) reporter genes encoding protein transporters that transport a radionuclide reporter probe into cells expressing the reporter gene (Yaghoubi et al., *Theranostics* 2(4):374-391, 2012). As used herein, a "PET reporter gene" includes any gene that encodes a protein capable of interacting with a PET reporter probe in a manner allowing for detection of the probe by molecular imaging. Exemplary PET reporter genes include, but are not limited to, herpes simplex virus (HSV) thymidine kinase (TK) and mutant forms thereof, varicella zoster virus (VSV) TK, human mitochondrial TK and mutants thereof, mutants of deoxycytidine kinase, dopamine 2 receptors mutants, human estrogen receptor α ligand binding domain (hERL), human somatostain receptor subtype 2 (hSSTr2), recombinant human carcinoembryonic antigen (CEA), engineered antibody fragments, humanized membrane anchored anti-polyethylene glycol (PEG), sodium iodide symporter (NIS), and human norepinephrine transporter (hNET) (see Yaghoubi et al. (2012) for a review of PET reporter genes and corresponding reporter probes).

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription. A "constitutive promoter" is a promoter that is continuously active and is not subject to regulation by external signals or molecules. In contrast, the activity of an "inducible promoter" is regulated by an external signal or molecule (for example, a transcription factor or tetracycline). A "tissue-specific promoter" is a promoter that is substantially active only in a particular tissue or tissues.

Protein IX (pIX): A minor component of the adenovirus capsid that associates with the hexon protein Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule, protein or virus is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids, proteins and viruses that have been altered solely by addition, substitution, or deletion of a portion of the natural nucleic acid molecule, protein or virus.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Stroma: The supportive tissues of an epithelial organ or tumor, consisting of connective tissues and blood vessels. Stromal cells are the cells that make up the stroma, primarily fibroblasts and pericytes. Tumor stroma is predominantly made up of fibroblasts, extracellular matrix, immune cells, vasculature and basement membrane (Bremnes et al., *J Thorac Oncol* 6:209-217, 2011). Tumor stromal cells are known to play a significant role in cancer growth and progression.

Subject: Living multi-cellular vertebrate organisms, a category that includes human and non-human mammals.

Synthetic: Produced by artificial means in a laboratory, for example a synthetic nucleic acid or protein can be chemically synthesized in a laboratory.

Therapeutic agent: A chemical compound, small molecule, recombinant virus or other composition, such as an antisense compound, antibody, peptide or nucleic acid molecule capable of inducing a desired therapeutic or prophylactic effect when properly administered to a subject.

Therapeutically effective amount: A quantity of a specified pharmaceutical or therapeutic agent (e.g. a recombinant virus) sufficient to achieve a desired effect in a subject, or in a cell, being treated with the agent. The effective amount of the agent can be dependent on several factors, including, but not limited to the subject or cells being treated, and the manner of administration of the therapeutic composition.

Transgene: A gene that has been inserted into the genome of a different organism (such as a virus). Transgenes can also be referred to as heterologous genes. As used herein, a "diagnostic transgene" refers to any transgene encoding a detectable product, such as, but not limited to, a fluorescent protein, an enzyme or a PET reporter. As used herein a "therapeutic transgene" refers to any transgene encoding product with a therapeutic application. In the context of the present disclosure, a therapeutic transgene can be, for example, an anti-cancer agent or an agent that disrupts or kills cells of the tumor stroma.

Uexon: An open reading frame located on the l strand (leftward transcription) between the early E3 region and the fiber gene (Tollefson et al., *J Virol* 81(23):12918-12926).

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

III. Overview of Several Embodiments

It is disclosed herein that a liver-detargeted synthetic adenovirus expressing a fiber protein with an Ad34 knob domain is capable of homing to sites of tumors. The synthetic adenoviruses can be used, for example, to deliver and express diagnostic or therapeutic transgenes in tumor cells, including tumor stromal cells.

Provided herein is a method of expressing a transgene in tumor cells of a subject. In some embodiments, the method includes administering to the subject a synthetic adenovirus that includes the transgene, a native or modified capsid that detargets the synthetic adenovirus from the liver, and an Ad34 fiber protein or a chimeric fiber protein comprising an Ad5 shaft domain and an Ad34 knob domain.

In some embodiments, the transgene is a diagnostic transgene. In some examples, the diagnostic transgene encodes a fluorescent protein, such as, but not limited to a green fluorescent protein (GFP), a yellow fluorescent protein (YFP), a cyan fluorescent protein (CFP), a red fluorescent protein (RFP), a blue fluorescent protein (BFP), or an orange fluorescent protein (for example, mOrange). In other examples, the diagnostic transgene encodes an enzyme, such as a luciferase. In yet other examples, the diagnostic transgene comprises a PET reporter gene.

In other embodiments, the transgene is a therapeutic transgene. In some examples, the therapeutic transgene encodes an anti-cancer agent. In specific examples, the anti-cancer agent is a pro-inflammatory molecule or cytokine, such as granulocyte macrophage colony stimulating factor (GM-CSF), CD40 ligand (CD40L), Fms-related tyrosine kinase 3 (FLT3) ligand, interleukin (IL)-1b, IL-2, IL-4, IL-6, IL-12, tumor necrosis factor (TNF)-α, an interferon, a chemokine, B7-1, intercellular adhesion molecule (ICAM)-1, lymphocyte function-associated antigen (LFA)-3, transforming growth factor (TGF)-β, platelet derived growth factor (PDGF) or epidermal growth factor (EGF). In other specific examples, the anti-cancer agent is an anti-angiogenic factor, such as an inhibitor of vascular endothelial growth factor (VEGF). In other specific examples, the anti-cancer agent is an inhibitor (such as a siRNA or shRNA inhibitor) of KRas. In other specific examples, the anti-cancer agent is an inhibitor of cytotoxic T lymphocyte-associated molecule (CTLA)-4, programmed cell death protein 1 (PD-1), programmed death-ligand 1 (PD-L1), carcinoembryonic antigen (CEA) or mucin 1 (MUC1). In some examples, the therapeutic transgene encodes an agent that disrupts or kills tumor stromal cells. In specific examples, the agent is Rexin-G, herpes simplex virus (HSV) thymidine kinase (TK), p53, TNF-α, Fas/FasL, or diphtheria toxin A.

Also provided herein is a method of diagnosing a subject as having a tumor. In some embodiments, the method includes administering to the subject a synthetic adenovirus that includes a diagnostic transgene, a native or modified capsid that detargets the synthetic adenovirus from the liver, and an Ad34 fiber protein or a chimeric fiber protein comprising an Ad5 shaft domain and an Ad34 knob domain.

In some embodiments, the diagnostic transgene is a PET reporter gene. In some examples, the PET reporter gene is a viral or human thymidine kinase (or mutant form thereof), a mutant of deoxycytidine kinase, a dopamine 2 receptor mutant, a human estrogen receptor α ligand binding domain (hERL), a human somatostain receptor subtype 2 (hSSTr2), a recombinant human CEA, an engineered antibody fragment, a humanized membrane anchored anti-polyethylene glycol (PEG), a sodium iodide symporter (NIS), or a human norepinephrine transporter (hNET).

In other embodiments, the diagnostic transgene encodes a fluorescent protein. In some examples, the fluorescent protein comprises a GFP, YFP, CFP, RFP, BFP, or orange fluorescent protein.

In other embodiments, the diagnostic transgene encodes an enzyme. In one example, the enzyme is a luciferase.

Further provided herein is a method of treating a tumor in a subject. In some embodiments, the method includes administering to the subject a synthetic adenovirus that includes a therapeutic transgene, a native or modified capsid that detargets the synthetic adenovirus from the liver, and an Ad34 fiber protein or a chimeric fiber protein comprising an Ad5 shaft domain and an Ad34 knob domain.

In some embodiments, the therapeutic transgene encodes an anti-cancer agent. In some examples, the anti-cancer agent is a pro-inflammatory molecule or cytokine, such as GM-CSF, CD40L, FLT3, IL-1b, IL-2, IL-4, IL-6, IL-12, TNF-α, an interferon, a chemokine, B7-1, ICAM-1, LFA-3, TGF-β, PDGF or EGF. In other examples, the anti-cancer agent is an anti-angiogenic factor, such as an inhibitor of VEGF. In other examples, the anti-cancer agent is an inhibitor (such as a siRNA or shRNA inhibitor) of KRas. In other examples, the anti-cancer agent is an inhibitor of CTLA-4, PD-1, CEA or MUC1. In other embodiments, the therapeutic transgene encodes an agent that disrupts or kills tumor stromal cells. In some examples, the agent is Rexin-G, HSV-TK, p53, TNF-α, Fas/FasL, or diphtheria toxin A.

In some embodiments of the methods disclosed herein, the synthetic adenovirus includes a modified capsid that detargets the virus from the liver. In some examples, the synthetic adenovirus comprises a modified hexon protein, such as an E451Q mutation (set forth herein as SEQ ID NO: 4). In other embodiments, the synthetic adenovirus has a native (unmodified) capsid that detargets the synthetic adenovirus from the liver (for example, a capsid from an adenovirus serotype that naturally does not infect the liver).

In some embodiments of the methods disclosed herein, the synthetic adenovirus further includes one or more binding sites, such as two or three binding sites, for a liver-specific microRNA. In some examples, the liver-specific microRNA is miR-122. In some examples, the one or more binding sites are in the 3'UTR of the transgene.

In some embodiments of the methods disclosed herein, the synthetic adenovirus further includes one or more binding sites, such as two or three binding sites, for a spleen-specific microRNA. In some examples, the spleen-specific microRNA is miR142-3p. In some examples, the one or more binding sites are in the 3'UTR of the transgene.

In some embodiments of the methods disclosed herein, the transgene is regulated by a tissue-specific promoter, such as a promoter active in the pancreas or the cells of the central nervous system. In other embodiments, the transgene is regulated by a tumor-specific promoter.

In some embodiments of the methods disclosed herein, the synthetic adenovirus is generated from an Ad5 vector genome. In some examples, the synthetic adenovirus comprises Ad5 capsid proteins and a chimeric fiber protein comprising an Ad5 shaft domain and an Ad34 knob domain.

In some embodiments of the methods disclosed herein, the tumor is a pancreatic tumor. In other embodiments, the tumor is a glioblastoma. In other embodiments, the tumor is a breast cancer, prostate cancer, gastrointestinal cancer, bone cancer or melanoma tumor.

In some embodiments of the methods disclosed herein, the tumor is characterized by a loss of p53 tumor suppressor activity. In some examples, the tumor exhibits mutations in p53. In some examples, the tumor exhibits loss of a wild-type p53 allele.

In some embodiments of the methods disclosed herein, the tumor is characterized by mutations in a Ras gene, such as KRas, HRas or NRas. In some embodiments of the methods disclosed herein, the tumor is characterized by alterations or mutations in neurofibromatosis type 1 (NF1), epidermal growth factor receptor (EGFR), BRCA1, BRCA2 or HER2.

In some embodiments of the methods disclosed herein, the genome of the synthetic adenovirus comprises a nucleotide sequence at least 80%, at least 85%, at least 90%, at least 95%, at least 96%, at least 97%, at least 98% or at least 99% identical to SEQ ID NO: 2. In some examples, the genome of the synthetic adenovirus comprises or consists of the nucleotide sequence of SEQ ID NO: 2.

In other embodiments of the methods disclosed herein, the genome of the synthetic adenovirus comprises a nucleotide sequence at least 80%, at least 85%, at least 90%, at least 95%, at least 96%, at least 97%, at least 98% or at least 99% identical to SEQ ID NO: 5. In some examples, the genome of the synthetic adenovirus comprises or consists of the nucleotide sequence of SEQ ID NO: 5.

Further provided herein are synthetic adenovirus genomes having at least 80%, at least 85%, at least 90%, at least 95%, at least 96%, at least 97%, at least 98% or at least 99% identical to SEQ ID NO: 2 or SEQ ID NO: 5. In some examples, the genome of the synthetic adenovirus comprises or consists of the nucleotide sequence of SEQ ID NO: 2 or SEQ ID NO: 5.

IV. Synthetic Adenoviruses

The Adsembly, AdSLICr and RapAD technologies enable the modular design and production of adenoviruses with unique capabilities (see PCT Publication Nos. WO2012/024351 and WO2013/138505, which are herein incorporated by reference in their entirety). The ability to design custom viruses with novel functions and properties opens up the potential to expand the utility of adenovirus as a vehicle to deliver therapeutic proteins by persuading the host to produce proteins in situ. This provides the unique capability to use human proteins that are difficult to manufacture for therapeutic purposes, and enable flexible delivery of almost any protein to diseased tissues.

The specific modifications disclosed herein are described with reference to the adenovirus 5 (Ad5) genome sequence, but may be used with any adenovirus serotype. Adenovirus is a natural multi-gene expression vehicle. The E1, E3, and E4 regions are either not necessary for replication in culture or can be complemented with available cell lines. Each of these regions has independent promoter elements that can be replaced with cellular promoters if necessary to drive the expression of multiple gene products via alternative splicing.

As disclosed herein, to create Ad5 expression vectors for in vivo use and transgene delivery, the E1A/E1B genes were deleted and replaced with at least one transgene. In some embodiments, the transgene is an EF1α driven luciferase-GFP fusion.

The synthetic adenoviruses disclosed herein may further include modifications that detarget the virus from the liver. Ad5 hexon can bind to Factor X in the blood, which can lead to its absorption by Kuppfer cells in the liver that prevent systemic dissemination and limiting inflammation. To overcome this, synthetic adenoviruses were engineered to include additional genomic modifications in the E1 and core modules that prevent adenovirus uptake and transgene expression in the liver, as described further below.

A. Ad34 Fiber and Chimeric Fiber Proteins for Retargeting

While the fiber proteins of Ad5 and many other serotypes have been shown to bind to the coxsackie adenovirus receptor (CAR) for cellular attachment, other serotypes have been shown to use CD46 (Gaggar et al., *Nat Med* 9:1408-1412, 2003), desmoglein 2 (Wang et al., *Nat Med* 17:96-104, 2011), sialic acid (Nilsson et al., *Nat Med* 17:105-109, 2011), or others (Arnberg, *Trends Pharmacol Sci* 33:442-448, 2012). The receptor usage of many serotypes has not been thoroughly examined and CD46 is not thought to be expressed in mature mice. Since the globular knob at the C-terminus of the fiber protein is typically responsible for receptor binding, a chimera was created by replacing the Ad5 fiber knob with that from Ad34 (see Example 1 below). The synthetic virus included an E1 module containing an E1A/E1B deletion and a luciferase-GFP fusion driven by an EF1α promoter. The synthetic adenovirus also included a liver detargeting modification in the hexon protein (E451Q) and binding sites in the 3'UTR of the transgene for a microRNA that is specifically expressed in the liver (miR-122) to prevent off-target expression of the transgene.

The data disclosed herein demonstrate the ability to combine modified parts from other serotypes in order to improve Ad5-based vectors. In this case allowing for rapid assembly of viruses that are optimized for entry into tumor cells.

B. Liver Detargeting Modifications

Natural Ad5 vectors will only infect the lungs (via inhalation) or liver (via intravenous administration). Ad5 hexon binds to Factor X in the blood, which leads its absorption by Kuppfer cells in the liver, preventing systemic dissemination and inducing virus-limiting inflammation. To overcome this and enable intravenous delivery of viruses that could travel to sites of tumors systemically, synthetic adenoviruses were engineered to include additional genomic modifications in the E1 and core modules that prevent uptake and expression in the liver.

To prevent virus uptake and sequestration in the liver through Ad5 hexon binding to Factor X, viruses were engineered with an additional mutation in hexon (E451Q) that prevents liver uptake. For example, AdSyn-CO171 does not accumulate in the liver and instead is able to target other organs, such as the spleen and lymph nodes. Thus, in some embodiments herein, the synthetic adenovirus comprises a modified hexon protein with an E451Q substitution.

To prevent off-target transgene expression in the liver, viruses were engineered to include binding sites in the 3' untranslated region (UTR) of the transgene for microRNAs that are specifically expressed in the liver. In particular embodiments, miR122 was selected as the liver-specific microRNA as its expression and binding sites are conserved in both human and mouse liver cells. In some examples, two micro-RNA binding sites for liver-specific miR122 were inserted in the 3'UTR of the transgene to prevent any residual transgene expression in the liver.

It is disclosed herein that a synthetic adenovirus with miR-122 binding sites and hexon mutation does not accumulate in the liver and instead is able to target tumors. In some embodiments, the one or more binding sites for the liver-specific microRNA are located in the 3'-UTR of the transgene. In some examples, the liver-specific microRNA is miR-122, miR-30 or miR-192.

Other mutations to the adenovirus hexon gene are contemplated herein to prevent adenovirus accumulation in the liver. For example, a synthetic adenovirus could be detargeted from the liver by replacing the nine hypervariable regions of hexon with those from different serotypes.

In some examples, the recombinant adenovirus comprises a hexon protein comprising or consisting of the amino acid sequence of SEQ ID NO: 3 or SEQ ID NO: 4.

C. Capsid Swaps for Evading Neutralizing Antibodies

The majority of the human population already has antibodies that recognize Ad5, the serotype most frequently used in research and therapeutic applications. Moreover, once a particular adenovirus serotype is used in a patient, new antibodies that recognize the viral capsid will be generated, making repeated administration of the same vector problematic. Therefore, the present disclosure further contemplates exploiting natural adenovirus modularity to create chimeric viruses capable of evading existing neutralizing antibodies. For example, the recombinant adenoviruses disclosed herein may further have complete 'capsid' module swaps (almost 60% of genome), which render them 'invisible' to pre-existing antibodies and enables repeated inoculations.

In some embodiments, the E1, E3 and E4 regions of the genome are derived from a first adenovirus serotype and the E2B, L1, L2, L3, E2A and L4 regions of the genome are derived from a second adenovirus serotype, such as Ad34. In some examples, the E1 region of the first adenovirus serotype is modified to encode a pIX protein from the second adenovirus serotype; and/or the E3 region of the first adenovirus serotype is modified to encode Uexon and fiber proteins from the second adenovirus serotype. In particular examples, the first adenovirus serotype is Ad5 and the second adenovirus serotype is Ad34.

D. Expression of Transgenes for Diagnostic and Therapeutic Applications

It is disclosed herein that recombinant adenoviruses comprising a chimeric fiber protein having an Ad34 knob domain and liver detargeting mutations are capable of targeting tumors. It is further disclosed that the recombinant adenoviruses are capable of expressing transgenes in tumor tissue, such as in tumor stromal cells. In one example, the transgene is a reporter, such as a luciferase-GFP reporter that enables detection of virus-transduced cells. In another example, the transgene is a therapeutic transgene, such as an anti-cancer molecule. The present disclosure provides synthetic adenoviruses that include diagnostic or therapeutic transgenes for the diagnosis and treatment of tumors.

Provided herein is a method of diagnosing a subject as having a tumor by administering to the subject a synthetic adenovirus that includes a diagnostic transgene, a native or modified capsid that detargets the synthetic adenovirus from the liver, and an Ad34 fiber protein or a chimeric fiber protein comprising an Ad5 shaft domain and an Ad34 knob domain. The diagnostic transgene can be, for example, a PET reporter gene, a fluorescent protein or an enzyme.

Also provided herein is a method of treating a tumor in a subject by administering to the subject a synthetic adenovirus that includes a therapeutic transgene, a native or modified capsid that detargets the synthetic adenovirus from the liver, and an Ad34 fiber protein or a chimeric fiber protein comprising an Ad5 shaft domain and an Ad34 knob domain. The therapeutic transgene can encode, for example, an anti-cancer agent or an agent that disrupts or kills tumor stromal cells.

In some embodiments, the transgene is inserted into the E1 or E3 region. Appropriate transgene insertion sites are well known in the art (see, for example, PCT Publication No. WO2012/024351).

The transgene, such as a gene encoding a fluorescent protein, is operably linked to a promoter. In some embodiments, the promoter is a heterologous promoter. In some examples, the promoter is the EF1$\alpha$ promoter. The selection of promoter is within the capabilities of one of skill in the art. In some cases, the promoter is an inducible promoter or a tissue-specific promoter. An exemplary tissue-specific promoter for expression in pancreatic tissue is Pdx1.

In some cases a single promoter is used to regulate expression of multiple genes, which can be achieved by use of an internal ribosomal entry site (IRES) or 2A peptide.

V. Pharmaceutical Compositions and Administration Thereof

Provided herein are compositions comprising a synthetic adenovirus (or one or more nucleic acids or vectors encoding the recombinant adenovirus). The compositions are, optionally, suitable for formulation and administration in vitro or in vivo. Optionally, the compositions comprise one or more of the recombinant adenovirus and a pharmaceutically acceptable carrier. Suitable carriers and their formulations are described in *Remington: The Science and Practice of Pharmacy,* 22$^{nd}$ Edition, Loyd V. Allen et al., editors, Pharmaceutical Press (2012). Pharmaceutically acceptable carriers include materials that are not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

The recombinant viruses (or one or more nucleic acids or vectors encoding the recombinant adenovirus) are administered in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, intratumoral or inhalation routes. The administration may be local or systemic. The compositions can be administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Thus, the compositions are administered in a number of ways depending on whether local or systemic treatment is desired, and on the area to be treated.

In some embodiments, the compositions for administration will include a recombinant adenovirus (or recombinant genome) as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Pharmaceutical formulations, particularly, of the recombinant viruses can be prepared by mixing the recombinant adenovirus (or one or more nucleic acids encoding the recombinant adenovirus) having the desired degree of purity with optional pharmaceutically acceptable carriers, excipients or stabilizers. Such formulations can be lyophilized formulations or aqueous solutions.

Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives, low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The recombinant adenovirus (or one or more nucleic acids encoding the recombinant adenovirus) can be formulated at any appropriate concentration of infectious units.

Formulations suitable for oral administration can consist of (a) liquid solutions, such as an effective amount of the recombinant adenovirus suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The recombinant adenovirus (or one or more nucleic acids encoding the recombinant adenovirus), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the provided methods, compositions can be administered, for example, by intravenous infusion, orally, topically, intraperitoneally, intravesically intratumorally, or intrathecally. Parenteral administration, intratumoral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. The pharmaceutical preparation is preferably in unit dosage form. In such form the preparation is subdivided into unit doses containing appropriate quantities of the active component. Thus, the pharmaceutical compositions can be administered in a variety of unit dosage forms depending upon the method of administration. For example, unit dosage forms suitable for oral administration include, but are not limited to, powder, tablets, pills, capsules and lozenges.

In some embodiments, the compositions include at least two different recombinant adenoviruses, such as recombinant adenoviruses that encode different transgenes. In some examples, the composition includes two, three, four, five or six different recombinant adenoviruses.

In therapeutic applications, recombinant adenoviruses or compositions thereof are administered to a subject in an effective amount or dose. Single or multiple administrations of the compositions may be administered as needed. A "patient" or "subject" includes both humans and other animals, particularly mammals. Thus, the methods are applicable to both human therapy and veterinary applications.

An effective amount of a recombinant adenovirus is determined on an individual basis and is based, at least in part, on the particular recombinant adenovirus used; the individual's size, age, gender and general health. For example, for administration to a human, at least $10^3$ plaque forming units (PFU) of a recombinant virus is used, such as at least $10^4$, at least $10^5$, at least $10^6$, at least $10^7$, at least $10^8$, at least $10^9$, at least $10^{10}$, at least $10^{11}$, or at least $10^{12}$ PFU, for example approximately $10^3$ to $10^{12}$ PFU of a recombinant virus is used, depending on the type, size and number of proliferating cells or neoplasms present. The effective amount can be from about 1.0 pfu/kg body weight to about $10^{15}$ pfu/kg body weight (e.g., from about $10^2$ pfu/kg body weight to about $10^{13}$ pfu/kg body weight). A recombinant adenovirus is administered in a single dose or in multiple doses (e.g., two, three, four, six, or more doses). Multiple doses can be administered concurrently or consecutively (e.g., over a period of days or weeks).

In some embodiments, the provided methods include administering to the subject one or more therapeutic agents, such as one or more agents for the treatment of cancer, such as pancreatic cancer or glioblastoma.

Administration of the synthetic adenoviruses disclosed herein that harbor a therapeutic transgene can be accompanied by administration of other anti-cancer agents or therapeutic treatments (such as surgical resection of a tumor). Any suitable anti-cancer agent can be administered in combination with the recombinant viruses disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens), CDK inhibitors and anti-angiogenesis agents. Other anti-cancer treatments include radiation therapy and other antibodies that specifically target cancer cells (e.g., biologics).

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

CDK (Cyclin-dependent kinase) inhibitors are agents that inhibit the function of CDKs. Non-limiting examples of CDK inhibitors for use in the provided methods include AG-024322, AT7519, AZD5438, flavopiridol, indisulam, P1446A-05, PD-0332991, and P276-00 (see e.g., Lapenna et al., *Nature Reviews,* 8:547-566, 2009). Other CDK inhibitors include LY2835219, Palbociclib, LEE011 (Novartis), pan-CDK inhibitor AT7519, seliciclib, CYC065, butyrolactone I, hymenialdisine, SU9516, CIN K4, PD0183812 or fascaplysin.

In some examples, the CDK inhibitor is a broad-range inhibitor (such as flavopiridol, olomoucine, roscovitine, kenpaullone, SNS-032, AT7519, AG-024322, (S)-Roscovitine or R547). In other examples, the CDK inhibitor is a specific inhibitor (such as fascaplysin, ryuvidine, purvalanol A, NU2058, BML-259, SU 9516, PD0332991 or P-276-00).

The choice of agent and dosage can be determined readily by one of skill in the art based on the given disease being treated. Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions.

The following examples are provided to illustrate certain particular features and/or embodiments. These examples should not be construed to limit the disclosure to the particular features or embodiments described.

EXAMPLES

Example 1

A Synthetic Adenovirus Expressing an Ad5/Ad34 Chimeric Fiber Protein and Liver Detargeting Modifications While the fiber proteins of Ad5 and many other serotypes have been shown to bind to CAR for cellular attachment, other serotypes have been shown to use CD46 (Gaggar et al., *Nat Med* 9:1408-1412, 2003), desmoglein 2 (Wang et al., *Nat Med* 17:96-104, 2011), sialic acid (Nilsson et al., *Nat Med* 17:105-109, 2011), or others (Arnberg, *Trends Pharmacol Sci* 33:442-448, 2012). The receptor usage of many serotypes has not been thoroughly examined and CD46 is not thought to be expressed in mature mice.

Adsembly/AdSLIC (see PCT Publication No. WO 2012/024351, incorporated herein by reference) was used to generate a synthetic adenovirus having a chimeric fiber protein. Since the globular knob at the C-terminus of the fiber protein is typically responsible for receptor binding, a virus with a chimeric fiber protein was created by replacing the Ad5 fiber knob with fiber knob from Ad34 (AdSyn-CO176). The control virus (AdSyn-CO171) contains an Ad5 fiber protein (i.e. both the shaft and knob domains are from Ad5). Both viruses were created with the same E1 module containing an E1A/E1B deletion and a luciferase-GFP fusion driven by an EF1$\alpha$ promoter (Table 1). The recombinant viruses also include liver detargeting modifications. Natural Ad5 vectors will only infect the lungs (via inhalation) or liver (via intravenous administration). Ad5 hexon binds to Factor X in the blood, which leads to its absorption by Kuppfer cells in the liver, preventing systemic dissemination and inducing limited inflammation. To overcome this and allow for systemic administration to alternative cell types, the synthetic adenoviruses were engineered to include additional genomic modifications in the E1 and core regions that prevent uptake and expression in the liver. Specifically, both viruses include binding sites in the 3'UTR of the transgene for a microRNA that is specifically expressed in the liver (miR-122) and an E451Q mutation in hexon.

TABLE 1

Adenoviruses with Chimeric Fiber Proteins and Liver Detargeting Modifications

| Virus Name | SEQ ID NO: | E1 | L3 | L5 | E4 |
|---|---|---|---|---|---|
| AdSyn-CO171 | 1 | ΔE1 + EF1α-luciferase-miR122 | hexon E451Q | wt | wt |
| AdSyn-CO176 | 2 | ΔE1 + EF1α-luciferase-miR122 | hexon E451Q | Ad34 knob Ad5 shaft fiber chimera | wt |

Example 2

A Synthetic Adenovirus Expressing the Ad34 Knob Domain Exhibits Tropism to Tumor Stroma This example describes the finding that AdSyn-CO176, expressing a chimeric fiber protein with an Ad34 knob domain, specifically traffics to tumor stroma.

Pancreatic Tumor Models

Figure 1B:
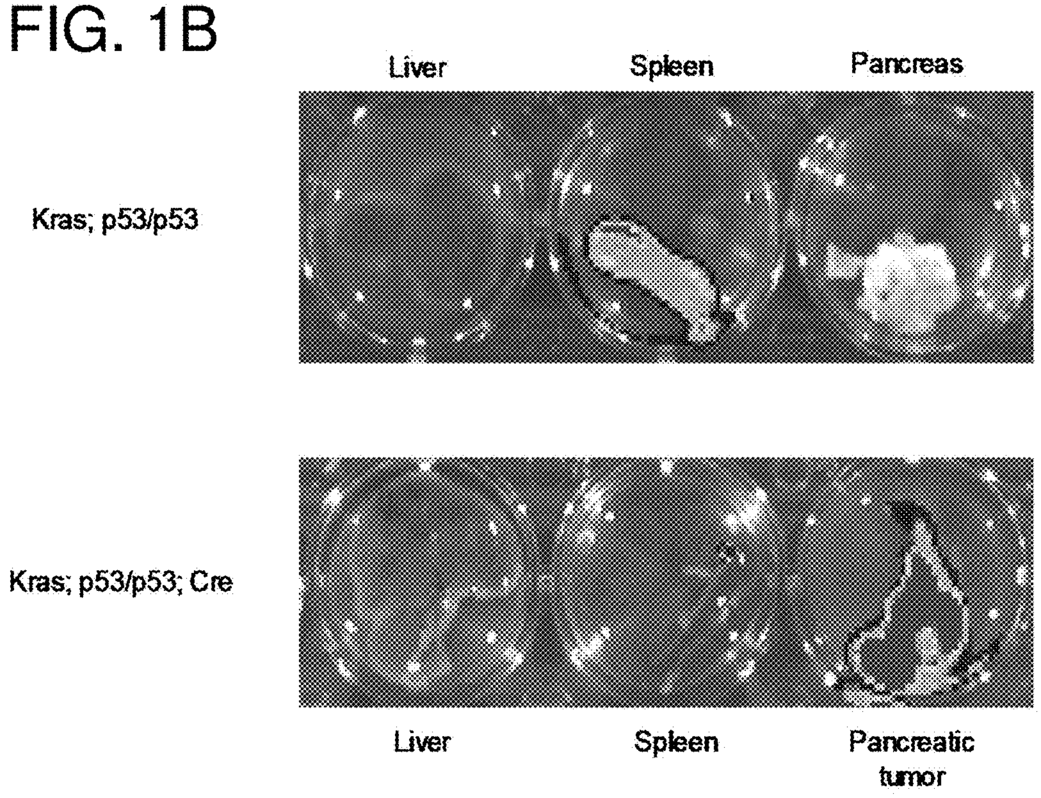

Shown in FIG. 1A is a schematic overview of the Cre-LoxP $Kras^{G12D}$/p53 pancreatic tumor model. Mice designated as “Kras; p53/p53” encode the $Kras^{G12D}$ oncogene downstream of the sequence encoding LoxP-stop codon-LoxP. The stop codon blocks the expression of mutant Kras ($Kras^{G12D}$) in the absence of Cre recombinase. However, in the presence of Cre recombinase, the stop codon is removed and allows for expression of the $Kras^{G12D}$ oncogene. In these same mice, both alleles of the p53 gene are flanked by LoxP sites (LoxP-p53-LoxP). Mice designated “p53/p53; Cre” also have both alleles of the p53 gene flanked by LoxP (LoxP-p53-LoxP), and they express the Cre recombinase transgene driven by the pancreatic and duodenal homeobox 1 (Pdx1) promoter. Pdx1 is a gene that is expressed specifically in the pancreatic cells, and thus both copies of p53 are deleted in the pancreatic cells. Breeding between the strains gives rise to offspring in which the Pdx1 promoter-driven Cre mediates the deletion of both alleles of the tumor suppressor p53 and activation of the mutant $Kras^{G12D}$ in pancreatic cells. Homozygous mice designated “Kras; p53/p53; Cre” develop pancreatic tumors in 5-7 weeks. AdSyn-CO176 was injected intravenously into Kras; p53/p53 and Kras; p53/p53; Cre mice. Seventy-two hours after the injection of virus, tissues were collected, incubated for 5 minutes with luciferin, and then scanned for 5 minutes using the IVIS™ imaging system. As shown in FIG. 1B, the Kras; p53/p53 mouse had a normal pancreas, and the luciferase signal was mainly from the spleen. In contrast, the Kras; p53/p53; Cre mouse had pancreatic tumors, and the signal was mainly from the pancreatic tumor.

Figure 2A:
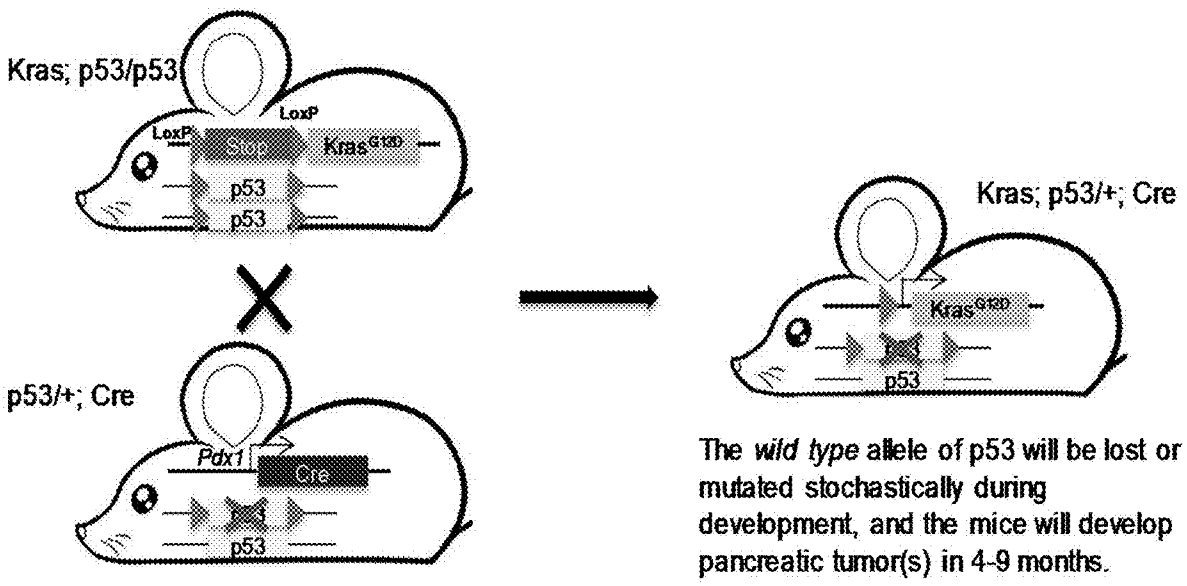
FIGS. 2A-2B. AdSyn-CO176 infected pancreatic tumor after the tail vein injection in a Cre-mediated genetic manipulation heterozygous model.
Figure 2B:
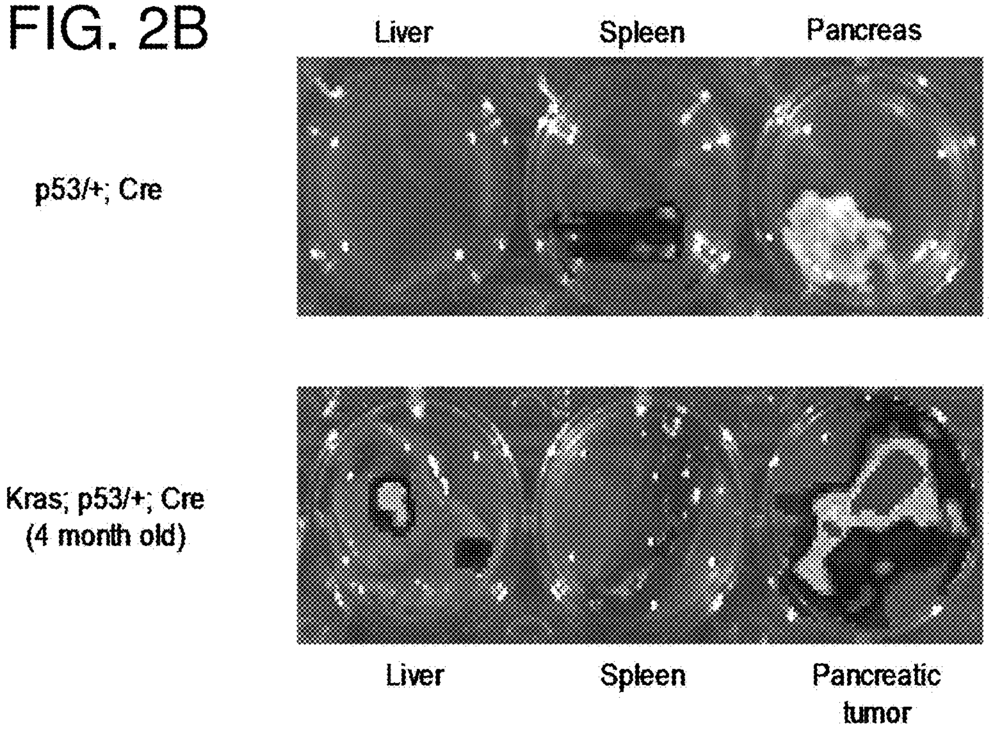

Another study was performed in a Cre-mediated genetic manipulation heterozygous model (FIG. 2A). Mice designated “p53/+; Cre” have one wild type p53 allele and one p53 allele flanked by LoxP sites (LoxP-p53-LoxP). Breeding between the Kras; p53/p53 and p53/+; Cre strains gives rise to offspring in which the Pdx1 promoter-driven Cre recombinase mediates the deletion of a single allele of the tumor suppressor p53 and activation of the mutant $Kras^{G12D}$ in pancreatic cells. These heterozygous mice, designated “Kras; p53/+; Cre,” develop tumors later in life (at 4-9 months of age) due to the fact that they have one wild type allele of p53. This wild type allele must be lost or mutated in order for pancreatic tumors to develop. AdSyn-CO176 was injected intravenously into 4-month old p53/+; Cre and Kras; p53/+; Cre mice. Seventy-two hours after the injection of virus, tissues were collected, incubated with luciferin for 5 minutes, and then scanned for 1 minute using the IVIS™ imaging system. The p53/+; Cre mouse had a normal pancreas, and the signal was mainly from spleen. In contrast, the Kras; p53/+; Cre mouse at 4 months of age had a pancreatic tumor, and the signal was mainly from the tumor and liver.

Figure 3A:
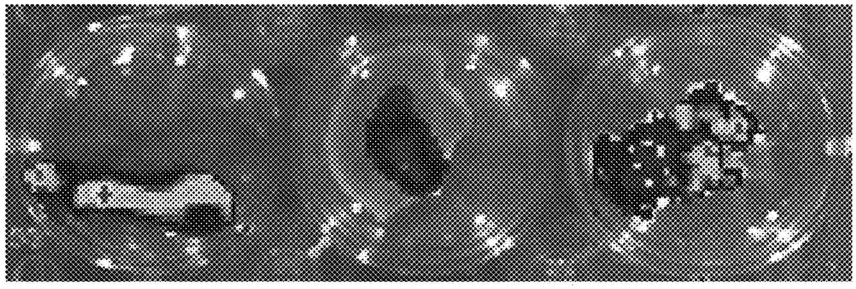
FIGS. 3A-3C. AdSyn-CO176 can infect and diagnose a pancreatic tumor at an early stage after tail vein injection. The heterozygous Kras; p53/+; Cre mice develop pancreatic tumors in 4-9 months. To test whether AdSyn-CO176 can infect pancreatic tumors at a very early stage of tumor development (before tumors are visible), AdSyn-176 was injected into Kras; p53/+; Cre mice at 2 months of age and luciferase expression was measured.
Figure 3B:
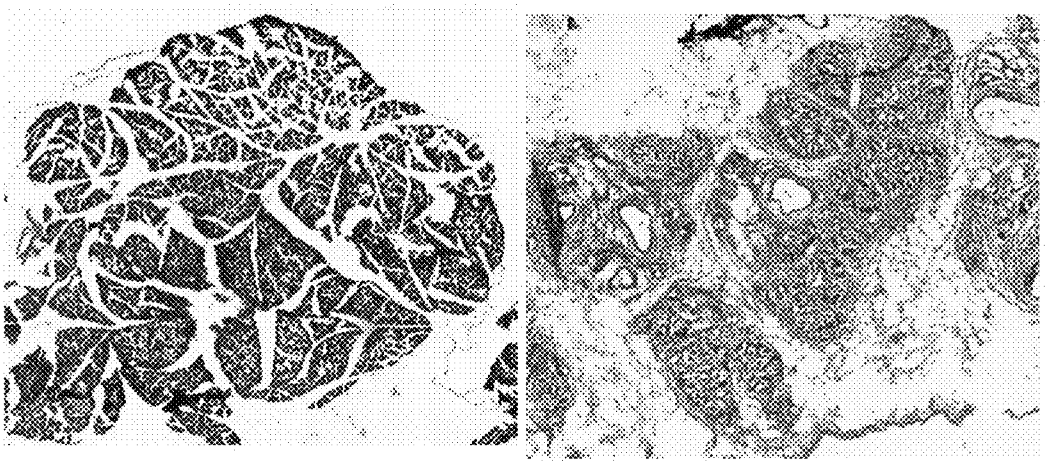
Figure 3C:
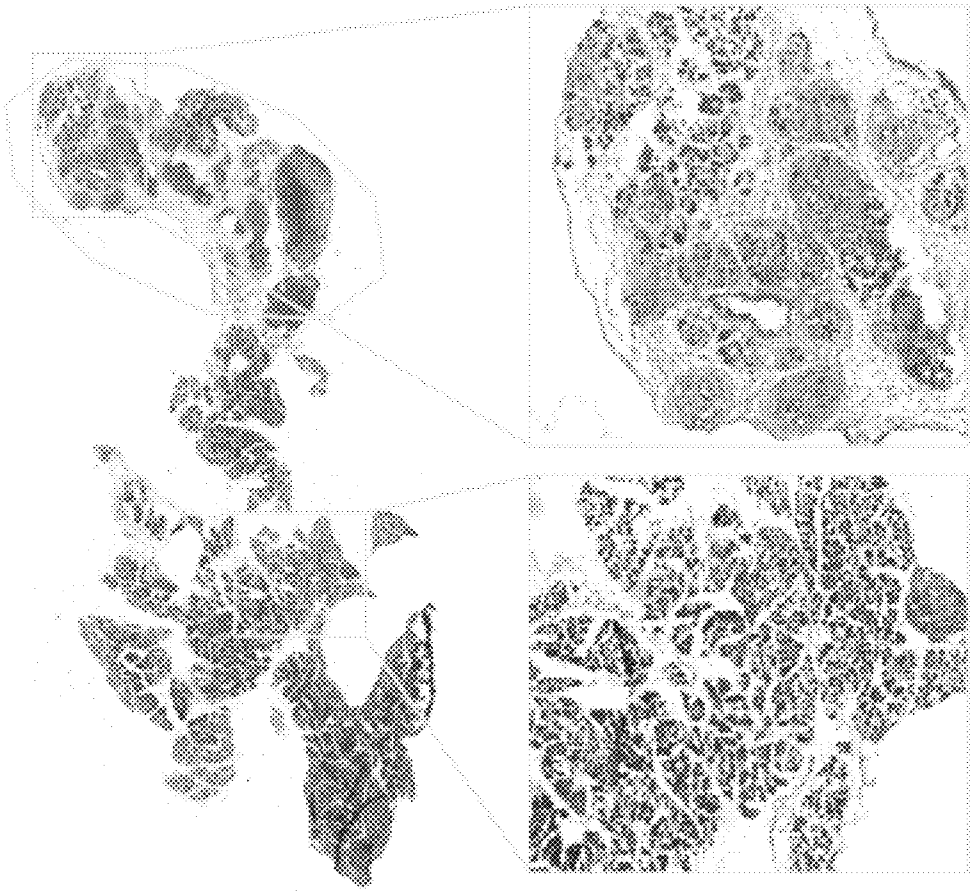

The heterozygous Kras; p53/+; Cre mice develop pancreatic tumors in 4-9 months. To test whether AdSyn-CO176 can infect pancreatic tumors at a very early stage of tumor development (before tumors are visible), AdSyn-CO176 was injected intravenously into Kras; p53/+; Cre mice at 2 months of age. Seventy-two hours after the injection of virus, tissues were collected, incubated with luciferin for 5 minutes, and scanned for 4 minutes using the IVIS™ imaging system. The pancreas of Kras; p53/+; Cre mouse at 2 months of age looked normal, but luciferase signal was found in this tissue (FIG. 3A). H&E staining was performed to evaluate histology of the pancreas following infection with AdSyn-CO176. For comparison, FIG. 3B shows the typical histology of normal pancreas tissue and pancreatic tumor tissue. H&E staining of the pancreas from a Kras; p53/+; Cre mouse at 2 months of age showed that a small part of the pancreas was developing the tumor (FIG. 3C, indicated by the polygon), while most of the pancreas tissue appeared normal. This result indicated that AdSyn-CO176 can infect pancreatic tumors at a very early stage.

Figure 4A:
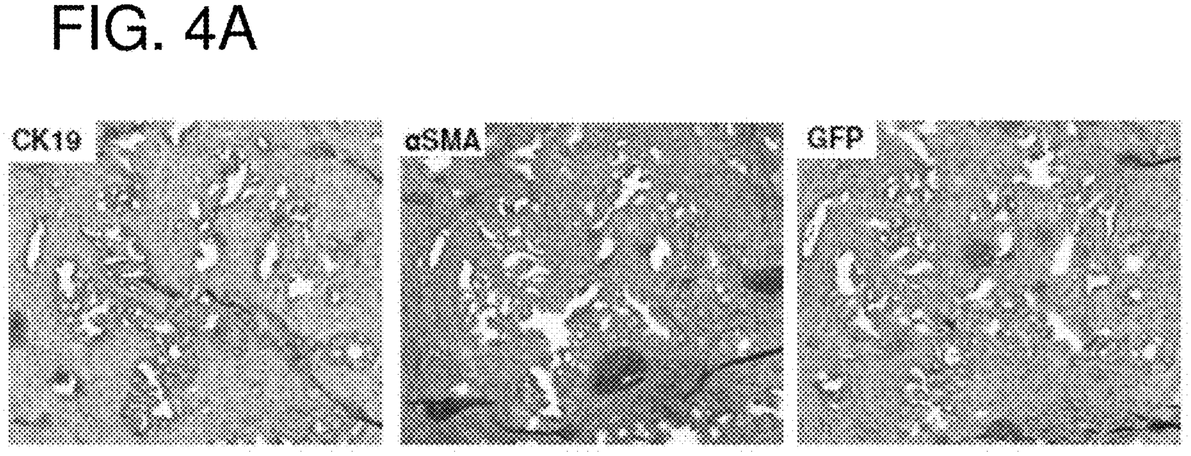
FIGS. 4A-4B. AdSyn-CO176 infects stromal cells in the pancreatic tumor. In pancreatic tumors, only 10% of the cells are cancer cells; the remaining 90% are stroma cells. As determined by immunohistochemistry (IHC) and immunofluorescence (IF) staining, the cells that were infected by AdSyn-CO176 were stromal cells.
Figure 4B:
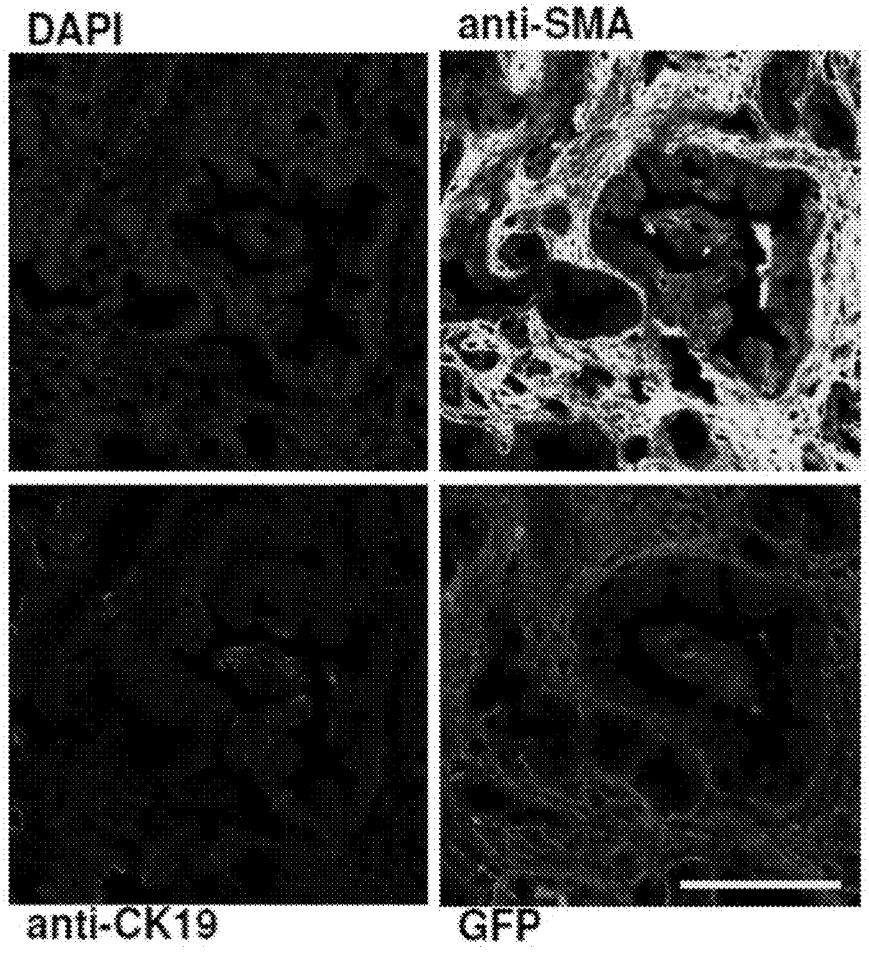

In pancreatic tumors, only 10% of the cells are cancer cells; the remaining 90% are stromal cells. To determine which cell type was targeted by AdSyn-CO176, IHC and IF staining were performed. CK19 is a marker of tumor cells, while smooth muscle actin (SMA) is a marker of stromal cells. IHC staining of a pancreatic tumor infected with AdSyn-CO176 showed that GFP, which was expressed from AdSyn-CO176, overlapped with SMA staining, indicating that AdSyn-CO176 targeted stromal cells (FIG. 4A). IF staining of a pancreatic tumor infected by AdSyn-CO176 also demonstrated that GFP overlapped with SMA staining (FIG. 4B), confirming that AdSyn-CO176 infects stromal cells.

Glioblastoma Model

Figure 5A:
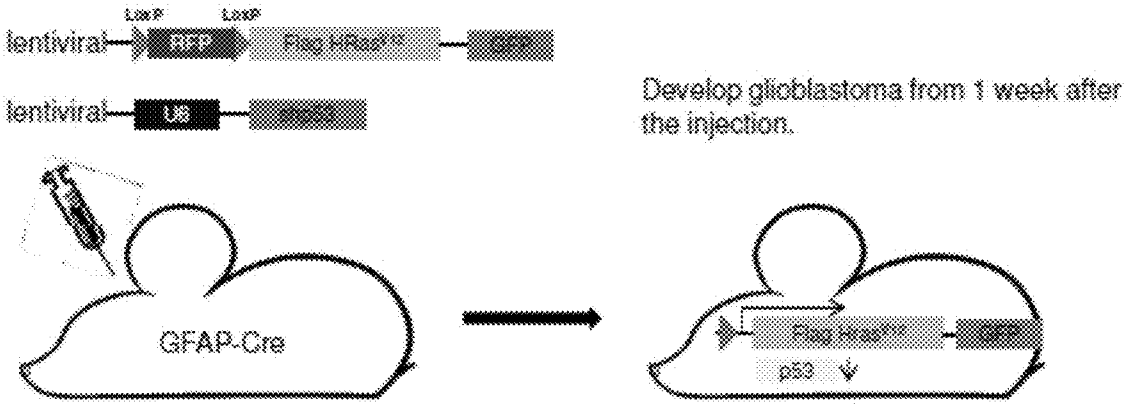
FIGS. 5A-5D. AdSyn-CO176 infected glioblastoma after tail vein injection. Synthetic adenovirus AdSyn-CO176 was injected into mice with glioblastoma by tail vein and the luciferase signal was found in the glioblastoma.
Figure 5B:
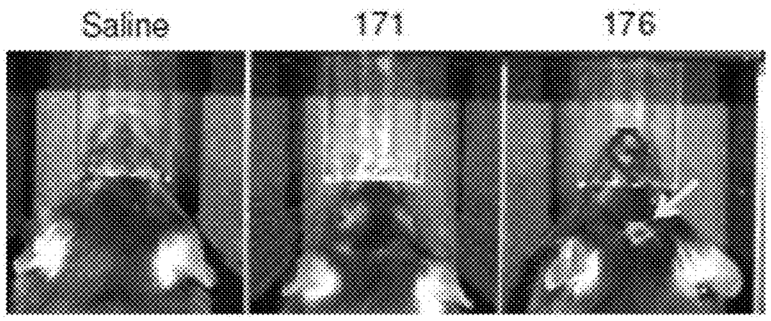

Shown in FIG. 5A is a schematic of a Cre-mediated genetic manipulation glioblastoma model. Lentiviruses were injected directly into the brain of GFAP-Cre mice. Glial fibrillary acidic protein (GFAP) promoter-driven Cre recombinase cleaves out RFP from the lentivirus-encoded gene and induces the expression of $HRas^{V12}$ and GFP primarily in astrocytes. Expression of lentivirus-encoded U6-p53 shRNA knocks down the expression of p53 in the brain cells that take up the virus. The expression of $HRas^{V12}$ and the knock down of p53 induces tumorigenesis in the brain from 1 week after the injection. GFP signal is used to indicate the formation of glioblastoma. Saline, AdSyn-CO171, or AdSyn-CO176 were injected via intravenous (IV) administration into GFAP-Cre mice that had received the tumor-inducing lentiviruses 4 weeks earlier. Forty-eight hours after the injection of virus, mice were scanned for 1 minute using the IVIS™ imaging system 5 minutes after the intraperitoneal injection of luciferin (FIG. 5B). A luciferase signal was detected in mice injected with AdSyn-CO176, but not in mice injected with saline or AdSyn-CO171.

Figure 5C:
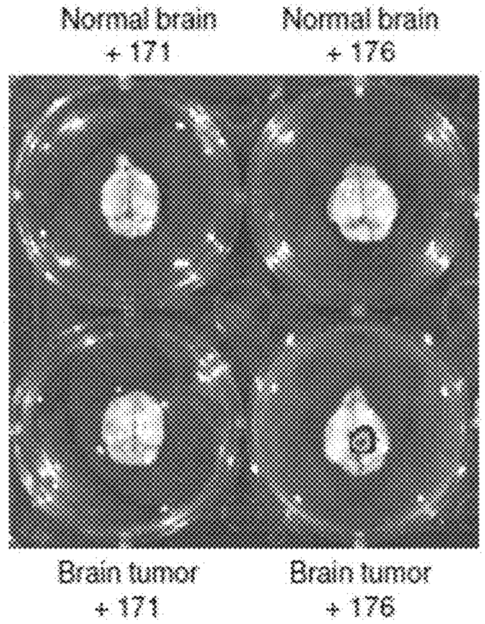
Figure 5D:
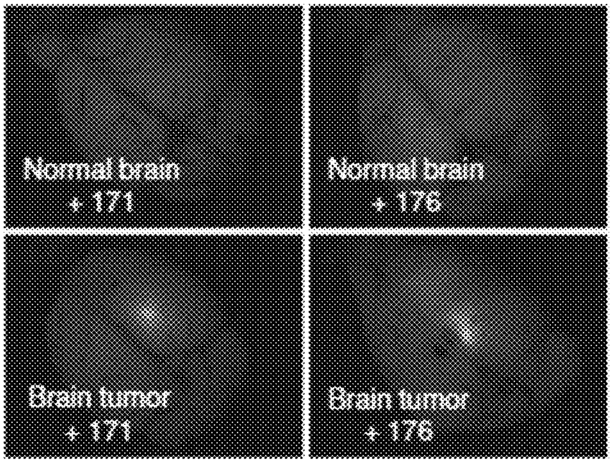

Wild type mice (normal brain) and GFAP-Cre mice that had received injection of tumor-inducing lentiviruses were injected with AdSyn-CO171 or AdSyn-CO176. Brain tissues were collected 72 hours after the injection of synthetic adenoviruses, incubated with luciferin for 5 minutes, and scanned for 5 minutes using the IVIS™ imaging system (FIG. 5C). Only the GFAP-Cre mouse injected with the tumor-inducing lentiviruses showed a luciferase signal from AdSyn-CO176. This demonstrates that AdSyn-CO176 traffics to the brain tissue only when a tumor is present. Brain tissues were also scanned for the GFP signal (FIG. 5D). The GFP signal is used to identify the glioblastoma. Both of the GFAP-Cre mice that received the tumor-inducing lentiviruses had the GFP signal in the brain, while no GFP was detected in wild type mice. The GFP signal overlapped with the luciferase signal perfectly in the GFAP-Cre mouse that received the tumor-inducing lentiviruses and AdSyn-CO176.

Figure 6A:
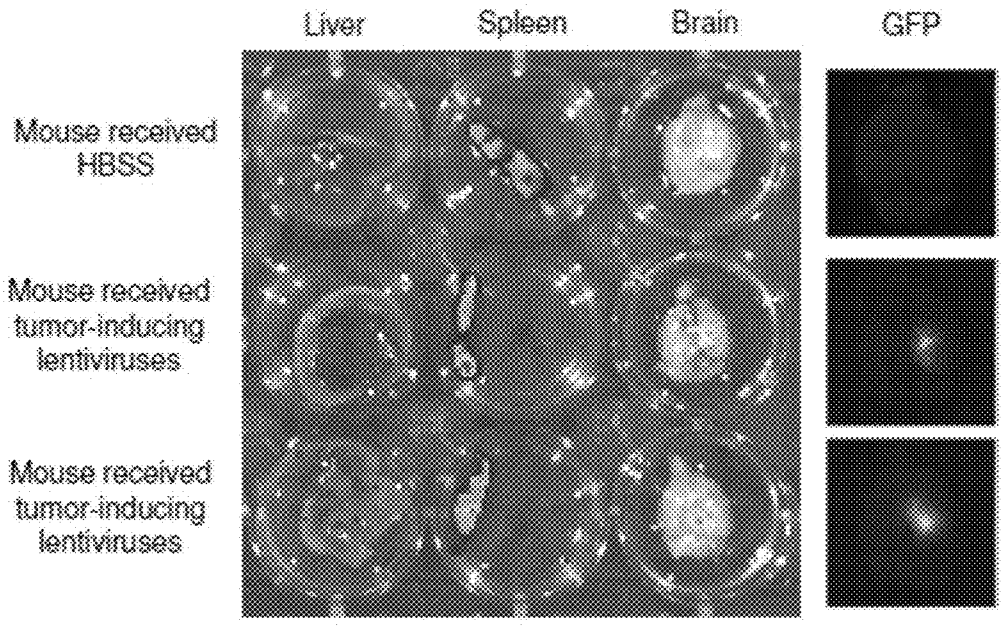
FIGS. 6A-6B. Trafficking of AdSyn-CO176 to glioblastoma is driven by the tumor, not injury. The injection of the tumor-inducing lentiviruses causes temporary injury to the brain at the injection site. Although the synthetic adenoviruses (AdSyn-CO171 and AdSyn-CO176) were injected 4 weeks after the initial injection of lentiviruses, it was still unclear whether trafficking of AdSyn-CO176 to the glioblastoma was driven by the tumor or by the injection site injury. To answer this question, GFAP-Cre mice were injected with synthetic adenovirus 4 weeks after either no injection, sham-injection or injection with tumor-inducing lentivirus.
Figure 6B:
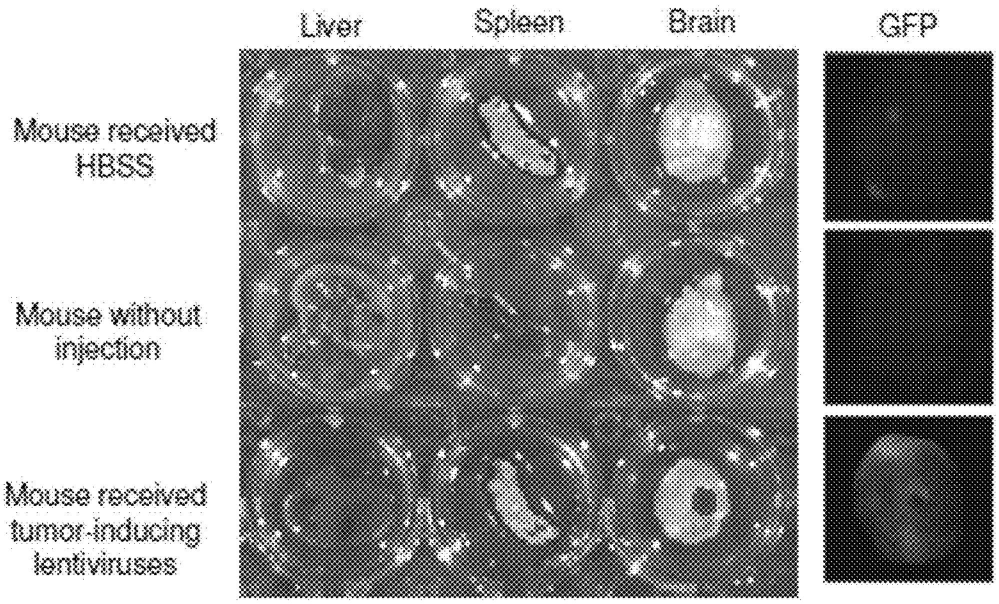

The injection of the tumor-inducing lentiviruses causes temporary injury to the brain at the injection site. Although the synthetic adenoviruses (AdSyn-CO171 and AdSyn-CO176) were injected 4 weeks after the initial injection of lentiviruses, it was still unclear whether trafficking of AdSyn-CO176 to the glioblastoma was driven by the tumor or by the injection site injury. To answer this question, GFAP-Cre mice were injected with synthetic adenovirus 4 weeks after either no injection, sham-injection or injection with tumor-inducing lentivirus. GFAP-Cre mice were injected with either Hanks' balanced salt solution (HBSS) or tumor-inducing lentiviruses. After 4 weeks, AdSyn-CO171 was injected intravenously. As shown in FIG. 6A, there was no luciferase signal from AdSyn-CO171 in the brain in either group of mice. GFAP-Cre mice were injected with HBSS or tumor-inducing lentiviruses, or received no injection. After 4 weeks, mice were injected intravenously with AdSyn-CO176. As shown in FIG. 6B, the luciferase signal was detected only in the brain of the mouse that received the tumor-inducing lentiviruses, while the mouse that received HBSS or no injection produced no signal. These results demonstrate that the specificity of AdSyn-CO176 is driven by the tumor and not injection site injury.

Example 3

AdSyn-CO176 Traffics to Human Glioblastoma Tumors in a Xenograft Model

This example describes the finding that a synthetic adenovirus expressing a chimeric fiber protein with an Ad34 knob domain is capable of targeting human glioblastoma tumors.

Figure 7A:
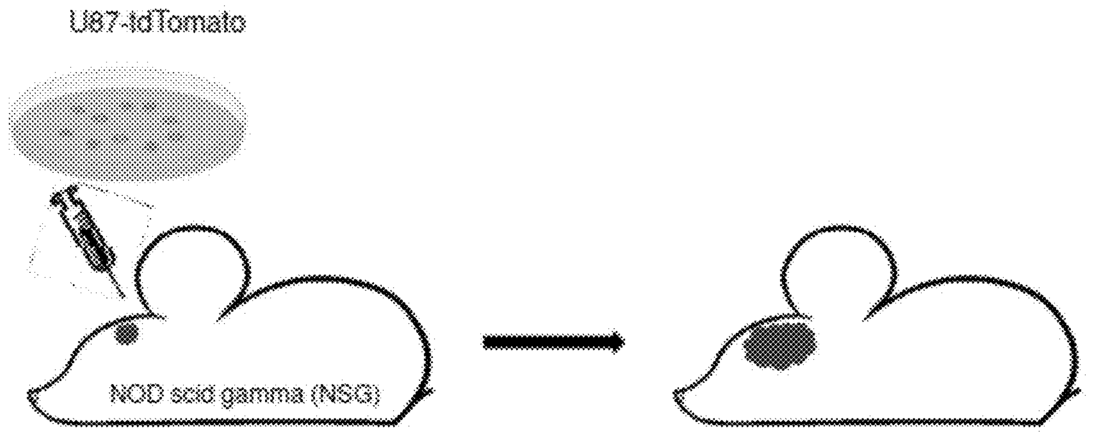
FIGS. 7A-7B. AdSyn-CO176 can traffic to human glioblastoma xenograft tumors.
Figure 7B:
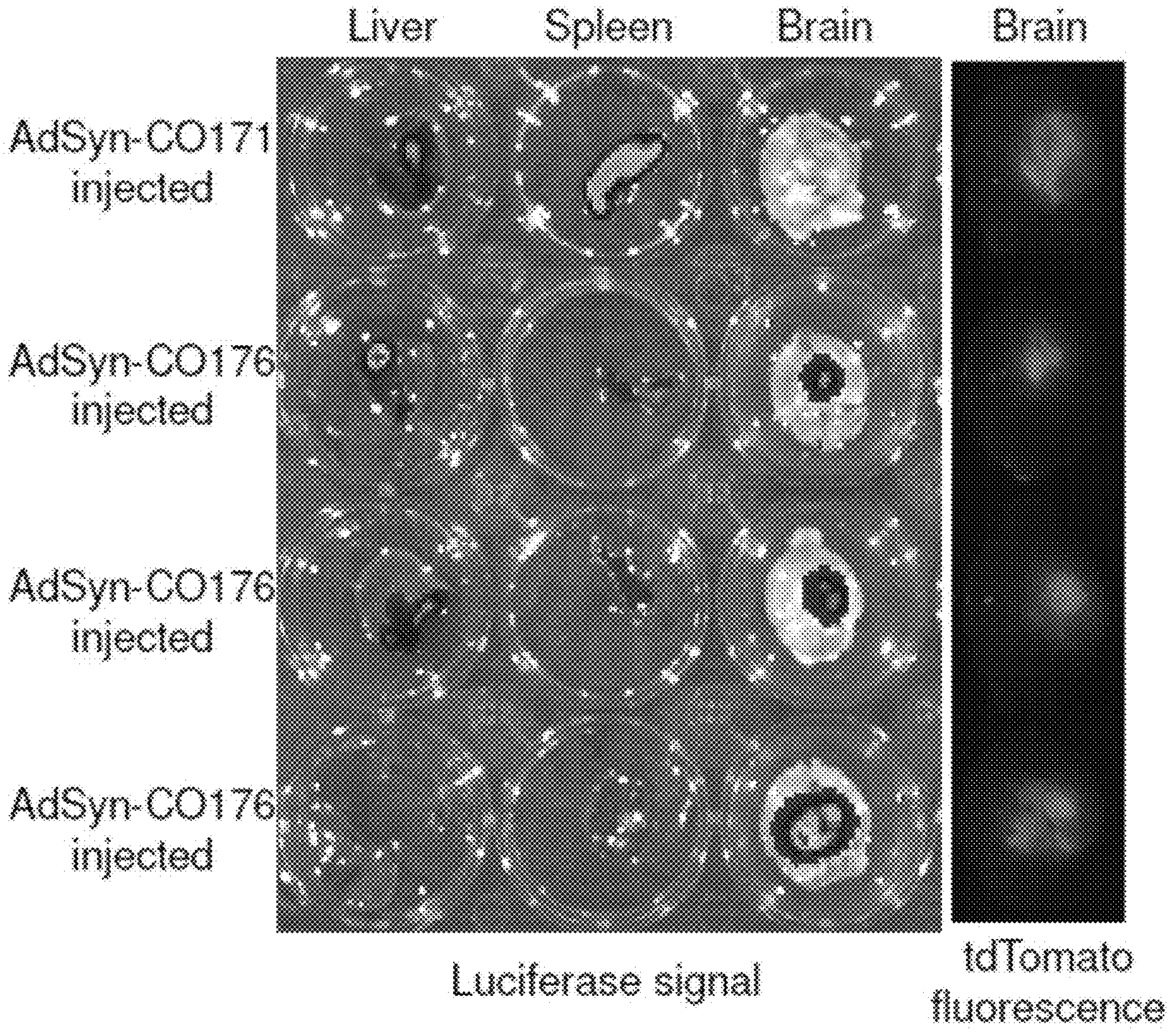

The U87-tdTomato cell line is a human glioblastoma cell line that expresses the tdTomato fluorescent protein as a reporter to enable monitoring of tumor growth. When U87-tdTomato cells are injected intracranially into NSG mice to generate glioblastoma tumors, it typically takes 4-8 weeks for tumors to develop (FIG. 7A). This glioblastoma xenograft model was used to determine whether AdSyn-CO176 could traffic to a human glioblastoma tumor. AdSyn-CO171 (SEQ ID NO: 1) and AdSyn-CO176 (SEQ ID NO: 2) were injected intravenously into NSG mice by tail vein injection four weeks after the mice had received an intracranial injection of U87-tdTomato cells. Forty-eight hours after the injection of viruses, liver, spleen and brain tissue were collected, incubated with luciferin for five minutes and then scanned for 1 minute using the IVIS™ imaging system. As shown in FIG. 7B, only the AdSyn-CO176 injected mice showed a luciferase signal in the brain, and this signal completely overlapped with tdTomato expression. Thus, these results demonstrate that AdSyn-CO176 can traffic to human glioblastoma tumors, while AdSyn-CO171 cannot.

Example 4

A Synthetic Adenovirus Targeting Tumor Stroma and Expressing a Therapeutic Transgene Reduces Tumor Size in an Animal Model This example demonstrates that a synthetic adenovirus expressing a chimeric fiber protein with an Ad34 knob domain and a therapeutic payload is capable of tracking to tumor stroma and reducing tumor size.

Studies were performed to determine whether a therapeutic transgene could be incorporated into AdSyn-CO176 (SEQ ID NO: 2) to enable treatment of tumors. To conduct this study, the KPCL (Kras$^{G12D}$; p53 knockout; Pdx1-Cre; firefly Luciferase) mouse model was used (FIG. 8A). KPCL mice are similar to homozygous "Kras; p53/p53; Cre" mice, which specifically express Kras$^{G12D}$ in the pancreas and have the p53 gene knocked out only in the pancreas. However, KPCL mice also specifically express firefly luciferase in the pancreas. The development of tumors in KPCL mice is also similar to the "Kras; p53/p53; Cre" mice.

Two additional synthetic adenoviruses were generated—AdSyn-CO987 (SEQ ID NO: 5) and AdSyn-CO989 (SEQ ID NO: 6). AdSyn-CO987 is a synthetic adenovirus based upon AdSyn-CO176. The herpes simplex virus-1 thymidine kinase (TK)/ganciclovir (GCV) suicide gene was cloned into AdSyn-CO176 to replace the firefly luciferase/GFP gene. A Renilla luciferase was also inserted just after TK in the genome of AdSyn-CO176. Control virus AdSyn-CO989 was generated by cloning TK-P2A-renilla luciferase into AdSyn-CO171 to replace the original firefly luciferase/GFP gene.

KPCL mice were injected intravenously via the tail vein with $1\times10^6$ PFU of AdSyn-CO987 or AdSyn-CO989 at 5-6 weeks of age. Two days later, the mice were i.p. or i.v. injected with GCV. Three control groups were used: AdSyn-CO989+GCV; AdSyn-CO987 followed with saline injection (AdSyn-CO987+saline); and GCV injection only (i.p. or i.v.). FIG. 8B provides a table showing the average survival of KPCL mice for each treatment group. Treatment with AdSyn-CO987+GCV extended mouse survival compared with controls.

The firefly luciferase signal expressed by tumors was analyzed during treatment to monitor tumor growth. The results are shown in FIG. 8C. The treatment for mouse Z619R was AdSyn-CO987+saline, which served as the control. Mice Z601R and Z607R were treated with AdSyn-CO987+GCV (i.p.). While the strength of the firefly luciferase signal increased in the control mouse Z619R (indicating an increase in tumor size), the signal decreased in mice Z601R and Z607R (indicating a reduction in tumor size).

Figure 9A:
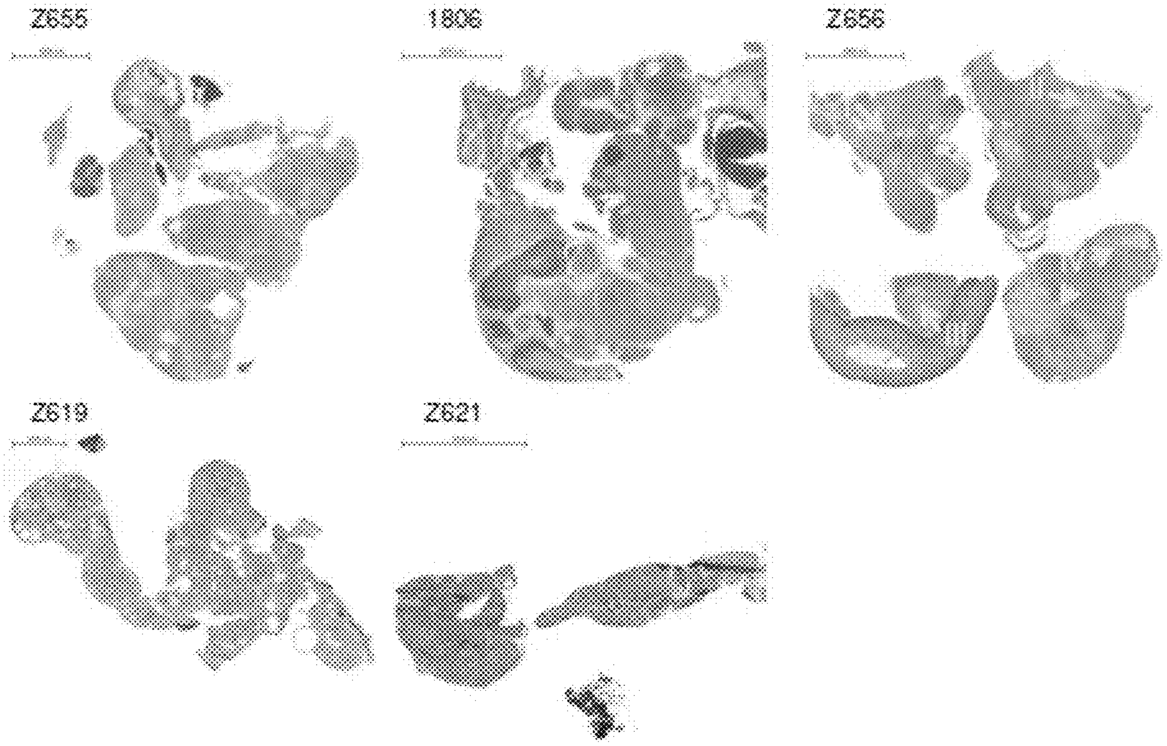
FIGS. 9A-9B. Histology of tumors in mice treated with AdSyn-CO987.
Figure 9B:
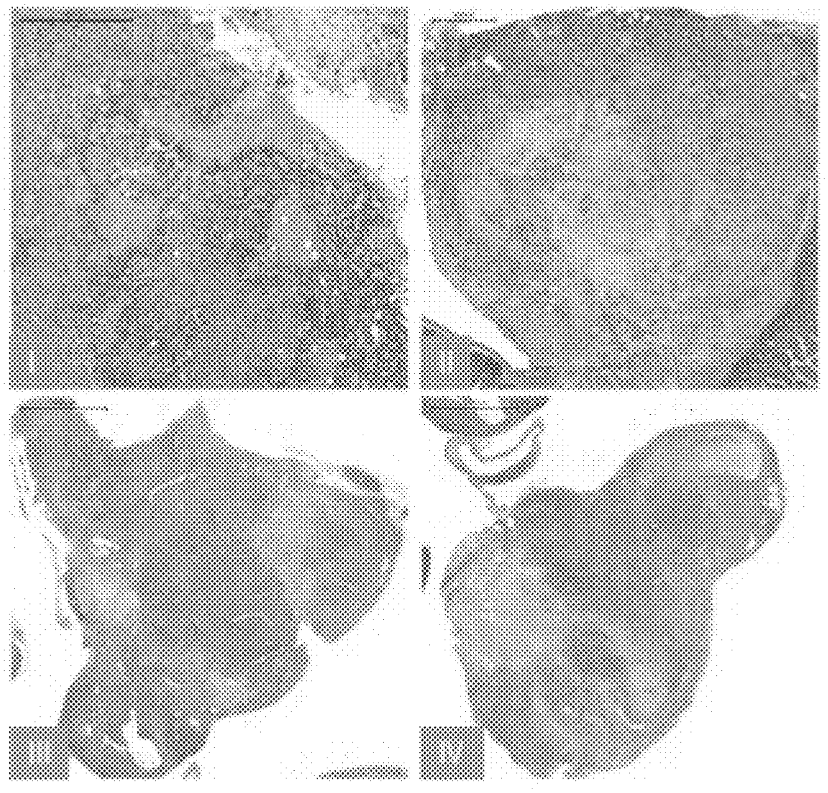

Histology of the pancreatic tumors was also evaluated by H&E staining (FIG. 9A). Mice Z655, 1806, Z619 and Z621 were all control mice. Mouse Z655 was treated with i.p. injected GCV only; mouse 1806 was treated with i.v. injected GCV only; mouse Z619 was treated with AdSyn-CO987+saline; and mouse Z621 received no treatment. Mouse Z656 received treatment with AdSyn-CO987+GCV i.v. Compared to the controls, the tumor from Z656 had more regions of necrosis (FIG. 9B).

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

The invention claimed is:

1. A method of expressing a transgene in stromal cells in a tumor, comprising infecting the stromal cells in the tumor with a synthetic adenovirus comprising:

the transgene inserted into the E1 region, wherein the transgene encodes an anti-cancer agent;

a native or modified capsid that detargets the synthetic adenovirus from the liver; and an adenovirus type 34 (Ad34) fiber protein or a chimeric fiber protein comprising an adenovirus type 5 (Ad5) shaft domain and an Ad34 knob domain, wherein the stromal cells in the tumor express the transgene.

2. The method of claim 1, wherein the synthetic adenovirus comprises a modified capsid that detargets the synthetic adenovirus from the liver.

3. The method of claim 1, wherein the synthetic adenovirus further comprises one or more binding sites for a liver-specific microRNA.

4. The method of claim 3, wherein the liver-specific microRNA is miR-122.

5. The method of claim 1, wherein the synthetic adenovirus further comprises one or more binding sites for a spleen-specific microRNA.

6. The method of claim 5, wherein the spleen-specific microRNA is miR142-3p.

7. The method of claim 1, wherein expression of the transgene is regulated by a tissue-specific promoter.

8. The method of claim 1, wherein the synthetic adenovirus comprises Ad5 capsid proteins and a chimeric fiber protein comprising an Ad5 shaft domain and an Ad34 knob domain.

9. The method of claim 1, wherein the tumor is a pancreatic tumor or a glioblastoma.

10. The method of claim 1, wherein the transgene encodes an anti-cancer agent selected from the group consisting of a pro-inflammatory molecule, a cytokine, an anti-angiogenic factor, an inhibitor of KRas, and an inhibitor of cytotoxic T lymphocyte-associated molecule (CTLA)-4, programmed cell death protein 1 (PD-1), carcinoembryonic antigen (CEA) and mucin 1 (MUC1).

11. The method of claim 1, wherein the anti-cancer agent disrupts or kills the stromal cells in the tumor.

12. The method of claim 1, wherein the transgene is operably linked to the EF1α promoter.

13. The method of claim 1, wherein the transgene encodes a pro-inflammatory molecule or cytokine selected from the group consisting of granulocyte macrophage colony stimulating factor (GM-CSF), CD40 ligand (CD40L), Fms-related tyrosine kinase 3 (FLT3) ligand, interleukin (IL)-1b, IL-2, IL-4, IL-6, IL-12, tumor necrosis factor (TNF)-α, an interferon, a chemokine, B7-1, intercellular adhesion molecule (ICAM)-1, lymphocyte function-associated antigen (LFA)-3, transforming growth factor (TGF)-β, platelet derived growth factor (PDGF), and epidermal growth factor (EGF).

14. The method of claim 13, wherein the transgene is operably linked to the EF1α promoter.

15. The method of claim 1, wherein the transgene encodes an inhibitor of vascular endothelial growth factor (VEGF).

16. The method of claim 15, wherein the transgene is operably linked to the EF1α promoter.

17. A method of reducing the size of a tumor in a subject, comprising infecting stromal cells in the tumor of the subject with a synthetic adenovirus comprising:

a therapeutic transgene inserted into the E1 region, wherein the therapeutic transgene encodes an anti-cancer agent;

a native or modified capsid that detargets the synthetic adenovirus from the liver; and an adenovirus type 34 (Ad34) fiber protein or a chimeric fiber protein comprising an adenovirus type 5 (Ad5) shaft domain and an Ad34 knob domain, wherein the stromal cells in the tumor express the transgene, and wherein expression of the transgene results in a reduction in the size of the tumor.

18. The method of claim 17, wherein the therapeutic transgene encodes an anti-cancer agent selected from the group consisting of a pro-inflammatory molecule, a cytokine, an anti-angiogenic factor, an inhibitor of KRas, and an inhibitor of cytotoxic T lymphocyte-associated molecule (CTLA)-4, programmed cell death protein 1 (PD-1), carcinoembryonic antigen (CEA), and mucin 1 (MUC1).

19. The method of claim 17, wherein the anti-cancer agent disrupts or kills the stromal cells in the tumor.

20. The method of claim 17, wherein the transgene is operably linked to the EF1α promoter.

21. The method of claim 17, wherein the tumor is a pancreatic tumor.

22. The method of claim 17, wherein the tumor is a glioblastoma.

23. A synthetic adenovirus genome, comprising a nucleotide sequence at least 95% identical to SEQ ID NO: 5.

24. The synthetic adenovirus genome of claim 23, comprising SEQ ID NO: 5.

* * * * *

SEQUENCE LISTING

<160> NUMBER OF SEQ ID NOS: 6

<210> SEQ ID NO 1
<211> LENGTH: 36913
<212> TYPE: DNA
<213> ORGANISM: Artificial Sequence
<220> FEATURE:
<223> OTHER INFORMATION: Synthetic adenovirus genome (AdSyn-CO171)

<400> SEQUENCE: 1
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattaaac cgtattaccg ccatgcattt aatggagtgc 480
ctcgtgaggc tccggtgccc gtcagtgggc agagcgcaca tcgcccacag tccccgagaa 540
gttgggggga ggggtcggca attgaaccgg tgcctagaga aggtggcgcg gggtaaactg 600
ggaaagtgat gtcgtgtact ggctccgcct ttttcccgag ggtgggggag aaccgtatat 660
aagtgcagta gtcgccgtga acgttctttt tcgcaacggg tttgccgcca gaacacaggt 720
aagtgccgtg tgtggttccc gcgggcctgg cctctttacg ggttatggcc cttgcgtgcc 780
ttgaattact tccacctggc tgcagtacgt gattcttgat cccgagcttc gggttggaag 840
tgggtgggag agttcgaggc cttgcgctta aggagcccct tcgcctcgtg cttgagttga 900
ggcctggcct gggcgctggg gccgccgcgt gcgaatctgg tggcaccttc gcgcctgtct 960
cgctgctttc gataagtctc tagccattta aaatttttga tgacctgctg cgacgctttt 1020
tttctggcaa gatagtcttg taaatgcggg ccaagatctg cacactggta tttcggtttt 1080
tggggccgcg ggcggcgacg gggcccgtgc gtcccagcgc acatgttcgg cgaggcgggg 1140
cctgcgagcg cggccaccga gaatcggacg ggggtagtct caagctggcc ggcctgctct 1200
ggtgcctggc ctcgcgccgc cgtgtatcgc cccgccctgg gcggcaaggc tggcccggtc 1260
ggcaccagtt gcgtgagcgg aaagatggcc gcttcccggc cctgctgcag ggagctcaaa 1320
atggaggacg cggcgctcgg gagagcgggc gggtgagtca cccacacaaa ggaaaagggc 1380
ctttccgtcc tcagccgtcg cttcatgtga ctccacggag taccgggcgc cgtccaggca 1440
cctcgattag ttctcgagct tttggagtac gtcgtcttta ggttgggggg aggggtttta 1500
tgcgatggag tttccccaca ctgagtgggt ggagactgaa gttaggccag cttggcactt 1560
gatgtaattc tccttggaat ttgccctttt tgagtttgga tcttggttca ttctcaagcc 1620
tcagacagtg gttcaaagtt tttttcttcc atttcaggtg tcgtgacgct agcgctaccg 1680
gactcagatc tcgagctcaa gcttcgaatt ctgcagtcga cggtaccgga tccatggaag 1740
acgccaaaaa cataaagaaa ggcccggcgc cattctatcc gctggaagat ggaaccgctg 1800
gagagcaact gcataaggct atgaagagat acgccctggt tcctggaaca attgctttta 1860
cagatgcaca tatcgaggtg gacatcactt acgctgagta cttcgaaatg tccgttcggt 1920
tggcagaagc tatgaaacga tatgggctga atacaaatca cagaatcgtc gtatgcagtg 1980
aaaactctct tcaattcttt atgccggtgt tgggcgcgtt atttatcgga gttgcagttg 2040

-continued cgcccgcgaa cgacatttat aatgaacgtg aattgctcaa cagtatgggc atttcgcagc 2100
ctaccgtggt gttcgtttcc aaaaaggggt tgcaaaaaat tttgaacgtg caaaaaaagc 2160
tcccaatcat ccaaaaaatt attatcatgg attctaaaac ggattaccag ggatttcagt 2220
cgatgtacac gttcgtcaca tctcatctac ctcccggttt taatgaatac gattttgtgc 2280
cagagtcctt cgatagggac aagacaattg cactgatcat gaactcctct ggatctactg 2340
gtctgcctaa aggtgtcgct ctgcctcata gaactgcctg cgtgagattc tcgcatgcca 2400
gagatcctat ttttggcaat caaatcattc cggatactgc gattttaagt gttgttccat 2460
tccatcacgg ttttggaatg tttactacac tcggatattt gatatgtgga tttcgagtcg 2520
tcttaatgta tagatttgaa gaagagctgt ttctgaggag ccttcaggat tacaagattc 2580
aaagtgcgct gctggtgcca accctattct ccttcttcgc caaaagcact ctgattgaca 2640
aatacgattt atctaattta cacgaaattg cttctggtgg cgctcccctc tctaaggaag 2700
tcggggaagc ggttgccaag aggttccatc tgccaggtat caggcaagga tatgggctca 2760
ctgagactac atcagctatt ctgattacac ccgaggggga tgataaaccg ggcgcggtcg 2820
gtaaagttgt tccatttttt gaagcgaagg ttgtggatct ggataccggg aaaacgctgg 2880
gcgttaatca aagaggcgaa ctgtgtgtga gaggtcctat gattatgtcc ggttatgtaa 2940
acaatccgga agcgaccaac gccttgattg acaaggatgg atggctacat tctggagaca 3000
tagcttactg ggacgaagac gaacacttct tcatcgttga ccgcctgaag tctctgatta 3060
agtacaaagg ctatcaggtg gctcccgctg aattggaatc catcttgctc caacacccca 3120
acatcttcga cgcaggtgtc gcaggtcttc ccgacgatga cgccggtgaa cttcccgccg 3180
ccgttgttgt tttggagcac ggaaagacga tgacggaaaa agagatcgtg gattacgtcg 3240
ccagtcaagt aacaaccgcg aaaaagttgc gcggaggagt tgtgtttgtg gacgaagtac 3300
cgaaaggtct taccggaaaa ctcgacgcaa gaaaaatcag agagatcctc ataaaggcca 3360
agaagggcgg aaagatcgcc gtggcagccg cagccaccat ggtgagcaag ggcgaggagc 3420
tgttcaccgg ggtggtgccc atcctggtcg agctggacgg cgacgtaaac ggccacaagt 3480
tcagcgtgtc cggcgagggc gagggcgatg ccacctacgg caagctgacc ctgaagttca 3540
tctgcaccac cggcaagctg cccgtgccct ggcccaccct cgtgaccacc ctgacctacg 3600
gcgtgcagtg cttcagccgc taccccgacc acatgaagca gcacgacttc ttcaagtccg 3660
ccatgcccga aggctacgtc caggagcgca ccatcttctt caaggacgac ggcaactaca 3720
agacccgcgc cgaggtgaag ttcgagggcg acaccctggt gaaccgcatc gagctgaagg 3780
gcatcgactt caaggaggac ggcaacatcc tggggcacaa gctggagtac aactacaaca 3840
gccacaacgt ctatatcatg gccgacaagc agaagaacgg catcaaggtg aacttcaaga 3900
tccgccacaa catcgaggac ggcagcgtgc agctcgccga ccactaccag cagaacaccc 3960
ccatcggcga cggccccgtg ctgctgcccg acaaccacta cctgagcacc cagtccgccc 4020
tgagcaaaga ccccaacgag aagcgcgatc acatggtcct gctggagttc gtgaccgccg 4080
ccgggatcac tctcggcatg gacgagctgt acaagtaaag cgactctaga tcataatcag 4140
ccataccaca acaccattgt cacactccaa tcgattcaaa caccattgtc acactccaac 4200
atttgtagag gttttacttg ctttaaaaaa cctcccacac ctccccctga acctgaaaca 4260
taaaatgaat gcaattgttg ttgttaactt gtttattgca gcttataatg gttacaaata 4320
aagcaatagc atcacaaatt tcacaaataa agcatttttt tcactgcatt ctagttgtgg 4380

-continued

```
tttgtccaaa ctcatcaatg taagtttaaa cggcgcgcct gaaatgtgtg ggcgtggctt   4440
aagggtggga aagaatatat aaggtggggg tcttatgtag ttttgtatct gttttgcagc   4500
agccgccgcc gccatgagca ccaactcgtt tgatggaagc attgtgagct catatttgac   4560
aacgcgcatg cccccatggg ccggggtgcg tcagaatgtg atgggctcca gcattgatgg   4620
tcgccccgtc ctgcccgcaa actctactac cttgacctac gagaccgtgt ctggaacgcc   4680
gttggagact gcagcctccg ccgccgcttc agccgctgca gccaccgccc gcgggattgt   4740
gactgacttt gctttcctga gcccgcttgc aagcagtgca gcttcccgtt catccgcccg   4800
cgatgacaag ttgacggctc ttttggcaca attggattct ttgacccggg aacttaatgt   4860
cgtttctcag cagctgttgg atctgcgcca gcaggtttct gccctgaagg cttcctcccc   4920
tcccaatgcg gtttaaaaca caacttttct atacaaagtt gtaaataaaa aaccagactc   4980
tgtttggatt tggatcaagc taagtgtctt gctgtcttta tttaggggtt ttgcgcgcgc   5040
ggtaggcccg ggaccagcgg tctcggtcgt tgagggtcct gtgtattttt tccaggacgt   5100
ggtaaaggtg actctggatg ttcagataca tgggcataag cccgtctctg gggtggaggt   5160
agcaccactg cagagcttca tgctgcgggg tggtgttgta gatgatccag tcgtagcagg   5220
agcgctgggc gtggtgccta aaaatgtctt tcagtagcaa gctgattgcc aggggcaggc   5280
ccttggtgta agtgtttaca aagcggttaa gctgggatgg gtgcatacgt ggggatatga   5340
gatgcatctt ggactgtatt tttaggttgg ctatgttccc agccatatcc ctccggggat   5400
tcatgttgtg cagaaccacc agcacagtgt atccggtgca cttgggaaat ttgtcatgta   5460
gcttagaagg aaatgcgtgg aagaacttgg agacgccctt gtgacctcca agattttcca   5520
tgcattcgtc cataatgatg gcaatgggcc cacgggcggc ggcctgggcg aagatatttc   5580
tgggatcact aacgtcatag ttgtgttcca ggatgagatc gtcataggcc atttttacaa   5640
agcgcgggcg gagggtgcca gactgcggta taatggttcc atccggccca ggggcgtagt   5700
taccctcaca gatttgcatt tcccacgctt tgagttcaga tggggggatc atgtctacct   5760
gcggggcgat gaagaaaacg gtttccgggg taggggagat cagctgggaa gaaagcaggt   5820
tcctgagcag ctgcgactta ccgcagccgg tgggcccgta aatcacacct attaccggct   5880
gcaactggta gttaagagag ctgcagctgc cgtcatccct gagcaggggg gccacttcgt   5940
taagcatgtc cctgactcgc atgttttccc tgaccaaatc cgccagaagg cgctcgccgc   6000
ccagcgatag cagttcttgc aaggaagcaa agtttttcaa cggtttgaga ccgtccgccg   6060
taggcatgct tttgagcgtt tgaccaagca gttccaggcg gtcccacagc tcggtcacct   6120
gctctacggc atctcgatcc agcatatctc ctcgtttcgc gggttggggc ggctttcgct   6180
gtacggcagt agtcggtgct cgtccagacg ggccagggtc atgtctttcc acgggcgcag   6240
ggtcctcgtc agcgtagtct gggtcacggt gaaggggtgc gctccgggct gcgcgctggc   6300
cagggtgcgc ttgaggctgg tcctgctggt gctgaagcgc tgccggtctt cgccctgcgc   6360
gtcggccagg tagcatttga ccatggtgtc atagtccagc ccctccgcgg cgtggccctt   6420
ggcgcgcagc ttgcccttgg aggaggcgcc gcacgagggg cagtgcagac ttttgagggc   6480
gtagagcttg ggcgcgagaa ataccgattc cggggagtag gcatccgcgc cgcaggcccc   6540
gcagacggtc tcgcattcca cgagccaggt gagctctggc cgttcggggt caaaaaccag   6600
gtttccccca tgctttttga tgcgtttctt acctctggtt tccatgagcc ggtgtccacg   6660
ctcggtgacg aaaaggctgt ccgtgtcccc gtatacagac ttgagaggcc tgtcctcgag   6720
cggtgttccg cggtcctcct cgtatagaaa ctcggaccac tctgagacaa aggctcgcgt   6780
```

-continued

```
ccaggccagc acgaaggagg ctaagtggga ggggtagcgg tcgttgtcca ctagggggtc   6840
cactcgctcc agggtgtgaa gacacatgtc gccctcttcg gcatcaagga aggtgattgg   6900
tttgtaggtg taggccacgt gaccgggtgt tcctgaaggg gggctataaa agggggtggg   6960
ggcgcgttcg tcctcactct cttccgcatc gctgtctgcg agggccagct gttggggtga   7020
gtactccctc tgaaaagcgg gcatgacttc tgcgctaaga ttgtcagttt ccaaaaacga   7080
ggaggatttg atattcacct ggcccgcggt gatgcctttg agggtggccg catccatctg   7140
gtcagaaaag acaatctttt tgttgtcaag cttggtggca aacgacccgt agagggcgtt   7200
ggacagcaac ttggcgatgg agcgcagggt ttggtttttg tcgcgatcgg cgcgctcctt   7260
ggccgcgatg tttagctgca cgtattcgcg cgcaacgcac cgccattcgg gaaagacggt   7320
ggtgcgctcg tcgggcacca ggtgcacgcg ccaaccgcgg ttgtgcaggg tgacaaggtc   7380
aacgctggtg gctacctctc cgcgtaggcg ctcgttggtc cagcagaggc ggccgccctt   7440
gcgcgagcag aatggcggta gggggtctag ctgcgtctcg tccggggggt ctgcgtccac   7500
ggtaaagacc ccgggcagca ggcgcgcgtc gaagtagtct atcttgcatc cttgcaagtc   7560
tagcgcctgc tgccatgcgc gggcggcaag cgcgcgctcg tatgggttga gtgggggacc   7620
ccatggcatg gggtgggtga gcgcggaggc gtacatgccg caaatgtcgt aaacgtagag   7680
gggctctctg agtattccaa gatatgtagg gtagcatctt ccaccgcgga tgctggcgcg   7740
cacgtaatcg tatagttcgt gcgagggagc gaggaggtcg ggaccgaggt tgctacgggc   7800
gggctgctct gctcggaaga ctatctgcct gaagatggca tgtgagttgg atgatatggt   7860
tggacgctgg aagacgttga agctggcgtc tgtgagacct accgcgtcac gcacgaagga   7920
ggcgtaggag tcgcgcagct tgttgaccag ctcggcggtg acctgcacgt ctagggcgca   7980
gtagtccagg gtttccttga tgatgtcata cttatcctgt cccttttttt tccacagctc   8040
gcggttgagg acaaactctt cgcggtcttt ccagtactct tggatcggaa acccgtcggc   8100
ctccgaacgg taagagccta gcatgtagaa ctggttgacg gcctggtagg cgcagcatcc   8160
cttttctacg ggtagcgcgt atgcctgcgc ggccttccgg agcgaggtgt gggtgagcgc   8220
aaaggtgtcc ctgaccatga ctttgaggta ctggtatttg aagtcagtgt cgtcgcatcc   8280
gccctgctcc cagagcaaaa agtccgtgcg ctttttggaa cgcggatttg gcagggcgaa   8340
ggtgacatcg ttgaagagta tctttcccgc gcgaggcata aagttgcgtg tgatgcggaa   8400
gggtcccggc acctcggaac ggttgttaat tacctgggcg gcgagcacga tctcgtcaaa   8460
gccgttgatg ttgtggccca caatgtaaag ttccaagaag cgcgggatgc ccttgatgga   8520
aggcaatttt ttaagttcct cgtaggtgag ctcttcaggg gagctgagcc cgtgctctga   8580
aagggcccag tctgcaagat gagggttgga agcgacgaat gagctccaca ggtcacgggc   8640
cattagcatt tgcaggtggt cgcgaaaggt cctaaactgg cgacctatgg ccattttttc   8700
tggggtgatg cagtagaagg taagcgggtc ttgttcccag cggtcccatc caaggttcgc   8760
ggctaggtct cgcgcggcag tcactagagg ctcatctccg ccgaacttca tgaccagcat   8820
gaagggcacg agctgcttcc caaaggcccc catccaagta taggtctcta catcgtaggt   8880
gacaaagaga cgctcggtgc gaggatgcga gccgatcggg aagaactgga tctcccgcca   8940
ccaattggag gagtggctat tgatgtggtg aaagtagaag tccctgcgac gggccgaaca   9000
ctcgtgctgg cttttgtaaa aacgtgcgca gtactggcag cggtgcacgg gctgtacatc   9060
ctgcacgagg ttgacctgac gaccgcgcac aaggaagcag agtgggaatt tgagcccctc   9120
```

-continued

```
gcctggcggg tttggctggt ggtcttctac ttcggctgct tgtccttgac cgtctggctg   9180
ctcgagggga gttacggtgg atcggaccac cacgccgcgc gagcccaaag tccagatgtc   9240
cgcgcgcggc ggtcggagct tgatgacaac atcgcgcaga tgggagctgt ccatggtctg   9300
gagctcccgc ggcgtcaggt caggcgggag ctcctgcagg tttacctcgc atagacgggt   9360
cagggcgcgg gctagatcca ggtgatacct aatttccagg ggctggttgg tggcggcgtc   9420
gatggcttgc aagaggccgc atccccgcgg cgcgactacg gtaccgcgcg gcgggcggtg   9480
ggccgcgggg gtgtccttgg atgatgcatc taaaagcggt gacgcgggcg agcccccgga   9540
ggtagggggg gctccggacc cgccgggaga gggggcaggg gcacgtcggc gccgcgcgcg   9600
ggcaggagct ggtgctgcgc gcgtaggttg ctggcgaacg cgacgacgcg gcggttgatc   9660
tcctgaatct ggcgcctctg cgtgaagacg acgggcccgg tgagcttgaa cctgaaagag   9720
agttcgacag aatcaatttc ggtgtcgttg acggcggcct ggcgcaaaat ctcctgcacg   9780
tctcctgagt tgtcttgata ggcgatctcg gccatgaact gctcgatctc ttcctcctgg   9840
agatctccgc gtccggctcg ctccacggtg gcggcgaggt cgttggaaat gcgggccatg   9900
agctgcgaga aggcgttgag gcctccctcg ttccagacgc ggctgtagac cacgccccct   9960
tcggcatcgc gggcgcgcat gaccacctgc gcgagattga gctccacgtg ccgggcgaag  10020
acggcgtagt ttcgcaggcg ctgaaagagg tagttgaggg tggtggcggt gtgttctgcc  10080
acgaagaagt acataaccca gcgtcgcaac gtggattcgt tgatatcccc caaggcctca  10140
aggcgctcca tggcctcgta gaagtccacg gcgaagttga aaaactggga gttgcgcgcc  10200
gacacggtta actcctcctc cagaagacgg atgagctcgg cgacagtgtc gcgcacctcg  10260
cgctcaaagg ctacaggggc ctcttcttct tcttcaatct cctcttccat aagggcctcc  10320
ccttcttctt cttctggcgg cggtggggga ggggggacac ggcggcgacg acggcgcacc  10380
gggaggcggt cgacaaagcg ctcgatcatc tccccgcggc gacggcgcat ggtctcggtg  10440
acggcgcggc cgttctcgcg ggggcgcagt tggaagacgc cgcccgtcat gtcccggtta  10500
tgggttggcg gggggctgcc atgcggcagg gatacggcgc taacgatgca tctcaacaat  10560
tgttgtgtag gtactccgcc gccgagggac ctgagcgagt ccgcatcgac cggatcggaa  10620
aacctctcga gaaaggcgtc taaccagtca cagtcgcaag gtaggctgag caccgtggcg  10680
ggcggcagcg ggcggcggtc ggggttgttt ctggcggagg tgctgctgat gatgtaatta  10740
aagtaggcgg tcttgagacg gcggatggtc gacagaagca ccatgtcctt gggtccggcc  10800
tgctgaatgc gcaggcggtc ggccatgccc caggcttcgt tttgacatcg gcgcaggtct  10860
ttgtagtagt cttgcatgag cctttctacc ggcacttctt cttctccttc ctcttgtcct  10920
gcatctcttg catctatcgc tgcggcggcg gcggagtttg gccgtaggtg gcgccctctt  10980
cctcccatgc gtgtgacccc gaagcccctc atcggctgaa gcagggctag gtcggcgaca  11040
acgcgctcgg ctaatatggc ctgctgcacc tgcgtgaggg tagactggaa gtcatccatg  11100
tccacaaagc ggtggtatgc gcccgtgttg atggtgtaag tgcagttggc cataacggac  11160
cagttaacgg tctggtgacc cggctgcgag agctcggtgt acctgagacg cgagtaagcc  11220
ctcgagtcaa atacgtagtc gttgcaagtc cgcaccaggt actggtatcc caccaaaaag  11280
tgcggcggcg gctggcggta gaggggccag cgtagggtgg ccggggctcc gggggcgaga  11340
tcttccaaca taaggcgatg atatccgtag atgtacctgg acatccaggt gatgccggcg  11400
gcggtggtgg aggcgcgcgg aaagtcgcgg acgcggttcc agatgttgcg cagcggcaaa  11460
aagtgctcca tggtcgggac gctctggccg gtcaggcgcg cgcaatcgtt gacgctctag  11520
```

-continued

```
accgtgcaaa aggagagcct gtaagcgggc actcttccgt ggtctggtgg ataaattcgc  11580
aagggtatca tggcggacga ccggggttcg agccccgtat ccggccgtcc gccgtgatcc  11640
atgcggttac cgcccgcgtg tcgaacccag gtgtgcgacg tcagacaacg ggggagtgct  11700
ccttttggct tccttccagg cgcggcggct gctgcgctag ctttttggc cactggccgc  11760
gcgcagcgta agcggttagg ctggaaagcg aaagcattaa gtggctcgct ccctgtagcc  11820
ggagggttat tttccaaggg ttgagtcgcg ggacccccgg ttcgagtctc ggaccggccg  11880
gactgcggcg aacgggggtt tgcctccccg tcatgcaaga ccccgcttgc aaattcctcc  11940
ggaaacaggg acgagcccct tttttgcttt tcccagatgc atccggtgct gcggcagatg  12000
cgcccccctc ctcagcagcg gcaagagcaa gagcagcggc agacatgcag ggcaccctcc  12060
cctcctccta ccgcgtcagg aggggcgaca tccgcggttg acgcggcagc agatggtgat  12120
tacgaacccc cgcggcgccg ggcccggcac tacctggact tggaggaggg cgagggcctg  12180
gcgcggctag gagcgccctc tcctgagcgg cacccaaggg tgcagctgaa gcgtgatacg  12240
cgtgaggcgt acgtgccgcg gcagaacctg tttcgcgacc gcgagggaga ggagcccgag  12300
gagatgcggg atcgaaagtt ccacgcaggg cgcgagctgc ggcatggcct gaatcgcgag  12360
cggttgctgc gcgaggagga ctttgagccc gacgcgcgaa ccgggattag tcccgcgcgc  12420
gcacacgtgg cggccgccga cctggtaacc gcatacgagc agacggtgaa ccaggagatt  12480
aactttcaaa aaagctttaa caaccacgtg cgtacgcttg tggcgcgcga ggaggtggct  12540
ataggactga tgcatctgtg ggactttgta agcgcgctgg agcaaaaccc aaatagcaag  12600
ccgctcatgg cgcagctgtt ccttatagtg cagcacagca gggacaacga ggcattcagg  12660
gatgcgctgc taaacatagt agagcccgag ggccgctggc tgctcgattt gataaacatc  12720
ctgcagagca tagtggtgca ggagcgcagc ttgagcctgg ctgacaaggt ggccgccatc  12780
aactattcca tgcttagcct gggcaagttt tacgcccgca agatatacca taccccttac  12840
gttcccatag acaaggaggt aaagatcgag gggttctaca tgcgcatggc gctgaaggtg  12900
cttaccttga gcgacgacct gggcgtttat cgcaacgagc gcatccacaa ggccgtgagc  12960
gtgagccggc ggcgcgagct cagcgaccgc gagctgatgc acagcctgca aagggccctg  13020
gctggcacgg gcagcggcga tagagaggcc gagtcctact ttgacgcggg cgctgacctg  13080
cgctgggccc caagccgacg cgccctggag gcagctgggg ccggacctgg gctggcggtg  13140
gcacccgcgc gcgctggcaa cgtcggcggc gtggaggaat atgacgagga cgatgagtac  13200
gagccagagg acggcgagta ctaagcggtg atgtttctga tcagatgatg caagacgcaa  13260
cggacccggc ggtgcgggcg gcgctgcaga gccagccgtc cggccttaac tccacggacg  13320
actggcgcca ggtcatggac cgcatcatgt cgctgactgc gcgcaatcct gacgcgttcc  13380
ggcagcagcc gcaggccaac cggctctccg caattctgga agcggtggtc ccggcgcgcg  13440
caaaccccac gcacgagaag gtgctggcga tcgtaaacgc gctggccgaa aacagggcca  13500
tccggcccga cgaggccggc ctggtctacg acgcgctgct tcagcgcgtg gctcgttaca  13560
acagcggcaa cgtgcagacc aacctggacc ggctggtggg ggatgtgcgc gaggccgtgg  13620
cgcagcgtga gcgcgcgcag cagcagggca acctgggctc catggttgca ctaaacgcct  13680
tcctgagtac acagcccgcc aacgtgccgc ggggacagga ggactacacc aactttgtga  13740
gcgcactgcg gctaatggtg actgagacac cgcaaagtga ggtgtaccag tctgggccag  13800
actatttttt ccagaccagt agacaaggcc tgcagaccgt aaacctgagc caggctttca  13860
```

-continued

```
aaaacttgca ggggctgtgg ggggtgcggg ctcccacagg cgaccgcgcg accgtgtcta  13920
gcttgctgac gcccaactcg cgcctgttgc tgctgctaat agcgcccttc acggacagtg  13980
gcagcgtgtc ccgggacaca tacctaggtc acttgctgac actgtaccgc gaggccatag  14040
gtcaggcgca tgtggacgag catactttcc aggagattac aagtgtcagc cgcgcgctgg  14100
ggcaggagga cacgggcagc ctggaggcaa ccctaaacta cctgctgacc aaccggcggc  14160
agaagatccc ctcgttgcac agtttaaaca gcgaggagga gcgcattttg cgctacgtgc  14220
agcagagcgt gagccttaac ctgatgcgcg acggggtaac gcccagcgtg gcgctggaca  14280
tgaccgcgcg caacatggaa ccgggcatgt atgcctcaaa ccggccgttt atcaaccgcc  14340
taatggacta cttgcatcgc gcggccgccg tgaaccccga gtatttcacc aatgccatct  14400
tgaacccgca ctggctaccg ccccctggtt tctacaccgg gggattcgag gtgcccgagg  14460
gtaacgatgg attcctctgg gacgacatag acgacagcgt gttttccccg caaccgcaga  14520
ccctgctaga gttgcaacag cgcgagcagg cagaggcggc gctgcgaaag gaaagcttcc  14580
gcaggccaag cagcttgtcc gatctaggcg ctgcggcccc gcggtcagat gctagtagcc  14640
catttccaag cttgataggg tctcttacca gcactcgcac cacccgcccg cgcctgctgg  14700
gcgaggagga gtacctaaac aactcgctgc tgcagccgca gcgcgaaaaa aacctgcctc  14760
cggcatttcc caacaacggg atagagagcc tagtggacaa gatgagtaga tggaagacgt  14820
acgcgcagga gcacagggac gtgccaggcc cgcgcccgcc cacccgtcgt caaaggcacg  14880
accgtcagcg gggtctggtg tgggaggacg atgactcggc agacgacagc agcgtcctgg  14940
atttgggagg gagtggcaac ccgtttgcgc accttcgccc caggctgggg agaatgtttt  15000
aaaaaaaaaa aaaaagcatg atgcaaaata aaaaactcac caaggccatg gcaccgagcg  15060
ttggttttct tgtattcccc ttagtatgcg gcgcgcggcg atgtatgagg aaggtcctcc  15120
tccctcctac gagagtgtgg tgagcgcggc gccagtggcg gcggcgctgg gttctccctt  15180
cgatgctccc ctggacccgc cgtttgtgcc tccgcggtac ctgcggccta ccggggggag  15240
aaacagcatc cgttactctg agttggcacc cctattcgac accacccgtg tgtacctggt  15300
ggacaacaag tcaacggatg tggcatccct gaactaccag aacgaccaca gcaactttct  15360
gaccacggtc attcaaaaca atgactacag cccgggggag gcaagcacac agaccatcaa  15420
tcttgacgac cggtcgcact ggggcggcga cctgaaaacc atcctgcata ccaacatgcc  15480
aaatgtgaac gagttcatgt ttaccaataa gtttaaggcg cgggtgatgg tgtcgcgctt  15540
gcctactaag gacaatcagg tggagctgaa atacgagtgg gtggagttca cgctgcccga  15600
gggcaactac tccgagacca tgaccataga ccttatgaac aacgcgatcg tggagcacta  15660
cttgaaagtg ggcagacaga acggggttct ggaaagcgac atcggggtaa agtttgacac  15720
ccgcaacttc agactggggt ttgaccccgt cactggtctt gtcatgcctg ggtatatac  15780
aaacgaagcc ttccatccag acatcatttt gctgccagga tgcggggtgg acttcaccca  15840
cagccgcctg agcaacttgt tgggcatccg caagcggcaa cccttccagg agggctttag  15900
gatcacctac gatgatctgg agggtggtaa cattcccgca ctgttggatg tggacgccta  15960
ccaggcgagc ttgaaagatg acaccgaaca gggcgggggt ggcgcaggcg gcagcaacag  16020
cagtggcagc ggcgcggaag agaactccaa cgcggcagcc gcggcaatgc agccggtgga  16080
ggacatgaac gatcatgcca ttcgcggcga cacctttgcc acacgggctg aggagaagcg  16140
cgctgaggcc gaagcagcgg ccgaagctgc cgcccccgct gcgcaacccg aggtcgagaa  16200
gcctcagaag aaaccggtga tcaaacccct gacagaggac agcaagaaac gcagttacaa  16260
```

```
cctaataagc aatgacagca ccttcaccca gtaccgcagc tggtaccttg catacaacta  16320
cggcgaccct cagaccggaa tccgctcatg gaccctgctt tgcactcctg acgtaacctg  16380
cggctcggag caggtctact ggtcgttgcc agacatgatg caagaccccg tgaccttccg  16440
ctccacgcgc cagatcagca actttccggt ggtgggcgcc gagctgttgc ccgtgcactc  16500
caagagcttc tacaacgacc aggccgtcta ctcccaactc atccgccagt ttacctctct  16560
gacccacgtg ttcaatcgct ttcccgagaa ccagattttg gcgcgcccgc cagcccccac  16620
catcaccacc gtcagtgaaa acgttcctgc tctcacagat cacgggacgc taccgctgcg  16680
caacagcatc ggaggagtcc agcgagtgac cattactgac gccagacgcc gcacctgccc  16740
ctacgtttac aaggccctgg gcatagtctc gccgcgcgtc ctatcgagcc gcactttttg  16800
agcaagcatg tccatcctta tatcgcccag caataacaca ggctggggcc tgcgcttccc  16860
aagcaagatg tttggcgggg ccaagaagcg ctccgaccaa cacccagtgc gcgtgcgcgg  16920
gcactaccgc gcgccctggg gcgcgcacaa acgcggccgc actgggcgca ccaccgtcga  16980
tgacgccatc gacgcggtgg tggaggaggc gcgcaactac acgcccacgc cgccaccagt  17040
gtccacagtg gacgcggcca ttcagaccgt ggtgcgcgga gcccggcgct atgctaaaat  17100
gaagagacgg cggaggcgcg tagcacgtcg ccaccgccgc cgacccggca ctgccgccca  17160
acgcgcggcg gcggccctgc ttaaccgcgc acgtcgcacc ggccgacggg cggccatgcg  17220
ggccgctcga aggctggccg cgggtattgt cactgtgccc cccaggtcca ggcgacgagc  17280
ggccgccgca gcagccgcgg ccattagtgc tatgactcag ggtcgcaggg gcaacgtgta  17340
ttgggtgcgc gactcggtta gcggcctgcg cgtgcccgtg cgcacccgcc ccccgcgcaa  17400
ctagattgca agaaaaaact acttagactc gtactgttgt atgtatccag cggcggcggc  17460
gcgcaacgaa gctatgtcca agcgcaaaat caaagaagag atgctccagg tcatcgcgcc  17520
ggagatctat ggcccccega agaaggaaga gcaggattac aagccccgaa agctaaagcg  17580
ggtcaaaaag aaaaagaaag atgatgatga tgaacttgac gacgaggtgg aactgctgca  17640
cgctaccgcg cccaggcgac gggtacagtg gaaaggtcga cgcgtaaaac gtgttttgcg  17700
acccggcacc accgtagtct ttacgcccgg tgagcgctcc acccgcacct acaagcgcgt  17760
gtatgatgag gtgtacggcg acgaggacct gcttgagcag gccaacgagc gcctcgggga  17820
gtttgcctac ggaaagcggc ataaggacat gctggcgttg ccgctggacg agggcaaccc  17880
aacacctagc ctaaagcccg taacactgca gcaggtgctg cccgcgcttg caccgtccga  17940
agaaaagcgc ggcctaaagc gcgagtctgg tgacttggca cccaccgtgc agctgatggt  18000
acccaagcgc cagcgactgg aagatgtctt ggaaaaaatg accgtggaac ctgggctgga  18060
gcccgaggtc cgcgtgcggc caatcaagca ggtggcgccg ggactgggcg tgcagaccgt  18120
ggacgttcag atacccacta ccagtagcac cagtattgcc accgccacag agggcatgga  18180
gacacaaacg tccccggttg cctcagcggt ggcggatgcc gcggtgcagg cggtcgctgc  18240
ggccgcgtcc aagacctcta cggaggtgca aacggacccg tggatgtttc gcgtttcagc  18300
cccccggcgc ccgcgccgtt cgaggaagta cggcgccgcc agcgcgctac tgcccgaata  18360
tgccctacat ccttccattg cgcctacccc cggctatcgt ggctacacct accgccccag  18420
aagacgagca actacccgac gccgaaccac cactggaacc cgccgccgcc gtcgccgtcg  18480
ccagcccgtg ctggccccga tttccgtgcg cagggtggct cgcgaaggag gcaggaccct  18540
ggtgctgcca acagcgcgct accaccccag catcgtttaa aagccggtct ttgtggttct  18600
```

-continued

```
tgcagatatg gccctcacct gccgcctccg tttcccggtg ccgggattcc gaggaagaat  18660
gcaccgtagg aggggcatgg ccggccacgg cctgacgggc ggcatgcgtc gtgcgcacca  18720
ccggcggcgg cgcgcgtcgc accgtcgcat gcgcggcggt atcctgcccc tccttattcc  18780
actgatcgcc gcggcgattg gcgccgtgcc cggaattgca tccgtggcct tgcaggcgca  18840
gagacactga ttaaaaacaa gttgcatgtg gaaaaatcaa aataaaaagt ctggactctc  18900
acgctcgctt ggtcctgtaa ctattttgta gaatggaaga catcaacttt gcgtctctgg  18960
ccccgcgaca cggctcgcgc ccgttcatgg gaaactggca agatatcggc accagcaata  19020
tgagcggtgg cgccttcagc tggggctcgc tgtggagcgg cattaaaaat ttcggttcca  19080
ccgttaagaa ctatggcagc aaggcctgga acagcagcac aggccagatg ctgagggata  19140
agttgaaaga gcaaaatttc caacaaaagg tggtagatgg cctggcctct ggcattagcg  19200
gggtggtgga cctggccaac caggcagtgc aaaataagat taacagtaag cttgatcccc  19260
gccctcccgt agaggagcct ccaccggccg tggagacagt gtctccagag gggcgtggcg  19320
aaaagcgtcc gcgccccgac agggaagaaa ctctggtgac gcaaatagac gagcctccct  19380
cgtacgagga ggcactaaag caaggcctgc ccaccacccg tcccatcgcg cccatggcta  19440
ccggagtgct gggccagcac acacccgtaa cgctggacct gcctcccccc gccgacaccc  19500
agcagaaacc tgtgctgcca ggcccgaccg ccgttgttgt aacccgtcct agccgcgcgt  19560
ccctgcgccg cgccgccagc ggtccgcgat cgttgcggcc cgtagccagt ggcaactggc  19620
aaagcacact gaacagcatc gtgggtctgg gggtgcaatc cctgaagcgc cgacgatgct  19680
tctgaatagc taacgtgtcg tatgtgtgtc atgtatgcgt ccatgtcgcc gccagaggag  19740
ctgctgagcc gccgcgcgcc cgctttccaa gatggctacc ccttcgatga tgccgcagtg  19800
gtcttacatg cacatctcgg gccaggacgc ctcggagtac ctgagccccg ggctggtgca  19860
gtttgcccgc gccaccgaga cgtacttcag cctgaataac aagtttagaa accccacggt  19920
ggcgcctacg cacgacgtga ccacagaccg gtcccagcgt ttgacgctgc ggttcatccc  19980
tgtggaccgt gaggatactg cgtactcgta caaggcgcgg ttcaccctag ctgtgggtga  20040
taaccgtgtg ctggacatgg cttccacgta ctttgacatc cgcggcgtgc tggacagggg  20100
ccctactttt aagccctact ctggcactgc ctacaacgcc ctggctccca agggtgcccc  20160
aaatccttgc gaatgggatg aagctgctac tgctcttgaa ataaacctag aagaagagga  20220
cgatgacaac gaagacgaag tagacgagca agctgagcag caaaaaactc acgtatttgg  20280
gcaggcgcct tattctggta taaatattac aaaggagggt attcaaatag gtgtcgaagg  20340
tcaaacacct aaatatgccg ataaaacatt tcaacctgaa cctcaaatag gagaatctca  20400
gtggtacgaa actgaaatta atcatgcagc tgggagagtc cttaaaaaga ctaccccaat  20460
gaaaccatgt tacggttcat atgcaaaacc cacaaatgaa aatggagggc aaggcattct  20520
tgtaaagcaa caaaatggaa agctagaaag tcaagtggaa atgcaatttt tctcaactac  20580
tgaggcgacc gcaggcaatg gtgataactt gactcctaaa gtggtattgt acagtgaaga  20640
tgtagatata gaaaccccag acactcatat ttcttacatg cccactatta aggaaggtaa  20700
ctcacgagaa ctaatgggcc aacaatctat gcccaacagg cctaattaca ttgcttttag  20760
ggacaatttt attggtctaa tgtattacaa cagcacgggt aatatgggtg ttctggcggg  20820
ccaagcatcg cagttgaatg ctgttgtaga tttgcaagac agaaacacag agctttcata  20880
ccagcttttg cttgattcca ttggtgatag aaccaggtac ttttctatgt ggaatcaggc  20940
tgttgacagc tatgatccag atgttagaat tattgaaaat catggaactg aagatgaact  21000
```

tccaaattac tgctttccac tgggaggtgt gattaataca gagactctta ccaaggtaaa 21060
acctaaaaca ggtcaggaaa atggatggga aaaagatgct acagaatttt cagataaaaa 21120
tcaaataaga gttggaaata attttgccat ggaaatcaat ctaaatgcca acctgtggag 21180
aaatttcctg tactccaaca tagcgctgta tttgcccgac aagctaaagt acagtccttc 21240
caacgtaaaa atttctgata acccaaacac ctacgactac atgaacaagc gagtggtggc 21300
tcccgggtta gtggactgct acattaacct tggagcacgc tggtcccttg actatatgga 21360
caacgtcaac ccatttaacc accaccgcaa tgctggcctg cgctaccgct caatgttgct 21420
gggcaatggt cgctatgtgc ccttccacat ccaggtgcct cagaagttct ttgccattaa 21480
aaacctcctt ctcctgccgg gctcatacac ctacgagtgg aacttcagga aggatgttaa 21540
catggttctg cagagctccc taggaaatga cctaagggtt gacggagcca gcattaagtt 21600
tgatagcatt tgcctttacg ccaccttctt ccccatggcc cacaacaccg cctccacgct 21660
tgaggccatg cttagaaacg acaccaacga ccagtccttt aacgactatc tctccgccgc 21720
caacatgctc taccctatac ccgccaacgc taccaacgtg cccatatcca tcccctcccg 21780
caactgggcg gctttccgcg gctgggcctt cacgcgcctt aagactaagg aaaccccatc 21840
actgggctcg ggctacgacc cttattacac ctactctggc tctataccct acctagatgg 21900
aaccttttac ctcaaccaca cctttaagaa ggtggccatt acctttgact cttctgtcag 21960
ctggcctggc aatgaccgcc tgcttacccc caacgagttt gaaattaagc gctcagttga 22020
cggggagggt tacaacgttg cccagtgtaa catgaccaaa gactggttcc tggtacaaat 22080
gctagctaac tacaacattg gctaccaggg cttctatatc ccagagagct acaaggaccg 22140
catgtactcc ttctttagaa acttccagcc catgagccgt caggtggtgg atgatactaa 22200
atacaaggac taccaacagg tgggcatcct acaccaacac aacaactctg gatttgttgg 22260
ctaccttgcc cccaccatgc gcgaaggaca ggcctaccct gctaacttcc cctatccgct 22320
tataggcaag accgcagttg acagcattac ccagaaaaag tttctttgcg atcgcaccct 22380
ttggcgcatc ccattctcca gtaactttat gtccatgggc gcactcacag acctgggcca 22440
aaaccttctc tacgccaact ccgcccacgc gctagacatg acttttgagg tggatcccat 22500
ggacgagccc acccttcttt atgttttgtt tgaagtcttt gacgtggtcc gtgtgcaccg 22560
gccgcaccgc ggcgtcatcg aaaccgtgta cctgcgcacg cccttctcgg ccggcaacgc 22620
cacaacataa agaagcaagc aacatcaaca acagctgccg ccatgggctc cagtgagcag 22680
gaactgaaag ccattgtcaa agatcttggt tgtgggccat attttttggg cacctatgac 22740
aagcgctttc caggctttgt ttctccacac aagctcgcct gcgccatagt caatacggcc 22800
ggtcgcgaga ctgggggcgt acactggatg gcctttgcct ggaacccgca ctcaaaaaca 22860
tgctacctct ttgagccctt tggcttttct gaccagcgac tcaagcaggt ttaccagttt 22920
gagtacgagt cactcctgcg ccgtagcgcc attgcttctt cccccgaccg ctgtataacg 22980
ctggaaaagt ccacccaaag cgtacagggg cccaactcgg ccgcctgtgg actattctgc 23040
tgcatgtttc tccacgcctt tgccaactgg ccccaaactc ccatggatca caacccccacc 23100
atgaacctta ttaccggggt acccaactcc atgctcaaca gtccccaggt acagcccacc 23160
ctgcgtcgca accaggaaca gctctacagc ttcctggagc gccactcgcc ctacttccgc 23220
agccacagtg cgcagattag gagcgccact tctttttgtc acttgaaaaa catgtaaaaa 23280
taatgtacta gagacacttt caataaaggc aaatgctttt atttgtacac tctcgggtga 23340
ttatttaccc ccacccttgc cgtctgcgcc gtttaaaaat caaaggggtt ctgccgcgca 23400
tcgctatgcg ccactggcag ggacacgttg cgatactggt gtttagtgct ccacttaaac 23460
tcaggcacaa ccatccgcgg cagctcggtg aagttttcac tccacaggct gcgcaccatc 23520
accaacgcgt ttagcaggtc gggcgccgat atcttgaagt cgcagttggg gcctccgccc 23580
tgcgcgcgcg agttgcgata cacagggttg cagcactgga acactatcag cgccgggtgg 23640
tgcacgctgg ccagcacgct cttgtcggag atcagatccg cgtccaggtc ctccgcgttg 23700
ctcagggcga acggagtcaa ctttggtagc tgccttccca aaaagggcgc gtgcccaggc 23760
tttgagttgc actcgcaccg tagtggcatc aaaaggtgac cgtgcccggt ctgggcgtta 23820
ggatacagcg cctgcataaa agccttgatc tgcttaaaag ccacctgagc ctttgcgcct 23880
tcagagaaga acatgccgca agacttgccg gaaaactgat tggccggaca ggccgcgtcg 23940
tgcacgcagc accttgcgtc ggtgttggag atctgcacca catttcggcc ccaccggttc 24000
ttcacgatct tggccttgct agactgctcc ttcagcgcgc gctgcccgtt ttcgctcgtc 24060
acatccattt caatcacgtg ctccttattt atcataatgc ttccgtgtag acacttaagc 24120
tcgccttcga tctcagcgca gcggtgcagc cacaacgcgc agcccgtggg ctcgtgatgc 24180
ttgtaggtca cctctgcaaa cgactgcagg tacgcctgca ggaatcgccc catcatcgtc 24240
acaaaggtct tgttgctggt gaaggtcagc tgcaacccgc ggtgctcctc gttcagccag 24300
gtcttgcata cggccgccag agcttccact tggtcaggca gtagtttgaa gttcgccttt 24360
agatcgttat ccacgtggta cttgtccatc agcgcgcgcg cagcctccat gcccttctcc 24420
cacgcagaca cgatcggcac actcagcggg ttcatcaccg taatttcact ttccgcttcg 24480
ctgggctctt cctcttcctc ttgcgtccgc ataccacgcg ccactgggtc gtcttcattc 24540
agccgccgca ctgtgcgctt acctcctttg ccatgcttga ttagcaccgg tgggttgctg 24600
aaacccacca tttgtagcgc cacatcttct ctttcttcct cgctgtccac gattacctct 24660
ggtgatggcg ggcgctcggg cttgggagaa gggcgcttct ttttcttctt gggcgcaatg 24720
gccaaatccg ccgccgaggt cgatggccgc gggctgggtg tgcgcggcac cagcgcgtct 24780
tgtgatgagt cttcctcgtc ctcggactcg atacgccgcc tcatccgctt ttttgggggc 24840
gcccggggag gcggcggcga cggggacggg gacgacacgt cctccatggt tgggggacgt 24900
cgcgccgcac cgcgtccgcg ctcgggggtg gtttcgcgct gctcctcttc ccgactggcc 24960
atttccttct cctataggca gaaaaagatc atggagtcag tcgagaagaa ggacagccta 25020
accgccccct ctgagttcgc caccaccgcc tccaccgatg ccgccaacgc gcctaccacc 25080
ttccccgtcg aggcaccccc gcttgaggag gaggaagtga ttatcgagca ggacccaggt 25140
tttgtaagcg aagacgacga ggaccgctca gtaccaacag aggataaaaa gcaagaccag 25200
gacaacgcag aggcaaacga ggaacaagtc gggcgggggg acgaaaggca tggcgactac 25260
ctagatgtgg gagacgacgt gctgttgaag catctgcagc gccagtgcgc cattatctgc 25320
gacgcgttgc aagagcgcag cgatgtgccc ctcgccatag cggatgtcag ccttgcctac 25380
gaacgccacc tattctcacc gcgcgtaccc cccaaacgcc aagaaaacgg cacatgcgag 25440
cccaacccgc gcctcaactt ctaccccgta tttgccgtgc cagaggtgct tgccacctat 25500
cacatctttt tccaaaactg caagataccc ctatcctgcc gtgccaaccg cagccgagcg 25560
gacaagcagc tggccttgcg gcagggcgct gtcatacctg atatcgcctc gctcaacgaa 25620
gtgccaaaaa tctttgaggg tcttggacgc gacgagaagc gcgcggcaaa cgctctgcaa 25680
caggaaaaca gcgaaaatga aagtcactct ggagtgttgg tggaactcga gggtgacaac 25740

-continued

```
gcgcgcctag ccgtactaaa acgcagcatc gaggtcaccc actttgccta cccggcactt  25800
aacctacccc ccaaggtcat gagcacagtc atgagtgagc tgatcgtgcg ccgtgcgcag  25860
cccctggaga gggatgcaaa tttgcaagaa caaacagagg agggcctacc cgcagttggc  25920
gacgagcagc tagcgcgctg gcttcaaacg cgcgagcctg ccgacttgga ggagcgacgc  25980
aaactaatga tggccgcagt gctcgttacc gtggagcttg agtgcatgca gcggttcttt  26040
gctgacccgg agatgcagcg caagctagag gaaacattgc actacacctt tcgacagggc  26100
tacgtacgcc aggcctgcaa gatctccaac gtggagctct gcaacctggt ctcctacctt  26160
ggaattttgc acgaaaaccg ccttgggcaa aacgtgcttc attccacgct caagggcgag  26220
gcgcgccgcg actacgtccg cgactgcgtt tacttatttc tatgctacac ctggcagacg  26280
gccatgggcg tttggcagca gtgcttggag gagtgcaacc tcaaggagct gcagaaactg  26340
ctaaagcaaa acttgaagga cctatggacg gccttcaacg agcgctccgt ggccgcgcac  26400
ctggcggaca tcattttccc cgaacgcctg cttaaaaccc tgcaacaggg tctgccagac  26460
ttcaccagtc aaagcatgtt gcagaacttt aggaacttta tcctagagcg ctcaggaatc  26520
ttgcccgcca cctgctgtgc acttcctagc gactttgtgc ccattaagta ccgcgaatgc  26580
cctccgccgc tttggggcca ctgctacctt ctgcagctag ccaactacct tgcctaccac  26640
tctgacataa tggaagacgt gagcggtgac ggtctactgg agtgtcactg tcgctgcaac  26700
ctatgcaccc cgcaccgctc cctggtttgc aattcgcagc tgcttaacga aagtcaaatt  26760
atcggtacct ttgagctgca gggtccctcg cctgacgaaa agtccgcggc tccggggttg  26820
aaactcactc cggggctgtg gacgtcggct taccttcgca aatttgtacc tgaggactac  26880
cacgcccacg agattaggtt ctacgaagac caatcccgcc cgccaaatgc ggagcttacc  26940
gcctgcgtca ttacccaggg ccacattctt ggccaattgc aagccatcaa caaagcccgc  27000
caagagtttc tgctacgaaa gggacggggg gtttacttgg acccccagtc cggcgaggag  27060
ctcaacccaa tcccccgcc gccgcagccc tatcagcagc agccgcgggc ccttgcttcc  27120
caggatggca cccaaaaaga agctgcagct gccgccgcca cccacggacg aggaggaata  27180
ctgggacagt caggcagagg aggttttgga cgaggaggag gaggacatga tggaagactg  27240
ggagagccta gacgaggaag cttccgaggt cgaagaggtg tcagacgaaa caccgtcacc  27300
ctcggtcgca ttcccctcgc cggcgcccca gaaatcggca accggttcca gcatggctac  27360
aacctccgct cctcaggcgc cgccggcact gcccgttcgc cgacccaacc gtagatggga  27420
caccactgga accagggccg gtaagtccaa gcagccgccg ccgttagccc aagagcaaca  27480
acagcgccaa ggctaccgct catggcgcgg gcacaagaac gccatagttg cttgcttgca  27540
agactgtggg ggcaacatct ccttcgcccg ccgctttctt ctctaccatc acggcgtggc  27600
cttcccccgt aacatcctgc attactaccg tcatctctac agcccatact gcaccggcgg  27660
cagcggcagc ggcagcaaca gcagcggcca cacagaagca aaggcgaccg gatagcaaga  27720
ctctgacaaa gcccaagaaa tccacagcgg cggcagcagc aggaggagga gcgctgcgtc  27780
tggcgcccaa cgaacccgta tcgacccgcg agcttagaaa caggattttt cccactctgt  27840
atgctatatt tcaacagagc aggggccaag aacaagagct gaaaataaaa aacaggtctc  27900
tgcgatccct cacccgcagc tgcctgtatc acaaaagcga agatcagctt cggcgcacgc  27960
tggaagacgc ggaggctctc ttcagtaaat actgcgcgct gactcttaag gactagtttc  28020
gcgccctttc tcaaatttaa gcgcgaaaac tacgtcatct ccagcggcca cacccggcgc  28080
```

-continued

```
cagcacctgt cgtcagcgcc atttcaactt tgtatacaaa agttgtgatg agcaaggaaa  28140
ttcccacgcc ctacatgtgg agttaccagc cacaaatggg acttgcggct ggagctgccc  28200
aagactactc aacccgaata aactacatga gcgcgggacc ccacatgata tcccgggtca  28260
acggaatacg cgcccaccga aaccgaattc tcctggaaca ggcggctatt accaccacac  28320
ctcgtaataa ccttaatccc cgtagttggc ccgctgccct ggtgtaccag gaaagtcccg  28380
ctcccaccac tgtggtactt cccagagacg cccaggccga agttcagatg actaactcag  28440
gggcgcagct tgcgggcggc tttcgtcaca gggtgcggtc gcccgggcag ggtataactc  28500
acctgacaat cagagggcga ggtattcagc tcaacgacga gtcggtgagc tcctcgcttg  28560
gtctccgtcc ggacgggaca tttcagatcg gcggcgccgg ccgctcttca ttcacgcctc  28620
gtcaggcaat cctaactctg cagacctcgt cctctgagcc gcgctctgga ggcattggaa  28680
ctctgcaatt tattgaggag tttgtgccat cggtctactt taaccccttc tcgggacctc  28740
ccggccacta tccggatcaa tttattccta actttgacgc ggtaaaggac tcggcggacg  28800
gctacgactg aatgttaagt ggagaggcag agcaactgcg cctgaaacac ctggtccact  28860
gtcgccgcca caagtgcttt gcccgcgact ccggtgagtt ttgctacttt gaattgcccg  28920
aggatcatat cgagggcccg gcgcacggcg tccggcttac cgcccaggga gagcttgccc  28980
gtagcctgat tcgggagttt acccagcgcc ccctgctagt tgagcgggac aggggaccct  29040
gtgttctcac tgtgatttgc aactgtccta accctggatt acatcaagat ctttgttgcc  29100
atctctgtgc tgagtataat aaatacagaa attaaaatat actggggctc ctatcgccat  29160
cctgtaaacg ccaccgtctt cacccgccca agcaaaccaa ggcgaacctt acctggtact  29220
tttaacatct ctccctctgt gatttacaac agtttcaacc cagacggagt gagtctacga  29280
gagaacctct ccgagctcag ctactccatc agaaaaaaca ccaccctcct tacctgccgg  29340
gaacgtacga gtgcgtcacc ggccgctgca ccacacctac cgcctgaccg taaaccagac  29400
tttttccgga cagacctcaa taactctgtt taccagaaca ggaggtgagc ttagaaaacc  29460
cttagggtat taggccaaag gcgcagctac tgtggggttt atgaacaatt caagcaactc  29520
tacgggctat tctaattcag gtttctctag aatcggggtt ggggttattc tctgtcttgt  29580
gattctcttt attcttatac taacgcttct ctgcctaagg ctcgccgcct gctgtgtgca  29640
catttgcatt tattgtcagc tttttaaacg ctggggtcgc cacccaagat gattaggtac  29700
ataatcctag gtttactcac ccttgcgtca gcccacggta ccacccaaaa ggtggatttt  29760
aaggagccag cctgtaatgt tacattcgca gctgaagcta atgagtgcac cactcttata  29820
aaatgcacca cagaacatga aaagctgctt attcgccaca aaaacaaaat tggcaagtat  29880
gctgtttatg ctatttggca gccaggtgac actacagagt ataatgttac agttttccag  29940
ggtaaaagtc ataaaacttt tatgtatact tttccatttt atgaaatgtg cgacattacc  30000
atgtacatga gcaaacagta taagttgtgg cccccacaaa attgtgtgga aaacactggc  30060
actttctgct gcactgctat gctaattaca gtgctcgctt tggtctgtac cctactctat  30120
attaaataca aaagcagacg cagctttatt gaggaaaaga aaatgcctta atttactaag  30180
ttacaaagct aatgtcacca ctaactgctt tactcgctgc ttgcaaaaca aattcaaaaa  30240
gttagcatta taattagaat aggatttaaa ccccccggtc atttcctgct caataccatt  30300
cccctgaaca attgactcta tgtgggatat gctccagcgc tacaaccttg aagtcaggct  30360
tcctggatgt cagcatctga ctttggccag cacctgtccc gcggatttgt tccagtccaa  30420
ctacagcgac ccaccctaac agagatgacc aacacaacca acgcggccgc cgctaccgga  30480
```

cttacatcta ccacaaatac accccaagtt tctgcctttg tcaataactg ggataacttg 30540
ggcatgtggt ggttctccat agcgcttatg tttgtatgcc ttattattat gtggctcatc 30600
tgctgcctaa agcgcaaacg cgcccgacca cccatctata gtcccatcat tgtgctacac 30660
ccaaacaatg atggaatcca tagattggac ggactgaaac acatgttctt ttctcttaca 30720
gtatgattaa atgagacatg attcctcgag tttttatatt actgaccctt gttgcgcttt 30780
tttgtgcgtg ctccacattg gctgcggttt ctcacatcga agtagactgc attccagcct 30840
tcacagtcta tttgctttac ggatttgtca ccctcacgct catctgcagc ctcatcactg 30900
tggtcatcgc ctttatccag tgcattgact gggtctgtgt gcgctttgca tatctcagac 30960
accatcccca gtacagggac aggactatag ctgagcttct tagaattctt taattatgaa 31020
atttactgtg acttttctgc tgattatttg caccctatct gcgttttgtt ccccgacctc 31080
caagcctcaa agacatatat catgcagatt cactcgtata tggaatattc caagttgcta 31140
caatgaaaaa agcgatcttt ccgaagcctg gttatatgca atcatctctg ttatggtgtt 31200
ctgcagtacc atcttagccc tagctatata tccctacctt gacattggct ggaacgcaat 31260
agatgccatg aaccacccaa ctttccccgc gcccgctatg cttccactgc aacaagttgt 31320
tgccggcggc tttgtcccag ccaatcagcc tcgcccacct tctcccaccc ccactgaaat 31380
cagctacttt aatctaacag gaggagatga ctgacaccct agatctagaa atggacggaa 31440
ttattacaga gcagcgcctg ctagaaagac gcagggcagc ggccgagcaa cagcgcatga 31500
atcaagagct ccaagacatg gttaacttgc accagtgcaa aaggggtatc ttttgtctgg 31560
taaagcaggc caaagtcacc tacgacagta ataccaccgg acaccgcctt agctacaagt 31620
tgccaaccaa gcgtcagaaa ttggtggtca tggtgggaga aaagcccatt accataactc 31680
agcactcggt agaaaccgaa ggctgcattc actcaccttg tcaaggacct gaggatctct 31740
gcacccttat taagaccctg tgcggtctca aagatcttat tccctttaac taataaaaaa 31800
aaataataaa gcatcactta cttaaaatca gttagcaaat ttctgtccag tttattcagc 31860
agcacctcct tgccctcctc ccagctctgg tattgcagct tcctcctggc tgcaaacttt 31920
ctccacaatc taaatggaat gtcagtttcc tcctgttcct gtccatccgc acccactatc 31980
ttcatgttgt tgcagatgaa gcgcgcaaga ccgtctgaag ataccttcaa ccccgtgtat 32040
ccatatgaca cggaaaccgg tcctccaact gtgccttttc ttactcctcc ctttgtatcc 32100
cccaatgggt ttcaagagag tccccctggg gtactctctt tgcgcctatc cgaacctcta 32160
gttacctcca atggcatgct tgcgctcaaa atgggcaacg gcctctctct ggacgaggcc 32220
ggcaacctta cctcccaaaa tgtaaccact gtgagcccac ctctcaaaaa aaccaagtca 32280
aacataaacc tggaaatatc tgcacccctc acagttacct cagaagccct aactgtggct 32340
gccgccgcac ctctaatggt cgcgggcaac acactcacca tgcaatcaca ggccccgcta 32400
accgtgcacg actccaaact tagcattgcc acccaaggac ccctcacagt gtcagaagga 32460
aagctagccc tgcaaacatc aggcccccctc accaccaccg atagcagtac ccttactatc 32520
actgcctcac cccctctaac tactgccact ggtagcttgg gcattgactt gaaagagccc 32580
atttatacac aaaatggaaa actaggacta aagtacgggg ctcctttgca tgtaacagac 32640
gacctaaaca ctttgaccgt agcaactggt ccaggtgtga ctattaataa tacttccttg 32700
caaactaaag ttactggagc cttgggtttt gattcacaag gcaatatgca acttaatgta 32760
gcaggaggac taaggattga ttctcaaaac agacgcctta tacttgatgt tagttatccg 32820

-continued

```
tttgatgctc aaaaccaact aaatctaaga ctaggacagg gccctctttt tataaactca  32880
gcccacaact tggatattaa ctacaacaaa ggcctttact tgtttacagc ttcaaacaat  32940
tccaaaaagc ttgaggttaa cctaagcact gccaaggggt tgatgtttga cgctacagcc  33000
atagccatta atgcaggaga tgggcttgaa tttggttcac ctaatgcacc aaacacaaat  33060
cccctcaaaa caaaaattgg ccatggccta gaatttgatt caaacaaggc tatggttcct  33120
aaactaggaa ctggccttag ttttgacagc acaggtgcca ttacagtagg aaacaaaaat  33180
aatgataagc taactttgtg gaccacacca gctccatctc ctaactgtag actaaatgca  33240
gagaaagatg ctaaactcac tttggtctta acaaaatgtg gcagtcaaat acttgctaca  33300
gtttcagttt tggctgttaa aggcagtttg gctccaatat ctggaacagt tcaaagtgct  33360
catcttatta taagatttga cgaaaatgga gtgctactaa acaattcctt cctggaccca  33420
gaatattgga actttagaaa tggagatctt actgaaggca cagcctatac aaacgctgtt  33480
ggatttatgc ctaacctatc agcttatcca aaatctcacg gtaaaactgc caaaagtaac  33540
attgtcagtc aagtttactt aaacggagac aaaactaaac ctgtaacact aaccattaca  33600
ctaaacggta cacaggaaac aggagacaca actccaagtg catactctat gtcattttca  33660
tgggactggt ctggccacaa ctacattaat gaaatatttg ccacatcctc ttacactttt  33720
tcatacattg cccaagaata aagaatcgtt tgtgttatgt ttcaacgtgt ttatttttca  33780
attgcagaaa atttcaagtc atttttcatt cagtagtata gccccaccac cacatagctt  33840
atacagatca ccgtacctca actttgtata ataaagttgt aatcaaactc acagaaccct  33900
agtattcaac ctgccacctc cctcccaaca cacagagtac acagtccttt ctccccggct  33960
ggccttaaaa agcatcatat catgggtaac agacatattc ttaggtgtta tattccacac  34020
ggtttcctgt cgagccaaac gctcatcagt gatattaata aactccccgg gcagctcact  34080
taagttcatg tcgctgtcca gctgctgagc cacaggctgc tgtccaactt gcggttgctt  34140
aacgggcggc gaaggagaag tccacgccta catgggggta gagtcataat cgtgcatcag  34200
gatagggcgg tggtgctgca gcagcgcgcg aataaactgc tgccgccgcc gctccgtcct  34260
gcaggaatac aacatggcag tggtctcctc agcgatgatt cgcaccgccc gcagcataag  34320
gcgccttgtc ctccgggcac agcagcgcac cctgatctca cttaaatcag cacagtaact  34380
gcagcacagc accacaatat tgttcaaaat cccacagtgc aaggcgctgt atccaaagct  34440
catggcgggg accacagaac ccacgtggcc atcataccac aagcgcaggt agattaagtg  34500
gcgacccctc ataaacacgc tggacataaa cattacctct tttggcatgt tgtaattcac  34560
cacctcccgg taccatataa acctctgatt aaacatggcg ccatccacca ccatcctaaa  34620
ccagctggcc aaaacctgcc cgccggctat acactgcagg gaaccgggac tggaacaatg  34680
acagtggaga gcccaggact cgtaaccatg gatcatcatg ctcgtcatga tatcaatgtt  34740
ggcacaacac aggcacacgt gcatacactt cctcaggatt acaagctcct cccgcgttag  34800
aaccatatcc cagggaacaa cccattcctg aatcagcgta aatcccacac tgcagggaag  34860
acctcgcacg taactcacgt tgtgcattgt caaagtgtta cattcgggca gcagcggatg  34920
atcctccagt atggtagcgc gggtttctgt ctcaaaagga ggtagacgat ccctactgta  34980
cggagtgcgc cgagacaacc gagatcgtgt tggtcgtagt gtcatgccaa atggaacgcc  35040
ggacgtagtc atatttcctg aagcaaaacc aggtgcgggc gtgacaaaca gatctgcgtc  35100
tccggtctcg ccgcttagat cgctctgtgt agtagttgta gtatatccac tctctcaaag  35160
catccaggcg ccccctggct tcgggttcta tgtaaactcc ttcatgcgcc gctgccctga  35220
```

```
taacatccac caccgcagaa taagccacac ccagccaacc tacacattcg ttctgcgagt  35280

cacacacggg aggagcggga agagctggaa gaaccatgtt ttttttttta ttccaaaaga  35340

ttatccaaaa cctcaaaatg aagatctatt aagtgaacgc gctcccctcc ggtggcgtgg  35400

tcaaactcta cagccaaaga acagataatg gcatttgtaa gatgttgcac aatggcttcc  35460

aaaaggcaaa cggccctcac gtccaagtgg acgtaaaggc taaacccttc agggtgaatc  35520

tcctctataa acattccagc accttcaacc atgcccaaat aattctcatc tcgccacctt  35580

ctcaatatat ctctaagcaa atcccgaata ttaagtccgg ccattgtaaa aatctgctcc  35640

agagcgccct ccaccttcag cctcaagcag cgaatcatga ttgcaaaaat tcaggttcct  35700

cacagacctg tataagattc aaaagcggaa cattaacaaa aataccgcga tcccgtaggt  35760

cccttcgcag ggccagctga acataatcgt gcaggtctgc acggaccagc gcggccactt  35820

ccccgccagg aaccatgaca aaagaaccca cactgattat gacacgcata ctcggagcta  35880

tgctaaccag cgtagccccg atgtaagctt gttgcatggg cggcgatata aaatgcaagg  35940

tgctgctcaa aaaatcaggc aaagcctcgc gcaaaaaaga aagcacatcg tagtcatgct  36000

catgcagata aaggcaggta agctccggaa ccaccacaga aaaagacacc atttttctct  36060

caaacatgtc tgcgggtttc tgcataaaca caaaataaaa taacaaaaaa acatttaaac  36120

attagaagcc tgtcttacaa caggaaaaac aacccttata agcataagac ggactacggc  36180

catgccggcg tgaccgtaaa aaaactggtc accgtgatta aaaagcacca ccgacagctc  36240

ctcggtcatg tccggagtca taatgtaaga ctcggtaaac acatcaggtt gattcacatc  36300

ggtcagtgct aaaaagcgac cgaaatagcc cgggggaata catacccgca ggcgtagaga  36360

caacattaca gcccccatag gaggtataac aaaattaata ggagagaaaa acacataaac  36420

acctgaaaaa ccctcctgcc taggcaaaat agcaccctcc cgctccagaa caacatacag  36480

cgcttccaca gcggcagcca taacagtcag ccttaccagt aaaaaagaaa acctattaaa  36540

aaaacaccac tcgacacggc accagctcaa tcagtcacag tgtaaaaaag ggccaagtgc  36600

agagcgagta tatataggac taaaaaatga cgtaacggtt aaagtccaca aaaaacaccc  36660

agaaaaccgc acgcgaacct acgcccagaa acgaaagcca aaaaacccac aacttcctca  36720

aatcgtcact tccgttttcc cacgttacgt cacttcccat tttaagaaaa ctacaattcc  36780

caacacatac aagttactcc gccctaaaac ctacgtcacc cgccccgttc ccacgccccg  36840

cgccacgtca caaactccac cccctcatta tcatattggc ttcaatccaa aataaggtat  36900

attattgatg atg                                                     36913
```

<210> SEQ ID NO 2
<211> LENGTH: 36943
<212> TYPE: DNA
<213> ORGANISM: Artificial Sequence
<220> FEATURE:
<223> OTHER INFORMATION: Synthetic adenovirus genome (AdSyn-CO176)

<400> SEQUENCE: 2

```
catcatcaat aatatacctt attttggatt gaagccaata tgataatgag gggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300
```

-continued

```
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattaaac cgtattaccg ccatgcattt aatggagtgc    480
ctcgtgaggc tccggtgccc gtcagtgggc agagcgcaca tcgcccacag tccccgagaa    540
gttgggggga ggggtcggca attgaaccgg tgcctagaga aggtggcgcg gggtaaactg    600
ggaaagtgat gtcgtgtact ggctccgcct ttttcccgag ggtgggggag aaccgtatat    660
aagtgcagta gtcgccgtga acgttctttt tcgcaacggg tttgccgcca gaacacaggt    720
aagtgccgtg tgtggttccc gcgggcctgg cctctttacg ggttatggcc cttgcgtgcc    780
ttgaattact tccacctggc tgcagtacgt gattcttgat cccgagcttc gggttggaag    840
tgggtgggag agttcgaggc cttgcgctta aggagcccct tcgcctcgtg cttgagttga    900
ggcctggcct gggcgctggg gccgccgcgt gcgaatctgg tggcaccttc gcgcctgtct    960
cgctgctttc gataagtctc tagccattta aaatttttga tgacctgctg cgacgctttt   1020
tttctggcaa gatagtcttg taaatgcggg ccaagatctg cacactggta tttcggtttt   1080
tggggccgcg ggcggcgacg gggcccgtgc gtcccagcgc acatgttcgg cgaggcgggg   1140
cctgcgagcg cggccaccga gaatcggacg ggggtagtct caagctggcc ggcctgctct   1200
ggtgcctggc ctcgcgccgc cgtgtatcgc cccgccctgg gcggcaaggc tggcccggtc   1260
ggcaccagtt gcgtgagcgg aaagatggcc gcttcccggc cctgctgcag ggagctcaaa   1320
atggaggacg cggcgctcgg gagagcgggc gggtgagtca cccacacaaa ggaaaagggc   1380
ctttccgtcc tcagccgtcg cttcatgtga ctccacggag taccgggcgc cgtccaggca   1440
cctcgattag ttctcgagct tttggagtac gtcgtcttta ggttgggggg aggggtttta   1500
tgcgatggag tttccccaca ctgagtgggt ggagactgaa gttaggccag cttggcactt   1560
gatgtaattc tccttggaat ttgccctttt tgagtttgga tcttggttca ttctcaagcc   1620
tcagacagtg gttcaaagtt tttttcttcc atttcaggtg tcgtgacgct agcgctaccg   1680
gactcagatc tcgagctcaa gcttcgaatt ctgcagtcga cggtaccgga tccatggaag   1740
acgccaaaaa cataaagaaa ggcccggcgc cattctatcc gctggaagat ggaaccgctg   1800
gagagcaact gcataaggct atgaagagat acgccctggt tcctggaaca attgctttta   1860
cagatgcaca tatcgaggtg gacatcactt acgctgagta cttcgaaatg tccgttcggt   1920
tggcagaagc tatgaaacga tatgggctga atacaaatca cagaatcgtc gtatgcagtg   1980
aaaactctct tcaattcttt atgccggtgt tgggcgcgtt atttatcgga gttgcagttg   2040
cgcccgcgaa cgacatttat aatgaacgtg aattgctcaa cagtatgggc atttcgcagc   2100
ctaccgtggt gttcgtttcc aaaaaggggt tgcaaaaaat tttgaacgtg caaaaaaagc   2160
tcccaatcat ccaaaaaatt attatcatgg attctaaaac ggattaccag ggatttcagt   2220
cgatgtacac gttcgtcaca tctcatctac ctcccggttt taatgaatac gattttgtgc   2280
cagagtcctt cgatagggac aagacaattg cactgatcat gaactcctct ggatctactg   2340
gtctgcctaa aggtgtcgct ctgcctcata gaactgcctg cgtgagattc tcgcatgcca   2400
gagatcctat ttttggcaat caaatcattc cggatactgc gattttaagt gttgttccat   2460
tccatcacgg ttttggaatg tttactacac tcggatattt gatatgtgga tttcgagtcg   2520
tcttaatgta tagatttgaa gaagagctgt ttctgaggag ccttcaggat tacaagattc   2580
aaagtgcgct gctggtgcca accctattct ccttcttcgc caaaagcact ctgattgaca   2640
aatacgattt atctaattta cacgaaattg cttctggtgg cgctcccctc tctaaggaag   2700
```

-continued

```
tcggggaagc ggttgccaag aggttccatc tgccaggtat caggcaagga tatgggctca   2760
ctgagactac atcagctatt ctgattacac ccgaggggga tgataaaccg ggcgcggtcg   2820
gtaaagttgt tccatttttt gaagcgaagg ttgtggatct ggataccggg aaaacgctgg   2880
gcgttaatca aagaggcgaa ctgtgtgtga gaggtcctat gattatgtcc ggttatgtaa   2940
acaatccgga agcgaccaac gccttgattg acaaggatgg atggctacat tctggagaca   3000
tagcttactg ggacgaagac gaacacttct tcatcgttga ccgcctgaag tctctgatta   3060
agtacaaagg ctatcaggtg gctcccgctg aattggaatc catcttgctc caacacccca   3120
acatcttcga cgcaggtgtc gcaggtcttc ccgacgatga cgccggtgaa cttcccgccg   3180
ccgttgttgt tttggagcac ggaaagacga tgacggaaaa agagatcgtg gattacgtcg   3240
ccagtcaagt aacaaccgcg aaaaagttgc gcggaggagt tgtgtttgtg gacgaagtac   3300
cgaaaggtct taccggaaaa ctcgacgcaa gaaaaatcag agagatcctc ataaaggcca   3360
agaagggcgg aaagatcgcc gtggcagccg cagccaccat ggtgagcaag ggcgaggagc   3420
tgttcaccgg ggtggtgccc atcctggtcg agctggacgg cgacgtaaac ggccacaagt   3480
tcagcgtgtc cggcgagggc gagggcgatg ccacctacgg caagctgacc ctgaagttca   3540
tctgcaccac cggcaagctg cccgtgccct ggcccaccct cgtgaccacc ctgacctacg   3600
gcgtgcagtg cttcagccgc taccccgacc acatgaagca gcacgacttc ttcaagtccg   3660
ccatgcccga aggctacgtc caggagcgca ccatcttctt caaggacgac ggcaactaca   3720
agacccgcgc cgaggtgaag ttcgagggcg acaccctggt gaaccgcatc gagctgaagg   3780
gcatcgactt caaggaggac ggcaacatcc tggggcacaa gctggagtac aactacaaca   3840
gccacaacgt ctatatcatg gccgacaagc agaagaacgg catcaaggtg aacttcaaga   3900
tccgccacaa catcgaggac ggcagcgtgc agctcgccga ccactaccag cagaacaccc   3960
ccatcggcga cggccccgtg ctgctgcccg acaaccacta cctgagcacc cagtccgccc   4020
tgagcaaaga ccccaacgag aagcgcgatc acatggtcct gctggagttc gtgaccgccg   4080
ccgggatcac tctcggcatg gacgagctgt acaagtaaag cgactctaga tcataatcag   4140
ccatacccaa acaccattgt cacactccaa tcgattcaaa caccattgtc acactccaac   4200
atttgtagag gttttacttg ctttaaaaaa cctcccacac ctccccctga acctgaaaca   4260
taaaatgaat gcaattgttg ttgttaactt gtttattgca gcttataatg gttacaaata   4320
aagcaatagc atcacaaatt tcacaaataa agcatttttt tcactgcatt ctagttgtgg   4380
tttgtccaaa ctcatcaatg taagtttaaa cggcgcgcct gaaatgtgtg ggcgtggctt   4440
aagggtggga aagaatatat aaggtggggg tcttatgtag ttttgtatct gttttgcagc   4500
agccgccgcc gccatgagca ccaactcgtt tgatggaagc attgtgagct catatttgac   4560
aacgcgcatg cccccatggg ccggggtgcg tcagaatgtg atgggctcca gcattgatgg   4620
tcgccccgtc ctgcccgcaa actctactac cttgacctac gagaccgtgt ctggaacgcc   4680
gttggagact gcagcctccg ccgccgcttc agccgctgca gccaccgccc gcgggattgt   4740
gactgacttt gctttcctga gcccgcttgc aagcagtgca gcttcccgtt catccgcccg   4800
cgatgacaag ttgacggctc ttttggcaca attggattct ttgacccggg aacttaatgt   4860
cgtttctcag cagctgttgg atctgcgcca gcaggtttct gccctgaagg cttcctcccc   4920
tcccaatgcg gtttaaaaca caacttttct atacaaagtt gtaaataaaa aaccagactc   4980
tgtttggatt tggatcaagc taagtgtctt gctgtcttta tttaggggtt ttgcgcgcgc   5040
```

-continued

```
ggtaggcccg ggaccagcgg tctcggtcgt tgagggtcct gtgtattttt tccaggacgt   5100
ggtaaaggtg actctggatg ttcagataca tgggcataag cccgtctctg ggtggaggt    5160
agcaccactg cagagcttca tgctgcgggg tggtgttgta gatgatccag tcgtagcagg   5220
agcgctgggc gtggtgccta aaaatgtctt tcagtagcaa gctgattgcc aggggcaggc   5280
ccttggtgta agtgtttaca aagcggttaa gctgggatgg gtgcatacgt ggggatatga   5340
gatgcatctt ggactgtatt tttaggttgg ctatgttccc agccatatcc ctccggggat   5400
tcatgttgtg cagaaccacc agcacagtgt atccggtgca cttgggaaat ttgtcatgta   5460
gcttagaagg aaatgcgtgg aagaacttgg agacgccctt gtgacctcca agattttcca   5520
tgcattcgtc cataatgatg gcaatgggcc cacgggcggc ggcctgggcg aagatatttc   5580
tgggatcact aacgtcatag ttgtgttcca ggatgagatc gtcataggcc atttttacaa   5640
agcgcgggcg gagggtgcca gactgcggta taatggttcc atccggccca ggggcgtagt   5700
taccctcaca gatttgcatt tcccacgctt tgagttcaga tgggggggatc atgtctacct   5760
gcggggcgat gaagaaaacg gtttccgggg taggggagat cagctgggaa gaaagcaggt   5820
tcctgagcag ctgcgactta ccgcagccgg tgggcccgta aatcacacct attaccggct   5880
gcaactggta gttaagagag ctgcagctgc cgtcatccct gagcaggggg gccacttcgt   5940
taagcatgtc cctgactcgc atgttttccc tgaccaaatc cgccagaagg cgctcgccgc   6000
ccagcgatag cagttcttgc aaggaagcaa agtttttcaa cggtttgaga ccgtccgccg   6060
taggcatgct tttgagcgtt tgaccaagca gttccaggcg gtcccacagc tcggtcacct   6120
gctctacggc atctcgatcc agcatatctc ctcgtttcgc gggttggggc ggctttcgct   6180
gtacggcagt agtcggtgct cgtccagacg ggccagggtc atgtctttcc acgggcgcag   6240
ggtcctcgtc agcgtagtct gggtcacggt gaaggggtgc gctccgggct gcgcgctggc   6300
cagggtgcgc ttgaggctgg tcctgctggt gctgaagcgc tgccggtctt cgccctgcgc   6360
gtcggccagg tagcatttga ccatggtgtc atagtccagc ccctccgcgg cgtggccctt   6420
ggcgcgcagc ttgcccttgg aggaggcgcc gcacgagggg cagtgcagac ttttgagggc   6480
gtagagcttg ggcgcgagaa ataccgattc cggggagtag gcatccgcgc cgcaggcccc   6540
gcagacggtc tcgcattcca cgagccaggt gagctctggc cgttcggggt caaaaaccag   6600
gtttccccca tgctttttga tgcgtttctt acctctggtt tccatgagcc ggtgtccacg   6660
ctcggtgacg aaaaggctgt ccgtgtcccc gtatacagac ttgagaggcc tgtcctcgag   6720
cggtgttccg cggtcctcct cgtatagaaa ctcggaccac tctgagacaa aggctcgcgt   6780
ccaggccagc acgaaggagg ctaagtggga ggggtagcgg tcgttgtcca ctagggggtc   6840
cactcgctcc agggtgtgaa gacacatgtc gccctcttcg gcatcaagga aggtgattgg   6900
tttgtaggtg taggccacgt gaccgggtgt tcctgaaggg gggctataaa agggggtggg   6960
ggcgcgttcg tcctcactct cttccgcatc gctgtctgcg agggccagct gttggggtga   7020
gtactccctc tgaaaagcgg gcatgacttc tgcgctaaga ttgtcagttt ccaaaaacga   7080
ggaggatttg atattcacct ggcccgcggt gatgcctttg agggtggccg catccatctg   7140
gtcagaaaag acaatctttt tgttgtcaag cttggtggca aacgacccgt agagggcgtt   7200
ggacagcaac ttggcgatgg agcgcagggt ttggtttttg tcgcgatcgg cgcgctcctt   7260
ggccgcgatg tttagctgca cgtattcgcg cgcaacgcac cgccattcgg gaaagacggt   7320
ggtgcgctcg tcgggcacca ggtgcacgcg ccaaccgcgg ttgtgcaggg tgacaaggtc   7380
aacgctggtg gctacctctc cgcgtaggcg ctcgttggtc cagcagaggc ggccgccctt   7440
```

-continued

```
gcgcgagcag aatggcggta gggggtctag ctgcgtctcg tccggggggt ctgcgtccac   7500
ggtaaagacc ccgggcagca ggcgcgcgtc gaagtagtct atcttgcatc cttgcaagtc   7560
tagcgcctgc tgccatgcgc gggcggcaag cgcgcgctcg tatgggttga gtgggggacc   7620
ccatggcatg gggtgggtga gcgcggaggc gtacatgccg caaatgtcgt aaacgtagag   7680
gggctctctg agtattccaa gatatgtagg gtagcatctt ccaccgcgga tgctggcgcg   7740
cacgtaatcg tatagttcgt gcgagggagc gaggaggtcg ggaccgaggt tgctacgggc   7800
gggctgctct gctcggaaga ctatctgcct gaagatggca tgtgagttgg atgatatggt   7860
tggacgctgg aagacgttga agctggcgtc tgtgagacct accgcgtcac gcacgaagga   7920
ggcgtaggag tcgcgcagct tgttgaccag ctcggcggtg acctgcacgt ctagggcgca   7980
gtagtccagg gtttccttga tgatgtcata cttatcctgt cccttttttt tccacagctc   8040
gcggttgagg acaaactctt cgcggtcttt ccagtactct tggatcggaa acccgtcggc   8100
ctccgaacgg taagagccta gcatgtagaa ctggttgacg gcctggtagg cgcagcatcc   8160
cttttctacg ggtagcgcgt atgcctgcgc ggccttccgg agcgaggtgt gggtgagcgc   8220
aaaggtgtcc ctgaccatga ctttgaggta ctggtatttg aagtcagtgt cgtcgcatcc   8280
gccctgctcc cagagcaaaa agtccgtgcg ctttttggaa cgcggatttg gcagggcgaa   8340
ggtgacatcg ttgaagagta tctttcccgc gcgaggcata aagttgcgtg tgatgcggaa   8400
gggtcccggc acctcggaac ggttgttaat tacctgggcg gcgagcacga tctcgtcaaa   8460
gccgttgatg ttgtggccca caatgtaaag ttccaagaag cgcgggatgc ccttgatgga   8520
aggcaatttt ttaagttcct cgtaggtgag ctcttcaggg gagctgagcc cgtgctctga   8580
aagggcccag tctgcaagat gagggttgga agcgacgaat gagctccaca ggtcacgggc   8640
cattagcatt tgcaggtggt cgcgaaaggt cctaaactgg cgacctatgg ccattttttc   8700
tggggtgatg cagtagaagg taagcgggtc ttgttcccag cggtcccatc caaggttcgc   8760
ggctaggtct cgcgcggcag tcactagagg ctcatctccg ccgaacttca tgaccagcat   8820
gaagggcacg agctgcttcc caaaggcccc catccaagta taggtctcta catcgtaggt   8880
gacaaagaga cgctcggtgc gaggatgcga gccgatcggg aagaactgga tctcccgcca   8940
ccaattggag gagtggctat tgatgtggtg aaagtagaag tccctgcgac gggccgaaca   9000
ctcgtgctgg cttttgtaaa aacgtgcgca gtactggcag cggtgcacgg gctgtacatc   9060
ctgcacgagg ttgacctgac gaccgcgcac aaggaagcag agtgggaatt tgagcccctc   9120
gcctggcggg tttggctggt ggtcttctac ttcggctgct tgtccttgac cgtctggctg   9180
ctcgagggga gttacggtgg atcggaccac cacgccgcgc gagcccaaag tccagatgtc   9240
cgcgcgcggc ggtcggagct tgatgacaac atcgcgcaga tgggagctgt ccatggtctg   9300
gagctcccgc ggcgtcaggt caggcgggag ctcctgcagg tttacctcgc atagacgggt   9360
cagggcgcgg gctagatcca ggtgatacct aatttccagg ggctggttgg tggcggcgtc   9420
gatggcttgc aagaggccgc atccccgcgg cgcgactacg gtaccgcgcg gcgggcggtg   9480
ggccgcgggg gtgtccttgg atgatgcatc taaaagcggt gacgcgggcg agcccccgga   9540
ggtagggggg gctccggacc cgccgggaga gggggcaggg gcacgtcggc gccgcgcgcg   9600
ggcaggagct ggtgctgcgc gcgtaggttg ctggcgaacg cgacgacgcg gcggttgatc   9660
tcctgaatct ggcgcctctg cgtgaagacg acgggcccgg tgagcttgaa cctgaaagag   9720
agttcgacag aatcaatttc ggtgtcgttg acggcggcct ggcgcaaaat ctcctgcacg   9780
```

-continued tctcctgagt tgtcttgata ggcgatctcg gccatgaact gctcgatctc ttcctcctgg 9840
agatctccgc gtccggctcg ctccacggtg gcggcgaggt cgttggaaat gcgggccatg 9900
agctgcgaga aggcgttgag gcctccctcg ttccagacgc ggctgtagac cacgcccccct 9960 tcggcatcgc gggcgcgcat gaccacctgc gcgagattga gctccacgtg ccgggcgaag 10020
acggcgtagt ttcgcaggcg ctgaaagagg tagttgaggg tggtggcggt gtgttctgcc 10080
acgaagaagt acataaccca gcgtcgcaac gtggattcgt tgatatcccc caaggcctca 10140
aggcgctcca tggcctcgta gaagtccacg gcgaagttga aaaactggga gttgcgcgcc 10200
gacacggtta actcctcctc cagaagacgg atgagctcgg cgacagtgtc gcgcacctcg 10260
cgctcaaagg ctacaggggc ctcttcttct tcttcaatct cctcttccat aagggcctcc 10320
ccttcttctt cttctggcgg cggtggggga gggggggacac ggcggcgacg acggcgcacc 10380
gggaggcggt cgacaaagcg ctcgatcatc tccccgcggc gacggcgcat ggtctcggtg 10440
acggcgcggc cgttctcgcg gggcgcagt tggaagacgc cgcccgtcat gtcccggtta 10500
tgggttggcg gggggctgcc atgcggcagg gatacggcgc taacgatgca tctcaacaat 10560
tgttgtgtag gtactccgcc gccgagggac ctgagcgagt ccgcatcgac cggatcggaa 10620
aacctctcga gaaaggcgtc taaccagtca cagtcgcaag gtaggctgag caccgtggcg 10680
ggcggcagcg ggcggcggtc ggggttgttt ctggcggagg tgctgctgat gatgtaatta 10740
aagtaggcgg tcttgagacg gcggatggtc gacagaagca ccatgtcctt gggtccggcc 10800
tgctgaatgc gcaggcggtc ggccatgccc caggcttcgt tttgacatcg gcgcaggtct 10860
ttgtagtagt cttgcatgag cctttctacc ggcacttctt cttctccttc ctcttgtcct 10920
gcatctcttg catctatcgc tgcggcggcg gcggagtttg gccgtaggtg gcgccctctt 10980
cctcccatgc gtgtgacccc gaagcccctc atcggctgaa gcagggctag gtcggcgaca 11040
acgcgctcgg ctaatatggc ctgctgcacc tgcgtgaggg tagactggaa gtcatccatg 11100
tccacaaagc ggtggtatgc gcccgtgttg atggtgtaag tgcagttggc cataacggac 11160
cagttaacgg tctggtgacc cggctgcgag agctcggtgt acctgagacg cgagtaagcc 11220
ctcgagtcaa atacgtagtc gttgcaagtc cgcaccaggt actggtatcc caccaaaaag 11280
tgcggcggcg gctggcggta gaggggccag cgtagggtgg ccggggctcc gggggcgaga 11340
tcttccaaca taaggcgatg atatccgtag atgtacctgg acatccaggt gatgccggcg 11400
gcggtggtgg aggcgcgcgg aaagtcgcgg acgcggttcc agatgttgcg cagcggcaaa 11460
aagtgctcca tggtcgggac gctctggccg gtcaggcgcg cgcaatcgtt gacgctctag 11520
accgtgcaaa aggagagcct gtaagcgggc actcttccgt ggtctggtgg ataaattcgc 11580
aagggtatca tggcggacga ccggggttcg agccccgtat ccggccgtcc gccgtgatcc 11640
atgcggttac cgcccgcgtg tcgaacccag gtgtgcgacg tcagacaacg ggggagtgct 11700
ccttttggct tccttccagg cgcggcggct gctgcgctag ctttttggc cactggccgc 11760 gcgcagcgta agcggttagg ctggaaagcg aaagcattaa gtggctcgct ccctgtagcc 11820
ggagggttat tttccaaggg ttgagtcgcg ggaccccgg ttcgagtctc ggaccggccg 11880
gactgcggcg aacgggggtt tgcctccccg tcatgcaaga ccccgcttgc aaattcctcc 11940
ggaaacaggg acgagcccct tttttgcttt tcccagatgc atccggtgct gcggcagatg 12000
cgcccccctc ctcagcagcg gcaagagcaa gagcagcggc agacatgcag ggcaccctcc 12060
cctcctccta ccgcgtcagg aggggcgaca tccgcggttg acgcggcagc agatggtgat 12120
tacgaacccc cgcggcgccg ggcccggcac tacctggact tggaggaggg cgagggcctg 12180

```
gcgcggctag gagcgccctc tcctgagcgg cacccaaggg tgcagctgaa gcgtgatacg  12240
cgtgaggcgt acgtgccgcg gcagaacctg tttcgcgacc gcgagggaga ggagcccgag  12300
gagatgcggg atcgaaagtt ccacgcaggg cgcgagctgc ggcatggcct gaatcgcgag  12360
cggttgctgc gcgaggagga ctttgagccc gacgcgcgaa ccgggattag tcccgcgcgc  12420
gcacacgtgg cggccgccga cctggtaacc gcatacgagc agacggtgaa ccaggagatt  12480
aactttcaaa aaagctttaa caaccacgtg cgtacgcttg tggcgcgcga ggaggtggct  12540
ataggactga tgcatctgtg ggactttgta agcgcgctgg agcaaaaccc aaatagcaag  12600
ccgctcatgg cgcagctgtt ccttatagtg cagcacagca gggacaacga ggcattcagg  12660
gatgcgctgc taaacatagt agagcccgag ggccgctggc tgctcgattt gataaacatc  12720
ctgcagagca tagtggtgca ggagcgcagc ttgagcctgg ctgacaaggt ggccgccatc  12780
aactattcca tgcttagcct gggcaagttt tacgcccgca agatatacca taccccttac  12840
gttcccatag acaaggaggt aaagatcgag gggttctaca tgcgcatggc gctgaaggtg  12900
cttaccttga gcgacgacct gggcgtttat cgcaacgagc gcatccacaa ggccgtgagc  12960
gtgagccggc ggcgcgagct cagcgaccgc gagctgatgc acagcctgca aagggccctg  13020
gctggcacgg gcagcggcga tagagaggcc gagtcctact ttgacgcggg cgctgacctg  13080
cgctgggccc caagccgacg cgccctggag gcagctgggg ccggacctgg gctggcggtg  13140
gcacccgcgc gcgctggcaa cgtcggcggc gtggaggaat atgacgagga cgatgagtac  13200
gagccagagg acggcgagta ctaagcggtg atgtttctga tcagatgatg caagacgcaa  13260
cggacccggc ggtgcgggcg gcgctgcaga gccagccgtc cggccttaac tccacggacg  13320
actggcgcca ggtcatggac cgcatcatgt cgctgactgc gcgcaatcct gacgcgttcc  13380
ggcagcagcc gcaggccaac cggctctccg caattctgga agcggtggtc ccggcgcgcg  13440
caaaccccac gcacgagaag gtgctggcga tcgtaaacgc gctggccgaa aacagggcca  13500
tccggcccga cgaggccggc ctggtctacg acgcgctgct tcagcgcgtg gctcgttaca  13560
acagcggcaa cgtgcagacc aacctggacc ggctggtggg ggatgtgcgc gaggccgtgg  13620
cgcagcgtga gcgcgcgcag cagcagggca acctgggctc catggttgca ctaaacgcct  13680
tcctgagtac acagcccgcc aacgtgccgc ggggacagga ggactacacc aactttgtga  13740
gcgcactgcg gctaatggtg actgagacac cgcaaagtga ggtgtaccag tctgggccag  13800
actatttttt ccagaccagt agacaaggcc tgcagaccgt aaacctgagc caggctttca  13860
aaaacttgca ggggctgtgg ggggtgcggg ctcccacagg cgaccgcgcg accgtgtcta  13920
gcttgctgac gcccaactcg cgcctgttgc tgctgctaat agcgcccttc acggacagtg  13980
gcagcgtgtc ccgggacaca tacctaggtc acttgctgac actgtaccgc gaggccatag  14040
gtcaggcgca tgtggacgag catactttcc aggagattac aagtgtcagc cgcgcgctgg  14100
ggcaggagga cacgggcagc ctggaggcaa ccctaaacta cctgctgacc aaccggcggc  14160
agaagatccc ctcgttgcac agtttaaaca gcgaggagga gcgcattttg cgctacgtgc  14220
agcagagcgt gagccttaac ctgatgcgcg acggggtaac gcccagcgtg gcgctggaca  14280
tgaccgcgcg caacatggaa ccgggcatgt atgcctcaaa ccggccgttt atcaaccgcc  14340
taatggacta cttgcatcgc gcggccgccg tgaaccccga gtatttcacc aatgccatct  14400
tgaacccgca ctggctaccg ccccctggtt tctacaccgg gggattcgag gtgcccgagg  14460
gtaacgatgg attcctctgg gacgacatag acgacagcgt gttttccccg caaccgcaga  14520
```

-continued

```
ccctgctaga gttgcaacag cgcgagcagg cagaggcggc gctgcgaaag gaaagcttcc  14580
gcaggccaag cagcttgtcc gatctaggcg ctgcggcccc gcggtcagat gctagtagcc  14640
catttccaag cttgataggg tctcttacca gcactcgcac cacccgcccg cgcctgctgg  14700
gcgaggagga gtacctaaac aactcgctgc tgcagccgca gcgcgaaaaa aacctgcctc  14760
cggcatttcc caacaacggg atagagagcc tagtggacaa gatgagtaga tggaagacgt  14820
acgcgcagga gcacagggac gtgccaggcc cgcgcccgcc cacccgtcgt caaaggcacg  14880
accgtcagcg gggtctggtg tgggaggacg atgactcggc agacgacagc agcgtcctgg  14940
atttgggagg gagtggcaac ccgtttgcgc accttcgccc caggctgggg agaatgtttt  15000
aaaaaaaaaa aaaaagcatg atgcaaaata aaaaactcac caaggccatg gcaccgagcg  15060
ttggttttct tgtattcccc ttagtatgcg gcgcgcggcg atgtatgagg aaggtcctcc  15120
tccctcctac gagagtgtgg tgagcgcggc gccagtggcg gcggcgctgg gttctccctt  15180
cgatgctccc ctggacccgc cgtttgtgcc tccgcggtac ctgcggccta ccggggggag  15240
aaacagcatc cgttactctg agttggcacc cctattcgac accacccgtg tgtacctggt  15300
ggacaacaag tcaacggatg tggcatccct gaactaccag aacgaccaca gcaactttct  15360
gaccacggtc attcaaaaca atgactacag cccgggggag gcaagcacac agaccatcaa  15420
tcttgacgac cggtcgcact ggggcggcga cctgaaaacc atcctgcata ccaacatgcc  15480
aaatgtgaac gagttcatgt ttaccaataa gtttaaggcg cgggtgatgg tgtcgcgctt  15540
gcctactaag gacaatcagg tggagctgaa atacgagtgg gtggagttca cgctgcccga  15600
gggcaactac tccgagacca tgaccataga ccttatgaac aacgcgatcg tggagcacta  15660
cttgaaagtg ggcagacaga acggggttct ggaaagcgac atcggggtaa agtttgacac  15720
ccgcaacttc agactggggt ttgaccccgt cactggtctt gtcatgcctg ggtatatac   15780
aaacgaagcc ttccatccag acatcatttt gctgccagga tgcggggtgg acttcaccca  15840
cagccgcctg agcaacttgt tgggcatccg caagcggcaa cccttccagg agggctttag  15900
gatcacctac gatgatctgg agggtggtaa cattcccgca ctgttggatg tggacgccta  15960
ccaggcgagc ttgaaagatg acaccgaaca gggcgggggt ggcgcaggcg gcagcaacag  16020
cagtggcagc ggcgcggaag agaactccaa cgcggcagcc gcggcaatgc agccggtgga  16080
ggacatgaac gatcatgcca ttcgcggcga cacctttgcc acacgggctg aggagaagcg  16140
cgctgaggcc gaagcagcgg ccgaagctgc cgcccccgct gcgcaacccg aggtcgagaa  16200
gcctcagaag aaaccggtga tcaaacccct gacagaggac agcaagaaac gcagttacaa  16260
cctaataagc aatgacagca ccttcaccca gtaccgcagc tggtaccttg catacaacta  16320
cggcgaccct cagaccggaa tccgctcatg gaccctgctt tgcactcctg acgtaacctg  16380
cggctcggag caggtctact ggtcgttgcc agacatgatg caagaccccg tgaccttccg  16440
ctccacgcgc cagatcagca actttccggt ggtgggcgcc gagctgttgc ccgtgcactc  16500
caagagcttc tacaacgacc aggccgtcta ctcccaactc atccgccagt ttacctctct  16560
gacccacgtg ttcaatcgct ttcccgagaa ccagattttg gcgcgcccgc cagcccccac  16620
catcaccacc gtcagtgaaa acgttcctgc tctcacagat cacgggacgc taccgctgcg  16680
caacagcatc ggaggagtcc agcgagtgac cattactgac gccagacgcc gcacctgccc  16740
ctacgtttac aaggccctgg gcatagtctc gccgcgcgtc ctatcgagcc gcactttttg  16800
agcaagcatg tccatcctta tatcgcccag caataacaca ggctggggcc tgcgcttccc  16860
aagcaagatg tttggcgggg ccaagaagcg ctccgaccaa cacccagtgc gcgtgcgcgg  16920
```

-continued

```
gcactaccgc gcgccctggg gcgcgcacaa acgcggccgc actgggcgca ccaccgtcga  16980
tgacgccatc gacgcggtgg tggaggaggc gcgcaactac acgcccacgc cgccaccagt  17040
gtccacagtg gacgcggcca ttcagaccgt ggtgcgcgga gcccggcgct atgctaaaat  17100
gaagagacgg cggaggcgcg tagcacgtcg ccaccgccgc cgacccggca ctgccgccca  17160
acgcgcggcg gcggccctgc ttaaccgcgc acgtcgcacc ggccgacggg cggccatgcg  17220
ggccgctcga aggctggccg cgggtattgt cactgtgccc cccaggtcca ggcgacgagc  17280
ggccgccgca gcagccgcgg ccattagtgc tatgactcag ggtcgcaggg gcaacgtgta  17340
ttgggtgcgc gactcggtta gcggcctgcg cgtgcccgtg cgcacccgcc ccccgcgcaa  17400
ctagattgca agaaaaaact acttagactc gtactgttgt atgtatccag cggcggcggc  17460
gcgcaacgaa gctatgtcca agcgcaaaat caaagaagag atgctccagg tcatcgcgcc  17520
ggagatctat ggcccccega agaaggaaga gcaggattac aagccccgaa agctaaagcg  17580
ggtcaaaaag aaaaagaaag atgatgatga tgaacttgac gacgaggtgg aactgctgca  17640
cgctaccgcg cccaggcgac gggtacagtg gaaaggtcga cgcgtaaaac gtgttttgcg  17700
acccggcacc accgtagtct ttacgcccgg tgagcgctcc acccgcacct acaagcgcgt  17760
gtatgatgag gtgtacggcg acgaggacct gcttgagcag gccaacgagc gcctcgggga  17820
gtttgcctac ggaaagcggc ataaggacat gctggcgttg ccgctggacg agggcaaccc  17880
aacacctagc ctaaagcccg taacactgca gcaggtgctg cccgcgcttg caccgtccga  17940
agaaaagcgc ggcctaaagc gcgagtctgg tgacttggca cccaccgtgc agctgatggt  18000
acccaagcgc cagcgactgg aagatgtctt ggaaaaaatg accgtggaac ctgggctgga  18060
gcccgaggtc cgcgtgcggc caatcaagca ggtggcgccg ggactgggcg tgcagaccgt  18120
ggacgttcag atacccacta ccagtagcac cagtattgcc accgccacag agggcatgga  18180
gacacaaacg tccccggttg cctcagcggt ggcggatgcc gcggtgcagg cggtcgctgc  18240
ggccgcgtcc aagacctcta cggaggtgca aacggacccg tggatgtttc gcgtttcagc  18300
cccccggcgc ccgcgccgtt cgaggaagta cggcgccgcc agcgcgctac tgcccgaata  18360
tgccctacat ccttccattg cgcctacccc cggctatcgt ggctacacct accgccccag  18420
aagacgagca actacccgac gccgaaccac cactggaacc cgccgccgcc gtcgccgtcg  18480
ccagcccgtg ctggccccga tttccgtgcg cagggtggct cgcgaaggag gcaggaccct  18540
ggtgctgcca acagcgcgct accaccccag catcgtttaa aagccggtct ttgtggttct  18600
tgcagatatg gccctcacct gccgcctccg tttcccggtg ccgggattcc gaggaagaat  18660
gcaccgtagg aggggcatgg ccggccacgg cctgacgggc ggcatgcgtc gtgcgcacca  18720
ccggcggcgg cgcgcgtcgc accgtcgcat gcgcggcggt atcctgcccc tccttattcc  18780
actgatcgcc gcggcgattg gcgccgtgcc cggaattgca tccgtggcct tgcaggcgca  18840
gagacactga ttaaaaacaa gttgcatgtg gaaaaatcaa aataaaaagt ctggactctc  18900
acgctcgctt ggtcctgtaa ctattttgta gaatggaaga catcaacttt gcgtctctgg  18960
ccccgcgaca cggctcgcgc ccgttcatgg gaaactggca agatatcggc accagcaata  19020
tgagcggtgg cgccttcagc tggggctcgc tgtggagcgg cattaaaaat ttcggttcca  19080
ccgttaagaa ctatggcagc aaggcctgga acagcagcac aggccagatg ctgagggata  19140
agttgaaaga gcaaaatttc caacaaaagg tggtagatgg cctggcctct ggcattagcg  19200
gggtggtgga cctggccaac caggcagtgc aaaataagat taacagtaag cttgatcccc  19260
```

-continued gccctcccgt agaggagcct ccaccggccg tggagacagt gtctccagag gggcgtggcg 19320
aaaagcgtcc gcgccccgac agggaagaaa ctctggtgac gcaaatagac gagcctccct 19380
cgtacgagga ggcactaaag caaggcctgc ccaccacccg tcccatcgcg cccatggcta 19440
ccggagtgct gggccagcac acacccgtaa cgctggacct gcctcccccc gccgacaccc 19500
agcagaaacc tgtgctgcca ggcccgaccg ccgttgttgt aacccgtcct agccgcgcgt 19560
ccctgcgccg cgccgccagc ggtccgcgat cgttgcggcc cgtagccagt ggcaactggc 19620
aaagcacact gaacagcatc gtgggtctgg gggtgcaatc cctgaagcgc cgacgatgct 19680
tctgaatagc taacgtgtcg tatgtgtgtc atgtatgcgt ccatgtcgcc gccagaggag 19740
ctgctgagcc gccgcgcgcc cgctttccaa gatggctacc ccttcgatga tgccgcagtg 19800
gtcttacatg cacatctcgg gccaggacgc ctcggagtac ctgagccccg ggctggtgca 19860
gtttgcccgc gccaccgaga cgtacttcag cctgaataac aagtttagaa accccacggt 19920
ggcgcctacg cacgacgtga ccacagaccg gtcccagcgt ttgacgctgc ggttcatccc 19980
tgtggaccgt gaggatactg cgtactcgta caaggcgcgg ttcaccctag ctgtgggtga 20040
taaccgtgtg ctggacatgg cttccacgta ctttgacatc cgcggcgtgc tggacagggg 20100
ccctactttt aagccctact ctggcactgc ctacaacgcc ctggctccca agggtgcccc 20160
aaatccttgc gaatgggatg aagctgctac tgctcttgaa ataaacctag aagaagagga 20220
cgatgacaac gaagacgaag tagacgagca agctgagcag caaaaaactc acgtatttgg 20280
gcaggcgcct tattctggta taaatattac aaaggagggt attcaaatag gtgtcgaagg 20340
tcaaacacct aaatatgccg ataaaacatt tcaacctgaa cctcaaatag gagaatctca 20400
gtggtacgaa actgaaatta atcatgcagc tgggagagtc cttaaaaaga ctaccccaat 20460
gaaaccatgt tacggttcat atgcaaaacc cacaaatgaa aatggagggc aaggcattct 20520
tgtaaagcaa caaaatggaa agctagaaag tcaagtggaa atgcaatttt tctcaactac 20580
tgaggcgacc gcaggcaatg gtgataactt gactcctaaa gtggtattgt acagtgaaga 20640
tgtagatata gaaaccccag acactcatat ttcttacatg cccactatta aggaaggtaa 20700
ctcacgagaa ctaatgggcc aacaatctat gcccaacagg cctaattaca ttgcttttag 20760
ggacaatttt attggtctaa tgtattacaa cagcacgggt aatatgggtg ttctggcggg 20820
ccaagcatcg cagttgaatg ctgttgtaga tttgcaagac agaaacacag agctttcata 20880
ccagcttttg cttgattcca ttggtgatag aaccaggtac ttttctatgt ggaatcaggc 20940
tgttgacagc tatgatccag atgttagaat tattgaaaat catggaactg aagatgaact 21000
tccaaattac tgctttccac tgggaggtgt gattaataca gagactctta ccaaggtaaa 21060
acctaaaaca ggtcaggaaa atggatggga aaaagatgct acagaatttt cagataaaaa 21120
tcaaataaga gttggaaata attttgccat ggaaatcaat ctaaatgcca acctgtggag 21180
aaatttcctg tactccaaca tagcgctgta tttgcccgac aagctaaagt acagtccttc 21240
caacgtaaaa atttctgata acccaaacac ctacgactac atgaacaagc gagtggtggc 21300
tcccgggtta gtggactgct acattaacct tggagcacgc tggtcccttg actatatgga 21360
caacgtcaac ccatttaacc accaccgcaa tgctggcctg cgctaccgct caatgttgct 21420
gggcaatggt cgctatgtgc ccttccacat ccaggtgcct cagaagttct ttgccattaa 21480
aaacctcctt ctcctgccgg gctcatacac ctacgagtgg aacttcagga aggatgttaa 21540
catggttctg cagagctccc taggaaatga cctaagggtt gacggagcca gcattaagtt 21600
tgatagcatt tgcctttacg ccaccttctt ccccatggcc cacaacaccg cctccacgct 21660

```
tgaggccatg cttagaaacg acaccaacga ccagtccttt aacgactatc tctccgccgc  21720
caacatgctc taccctatac ccgccaacgc taccaacgtg cccatatcca tcccctcccg  21780
caactgggcg gctttccgcg gctgggcctt cacgcgcctt aagactaagg aaaccccatc  21840
actgggctcg ggctacgacc cttattacac ctactctggc tctataccct acctagatgg  21900
aacctttac ctcaaccaca cctttaagaa ggtggccatt acctttgact cttctgtcag  21960
ctggcctggc aatgaccgcc tgcttacccc caacgagttt gaaattaagc gctcagttga  22020
cggggagggt tacaacgttg cccagtgtaa catgaccaaa gactggttcc tggtacaaat  22080
gctagctaac tacaacattg gctaccaggg cttctatatc ccagagagct acaaggaccg  22140
catgtactcc ttctttagaa acttccagcc catgagccgt caggtggtgg atgatactaa  22200
atacaaggac taccaacagg tgggcatcct acaccaacac aacaactctg gatttgttgg  22260
ctaccttgcc cccaccatgc gcgaaggaca ggcctaccct gctaacttcc cctatccgct  22320
tataggcaag accgcagttg acagcattac ccagaaaaag tttctttgcg atcgcaccct  22380
ttggcgcatc ccattctcca gtaactttat gtccatgggc gcactcacag acctgggcca  22440
aaaccttctc tacgccaact ccgcccacgc gctagacatg acttttgagg tggatcccat  22500
ggacgagccc acccttcttt atgttttgtt tgaagtcttt gacgtggtcc gtgtgcaccg  22560
gccgcaccgc ggcgtcatcg aaaccgtgta cctgcgcacg cccttctcgg ccggcaacgc  22620
cacaacataa agaagcaagc aacatcaaca acagctgccg ccatgggctc cagtgagcag  22680
gaactgaaag ccattgtcaa agatcttggt tgtgggccat atttttgggc cacctatgac  22740
aagcgctttc caggctttgt ttctccacac aagctcgcct gcgccatagt caatacggcc  22800
ggtcgcgaga ctgggggcgt acactggatg gcctttgcct ggaacccgca ctcaaaaaca  22860
tgctacctct ttgagccctt tggcttttct gaccagcgac tcaagcaggt ttaccagttt  22920
gagtacgagt cactcctgcg ccgtagcgcc attgcttctt cccccgaccg ctgtataacg  22980
ctggaaaagt ccacccaaag cgtacagggg cccaactcgg ccgcctgtgg actattctgc  23040
tgcatgtttc tccacgcctt tgccaactgg ccccaaactc ccatggatca caaccccacc  23100
atgaacctta ttaccggggt acccaactcc atgctcaaca gtccccaggt acagcccacc  23160
ctgcgtcgca accaggaaca gctctacagc ttcctggagc gccactcgcc ctacttccgc  23220
agccacagtg cgcagattag gagcgccact tctttttgtc acttgaaaaa catgtaaaaa  23280
taatgtacta gagacacttt caataaaggc aaatgctttt atttgtacac tctcgggtga  23340
ttatttaccc ccacccttgc cgtctgcgcc gtttaaaaat caaaggggtt ctgccgcgca  23400
tcgctatgcg ccactggcag ggacacgttg cgatactggt gtttagtgct ccacttaaac  23460
tcaggcacaa ccatccgcgg cagctcggtg aagttttcac tccacaggct gcgcaccatc  23520
accaacgcgt ttagcaggtc gggcgccgat atcttgaagt cgcagttggg gcctccgccc  23580
tgcgcgcgcg agttgcgata cacagggttg cagcactgga acactatcag cgccgggtgg  23640
tgcacgctgg ccagcacgct cttgtcggag atcagatccg cgtccaggtc ctccgcgttg  23700
ctcagggcga acggagtcaa ctttggtagc tgccttccca aaaagggcgc gtgcccaggc  23760
tttgagttgc actcgcaccg tagtggcatc aaaaggtgac cgtgcccggt ctgggcgtta  23820
ggatacagcg cctgcataaa agccttgatc tgcttaaaag ccacctgagc ctttgcgcct  23880
tcagagaaga acatgccgca agacttgccg gaaaactgat tggccggaca ggccgcgtcg  23940
tgcacgcagc accttgcgtc ggtgttggag atctgcacca catttcggcc ccaccggttc  24000
```

ttcacgatct tggccttgct agactgctcc ttcagcgcgc gctgcccgtt ttcgctcgtc 24060
acatccattt caatcacgtg ctccttattt atcataatgc ttccgtgtag acacttaagc 24120
tcgccttcga tctcagcgca gcggtgcagc cacaacgcgc agcccgtggg ctcgtgatgc 24180
ttgtaggtca cctctgcaaa cgactgcagg tacgcctgca ggaatcgccc catcatcgtc 24240
acaaaggtct tgttgctggt gaaggtcagc tgcaacccgc ggtgctcctc gttcagccag 24300
gtcttgcata cggccgccag agcttccact tggtcaggca gtagtttgaa gttcgccttt 24360
agatcgttat ccacgtggta cttgtccatc agcgcgcgcg cagcctccat gcccttctcc 24420
cacgcagaca cgatcggcac actcagcggg ttcatcaccg taatttcact ttccgcttcg 24480
ctgggctctt cctcttcctc ttgcgtccgc ataccacgcg ccactgggtc gtcttcattc 24540
agccgccgca ctgtgcgctt acctcctttg ccatgcttga ttagcaccgg tgggttgctg 24600
aaacccacca tttgtagcgc cacatcttct ctttcttcct cgctgtccac gattacctct 24660
ggtgatggcg ggcgctcggg cttgggagaa gggcgcttct ttttcttctt gggcgcaatg 24720
gccaaatccg ccgccgaggt cgatggccgc gggctgggtg tgcgcggcac cagcgcgtct 24780
tgtgatgagt cttcctcgtc ctcggactcg atacgccgcc tcatccgctt ttttgggggc 24840
gcccggggag gcggcggcga cggggacggg gacgacacgt cctccatggt tgggggacgt 24900
cgcgccgcac cgcgtccgcg ctcgggggtg gtttcgcgct gctcctcttc ccgactggcc 24960
atttccttct cctataggca gaaaaagatc atggagtcag tcgagaagaa ggacagccta 25020
accgccccct ctgagttcgc caccaccgcc tccaccgatg ccgccaacgc gcctaccacc 25080
ttccccgtcg aggcaccccc gcttgaggag gaggaagtga ttatcgagca ggacccaggt 25140
tttgtaagcg aagacgacga ggaccgctca gtaccaacag aggataaaaa gcaagaccag 25200
gacaacgcag aggcaaacga ggaacaagtc gggcgggggg acgaaaggca tggcgactac 25260
ctagatgtgg gagacgacgt gctgttgaag catctgcagc gccagtgcgc cattatctgc 25320
gacgcgttgc aagagcgcag cgatgtgccc ctcgccatag cggatgtcag ccttgcctac 25380
gaacgccacc tattctcacc gcgcgtaccc cccaaacgcc aagaaaacgg cacatgcgag 25440
cccaacccgc gcctcaactt ctaccccgta tttgccgtgc cagaggtgct tgccacctat 25500
cacatctttt tccaaaactg caagataccc ctatcctgcc gtgccaaccg cagccgagcg 25560
gacaagcagc tggccttgcg gcagggcgct gtcatacctg atatcgcctc gctcaacgaa 25620
gtgccaaaaa tctttgaggg tcttggacgc gacgagaagc gcgcggcaaa cgctctgcaa 25680
caggaaaaca gcgaaaatga aagtcactct ggagtgttgg tggaactcga gggtgacaac 25740
gcgcgcctag ccgtactaaa acgcagcatc gaggtcaccc actttgccta cccggcactt 25800
aacctacccc ccaaggtcat gagcacagtc atgagtgagc tgatcgtgcg ccgtgcgcag 25860
cccctggaga gggatgcaaa tttgcaagaa caaacagagg agggcctacc cgcagttggc 25920
gacgagcagc tagcgcgctg gcttcaaacg cgcgagcctg ccgacttgga ggagcgacgc 25980
aaactaatga tggccgcagt gctcgttacc gtggagcttg agtgcatgca gcggttcttt 26040
gctgacccgg agatgcagcg caagctagag gaaacattgc actacacctt tcgacagggc 26100
tacgtacgcc aggcctgcaa gatctccaac gtggagctct gcaacctggt ctcctacctt 26160
ggaattttgc acgaaaaccg ccttgggcaa aacgtgcttc attccacgct caagggcgag 26220
gcgcgccgcg actacgtccg cgactgcgtt tacttatttc tatgctacac ctggcagacg 26280
gccatgggcg tttggcagca gtgcttggag gagtgcaacc tcaaggagct gcagaaactg 26340
ctaaagcaaa acttgaagga cctatggacg gccttcaacg agcgctccgt ggccgcgcac 26400

-continued ctggcggaca tcattttccc cgaacgcctg cttaaaaccc tgcaacaggg tctgccagac 26460
ttcaccagtc aaagcatgtt gcagaacttt aggaacttta tcctagagcg ctcaggaatc 26520
ttgcccgcca cctgctgtgc acttcctagc gactttgtgc ccattaagta ccgcgaatgc 26580
cctccgccgc tttggggcca ctgctacctt ctgcagctag ccaactacct tgcctaccac 26640
tctgacataa tggaagacgt gagcggtgac ggtctactgg agtgtcactg tcgctgcaac 26700
ctatgcaccc cgcaccgctc cctggtttgc aattcgcagc tgcttaacga aagtcaaatt 26760
atcggtacct ttgagctgca gggtccctcg cctgacgaaa agtccgcggc tccggggttg 26820
aaactcactc cggggctgtg gacgtcggct taccttcgca aatttgtacc tgaggactac 26880
cacgcccacg agattaggtt ctacgaagac caatcccgcc cgccaaatgc ggagcttacc 26940
gcctgcgtca ttacccaggg ccacattctt ggccaattgc aagccatcaa caaagcccgc 27000
caagagtttc tgctacgaaa gggacggggg gtttacttgg acccccagtc cggcgaggag 27060
ctcaacccaa tcccccgcc gccgcagccc tatcagcagc agccgcgggc ccttgcttcc 27120
caggatggca cccaaaaaga agctgcagct gccgccgcca cccacggacg aggaggaata 27180
ctgggacagt caggcagagg aggttttgga cgaggaggag gaggacatga tggaagactg 27240
ggagagccta gacgaggaag cttccgaggt cgaagaggtg tcagacgaaa caccgtcacc 27300
ctcggtcgca ttcccctcgc cggcgcccca gaaatcggca accggttcca gcatggctac 27360
aacctccgct cctcaggcgc cgccggcact gcccgttcgc cgacccaacc gtagatggga 27420
caccactgga accagggccg gtaagtccaa gcagccgccg ccgttagccc aagagcaaca 27480
acagcgccaa ggctaccgct catggcgcgg gcacaagaac gccatagttg cttgcttgca 27540
agactgtggg ggcaacatct ccttcgcccg ccgctttctt ctctaccatc acggcgtggc 27600
cttcccccgt aacatcctgc attactaccg tcatctctac agcccatact gcaccggcgg 27660
cagcggcagc ggcagcaaca gcagcggcca cacagaagca aaggcgaccg gatagcaaga 27720
ctctgacaaa gcccaagaaa tccacagcgg cggcagcagc aggaggagga gcgctgcgtc 27780
tggcgcccaa cgaacccgta tcgacccgcg agcttagaaa caggattttt cccactctgt 27840
atgctatatt tcaacagagc aggggccaag aacaagagct gaaaataaaa aacaggtctc 27900
tgcgatccct cacccgcagc tgcctgtatc acaaaagcga agatcagctt cggcgcacgc 27960
tggaagacgc ggaggctctc ttcagtaaat actgcgcgct gactcttaag gactagtttc 28020
gcgccctttc tcaaatttaa gcgcgaaaac tacgtcatct ccagcggcca cacccggcgc 28080
cagcacctgt cgtcagcgcc atttcaactt tgtatacaaa agttgtgatg agcaaggaaa 28140
ttcccacgcc ctacatgtgg agttaccagc cacaaatggg acttgcggct ggagctgccc 28200
aagactactc aacccgaata aactacatga gcgcgggacc ccacatgata tcccggtca 28260 acggaatacg cgcccaccga aaccgaattc tcctggaaca ggcggctatt accaccacac 28320
ctcgtaataa ccttaatccc cgtagttggc ccgctgccct ggtgtaccag gaaagtcccg 28380
ctcccaccac tgtggtactt cccagagacg cccaggccga agttcagatg actaactcag 28440
gggcgcagct tgcgggcggc tttcgtcaca gggtgcggtc gcccgggcag ggtataactc 28500
acctgacaat cagagggcga ggtattcagc tcaacgacga gtcggtgagc tcctcgcttg 28560
gtctccgtcc ggacgggaca tttcagatcg gcggcgccgg ccgctcttca ttcacgcctc 28620
gtcaggcaat cctaactctg cagacctcgt cctctgagcc gcgctctgga ggcattggaa 28680
ctctgcaatt tattgaggag tttgtgccat cggtctactt taacccctc tcgggacctc 28740

-continued

```
ccggccacta tccggatcaa tttattccta actttgacgc ggtaaaggac tcggcggacg  28800
gctacgactg aatgttaagt ggagaggcag agcaactgcg cctgaaacac ctggtccact  28860
gtcgccgcca caagtgcttt gcccgcgact ccggtgagtt ttgctacttt gaattgcccg  28920
aggatcatat cgagggcccg gcgcacggcg tccggcttac cgcccaggga gagcttgccc  28980
gtagcctgat tcgggagttt acccagcgcc ccctgctagt tgagcgggac aggggaccct  29040
gtgttctcac tgtgatttgc aactgtccta accctggatt acatcaagat ctttgttgcc  29100
atctctgtgc tgagtataat aaatacagaa attaaaatat actggggctc ctatcgccat  29160
cctgtaaacg ccaccgtctt cacccgccca agcaaaccaa ggcgaacctt acctggtact  29220
tttaacatct ctccctctgt gatttacaac agtttcaacc cagacggagt gagtctacga  29280
gagaacctct ccgagctcag ctactccatc agaaaaaaca ccaccctcct tacctgccgg  29340
gaacgtacga gtgcgtcacc ggccgctgca ccacacctac cgcctgaccg taaaccagac  29400
tttttccgga cagacctcaa taactctgtt taccagaaca ggaggtgagc ttagaaaacc  29460
cttagggtat taggccaaag gcgcagctac tgtggggttt atgaacaatt caagcaactc  29520
tacgggctat tctaattcag gtttctctag aatcggggtt ggggttattc tctgtcttgt  29580
gattctcttt attcttatac taacgcttct ctgcctaagg ctcgccgcct gctgtgtgca  29640
catttgcatt tattgtcagc tttttaaacg ctggggtcgc cacccaagat gattaggtac  29700
ataatcctag gtttactcac ccttgcgtca gcccacggta ccacccaaaa ggtggatttt  29760
aaggagccag cctgtaatgt tacattcgca gctgaagcta atgagtgcac cactcttata  29820
aaatgcacca cagaacatga aaagctgctt attcgccaca aaaacaaaat tggcaagtat  29880
gctgtttatg ctatttggca gccaggtgac actacagagt ataatgttac agttttccag  29940
ggtaaaagtc ataaaacttt tatgtatact tttccatttt atgaaatgtg cgacattacc  30000
atgtacatga gcaaacagta taagttgtgg cccccacaaa attgtgtgga aaacactggc  30060
actttctgct gcactgctat gctaattaca gtgctcgctt tggtctgtac cctactctat  30120
attaaataca aaagcagacg cagctttatt gaggaaaaga aatgccttta atttactaag  30180
ttacaaagct aatgtcacca ctaactgctt tactcgctgc ttgcaaaaca aattcaaaaa  30240
gttagcatta taattagaat aggatttaaa ccccccggtc atttcctgct caataccatt  30300
cccctgaaca attgactcta tgtgggatat gctccagcgc tacaaccttg aagtcaggct  30360
tcctggatgt cagcatctga ctttggccag cacctgtccc gcggatttgt tccagtccaa  30420
ctacagcgac ccaccctaac agagatgacc aacacaacca acgcggccgc cgctaccgga  30480
cttacatcta ccacaaatac accccaagtt tctgcctttg tcaataactg ggataacttg  30540
ggcatgtggt ggttctccat agcgcttatg tttgtatgcc ttattattat gtggctcatc  30600
tgctgcctaa agcgcaaacg cgcccgacca cccatctata gtcccatcat tgtgctacac  30660
ccaaacaatg atggaatcca tagattggac ggactgaaac acatgttctt ttctcttaca  30720
gtatgattaa atgagacatg attcctcgag tttttatatt actgaccctt gttgcgcttt  30780
tttgtgcgtg ctccacattg gctgcggttt ctcacatcga agtagactgc attccagcct  30840
tcacagtcta tttgctttac ggatttgtca ccctcacgct catctgcagc ctcatcactg  30900
tggtcatcgc ctttatccag tgcattgact gggtctgtgt gcgctttgca tatctcagac  30960
accatcccca gtacagggac aggactatag ctgagcttct tagaattctt taattatgaa  31020
atttactgtg acttttctgc tgattatttg caccctatct gcgttttgtt ccccgacctc  31080
caagcctcaa agacatatat catgcagatt cactcgtata tggaatattc caagttgcta  31140
```

-continued

```
caatgaaaaa agcgatcttt ccgaagcctg gttatatgca atcatctctg ttatggtgtt  31200
ctgcagtacc atcttagccc tagctatata tccctacctt gacattggct ggaacgcaat  31260
agatgccatg aaccacccaa ctttccccgc gcccgctatg cttccactgc aacaagttgt  31320
tgccggcggc tttgtcccag ccaatcagcc tcgcccacct tctcccaccc ccactgaaat  31380
cagctacttt aatctaacag gaggagatga ctgacaccct agatctagaa atggacggaa  31440
ttattacaga gcagcgcctg ctagaaagac gcagggcagc ggccgagcaa cagcgcatga  31500
atcaagagct ccaagacatg gttaacttgc accagtgcaa aaggggtatc ttttgtctgg  31560
taaagcaggc caaagtcacc tacgacagta ataccaccgg acaccgcctt agctacaagt  31620
tgccaaccaa gcgtcagaaa ttggtggtca tggtgggaga aaagcccatt accataactc  31680
agcactcggt agaaaccgaa ggctgcattc actcaccttg tcaaggacct gaggatctct  31740
gcacccttat taagaccctg tgcggtctca aagatcttat tccctttaac taataaaaaa  31800
aaataataaa gcatcactta cttaaaatca gttagcaaat ttctgtccag tttattcagc  31860
agcacctcct tgccctcctc ccagctctgg tattgcagct tcctcctggc tgcaaacttt  31920
ctccacaatc taaatggaat gtcagtttcc tcctgttcct gtccatccgc acccactatc  31980
ttcatgttgt tgcagatgaa gcgcgcaaga ccgtctgaag ataccttcaa ccccgtgtat  32040
ccatatgaca cggaaaccgg tcctccaact gtgccttttc ttactcctcc ctttgtatcc  32100
cccaatgggt ttcaagagag tcccccctggg gtactctctt tgcgcctatc cgaacctcta  32160
gttacctcca atggcatgct tgcgctcaaa atgggcaacg gcctctctct ggacgaggcc  32220
ggcaacctta cctcccaaaa tgtaaccact gtgagcccac ctctcaaaaa aaccaagtca  32280
aacataaacc tggaaatatc tgcacccctc acagttacct cagaagccct aactgtggct  32340
gccgccgcac ctctaatggt cgcgggcaac acactcacca tgcaatcaca ggccccgcta  32400
accgtgcacg actccaaact tagcattgcc acccaaggac ccctcacagt gtcagaagga  32460
aagctagccc tgcaaacatc aggcccctc accaccaccg atagcagtac ccttactatc  32520
actgcctcac cccctctaac tactgccact ggtagcttgg gcattgactt gaaagagccc  32580
atttatacac aaaatggaaa actaggacta aagtacgggg ctcctttgca tgtaacagac  32640
gacctaaaca ctttgaccgt agcaactggt ccaggtgtga ctattaataa tacttccttg  32700
caaactaaag ttactggagc cttgggtttt gattcacaag gcaatatgca acttaatgta  32760
gcaggaggac taaggattga ttctcaaaac agacgcctta tacttgatgt tagttatccg  32820
tttgatgctc aaaaccaact aaatctaaga ctaggacagg gccctctttt tataaactca  32880
gcccacaact tggatattaa ctacaacaaa ggcctttact tgtttacagc ttcaaacaat  32940
tccaaaaagc ttgaggttaa cctaagcact gccaaggggt tgatgtttga cgctacagcc  33000
atagccatta atgcaggaga tgggcttgaa tttggttcac ctaatgcacc aaacacaaat  33060
cccctcaaaa caaaaattgg ccatggccta gaatttgatt caaacaaggc tatggttcct  33120
aaactaggaa ctggccttag ttttgacagc acaggtgcca ttacagtagg aaacaaaaat  33180
aatgataagc taactttatg gactggaata aaccctccac ctaactgtca aattgtggaa  33240
aacactaata caaatgatgg caaacttact ttagtattag taaaaaacgg agggcttgtt  33300
aatggctacg tgtctctagt tggtgtatca gacactgtga accaaatgtt cacacaaaag  33360
acagcaaaca tccaattaag attatatttt gactcttctg gaaatctatt aactgatgaa  33420
tcagacttaa aaattccact taaaaataaa tcttctacag cgaccagtga aactgtagcc  33480
```

-continued

```
agcagcaaag cctttatgcc aagtactaca gcttatccct tcaacaccac tactagggat  33540
agtgaaaact acattcatgg aatatgttac tacatgacta gttatgatag aagtctattt  33600
cccttgaaca tttctataat gctaaacagc cgtatgattt cttccaatgt tgcctatgcc  33660
atacaatttg aatggaatct aaatgcaagt gaatctccag aaagcaacat agctacgctg  33720
accacatccc cctttttctt ttcttacatt acagaagacg acaactaata aagaatcgtt  33780
tgtgttatgt ttcaacgtgt ttatttttca attgcagaaa atttcaagtc atttttcatt  33840
cagtagtata gccccaccac cacatagctt atacagatca ccgtacctca actttgtata  33900
ataaagttgt aatcaaactc acagaaccct agtattcaac ctgccacctc cctcccaaca  33960
cacagagtac acagtccttt ctccccggct ggccttaaaa agcatcatat catgggtaac  34020
agacatattc ttaggtgtta tattccacac ggtttcctgt cgagccaaac gctcatcagt  34080
gatattaata aactccccgg gcagctcact taagttcatg tcgctgtcca gctgctgagc  34140
cacaggctgc tgtccaactt gcggttgctt aacgggcggc gaaggagaag tccacgccta  34200
catgggggta gagtcataat cgtgcatcag gatagggcgg tggtgctgca gcagcgcgcg  34260
aataaactgc tgccgccgcc gctccgtcct gcaggaatac aacatggcag tggtctcctc  34320
agcgatgatt cgcaccgccc gcagcataag gcgccttgtc ctccgggcac agcagcgcac  34380
cctgatctca cttaaatcag cacagtaact gcagcacagc accacaatat tgttcaaaat  34440
cccacagtgc aaggcgctgt atccaaagct catggcgggg accacagaac ccacgtggcc  34500
atcataccac aagcgcaggt agattaagtg gcgacccctc ataaacacgc tggacataaa  34560
cattacctct tttggcatgt tgtaattcac cacctcccgg taccatataa acctctgatt  34620
aaacatggcg ccatccacca ccatcctaaa ccagctggcc aaaacctgcc cgccggctat  34680
acactgcagg gaaccgggac tggaacaatg acagtggaga gcccaggact cgtaaccatg  34740
gatcatcatg ctcgtcatga tatcaatgtt ggcacaacac aggcacacgt gcatacactt  34800
cctcaggatt acaagctcct cccgcgttag aaccatatcc cagggaacaa cccattcctg  34860
aatcagcgta aatcccacac tgcagggaag acctcgcacg taactcacgt tgtgcattgt  34920
caaagtgtta cattcgggca gcagcggatg atcctccagt atggtagcgc gggtttctgt  34980
ctcaaaagga ggtagacgat ccctactgta cggagtgcgc cgagacaacc gagatcgtgt  35040
tggtcgtagt gtcatgccaa atggaacgcc ggacgtagtc atatttcctg aagcaaaacc  35100
aggtgcgggc gtgacaaaca gatctgcgtc tccggtctcg ccgcttagat cgctctgtgt  35160
agtagttgta gtatatccac tctctcaaag catccaggcg ccccctggct tcgggttcta  35220
tgtaaactcc ttcatgcgcc gctgccctga taacatccac caccgcagaa taagccacac  35280
ccagccaacc tacacattcg ttctgcgagt cacacacggg aggagcggga agagctggaa  35340
gaaccatgtt tttttttta ttccaaaaga ttatccaaaa cctcaaaatg aagatctatt  35400
aagtgaacgc gctcccctcc ggtggcgtgg tcaaactcta cagccaaaga acagataatg  35460
gcatttgtaa gatgttgcac aatggcttcc aaaaggcaaa cggccctcac gtccaagtgg  35520
acgtaaaggc taaacccttc agggtgaatc tcctctataa acattccagc accttcaacc  35580
atgcccaaat aattctcatc tcgccacctt ctcaatatat ctctaagcaa atcccgaata  35640
ttaagtccgg ccattgtaaa aatctgctcc agagcgccct ccaccttcag cctcaagcag  35700
cgaatcatga ttgcaaaaat tcaggttcct cacagacctg tataagattc aaaagcggaa  35760
cattaacaaa aataccgcga tcccgtaggt cccttcgcag ggccagctga acataatcgt  35820
gcaggtctgc acggaccagc gcggccactt ccccgccagg aaccatgaca aaagaaccca  35880
```

```
cactgattat gacacgcata ctcggagcta tgctaaccag cgtagccccg atgtaagctt  35940

gttgcatggg cggcgatata aaatgcaagg tgctgctcaa aaaatcaggc aaagcctcgc  36000

gcaaaaaaga aagcacatcg tagtcatgct catgcagata aaggcaggta agctccggaa  36060

ccaccacaga aaaagacacc atttttctct caaacatgtc tgcgggtttc tgcataaaca  36120

caaaataaaa taacaaaaaa acatttaaac attagaagcc tgtcttacaa caggaaaaac  36180

aacccttata agcataagac ggactacggc catgccggcg tgaccgtaaa aaaactggtc  36240

accgtgatta aaaagcacca ccgacagctc ctcggtcatg tccggagtca taatgtaaga  36300

ctcggtaaac acatcaggtt gattcacatc ggtcagtgct aaaaagcgac cgaaatagcc  36360

cgggggaata catacccgca ggcgtagaga caacattaca gcccccatag gaggtataac  36420

aaaattaata ggagagaaaa acacataaac acctgaaaaa ccctcctgcc taggcaaaat  36480

agcaccctcc cgctccagaa caacatacag cgcttccaca gcggcagcca taacagtcag  36540

ccttaccagt aaaaaagaaa acctattaaa aaaacaccac tcgacacggc accagctcaa  36600

tcagtcacag tgtaaaaaag ggccaagtgc agagcgagta tatataggac taaaaaatga  36660

cgtaacggtt aaagtccaca aaaaacaccc agaaaaccgc acgcgaacct acgcccagaa  36720

acgaaagcca aaaaacccac aacttcctca aatcgtcact tccgttttcc cacgttacgt  36780

cacttcccat tttaagaaaa ctacaattcc caacacatac aagttactcc gccctaaaac  36840

ctacgtcacc cgccccgttc ccacgccccg cgccacgtca caaactccac cccctcatta  36900

tcatattggc ttcaatccaa aataaggtat attattgatg atg                    36943


<210> SEQ ID NO 3
<211> LENGTH: 952
<212> TYPE: PRT
<213> ORGANISM: Adenovirus type 5

<400> SEQUENCE: 3

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Ala Thr Ala Leu Glu Ile
    130                 135                 140

Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
```

-continued

```
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Thr Thr Glu Ala
            260                 265                 270

Thr Ala Gly Asn Gly Asp Asn Leu Thr Pro Lys Val Val Leu Tyr Ser
        275                 280                 285

Glu Asp Val Asp Ile Glu Thr Pro Asp Thr His Ile Ser Tyr Met Pro
    290                 295                 300

Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
                325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
        355                 360                 365

Ser Tyr Gln Leu Leu Leu Asp Ser Ile Gly Asp Arg Thr Arg Tyr Phe
    370                 375                 380

Ser Met Trp Asn Gln Ala Val Asp Ser Tyr Asp Pro Asp Val Arg Ile
385                 390                 395                 400

Ile Glu Asn His Gly Thr Glu Asp Glu Leu Pro Asn Tyr Cys Phe Pro
                405                 410                 415

Leu Gly Gly Val Ile Asn Thr Glu Thr Leu Thr Lys Val Lys Pro Lys
            420                 425                 430

Thr Gly Gln Glu Asn Gly Trp Glu Lys Asp Ala Thr Glu Phe Ser Asp
        435                 440                 445

Lys Asn Glu Ile Arg Val Gly Asn Asn Phe Ala Met Glu Ile Asn Leu
    450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Ser Pro Ser Asn Val Lys Ile Ser Asp
                485                 490                 495

Asn Pro Asn Thr Tyr Asp Tyr Met Asn Lys Arg Val Val Ala Pro Gly
            500                 505                 510

Leu Val Asp Cys Tyr Ile Asn Leu Gly Ala Arg Trp Ser Leu Asp Tyr
        515                 520                 525

Met Asp Asn Val Asn Pro Phe Asn His His Arg Asn Ala Gly Leu Arg
    530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
                565                 570                 575

Gly Ser Tyr Thr Tyr Glu Trp Asn Phe Arg Lys Asp Val Asn Met Val
            580                 585                 590

Leu Gln Ser Ser Leu Gly Asn Asp Leu Arg Val Asp Gly Ala Ser Ile
        595                 600                 605
```

```
Lys Phe Asp Ser Ile Cys Leu Tyr Ala Thr Phe Phe Pro Met Ala His
    610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
                645                 650                 655

Pro Ala Asn Ala Thr Asn Val Pro Ile Ser Ile Pro Ser Arg Asn Trp
            660                 665                 670

Ala Ala Phe Arg Gly Trp Ala Phe Thr Arg Leu Lys Thr Lys Glu Thr
        675                 680                 685

Pro Ser Leu Gly Ser Gly Tyr Asp Pro Tyr Tyr Thr Tyr Ser Gly Ser
    690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
                725                 730                 735

Leu Leu Thr Pro Asn Glu Phe Glu Ile Lys Arg Ser Val Asp Gly Glu
            740                 745                 750

Gly Tyr Asn Val Ala Gln Cys Asn Met Thr Lys Asp Trp Phe Leu Val
        755                 760                 765

Gln Met Leu Ala Asn Tyr Asn Ile Gly Tyr Gln Gly Phe Tyr Ile Pro
    770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                805                 810                 815

Val Gly Ile Leu His Gln His Asn Asn Ser Gly Phe Val Gly Tyr Leu
            820                 825                 830

Ala Pro Thr Met Arg Glu Gly Gln Ala Tyr Pro Ala Asn Phe Pro Tyr
        835                 840                 845

Pro Leu Ile Gly Lys Thr Ala Val Asp Ser Ile Thr Gln Lys Lys Phe
    850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
                885                 890                 895

Ser Ala His Ala Leu Asp Met Thr Phe Glu Val Asp Pro Met Asp Glu
            900                 905                 910

Pro Thr Leu Leu Tyr Val Leu Phe Glu Val Phe Asp Val Val Arg Val
        915                 920                 925

His Arg Pro His Arg Gly Val Ile Glu Thr Val Tyr Leu Arg Thr Pro
    930                 935                 940

Phe Ser Ala Gly Asn Ala Thr Thr
945                 950


<210> SEQ ID NO 4
<211> LENGTH: 952
<212> TYPE: PRT
<213> ORGANISM: Artificial Sequence
<220> FEATURE:
<223> OTHER INFORMATION: Synthetic polypeptide

<400> SEQUENCE: 4

Met Ala Thr Pro Ser Met Met Pro Gln Trp Ser Tyr Met His Ile Ser
1               5                   10                  15
```

-continued

```
Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Ala Thr Ala Leu Glu Ile
    130                 135                 140

Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Thr Thr Glu Ala
            260                 265                 270

Thr Ala Gly Asn Gly Asp Asn Leu Thr Pro Lys Val Val Leu Tyr Ser
        275                 280                 285

Glu Asp Val Asp Ile Glu Thr Pro Asp Thr His Ile Ser Tyr Met Pro
    290                 295                 300

Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
                325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
        355                 360                 365

Ser Tyr Gln Leu Leu Leu Asp Ser Ile Gly Asp Arg Thr Arg Tyr Phe
    370                 375                 380

Ser Met Trp Asn Gln Ala Val Asp Ser Tyr Asp Pro Asp Val Arg Ile
385                 390                 395                 400

Ile Glu Asn His Gly Thr Glu Asp Glu Leu Pro Asn Tyr Cys Phe Pro
                405                 410                 415

Leu Gly Gly Val Ile Asn Thr Glu Thr Leu Thr Lys Val Lys Pro Lys
            420                 425                 430
```

-continued

```
Thr Gly Gln Glu Asn Gly Trp Glu Lys Asp Ala Thr Glu Phe Ser Asp
        435                 440                 445

Lys Asn Gln Ile Arg Val Gly Asn Asn Phe Ala Met Glu Ile Asn Leu
    450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Ser Pro Ser Asn Val Lys Ile Ser Asp
                485                 490                 495

Asn Pro Asn Thr Tyr Asp Tyr Met Asn Lys Arg Val Val Ala Pro Gly
            500                 505                 510

Leu Val Asp Cys Tyr Ile Asn Leu Gly Ala Arg Trp Ser Leu Asp Tyr
        515                 520                 525

Met Asp Asn Val Asn Pro Phe Asn His His Arg Asn Ala Gly Leu Arg
    530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
                565                 570                 575

Gly Ser Tyr Thr Tyr Glu Trp Asn Phe Arg Lys Asp Val Asn Met Val
            580                 585                 590

Leu Gln Ser Ser Leu Gly Asn Asp Leu Arg Val Asp Gly Ala Ser Ile
        595                 600                 605

Lys Phe Asp Ser Ile Cys Leu Tyr Ala Thr Phe Phe Pro Met Ala His
    610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
                645                 650                 655

Pro Ala Asn Ala Thr Asn Val Pro Ile Ser Ile Pro Ser Arg Asn Trp
            660                 665                 670

Ala Ala Phe Arg Gly Trp Ala Phe Thr Arg Leu Lys Thr Lys Glu Thr
        675                 680                 685

Pro Ser Leu Gly Ser Gly Tyr Asp Pro Tyr Tyr Thr Tyr Ser Gly Ser
    690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
                725                 730                 735

Leu Leu Thr Pro Asn Glu Phe Glu Ile Lys Arg Ser Val Asp Gly Glu
            740                 745                 750

Gly Tyr Asn Val Ala Gln Cys Asn Met Thr Lys Asp Trp Phe Leu Val
        755                 760                 765

Gln Met Leu Ala Asn Tyr Asn Ile Gly Tyr Gln Gly Phe Tyr Ile Pro
    770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                805                 810                 815

Val Gly Ile Leu His Gln His Asn Asn Ser Gly Phe Val Gly Tyr Leu
            820                 825                 830

Ala Pro Thr Met Arg Glu Gly Gln Ala Tyr Pro Ala Asn Phe Pro Tyr
        835                 840                 845

Pro Leu Ile Gly Lys Thr Ala Val Asp Ser Ile Thr Gln Lys Lys Phe
```

-continued 850 855 860

Leu Cys Asp Arg Thr Leu Trp Arg Ile Pro Phe Ser Ser Asn Phe Met
865 870 875 880

Ser Met Gly Ala Leu Thr Asp Leu Gly Gln Asn Leu Leu Tyr Ala Asn
885 890 895

Ser Ala His Ala Leu Asp Met Thr Phe Glu Val Asp Pro Met Asp Glu
900 905 910

Pro Thr Leu Leu Tyr Val Leu Phe Glu Val Phe Asp Val Val Arg Val
915 920 925

His Arg Pro His Arg Gly Val Ile Glu Thr Val Tyr Leu Arg Thr Pro
930 935 940

Phe Ser Ala Gly Asn Ala Thr Thr
945 950

<210> SEQ ID NO 5
<211> LENGTH: 41258
<212> TYPE: DNA
<213> ORGANISM: Artificial Sequence
<220> FEATURE:
<223> OTHER INFORMATION: Synthetic adenovirus genome (AdSyn-CO987)

<400> SEQUENCE: 5
gttccactga gcgtcagacc ccttaataag atgatcttct tgagatcgtt ttggtctgcg 60
cgtaatctct tgctctgaaa acgaaaaaac cgccttgcag ggcggttttt cgaaggttct 120
ctgagctacc aactctttga accgaggtaa ctggcttgga ggagcgcagt caccaaaact 180
tgtcctttca gtttagcctt aaccggcgca tgacttcaag actaactcct ctaaatcaat 240
taccagtggc tgctgccagt ggtgcttttg catgtctttc cgggttggac tcaagacgat 300
agttaccgga taaggcgcag cggtcggact gaacgggggg ttcgtgcata cagtccagct 360
tggagcgaac tgcctacccg gaactgagtg tcaggcgtgg aatgagacaa acgcggccat 420
aacagcggaa tgacaccggt aaaccgaaag gcaggaacag gagagcgcac gagggagccg 480
ccaggggaaa cgcctggtat ctttatagtc ctgtcgggtt tcgccaccac tgatttgagc 540
gtcagatttc gtgatgcttg tcaggggggc ggagcctatg gaaaaacggc tttgccgcgg 600
ccctctcact tccctgttaa gtatcttcct ggcatcttcc aggaaatctc cgccccgttc 660
gtaagccatt tccgctcgcc gcagtcgaac gaccgagcgt agcgagtcag tgagcgagga 720
agcggaatat atcctgtatc acatattctg ctgacgcacc ggtgcagcct tttttctcct 780
gccacatgaa gcacttcact gacaccctca tcagtgccaa catagtaagc cagtatacac 840
tccgctagcg ctgaggtctg cctcgtgaag aaggtgttgc tgactcatac caggcctgaa 900
tcgccccatc atccagccag aaagtgaggg agccacggtt gatgagagct ttgttgtagg 960
tggaccagtt ggtgattttg aacttttgct ttgccacgga acggtctgcg ttgtcgggaa 1020
gatgcgtgat ctgatccttc aactcagcaa aagttcgatt tattcaacaa agccacgttg 1080
tgtctcaaaa tctctgatgt tacattgcac aagataaaaa tatatcatca tgaacaataa 1140
aactgtctgc ttacataaac agtaatacaa ggggtgttga tactctcagt acaatctgct 1200
ctgatgccgc atagttaagc cagtatctgc tccctgcttg tgtgttggag gtcgctgagt 1260
agtgcgcgag caaaatttaa gctacaacaa ggcaaggctt gaccgacaat tgcatgaaga 1320
atctgcttag ggttaggcgt tttgcgctgc ttcgcgatgt acgggccaga tatacgcgta 1380
tctgagggga ctagggtgtg tttaggcgaa aagcggggct tcggttgtac gcggttagga 1440
gtcccctcag gatatagtag tttcgctttt gcatagggag ggggaaatgt agtcttatgc 1500
aatactcttg tagtcttgca acatggtaac gatgagttag caacatgcct tacaaggaga 1560
gaaaaagcac cgtgcatgcc gattggtgga agtaaggtgg tacgatcgtg ccttattagg 1620
aaggcaacag acgggtctga catggattgg acgaaccact gaattccgca ttgcagagat 1680
attgtattta agtgcctagc tcgatacaat aaacgccatt tgaccattca ccacattggt 1740
gtgcacctcc aagctgggta cggatccggc cttgccggcc tcgagcggcc gctagcgccg 1800
ccactatggg atcaagatcg ccaaaaaaga agagaaaggt gccgaagaag catgcagcac 1860
caccaaaaaa aaaacgaaaa gtagaagacc cacgatttat gtacccatac gatgttcctg 1920
actatgcggg tatgaaaaac atcaaaaaaa accaggtaat gaacctgggt ccgaactcta 1980
aactgctgaa agaatacaaa tcccagctga tcgaactgaa catcgaacag ttcgaagcag 2040
gtatcggtct gatcctgggt gatgcttaca tccgttctcg tgatgaaggt aaaacctact 2100
gtatgcagtt cgagtggaaa aacaaagcat acatggacca cgtatgtctg ctgtacgatc 2160
agtgggtact gtccccgccg cacaaaaaag aacgtgttaa ccacctgggt aacctggtaa 2220
tcacctgggg cgcccagact ttcaaacacc aagctttcaa caaactggct aacctgttca 2280
tcgttaacaa caaaaaaacc atcccgaaca acctggttga aaactacctg accccgatgt 2340
ctctggcata ctggttcatg gatgatggtg gtaaatggga ttacaacaaa aactctacca 2400
acaaatcgat cgtactgaac acccagtctt tcactttcga agaagtagaa tacctggtta 2460
agggtctgcg taacaaattc caactgaact gttacgtaaa aatcaacaaa aacaaaccga 2520
tcatctacat cgattctatg tcttacctga tcttctacaa cctgatcaaa ccgtacctga 2580
tcccgcagat gatgtacaaa ctgccgaaca ctatctcctc cgaaactttc ctgaaataag 2640
gtaccgatcc agacatgata agatacattg atgagtttgg acaaaccaca actagaatgc 2700
agtgaaaaaa atgctttatt tgtgaaattt gtgatgctat tgctttattt gtaaccatta 2760
taagctgcaa taaacaagtt aacaacaaca attgcattca ttttatgttt caggttcagg 2820
gggaggtgtg ggaggttttt taaagcaagt aaaacctcta caaatgtggt atggctgatt 2880
atgatcatcg taaacttggt ctgacagtta ccaatgctta atcagtgagg cacctatctc 2940
agcgatctgt ctatttcgtt catccatagt tgcctgactc cccgtcgtgt agataactac 3000
gatacgggag ggcttaccat ctggccccag tgctgcaatg ataccgcgag acccacgctc 3060
accggctcca gatttatcag caataaacca gccagccgga agggccgagc gcagaagtgg 3120
tcctgcaact ttatccgcct ccatccagtc tattaattgt tgccgggaag ctagagtaag 3180
tagttcgcca gttaatagtt tgcgcaacgt tgttgccatt gctacaggca tcgtggtgtc 3240
acgctcgtcg tttggtatgg cttcattcag ctccggttcc caacgatcaa ggcgagttac 3300
atgatccccc atgttgtgca aaaaagcggt tagctccttc ggtcctccga tcgttgtcag 3360
aagtaagttg gccgcagtgt tatcactcat ggttatggca gcactgcata attctcttac 3420
tgtcatgcca tccgtaagat gcttttctgt gactggtgag tactcaacca agtcattctg 3480
agaatagtgt atgcggcgac cgagttgctc ttgcccggcg tcaatacggg ataataccgc 3540
gccacatagc agaactttaa aagtgctcat cattggaaaa cgttcttcgg ggcgaaaact 3600
ctcaaggatc ttaccgctgt tgagatccag ttcgatgtaa cccactcgtg cacccaactg 3660
atcttcagca tcttttactt tcaccagcgt ttctgggtga gcaaaaacag gaaggcaaaa 3720
tgccgcaaaa aagggaataa gggcgacacg gaaatgttga atactcatac tcttcctttt 3780
tcaatattat tgaagcattt atcagggtta ttgtctcatg agcggataca tatttgaatg 3840

-continued

```
tatttagaaa aataaacaaa taggggttcc gcgcacattt ccccgaaaag tgccacctga   3900
cgtctaagaa accattatta tcatgacatt aacctataaa aataggcgta tcacgaggcc   3960
ctttcgtctc gcgcgtttcg gtgatgacgg tgaaaacctc tgacacatgc agctcccgga   4020
gacggtcaca gcttgtctgt aagcggatgc cgggagcaga caagcccgtc agggcgcgtc   4080
agcgggtgtt ggcgggtgtc ggggctggct taactatgcg gcatcagagc agattgtact   4140
gagagtgcac catatgcggt gtgaaatacc gcacagatgc gtaaggagaa aataccgcat   4200
caggcgccat tcgccattca ggctgcgcaa ctgttgggaa gggcgatcgg tgcgggcctc   4260
ttcgctatta cgccagctgg cgaaaggggg atgtgctgca aggcgattaa gttgggtaac   4320
gccagggttt tcccagtcac gacgttgtaa aacgacggcc agtgaattac aactttgtac   4380
aaaaaagcag attaccctgt tatccctaca tcatcaataa tataccttat tttggattga   4440
agccaatatg ataatgaggg ggtggagttt gtgacgtggc gcggggcgtg ggaacggggc   4500
gggtgacgta gtagtgtggc ggaagtgtga tgttgcaagt gtggcggaac acatgtaagc   4560
gacggatgtg gcaaaagtga cgtttttggt gtgcgccggt gtacacagga agtgacaatt   4620
ttcgcgcggt tttaggcgga tgttgtagta aatttgggcg taaccgagta agatttggcc   4680
attttcgcgg gaaaactgaa taagaggaag tgaaatctga ataattttgt gttactcata   4740
gcgcgtaata tttgtctagg gccgcgggga ctttgaccgt ttacgtggag actcgcccag   4800
gtgtttttct caggtgtttt ccgcgttccg ggtcaaagtt ggcgttttat tattaaaccg   4860
tattaccgcc atgcatttaa tggagtgcct cgtgaggctc cggtgcccgt cagtgggcag   4920
agcgcacatc gcccacagtc cccgagaagt tggggggagg ggtcggcaat tgaaccggtg   4980
cctagagaag gtggcgcggg gtaaactggg aaagtgatgt cgtgtactgg ctccgccttt   5040
ttcccgaggg tgggggagaa ccgtatataa gtgcagtagt cgccgtgaac gttctttttc   5100
gcaacgggtt tgccgccaga acacaggtaa gtgccgtgtg tggttcccgc gggcctggcc   5160
tctttacggg ttatggccct tgcgtgcctt gaattacttc cacctggctg cagtacgtga   5220
ttcttgatcc cgagcttcgg gttggaagtg ggtgggagag ttcgaggcct tgcgcttaag   5280
gagccccttc gcctcgtgct tgagttgagg cctggcctgg gcgctggggc cgccgcgtgc   5340
gaatctggtg gcaccttcgc gcctgtctcg ctgctttcga taagtctcta gccatttaaa   5400
atttttgatg acctgctgcg acgctttttt tctggcaaga tagtcttgta aatgcgggcc   5460
aagatctgca cactggtatt tcggtttttg gggccgcggg cggcgacggg gcccgtgcgt   5520
cccagcgcac atgttcggcg aggcggggcc tgcgagcgcg gccaccgaga atcggacggg   5580
ggtagtctca agctggccgg cctgctctgg tgcctggcct cgcgccgccg tgtatcgccc   5640
cgccctgggc ggcaaggctg gcccggtcgg caccagttgc gtgagcggaa agatggccgc   5700
ttcccggccc tgctgcaggg agctcaaaat ggaggacgcg gcgctcggga gagcgggcgg   5760
gtgagtcacc cacacaaagg aaaagggcct ttccgtcctc agccgtcgct tcatgtgact   5820
ccacggagta ccgggcgccg tccaggcacc tcgattagtt ctcgagcttt tggagtacgt   5880
cgtctttagg ttggggggag gggttttatg cgatggagtt tccccacact gagtgggtgg   5940
agactgaagt taggccagct tggcacttga tgtaattctc cttggaattt gccctttttg   6000
agtttggatc ttggttcatt ctcaagcctc agacagtggt tcaaagtttt tttcttccat   6060
ttcaggtgtc gtgacgctag cgctaccgga ctcagatctc gagctcaagc ttcgaattct   6120
gcagcaccat ggactataaa gatgacgacg acaaggcttc gtaccccggc catcagcacg   6180
cgtctgcgtt cgaccaggct gcgcgttctc gcggccatag caaccgacgt acggcgttgc   6240
```

```
gccctcgccg gcagcaagaa gccacggaag tccgcccgga gcagaaaatg cccacgctac   6300
tgcgggttta tatagacggt ccccacggga tggggaaaac caccaccacg caactgctgg   6360
tggccctggg ttcgcgcgac gatatcgtct acgtacccga gccgatgact tactggcggg   6420
tgctgggggc ttccgagaca atcgcgaaca tctacaccac acaacaccgc cttgaccagg   6480
gtgagatatc ggccggggac gcggcggtgg taatgacaag cgcccagata acaatgggca   6540
tgccttatgc cgtgaccgac gccgttctgg ctcctcatat cggggggag gctgggagct    6600
cacatgcccc gcccccggcc ctcaccctca tcttcgaccg ccatcccatc gccgccctcc   6660
tgtgctaccc ggccgcgcga taccttatgg gcagcatgac cccccaggcc gtgctggcgt   6720
tcgtggccct catcccgccg accttgcccg gcacaaacat cgtgttgggg gcccttccgg   6780
aggacagaca catcgaccgc ctggccaaac gccagcgccc cggcgagcgg cttgacctgg   6840
ctatgctggc cgcgattcgc cgcgtttacg ggctgcttgc caatacggtg cggtatctgc   6900
agggcggcgg gtcgtggcgg gaggattggg gacagctttc ggggacggcc gtgccgcccc   6960
agggtgccga gccccagagc aacgcgggcc cacgacccca tatcggggac acgttattta   7020
ccctgtttcg ggcccccgag ttgctggccc ccaacggcga cctgtacaac gtgtttgcct   7080
gggccttgga cgtcttggcc aaacgcctcc gtcccatgca cgtctttatc ctggattacg   7140
accaatcgcc cgccggctgc cgggacgccc tgctgcaact tacctccggg atgatccaga   7200
cccacgtcac caccccaggc tccataccga cgatctgcga cctggcgcgc acgtttgccc   7260
gggagatggg ggaggctaac ggaagcggag ctactaactt cagcctgctg aagcaggctg   7320
gtgacgtcga ggagaatcct ggcccaatga cttcgaaagt ttatgatcca gaacaaagga   7380
aacggatgat aactggtccg cagtggtggg ccagatgtaa acaaatgaat gttcttgatt   7440
catttattaa ttattatgat tcagaaaaac atgcagaaaa tgctgttatt tttttacatg   7500
gtaacgcggc ctcttcttat ttatggcgac atgttgtgcc acatattgag ccagtagcgc   7560
ggtgtattat accagacctt attggtatgg gcaaatcagg caaatctggt aatggttctt   7620
ataggttact tgatcattac aaatatctta ctgcatggtt tgaacttctt aatttaccaa   7680
agaagatcat tttgtcggc catgattggg gtgcttgttt ggcatttcat tatagctatg    7740
agcatcaaga taagatcaaa gcaatagttc acgctgaaag tgtagtagat gtgattgaat   7800
catgggatga atggcctgat attgaagaag atattgcgtt gatcaaatct gaagaaggag   7860
aaaaaatggt tttggagaat aacttcttcg tggaaaccat gttgccatca aaaatcatga   7920
gaaagttaga accagaagaa tttgcagcat atcttgaacc attcaaagag aaaggtgaag   7980
ttcgtcgtcc aacattatca tggcctcgtg aaatcccgtt agtaaaaggt ggtaaacctg   8040
acgttgtaca aattgttagg aattataatg cttatctacg tgcaagtgat gatttaccaa   8100
aaatgtttat tgaatcggac ccaggattct tttccaatgc tattgttgaa ggtgccaaga   8160
agtttcctaa tactgaattt gtcaaagtaa aaggtcttca tttttcgcaa gaagatgcac   8220
ctgatgaaat gggaaaatat atcaaatcgt tcgttgagcg agttctcaaa aatgaacaat   8280
aaggagcgac tctagatcat aatcagccat accacatttg tagaggtttt acttgcttta   8340
aaaaacctcc cacacctccc cctgaacctg aaacataaaa tgaatgcaat tgttgttgtt   8400
aacttgttta ttgcagctta taatggttac aaataaagca atagcatcac aaatttcaca   8460
aataaagcat ttttttcact gcattctagt tgtggtttgt ccaaactcat caatgtaagt   8520
ttaaacggcg cgcctgaaat gtgtgggcgt ggcttaaggg tgggaaagaa tatataaggt   8580
```

-continued

```
gggggtctta tgtagttttg tatctgtttt gcagcagccg ccgccgccat gagcaccaac   8640
tcgtttgatg gaagcattgt gagctcatat ttgacaacgc gcatgccccc atgggccggg   8700
gtgcgtcaga atgtgatggg ctccagcatt gatggtcgcc ccgtcctgcc cgcaaactct   8760
actaccttga cctacgagac cgtgtctgga acgccgttgg agactgcagc ctccgccgcc   8820
gcttcagccg ctgcagccac cgcccgcggg attgtgactg actttgcttt cctgagcccg   8880
cttgcaagca gtgcagcttc ccgttcatcc gcccgcgatg acaagttgac ggctcttttg   8940
gcacaattgg attctttgac ccgggaactt aatgtcgttt ctcagcagct gttggatctg   9000
cgccagcagg tttctgccct gaaggcttcc tcccctccca atgcggttta aaacacaact   9060
tttctataca aagttgtaaa taaaaaacca gactctgttt ggatttggat caagctaagt   9120
gtcttgctgt ctttatttag gggttttgcg cgcgcggtag gcccgggacc agcggtctcg   9180
gtcgttgagg gtcctgtgta ttttttccag gacgtggtaa aggtgactct ggatgttcag   9240
atacatgggc ataagcccgt ctctggggtg gaggtagcac cactgcagag cttcatgctg   9300
cggggtggtg ttgtagatga tccagtcgta gcaggagcgc tgggcgtggt gcctaaaaat   9360
gtctttcagt agcaagctga ttgccagggg caggcccttg gtgtaagtgt ttacaaagcg   9420
gttaagctgg gatgggtgca tacgtgggga tatgagatgc atcttggact gtatttttag   9480
gttggctatg ttcccagcca tatccctccg gggattcatg ttgtgcagaa ccaccagcac   9540
agtgtatccg gtgcacttgg gaaatttgtc atgtagctta gaaggaaatg cgtggaagaa   9600
cttggagacg cccttgtgac ctccaagatt ttccatgcat tcgtccataa tgatggcaat   9660
gggcccacgg gcggcggcct gggcgaagat atttctggga tcactaacgt catagttgtg   9720
ttccaggatg agatcgtcat aggccatttt tacaaagcgc gggcggaggg tgccagactg   9780
cggtataatg gttccatccg gcccaggggc gtagttaccc tcacagattt gcatttccca   9840
cgctttgagt tcagatgggg ggatcatgtc tacctgcggg gcgatgaaga aaacggtttc   9900
cggggtaggg gagatcagct gggaagaaag caggttcctg agcagctgcg acttaccgca   9960
gccggtgggc ccgtaaatca cacctattac cggctgcaac tggtagttaa gagagctgca  10020
gctgccgtca tccctgagca ggggggccac ttcgttaagc atgtccctga ctcgcatgtt  10080
ttccctgacc aaatccgcca gaaggcgctc gccgcccagc gatagcagtt cttgcaagga  10140
agcaaagttt ttcaacggtt tgagaccgtc cgccgtaggc atgcttttga gcgtttgacc  10200
aagcagttcc aggcggtccc acagctcggt cacctgctct acggcatctc gatccagcat  10260
atctcctcgt ttcgcgggtt ggggcggctt tcgctgtacg gcagtagtcg gtgctcgtcc  10320
agacgggcca gggtcatgtc tttccacggg cgcagggtcc tcgtcagcgt agtctgggtc  10380
acggtgaagg ggtgcgctcc gggctgcgcg ctggccaggg tgcgcttgag gctggtcctg  10440
ctggtgctga agcgctgccg gtcttcgccc tgcgcgtcgg ccaggtagca tttgaccatg  10500
gtgtcatagt ccagcccctc cgcggcgtgg cccttggcgc gcagcttgcc cttggaggag  10560
gcgccgcacg aggggcagtg cagacttttg agggcgtaga gcttgggcgc gagaaatacc  10620
gattccgggg agtaggcatc cgcgccgcag gccccgcaga cggtctcgca ttccacgagc  10680
caggtgagct ctggccgttc ggggtcaaaa accaggtttc ccccatgctt tttgatgcgt  10740
ttcttacctc tggtttccat gagccggtgt ccacgctcgg tgacgaaaag gctgtccgtg  10800
tccccgtata cagacttgag aggcctgtcc tcgagcggtg ttccgcggtc ctcctcgtat  10860
agaaactcgg accactctga gacaaaggct cgcgtccagg ccagcacgaa ggaggctaag  10920
tgggaggggt agcggtcgtt gtccactagg gggtccactc gctccagggt gtgaagacac  10980
```

-continued atgtcgccct cttcggcatc aaggaaggtg attggtttgt aggtgtaggc cacgtgaccg 11040
ggtgttcctg aaggggggct ataaaagggg gtgggggcgc gttcgtcctc actctcttcc 11100
gcatcgctgt ctgcgagggc cagctgttgg ggtgagtact ccctctgaaa agcgggcatg 11160
acttctgcgc taagattgtc agtttccaaa aacgaggagg atttgatatt cacctggccc 11220
gcggtgatgc ctttgagggt ggccgcatcc atctggtcag aaaagacaat ctttttgttg 11280
tcaagcttgg tggcaaacga cccgtagagg gcgttggaca gcaacttggc gatggagcgc 11340
agggtttggt ttttgtcgcg atcggcgcgc tccttggccg cgatgtttag ctgcacgtat 11400
tcgcgcgcaa cgcaccgcca ttcgggaaag acggtggtgc gctcgtcggg caccaggtgc 11460
acgcgccaac cgcggttgtg cagggtgaca aggtcaacgc tggtggctac ctctccgcgt 11520
aggcgctcgt tggtccagca gaggcggccg cccttgcgcg agcagaatgg cggtaggggg 11580
tctagctgcg tctcgtccgg ggggtctgcg tccacggtaa agaccccggg cagcaggcgc 11640
gcgtcgaagt agtctatctt gcatccttgc aagtctagcg cctgctgcca tgcgcgggcg 11700
gcaagcgcgc gctcgtatgg gttgagtggg ggaccccatg gcatggggtg ggtgagcgcg 11760
gaggcgtaca tgccgcaaat gtcgtaaacg tagaggggct ctctgagtat tccaagatat 11820
gtagggtagc atcttccacc gcggatgctg gcgcgcacgt aatcgtatag ttcgtgcgag 11880
ggagcgagga ggtcgggacc gaggttgcta cgggcgggct gctctgctcg gaagactatc 11940
tgcctgaaga tggcatgtga gttggatgat atggttggac gctggaagac gttgaagctg 12000
gcgtctgtga gacctaccgc gtcacgcacg aaggaggcgt aggagtcgcg cagcttgttg 12060
accagctcgg cggtgacctg cacgtctagg gcgcagtagt ccagggtttc cttgatgatg 12120
tcatacttat cctgtccctt ttttttccac agctcgcggt tgaggacaaa ctcttcgcgg 12180
tctttccagt actcttggat cggaaacccg tcggcctccg aacggtaaga gcctagcatg 12240
tagaactggt tgacggcctg gtaggcgcag catccctttt ctacgggtag cgcgtatgcc 12300
tgcgcggcct tccggagcga ggtgtgggtg agcgcaaagg tgtccctgac catgactttg 12360
aggtactggt atttgaagtc agtgtcgtcg catccgccct gctcccagag caaaaagtcc 12420
gtgcgctttt tggaacgcgg atttggcagg gcgaaggtga catcgttgaa gagtatcttt 12480
cccgcgcgag gcataaagtt gcgtgtgatg cggaagggtc ccggcacctc ggaacggttg 12540
ttaattacct gggcggcgag cacgatctcg tcaaagccgt tgatgttgtg gcccacaatg 12600
taaagttcca agaagcgcgg gatgcccttg atggaaggca attttttaag ttcctcgtag 12660
gtgagctctt caggggagct gagcccgtgc tctgaaaggg cccagtctgc aagatgaggg 12720
ttggaagcga cgaatgagct ccacaggtca cgggccatta gcatttgcag gtggtcgcga 12780
aaggtcctaa actggcgacc tatggccatt ttttctgggg tgatgcagta gaaggtaagc 12840
gggtcttgtt cccagcggtc ccatccaagg ttcgcggcta ggtctcgcgc ggcagtcact 12900
agaggctcat ctccgccgaa cttcatgacc agcatgaagg gcacgagctg cttcccaaag 12960
gcccccatcc aagtataggt ctctacatcg taggtgacaa agagacgctc ggtgcgagga 13020
tgcgagccga tcgggaagaa ctggatctcc cgccaccaat tggaggagtg gctattgatg 13080
tggtgaaagt agaagtccct gcgacgggcc gaacactcgt gctggctttt gtaaaaacgt 13140
gcgcagtact ggcagcggtg cacgggctgt acatcctgca cgaggttgac ctgacgaccg 13200
cgcacaagga agcagagtgg gaatttgagc ccctcgcctg gcgggtttgg ctggtggtct 13260
tctacttcgg ctgcttgtcc ttgaccgtct ggctgctcga ggggagttac ggtggatcgg 13320

-continued

```
accaccacgc cgcgcgagcc caaagtccag atgtccgcgc gcggcggtcg gagcttgatg  13380
acaacatcgc gcagatggga gctgtccatg gtctggagct cccgcggcgt caggtcaggc  13440
gggagctcct gcaggtttac ctcgcataga cgggtcaggg cgcgggctag atccaggtga  13500
tacctaattt ccaggggctg gttggtggcg gcgtcgatgg cttgcaagag gccgcatccc  13560
cgcggcgcga ctacggtacc gcgcggcggg cggtgggccg cgggggtgtc cttggatgat  13620
gcatctaaaa gcggtgacgc gggcgagccc ccggaggtag ggggggctcc ggacccgccg  13680
ggagaggggg caggggcacg tcggcgccgc gcgcgggcag gagctggtgc tgcgcgcgta  13740
ggttgctggc gaacgcgacg acgcggcggt tgatctcctg aatctggcgc ctctgcgtga  13800
agacgacggg cccggtgagc ttgaacctga aagagagttc gacagaatca atttcggtgt  13860
cgttgacggc ggcctggcgc aaaatctcct gcacgtctcc tgagttgtct tgataggcga  13920
tctcggccat gaactgctcg atctcttcct cctggagatc tccgcgtccg gctcgctcca  13980
cggtggcggc gaggtcgttg gaaatgcggg ccatgagctg cgagaaggcg ttgaggcctc  14040
cctcgttcca gacgcggctg tagaccacgc cccttcggc atcgcgggcg cgcatgacca  14100
cctgcgcgag attgagctcc acgtgccggg cgaagacggc gtagtttcgc aggcgctgaa  14160
agaggtagtt gagggtggtg gcggtgtgtt ctgccacgaa gaagtacata acccagcgtc  14220
gcaacgtgga ttcgttgata tcccccaagg cctcaaggcg ctccatggcc tcgtagaagt  14280
ccacggcgaa gttgaaaaac tgggagttgc gcgccgacac ggttaactcc tcctccagaa  14340
gacggatgag ctcggcgaca gtgtcgcgca cctcgcgctc aaaggctaca ggggcctctt  14400
cttcttcttc aatctcctct tccataaggg cctccccttc ttcttcttct ggcggcggtg  14460
ggggaggggg gacacggcgg cgacgacggc gcaccgggag gcggtcgaca aagcgctcga  14520
tcatctcccc gcggcgacgg cgcatggtct cggtgacggc gcggccgttc tcgcgggggc  14580
gcagttggaa gacgccgccc gtcatgtccc ggttatgggt tggcgggggg ctgccatgcg  14640
gcagggatac ggcgctaacg atgcatctca acaattgttg tgtaggtact ccgccgccga  14700
gggacctgag cgagtccgca tcgaccggat cggaaaacct ctcgagaaag gcgtctaacc  14760
agtcacagtc gcaaggtagg ctgagcaccg tggcgggcgg cagcgggcgg cggtcggggt  14820
tgtttctggc ggaggtgctg ctgatgatgt aattaaagta ggcggtcttg agacggcgga  14880
tggtcgacag aagcaccatg tccttgggtc cggcctgctg aatgcgcagg cggtcggcca  14940
tgccccaggc ttcgttttga catcggcgca ggtctttgta gtagtcttgc atgagccttt  15000
ctaccggcac ttcttcttct ccttcctctt gtcctgcatc tcttgcatct atcgctgcgg  15060
cggcggcgga gtttggccgt aggtggcgcc ctcttcctcc catgcgtgtg accccgaagc  15120
ccctcatcgg ctgaagcagg gctaggtcgg cgacaacgcg ctcggctaat atggcctgct  15180
gcacctgcgt gagggtagac tggaagtcat ccatgtccac aaagcggtgg tatgcgcccg  15240
tgttgatggt gtaagtgcag ttggccataa cggaccagtt aacggtctgg tgacccggct  15300
gcgagagctc ggtgtacctg agacgcgagt aagccctcga gtcaaatacg tagtcgttgc  15360
aagtccgcac caggtactgg tatcccacca aaaagtgcgg cggcggctgg cggtagaggg  15420
gccagcgtag ggtggccggg gctccggggg cgagatcttc caacataagg cgatgatatc  15480
cgtagatgta cctggacatc caggtgatgc cggcggcggt ggtggaggcg cgcggaaagt  15540
cgcggacgcg gttccagatg ttgcgcagcg gcaaaaagtg ctccatggtc gggacgctct  15600
ggccggtcag gcgcgcgcaa tcgttgacgc tctagaccgt gcaaaaggag agcctgtaag  15660
cgggcactct tccgtggtct ggtggataaa ttcgcaaggg tatcatggcg gacgaccggg  15720
```

```
gttcgagccc cgtatccggc cgtccgccgt gatccatgcg gttaccgccc gcgtgtcgaa  15780
cccaggtgtg cgacgtcaga caacggggga gtgctccttt tggcttcctt ccaggcgcgg  15840
cggctgctgc gctagctttt ttggccactg gccgcgcgca gcgtaagcgg ttaggctgga  15900
aagcgaaagc attaagtggc tcgctccctg tagccggagg gttattttcc aagggttgag  15960
tcgcgggacc cccggttcga gtctcggacc ggccggactg cggcgaacgg gggtttgcct  16020
ccccgtcatg caagaccccg cttgcaaatt cctccggaaa cagggacgag ccccttttt  16080
gcttttccca gatgcatccg gtgctgcggc agatgcgccc ccctcctcag cagcggcaag  16140
agcaagagca gcggcagaca tgcagggcac cctcccctcc tcctaccgcg tcaggagggg  16200
cgacatccgc ggttgacgcg gcagcagatg gtgattacga acccccgcgg cgccgggccc  16260
ggcactacct ggacttggag gagggcgagg gcctggcgcg gctaggagcg ccctctcctg  16320
agcggcaccc aagggtgcag ctgaagcgtg atacgcgtga ggcgtacgtg ccgcggcaga  16380
acctgtttcg cgaccgcgag ggagaggagc ccgaggagat gcgggatcga aagttccacg  16440
cagggcgcga gctgcggcat ggcctgaatc gcgagcggtt gctgcgcgag gaggactttg  16500
agcccgacgc gcgaaccggg attagtcccg cgcgcgcaca cgtggcggcc gccgacctgg  16560
taaccgcata cgagcagacg gtgaaccagg agattaactt tcaaaaaagc tttaacaacc  16620
acgtgcgtac gcttgtggcg cgcgaggagg tggctatagg actgatgcat ctgtgggact  16680
ttgtaagcgc gctggagcaa aacccaaata gcaagccgct catggcgcag ctgttcctta  16740
tagtgcagca cagcagggac aacgaggcat tcagggatgc gctgctaaac atagtagagc  16800
ccgagggccg ctggctgctc gatttgataa acatcctgca gagcatagtg gtgcaggagc  16860
gcagcttgag cctggctgac aaggtggccg ccatcaacta ttccatgctt agcctgggca  16920
agttttacgc ccgcaagata taccataccc cttacgttcc catagacaag gaggtaaaga  16980
tcgaggggtt ctacatgcgc atggcgctga aggtgcttac cttgagcgac gacctgggcg  17040
tttatcgcaa cgagcgcatc cacaaggccg tgagcgtgag ccggcggcgc gagctcagcg  17100
accgcgagct gatgcacagc ctgcaaaggg ccctggctgg cacgggcagc ggcgatagag  17160
aggccgagtc ctactttgac gcgggcgctg acctgcgctg ggccccaagc cgacgcgccc  17220
tggaggcagc tggggccgga cctgggctgg cggtggcacc cgcgcgcgct ggcaacgtcg  17280
gcggcgtgga ggaatatgac gaggacgatg agtacgagcc agaggacggc gagtactaag  17340
cggtgatgtt tctgatcaga tgatgcaaga cgcaacggac ccggcggtgc gggcggcgct  17400
gcagagccag ccgtccggcc ttaactccac ggacgactgg cgccaggtca tggaccgcat  17460
catgtcgctg actgcgcgca atcctgacgc gttccggcag cagccgcagg ccaaccggct  17520
ctccgcaatt ctggaagcgg tggtcccggc gcgcgcaaac cccacgcacg agaaggtgct  17580
ggcgatcgta aacgcgctgg ccgaaaacag ggccatccgg cccgacgagg ccggcctggt  17640
ctacgacgcg ctgcttcagc gcgtggctcg ttacaacagc ggcaacgtgc agaccaacct  17700
ggaccggctg gtgggggatg tgcgcgaggc cgtggcgcag cgtgagcgcg cgcagcagca  17760
gggcaacctg ggctccatgg ttgcactaaa cgccttcctg agtacacagc ccgccaacgt  17820
gccgcgggga caggaggact acaccaactt tgtgagcgca ctgcggctaa tggtgactga  17880
gacaccgcaa agtgaggtgt accagtctgg gccagactat tttttccaga ccagtagaca  17940
aggcctgcag accgtaaacc tgagccaggc tttcaaaaac ttgcaggggc tgtgggggt  18000
gcgggctccc acaggcgacc gcgcgaccgt gtctagcttg ctgacgccca actcgcgcct  18060
```

-continued

```
gttgctgctg ctaatagcgc ccttcacgga cagtggcagc gtgtcccggg acacatacct  18120
aggtcacttg ctgacactgt accgcgaggc cataggtcag gcgcatgtgg acgagcatac  18180
tttccaggag attacaagtg tcagccgcgc gctggggcag gaggacacgg gcagcctgga  18240
ggcaacccta aactacctgc tgaccaaccg gcggcagaag atcccctcgt tgcacagttt  18300
aaacagcgag gaggagcgca ttttgcgcta cgtgcagcag agcgtgagcc ttaacctgat  18360
gcgcgacggg gtaacgccca gcgtggcgct ggacatgacc gcgcgcaaca tggaaccggg  18420
catgtatgcc tcaaaccggc cgtttatcaa ccgcctaatg gactacttgc atcgcgcggc  18480
cgccgtgaac cccgagtatt tcaccaatgc catcttgaac ccgcactggc taccgccccc  18540
tggtttctac accgggggat tcgaggtgcc cgagggtaac gatggattcc tctgggacga  18600
catagacgac agcgtgtttt ccccgcaacc gcagaccctg ctagagttgc aacagcgcga  18660
gcaggcagag gcggcgctgc gaaaggaaag cttccgcagg ccaagcagct tgtccgatct  18720
aggcgctgcg gccccgcggt cagatgctag tagcccattt ccaagcttga tagggtctct  18780
taccagcact cgcaccaccc gcccgcgcct gctgggcgag gaggagtacc taaacaactc  18840
gctgctgcag ccgcagcgcg aaaaaaacct gcctccggca tttcccaaca acgggataga  18900
gagcctagtg gacaagatga gtagatggaa gacgtacgcg caggagcaca gggacgtgcc  18960
aggcccgcgc ccgcccaccc gtcgtcaaag gcacgaccgt cagcggggtc tggtgtggga  19020
ggacgatgac tcggcagacg acagcagcgt cctggatttg ggagggagtg gcaacccgtt  19080
tgcgcacctt cgccccaggc tggggagaat gttttaaaaa aaaaaaaaaa gcatgatgca  19140
aaataaaaaa ctcaccaagg ccatggcacc gagcgttggt tttcttgtat tcccccttagt  19200
atgcggcgcg cggcgatgta tgaggaaggt cctcctccct cctacgagag tgtggtgagc  19260
gcggcgccag tggcggcggc gctgggttct cccttcgatg ctcccctgga cccgccgttt  19320
gtgcctccgc ggtacctgcg gcctaccggg gggagaaaca gcatccgtta ctctgagttg  19380
gcacccctat tcgacaccac ccgtgtgtac ctggtggaca acaagtcaac ggatgtggca  19440
tccctgaact accagaacga ccacagcaac tttctgacca cggtcattca aaacaatgac  19500
tacagcccgg gggaggcaag cacacagacc atcaatcttg acgaccggtc gcactggggc  19560
ggcgacctga aaaccatcct gcataccaac atgccaaatg tgaacgagtt catgtttacc  19620
aataagttta aggcgcgggt gatggtgtcg cgcttgccta ctaaggacaa tcaggtggag  19680
ctgaaatacg agtgggtgga gttcacgctg cccgagggca actactccga gaccatgacc  19740
atagacctta tgaacaacgc gatcgtggag cactacttga aagtgggcag acagaacggg  19800
gttctggaaa gcgacatcgg ggtaaagttt gacacccgca acttcagact ggggtttgac  19860
cccgtcactg gtcttgtcat gcctggggta tatacaaacg aagccttcca tccagacatc  19920
attttgctgc caggatgcgg ggtggacttc acccacagcc gcctgagcaa cttgttgggc  19980
atccgcaagc ggcaaccctt ccaggagggc tttaggatca cctacgatga tctggagggt  20040
ggtaacattc ccgcactgtt ggatgtggac gcctaccagg cgagcttgaa agatgacacc  20100
gaacagggcg ggggtggcgc aggcggcagc aacagcagtg gcagcggcgc ggaagagaac  20160
tccaacgcgg cagccgcggc aatgcagccg gtggaggaca tgaacgatca tgccattcgc  20220
ggcgacacct ttgccacacg ggctgaggag aagcgcgctg aggccgaagc agcggccgaa  20280
gctgccgccc ccgctgcgca acccgaggtc gagaagcctc agaagaaacc ggtgatcaaa  20340
cccctgacag aggacagcaa gaaacgcagt tacaacctaa taagcaatga cagcaccttc  20400
acccagtacc gcagctggta ccttgcatac aactacggcg accctcagac cggaatccgc  20460
```

```
tcatggaccc tgctttgcac tcctgacgta acctgcggct cggagcaggt ctactggtcg  20520
ttgccagaca tgatgcaaga ccccgtgacc ttccgctcca cgcgccagat cagcaacttt  20580
ccggtggtgg gcgccgagct gttgcccgtg cactccaaga gcttctacaa cgaccaggcc  20640
gtctactccc aactcatccg ccagtttacc tctctgaccc acgtgttcaa tcgctttccc  20700
gagaaccaga ttttggcgcg cccgccagcc cccaccatca ccaccgtcag tgaaaacgtt  20760
cctgctctca cagatcacgg gacgctaccg ctgcgcaaca gcatcggagg agtccagcga  20820
gtgaccatta ctgacgccag acgccgcacc tgcccctacg tttacaaggc cctgggcata  20880
gtctcgccgc gcgtcctatc gagccgcact ttttgagcaa gcatgtccat ccttatatcg  20940
cccagcaata acacaggctg gggcctgcgc ttcccaagca agatgtttgg cggggccaag  21000
aagcgctccg accaacaccc agtgcgcgtg cgcgggcact accgcgcgcc ctggggcgcg  21060
cacaaacgcg gccgcactgg gcgcaccacc gtcgatgacg ccatcgacgc ggtggtggag  21120
gaggcgcgca actacacgcc cacgccgcca ccagtgtcca cagtggacgc ggccattcag  21180
accgtggtgc gcggagcccg gcgctatgct aaaatgaaga gacggcggag gcgcgtagca  21240
cgtcgccacc gccgccgacc cggcactgcc gcccaacgcg cggcggcggc cctgcttaac  21300
cgcgcacgtc gcaccggccg acgggcggcc atgcgggccg ctcgaaggct ggccgcgggt  21360
attgtcactg tgccccccag gtccaggcga cgagcggccg ccgcagcagc cgcggccatt  21420
agtgctatga ctcagggtcg caggggcaac gtgtattggg tgcgcgactc ggttagcggc  21480
ctgcgcgtgc ccgtgcgcac ccgcccccccg cgcaactaga ttgcaagaaa aaactactta  21540
gactcgtact gttgtatgta tccagcggcg gcggcgcgca acgaagctat gtccaagcgc  21600
aaaatcaaag aagagatgct ccaggtcatc gcgccggaga tctatggccc cccgaagaag  21660
gaagagcagg attacaagcc ccgaaagcta aagcgggtca aaaagaaaaa gaaagatgat  21720
gatgatgaac ttgacgacga ggtggaactg ctgcacgcta ccgcgcccag gcgacgggta  21780
cagtggaaag gtcgacgcgt aaaacgtgtt ttgcgacccg gcaccaccgt agtctttacg  21840
cccggtgagc gctccacccg cacctacaag cgcgtgtatg atgaggtgta cggcgacgag  21900
gacctgcttg agcaggccaa cgagcgcctc ggggagtttg cctacggaaa gcggcataag  21960
gacatgctgg cgttgccgct ggacgagggc aacccaaacac ctagcctaaa gcccgtaaca  22020
ctgcagcagg tgctgcccgc gcttgcaccg tccgaagaaa agcgcggcct aaagcgcgag  22080
tctggtgact tggcacccac cgtgcagctg atggtaccca agcgccagcg actggaagat  22140
gtcttggaaa aaatgaccgt ggaacctggg ctggagcccg aggtccgcgt gcggccaatc  22200
aagcaggtgg cgccgggact gggcgtgcag accgtggacg ttcagatacc cactaccagt  22260
agcaccagta ttgccaccgc cacagagggc atggagacac aaacgtcccc ggttgcctca  22320
gcggtggcgg atgccgcggt gcaggcggtc gctgcggccg cgtccaagac ctctacggag  22380
gtgcaaacgg acccgtggat gtttcgcgtt tcagcccccc ggcgcccgcg ccgttcgagg  22440
aagtacggcg ccgccagcgc gctactgccc gaatatgccc tacatccttc cattgcgcct  22500
acccccggct atcgtggcta cacctaccgc cccagaagac gagcaactac ccgacgccga  22560
accaccactg gaacccgccg ccgccgtcgc cgtcgccagc ccgtgctggc cccgatttcc  22620
gtgcgcaggg tggctcgcga aggaggcagg accctggtgc tgccaacagc gcgctaccac  22680
cccagcatcg tttaaaagcc ggtctttgtg gttcttgcag atatggccct cacctgccgc  22740
ctccgtttcc cggtgccggg attccgagga agaatgcacc gtaggagggg catggccggc  22800
```

-continued

```
cacggcctga cgggcggcat gcgtcgtgcg caccaccggc ggcggcgcgc gtcgcaccgt  22860
cgcatgcgcg gcggtatcct gcccctcctt attccactga tcgccgcggc gattggcgcc  22920
gtgcccggaa ttgcatccgt ggccttgcag gcgcagagac actgattaaa aacaagttgc  22980
atgtggaaaa atcaaaataa aaagtctgga ctctcacgct cgcttggtcc tgtaactatt  23040
ttgtagaatg gaagacatca actttgcgtc tctggccccg cgacacggct cgcgcccgtt  23100
catgggaaac tggcaagata tcggcaccag caatatgagc ggtggcgcct tcagctgggg  23160
ctcgctgtgg agcggcatta aaaatttcgg ttccaccgtt aagaactatg gcagcaaggc  23220
ctggaacagc agcacaggcc agatgctgag ggataagttg aaagagcaaa atttccaaca  23280
aaaggtggta gatggcctgg cctctggcat tagcggggtg gtggacctgg ccaaccaggc  23340
agtgcaaaat aagattaaca gtaagcttga tccccgccct cccgtagagg agcctccacc  23400
ggccgtggag acagtgtctc cagaggggcg tggcgaaaag cgtccgcgcc ccgacaggga  23460
agaaactctg gtgacgcaaa tagacgagcc tccctcgtac gaggaggcac taaagcaagg  23520
cctgcccacc acccgtccca tcgcgcccat ggctaccgga gtgctgggcc agcacacacc  23580
cgtaacgctg gacctgcctc cccccgccga cacccagcag aaacctgtgc tgccaggccc  23640
gaccgccgtt gttgtaaccc gtcctagccg cgcgtccctg cgccgcgccg ccagcggtcc  23700
gcgatcgttg cggcccgtag ccagtggcaa ctggcaaagc acactgaaca gcatcgtggg  23760
tctgggggtg caatccctga agcgccgacg atgcttctga atagctaacg tgtcgtatgt  23820
gtgtcatgta tgcgtccatg tcgccgccag aggagctgct gagccgccgc gcgcccgctt  23880
tccaagatgg ctaccccttc gatgatgccg cagtggtctt acatgcacat ctcgggccag  23940
gacgcctcgg agtacctgag ccccgggctg gtgcagtttg cccgcgccac cgagacgtac  24000
ttcagcctga ataacaagtt tagaaacccc acggtggcgc ctacgcacga cgtgaccaca  24060
gaccggtccc agcgtttgac gctgcggttc atccctgtgg accgtgagga tactgcgtac  24120
tcgtacaagg cgcggttcac cctagctgtg ggtgataacc gtgtgctgga catggcttcc  24180
acgtactttg acatccgcgg cgtgctggac aggggcccta cttttaagcc ctactctggc  24240
actgcctaca acgccctggc tcccaagggt gccccaaatc cttgcgaatg ggatgaagct  24300
gctactgctc ttgaaataaa cctagaagaa gaggacgatg acaacgaaga cgaagtagac  24360
gagcaagctg agcagcaaaa aactcacgta tttgggcagg cgccttattc tggtataaat  24420
attacaaagg agggtattca aataggtgtc gaaggtcaaa cacctaaata tgccgataaa  24480
acatttcaac ctgaacctca aataggagaa tctcagtggt acgaaactga aattaatcat  24540
gcagctggga gagtccttaa aaagactacc ccaatgaaac catgttacgg ttcatatgca  24600
aaacccacaa atgaaaatgg agggcaaggc attcttgtaa agcaacaaaa tggaaagcta  24660
gaaagtcaag tggaaatgca atttttctca actactgagg cgaccgcagg caatggtgat  24720
aacttgactc ctaaagtggt attgtacagt gaagatgtag atatagaaac cccagacact  24780
catatttctt acatgcccac tattaaggaa ggtaactcac gagaactaat gggccaacaa  24840
tctatgccca acaggcctaa ttacattgct tttagggaca attttattgg tctaatgtat  24900
tacaacagca cgggtaatat gggtgttctg gcgggccaag catcgcagtt gaatgctgtt  24960
gtagatttgc aagacagaaa cacagagctt tcataccagc ttttgcttga ttccattggt  25020
gatagaacca ggtacttttc tatgtggaat caggctgttg acagctatga tccagatgtt  25080
agaattattg aaaatcatgg aactgaagat gaacttccaa attactgctt tccactggga  25140
ggtgtgatta atacagagac tcttaccaag gtaaaaccta aaacaggtca ggaaaatgga  25200
```

```
tgggaaaaag atgctacaga attttcagat aaaaatcaaa taagagttgg aaataatttt  25260
gccatggaaa tcaatctaaa tgccaacctg tggagaaatt tcctgtactc caacatagcg  25320
ctgtatttgc ccgacaagct aaagtacagt ccttccaacg taaaaatttc tgataaccca  25380
aacacctacg actacatgaa caagcgagtg gtggctcccg ggttagtgga ctgctacatt  25440
aaccttggag cacgctggtc ccttgactat atggacaacg tcaacccatt taaccaccac  25500
cgcaatgctg gcctgcgcta ccgctcaatg ttgctgggca atggtcgcta tgtgcccttc  25560
cacatccagg tgcctcagaa gttctttgcc attaaaaacc tccttctcct gccgggctca  25620
tacacctacg agtggaactt caggaaggat gttaacatgg ttctgcagag ctccctagga  25680
aatgacctaa gggttgacgg agccagcatt aagtttgata gcatttgcct ttacgccacc  25740
ttcttcccca tggcccacaa caccgcctcc acgcttgagg ccatgcttag aaacgacacc  25800
aacgaccagt cctttaacga ctatctctcc gccgccaaca tgctctaccc tatacccgcc  25860
aacgctacca acgtgcccat atccatcccc tcccgcaact gggcggcttt ccgcggctgg  25920
gccttcacgc gccttaagac taaggaaacc ccatcactgg gctcgggcta cgacccttat  25980
tacacctact ctggctctat accctaccta gatggaacct tttacctcaa ccacaccttt  26040
aagaaggtgg ccattacctt tgactcttct gtcagctggc ctggcaatga ccgcctgctt  26100
acccccaacg agtttgaaat taagcgctca gttgacgggg agggttacaa cgttgcccag  26160
tgtaacatga ccaaagactg gttcctggta caaatgctag ctaactacaa cattggctac  26220
cagggcttct atatcccaga gagctacaag gaccgcatgt actccttctt tagaaacttc  26280
cagcccatga gccgtcaggt ggtggatgat actaaataca aggactacca acaggtgggc  26340
atcctacacc aacacaacaa ctctggattt gttggctacc ttgcccccac catgcgcgaa  26400
ggacaggcct accctgctaa cttcccctat ccgcttatag gcaagaccgc agttgacagc  26460
attacccaga aaaagtttct ttgcgatcgc accctttggc gcatcccatt ctccagtaac  26520
tttatgtcca tgggcgcact cacagacctg ggccaaaacc ttctctacgc caactccgcc  26580
cacgcgctag acatgacttt tgaggtggat cccatggacg agcccaccct tctttatgtt  26640
ttgtttgaag tctttgacgt ggtccgtgtg caccggccgc accgcggcgt catcgaaacc  26700
gtgtacctgc gcacgccctt ctcggccggc aacgccacaa cataaagaag caagcaacat  26760
caacaacagc tgccgccatg ggctccagtg agcaggaact gaaagccatt gtcaaagatc  26820
ttggttgtgg gccatatttt ttgggcacct atgacaagcg ctttccaggc tttgtttctc  26880
cacacaagct cgcctgcgcc atagtcaata cggccggtcg cgagactggg ggcgtacact  26940
ggatggcctt tgcctggaac ccgcactcaa aaacatgcta cctctttgag ccctttggct  27000
tttctgacca gcgactcaag caggtttacc agtttgagta cgagtcactc ctgcgccgta  27060
gcgccattgc ttcttccccc gaccgctgta taacgctgga aaagtccacc caaagcgtac  27120
aggggcccaa ctcggccgcc tgtggactat tctgctgcat gtttctccac gcctttgcca  27180
actggcccca aactcccatg gatcacaacc ccaccatgaa ccttattacc ggggtaccca  27240
actccatgct caacagtccc caggtacagc ccaccctgcg tcgcaaccag gaacagctct  27300
acagcttcct ggagcgccac tcgccctact tccgcagcca cagtgcgcag attaggagcg  27360
ccacttcttt ttgtcacttg aaaaacatgt aaaaataatg tactagagac actttcaata  27420
aaggcaaatg cttttatttg tacactctcg ggtgattatt tacccccacc cttgccgtct  27480
gcgccgttta aaaatcaaag ggttctgccg cgcatcgct atgcgccact ggcagggaca  27540
```

-continued

```
cgttgcgata ctggtgttta gtgctccact taaactcagg cacaaccatc cgcggcagct  27600
cggtgaagtt ttcactccac aggctgcgca ccatcaccaa cgcgtttagc aggtcgggcg  27660
ccgatatctt gaagtcgcag ttggggcctc cgccctgcgc gcgcgagttg cgatacacag  27720
ggttgcagca ctggaacact atcagcgccg ggtggtgcac gctggccagc acgctcttgt  27780
cggagatcag atccgcgtcc aggtcctccg cgttgctcag ggcgaacgga gtcaactttg  27840
gtagctgcct tcccaaaaag ggcgcgtgcc caggctttga gttgcactcg caccgtagtg  27900
gcatcaaaag gtgaccgtgc ccggtctggg cgttaggata cagcgcctgc ataaaagcct  27960
tgatctgctt aaaagccacc tgagcctttg cgccttcaga gaagaacatg ccgcaagact  28020
tgccggaaaa ctgattggcc ggacaggccg cgtcgtgcac gcagcacctt gcgtcggtgt  28080
tggagatctg caccacattt cggccccacc ggttcttcac gatcttggcc ttgctagact  28140
gctccttcag cgcgcgctgc ccgttttcgc tcgtcacatc catttcaatc acgtgctcct  28200
tatttatcat aatgcttccg tgtagacact taagctcgcc ttcgatctca gcgcagcggt  28260
gcagccacaa cgcgcagccc gtgggctcgt gatgcttgta ggtcacctct gcaaacgact  28320
gcaggtacgc ctgcaggaat cgccccatca tcgtcacaaa ggtcttgttg ctggtgaagg  28380
tcagctgcaa cccgcggtgc tcctcgttca gccaggtctt gcatacggcc gccagagctt  28440
ccacttggtc aggcagtagt ttgaagttcg cctttagatc gttatccacg tggtacttgt  28500
ccatcagcgc gcgcgcagcc tccatgccct tctcccacgc agacacgatc ggcacactca  28560
gcgggttcat caccgtaatt tcactttccg cttcgctggg ctcttcctct tcctcttgcg  28620
tccgcatacc acgcgccact gggtcgtctt cattcagccg ccgcactgtg cgcttacctc  28680
ctttgccatg cttgattagc accggtgggt tgctgaaacc caccatttgt agcgccacat  28740
cttctctttc ttcctcgctg tccacgatta cctctggtga tggcgggcgc tcgggcttgg  28800
gagaagggcg cttctttttc ttcttgggcg caatggccaa atccgccgcc gaggtcgatg  28860
gccgcgggct gggtgtgcgc ggcaccagcg cgtcttgtga tgagtcttcc tcgtcctcgg  28920
actcgatacg ccgcctcatc cgcttttttg ggggcgcccg gggaggcggc ggcgacgggg  28980
acggggacga cacgtcctcc atggttgggg gacgtcgcgc cgcaccgcgt ccgcgctcgg  29040
gggtggtttc gcgctgctcc tcttcccgac tggccatttc cttctcctat aggcagaaaa  29100
agatcatgga gtcagtcgag aagaaggaca gcctaaccgc cccctctgag ttcgccacca  29160
ccgcctccac cgatgccgcc aacgcgccta ccaccttccc cgtcgaggca cccccgcttg  29220
aggaggagga agtgattatc gagcaggacc caggttttgt aagcgaagac gacgaggacc  29280
gctcagtacc aacagaggat aaaaagcaag accaggacaa cgcagaggca aacgaggaac  29340
aagtcgggcg gggggacgaa aggcatggcg actacctaga tgtgggagac gacgtgctgt  29400
tgaagcatct gcagcgccag tgcgccatta tctgcgacgc gttgcaagag cgcagcgatg  29460
tgcccctcgc catagcggat gtcagccttg cctacgaacg ccacctattc tcaccgcgcg  29520
tacccccaa acgccaagaa aacggcacat gcgagcccaa cccgcgcctc aacttctacc  29580
ccgtatttgc cgtgccagag gtgcttgcca cctatcacat ctttttccaa aactgcaaga  29640
taccctatc ctgccgtgcc aaccgcagcc gagcggacaa gcagctggcc ttgcggcagg  29700
gcgctgtcat acctgatatc gcctcgctca acgaagtgcc aaaaatcttt gagggtcttg  29760
gacgcgacga gaagcgcgcg gcaaacgctc tgcaacagga aaacagcgaa aatgaaagtc  29820
actctggagt gttggtggaa ctcgagggtg acaacgcgcg cctagccgta ctaaaacgca  29880
gcatcgaggt cacccacttt gcctacccgg cacttaacct accccccaag gtcatgagca  29940
```

```
cagtcatgag tgagctgatc gtgcgccgtg cgcagcccct ggagagggat gcaaatttgc  30000
aagaacaaac agaggagggc ctacccgcag ttggcgacga gcagctagcg cgctggcttc  30060
aaacgcgcga gcctgccgac ttggaggagc gacgcaaact aatgatggcc gcagtgctcg  30120
ttaccgtgga gcttgagtgc atgcagcggt tctttgctga cccggagatg cagcgcaagc  30180
tagaggaaac attgcactac acctttcgac agggctacgt acgccaggcc tgcaagatct  30240
ccaacgtgga gctctgcaac ctggtctcct accttggaat tttgcacgaa aaccgccttg  30300
ggcaaaacgt gcttcattcc acgctcaagg gcgaggcgcg ccgcgactac gtccgcgact  30360
gcgtttactt atttctatgc tacacctggc agacggccat gggcgtttgg cagcagtgct  30420
tggaggagtg caacctcaag gagctgcaga aactgctaaa gcaaaacttg aaggacctat  30480
ggacggcctt caacgagcgc tccgtggccg cgcacctggc ggacatcatt ttccccgaac  30540
gcctgcttaa aaccctgcaa cagggtctgc cagacttcac cagtcaaagc atgttgcaga  30600
actttaggaa ctttatccta gagcgctcag gaatcttgcc cgccacctgc tgtgcacttc  30660
ctagcgactt tgtgcccatt aagtaccgcg aatgccctcc gccgctttgg ggccactgct  30720
accttctgca gctagccaac taccttgcct accactctga cataatggaa gacgtgagcg  30780
gtgacggtct actggagtgt cactgtcgct gcaacctatg caccccgcac cgctccctgg  30840
tttgcaattc gcagctgctt aacgaaagtc aaattatcgg tacctttgag ctgcagggtc  30900
cctcgcctga cgaaaagtcc gcggctccgg ggttgaaact cactccgggg ctgtggacgt  30960
cggcttacct tcgcaaattt gtacctgagg actaccacgc ccacgagatt aggttctacg  31020
aagaccaatc ccgcccgcca aatgcggagc ttaccgcctg cgtcattacc cagggccaca  31080
ttcttggcca attgcaagcc atcaacaaag cccgccaaga gtttctgcta cgaaagggac  31140
gggggggtta cttggacccc cagtccggcg aggagctcaa cccaatcccc ccgccgccgc  31200
agccctatca gcagcagccg cgggcccttg cttcccagga tggcacccaa aaagaagctg  31260
cagctgccgc cgccacccac ggacgaggag gaatactggg acagtcaggc agaggaggtt  31320
ttggacgagg aggaggagga catgatggaa gactgggaga gcctagacga ggaagcttcc  31380
gaggtcgaag aggtgtcaga cgaaacaccg tcaccctcgg tcgcattccc ctcgccggcg  31440
ccccagaaat cggcaaccgg ttccagcatg gctacaacct ccgctcctca ggcgccgccg  31500
gcactgcccg ttcgccgacc caaccgtaga tgggacacca ctggaaccag ggccggtaag  31560
tccaagcagc cgccgccgtt agcccaagag caacaacagc gccaaggcta ccgctcatgg  31620
cgcgggcaca agaacgccat agttgcttgc ttgcaagact gtgggggcaa catctccttc  31680
gcccgccgct ttcttctcta ccatcacggc gtggccttcc cccgtaacat cctgcattac  31740
taccgtcatc tctacagccc atactgcacc ggcggcagcg gcagcggcag caacagcagc  31800
ggccacacag aagcaaaggc gaccggatag caagactctg acaaagccca agaaatccac  31860
agcggcggca gcagcaggag gaggagcgct gcgtctggcg cccaacgaac ccgtatcgac  31920
ccgcgagctt agaaacagga tttttcccac tctgtatgct atatttcaac agagcagggg  31980
ccaagaacaa gagctgaaaa taaaaaacag gtctctgcga tccctcaccc gcagctgcct  32040
gtatcacaaa agcgaagatc agcttcggcg cacgctggaa gacgcggagg ctctcttcag  32100
taaatactgc gcgctgactc ttaaggacta gtttcgcgcc ctttctcaaa tttaagcgcg  32160
aaaactacgt catctccagc ggccacaccc ggcgccagca cctgtcgtca gcgccatttc  32220
aactttgtat acaaaagttg tgatgagcaa ggaaattccc acgccctaca tgtggagtta  32280
```

-continued

```
ccagccacaa atgggacttg cggctggagc tgcccaagac tactcaaccc gaataaacta  32340
catgagcgcg ggaccccaca tgatatcccg ggtcaacgga atacgcgccc accgaaaccg  32400
aattctcctg gaacaggcgg ctattaccac cacacctcgt aataacctta atccccgtag  32460
ttggcccgct gccctggtgt accaggaaag tcccgctccc accactgtgg tacttcccag  32520
agacgcccag gccgaagttc agatgactaa ctcaggggcg cagcttgcgg gcggctttcg  32580
tcacagggtg cggtcgcccg ggcagggtat aactcacctg acaatcagag ggcgaggtat  32640
tcagctcaac gacgagtcgg tgagctcctc gcttggtctc cgtccggacg ggacatttca  32700
gatcggcggc gccggccgct cttcattcac gcctcgtcag gcaatcctaa ctctgcagac  32760
ctcgtcctct gagccgcgct ctggaggcat tggaactctg caatttattg aggagtttgt  32820
gccatcggtc tactttaacc ccttctcggg acctcccggc cactatccgg atcaatttat  32880
tcctaacttt gacgcggtaa aggactcggc ggacggctac gactgaatgt taagtggaga  32940
ggcagagcaa ctgcgcctga aacacctggt ccactgtcgc cgccacaagt gctttgcccg  33000
cgactccggt gagttttgct actttgaatt gcccgaggat catatcgagg gcccggcgca  33060
cggcgtccgg cttaccgccc agggagagct tgcccgtagc ctgattcggg agtttaccca  33120
gcgcccccctg ctagttgagc gggacagggg accctgtgtt ctcactgtga tttgcaactg  33180
tcctaaccct ggattacatc aagatctttg ttgccatctc tgtgctgagt ataataaata  33240
cagaaattaa aatatactgg ggctcctatc gccatcctgt aaacgccacc gtcttcaccc  33300
gcccaagcaa accaaggcga accttacctg gtacttttaa catctctccc tctgtgattt  33360
acaacagttt caacccagac ggagtgagtc tacgagagaa cctctccgag ctcagctact  33420
ccatcagaaa aaacaccacc ctccttacct gccgggaacg tacgagtgcg tcaccggccg  33480
ctgcaccaca cctaccgcct gaccgtaaac cagacttttt ccggacagac ctcaataact  33540
ctgtttacca gaacaggagg tgagcttaga aaacccttag ggtattaggc caaaggcgca  33600
gctactgtgg ggtttatgaa caattcaagc aactctacgg gctattctaa ttcaggtttc  33660
tctagaatcg ggttggggt tattctctgt cttgtgattc tctttattct tatactaacg  33720
cttctctgcc taaggctcgc cgcctgctgt gtgcacattt gcatttattg tcagcttttt  33780
aaacgctggg gtcgccaccc aagatgatta ggtacataat cctaggttta ctcacccttg  33840
cgtcagccca cggtaccacc caaaaggtgg attttaagga gccagcctgt aatgttacat  33900
tcgcagctga agctaatgag tgcaccactc ttataaaatg caccacagaa catgaaaagc  33960
tgcttattcg ccacaaaaac aaaattggca agtatgctgt ttatgctatt tggcagccag  34020
gtgacactac agagtataat gttacagttt tccagggtaa aagtcataaa acttttatgt  34080
atacttttcc attttatgaa atgtgcgaca ttaccatgta catgagcaaa cagtataagt  34140
tgtggccccc acaaaattgt gtggaaaaca ctggcacttt ctgctgcact gctatgctaa  34200
ttacagtgct cgctttggtc tgtaccctac tctatattaa atacaaaagc agacgcagct  34260
ttattgagga aaagaaaatg ccttaattta ctaagttaca aagctaatgt caccactaac  34320
tgctttactc gctgcttgca aaacaaattc aaaaagttag cattataatt agaataggat  34380
ttaaaccccc cggtcatttc ctgctcaata ccattcccct gaacaattga ctctatgtgg  34440
gatatgctcc agcgctacaa ccttgaagtc aggcttcctg gatgtcagca tctgactttg  34500
gccagcacct gtcccgcgga tttgttccag tccaactaca gcgacccacc ctaacagaga  34560
tgaccaacac aaccaacgcg gccgccgcta ccggacttac atctaccaca aatacacccc  34620
aagtttctgc ctttgtcaat aactgggata acttgggcat gtggtggttc tccatagcgc  34680
```

```
ttatgtttgt atgccttatt attatgtggc tcatctgctg cctaaagcgc aaacgcgccc  34740
gaccacccat ctatagtccc atcattgtgc tacacccaaa caatgatgga atccatagat  34800
tggacggact gaaacacatg ttcttttctc ttacagtatg attaaatgag acatgattcc  34860
tcgagttttt atattactga cccttgttgc gctttttgt gcgtgctcca cattggctgc  34920
ggtttctcac atcgaagtag actgcattcc agccttcaca gtctatttgc tttacggatt  34980
tgtcaccctc acgctcatct gcagcctcat cactgtggtc atcgccttta tccagtgcat  35040
tgactgggtc tgtgtgcgct ttgcatatct cagacaccat ccccagtaca gggacaggac  35100
tatagctgag cttcttagaa ttctttaatt atgaaattta ctgtgacttt tctgctgatt  35160
atttgcaccc tatctgcgtt ttgttccccg acctccaagc ctcaaagaca tatatcatgc  35220
agattcactc gtatatggaa tattccaagt tgctacaatg aaaaaagcga tctttccgaa  35280
gcctggttat atgcaatcat ctctgttatg gtgttctgca gtaccatctt agccctagct  35340
atatatccct accttgacat tggctggaac gcaatagatg ccatgaacca cccaactttc  35400
cccgcgcccg ctatgcttcc actgcaacaa gttgttgccg gcggctttgt cccagccaat  35460
cagcctcgcc caccttctcc cacccccact gaaatcagct actttaatct aacaggagga  35520
gatgactgac accctagatc tagaaatgga cggaattatt acagagcagc gcctgctaga  35580
aagacgcagg gcagcggccg agcaacagcg catgaatcaa gagctccaag acatggttaa  35640
cttgcaccag tgcaaaaggg gtatcttttg tctggtaaag caggccaaag tcacctacga  35700
cagtaatacc accggacacc gccttagcta caagttgcca accaagcgtc agaaattggt  35760
ggtcatggtg ggagaaaagc ccattaccat aactcagcac tcggtagaaa ccgaaggctg  35820
cattcactca ccttgtcaag gacctgagga tctctgcacc cttattaaga ccctgtgcgg  35880
tctcaaagat cttattccct ttaactaata aaaaaaaata ataaagcatc acttacttaa  35940
aatcagttag caaatttctg tccagtttat tcagcagcac ctccttgccc tcctcccagc  36000
tctggtattg cagcttcctc ctggctgcaa actttctcca caatctaaat ggaatgtcag  36060
tttcctcctg ttcctgtcca tccgcaccca ctatcttcat gttgttgcag atgaagcgcg  36120
caagaccgtc tgaagatacc ttcaaccccg tgtatccata tgacacggaa accggtcctc  36180
caactgtgcc ttttcttact cctccctttg tatcccccaa tgggtttcaa gagagtcccc  36240
ctggggtact ctctttgcgc ctatccgaac ctctagttac ctccaatggc atgcttgcgc  36300
tcaaaatggg caacggcctc tctctggacg aggccggcaa ccttacctcc caaaatgtaa  36360
ccactgtgag cccacctctc aaaaaaacca agtcaaacat aaacctggaa atatctgcac  36420
ccctcacagt tacctcagaa gccctaactg tggctgccgc cgcacctcta atggtcgcgg  36480
gcaacacact caccatgcaa tcacaggccc cgctaaccgt gcacgactcc aaacttagca  36540
ttgccaccca aggacccctc acagtgtcag aaggaaagct agccctgcaa acatcaggcc  36600
ccctcaccac caccgatagc agtaccctta ctatcactgc ctcacccccct ctaactactg  36660
ccactggtag cttgggcatt gacttgaaag agcccattta tacacaaaat ggaaaactag  36720
gactaaagta cggggctcct ttgcatgtaa cagacgacct aaacactttg accgtagcaa  36780
ctggtccagg tgtgactatt aataatactt ccttgcaaac taaagttact ggagccttgg  36840
gttttgattc acaaggcaat atgcaactta atgtagcagg aggactaagg attgattctc  36900
aaaacagacg ccttatactt gatgttagtt atccgtttga tgctcaaaac caactaaatc  36960
taagactagg acagggccct ctttttataa actcagccca caacttggat attaactaca  37020
```

-continued

```
acaaaggcct ttacttgttt acagcttcaa acaattccaa aaagcttgag gttaacctaa  37080
gcactgccaa ggggttgatg tttgacgcta cagccatagc cattaatgca ggagatgggc  37140
ttgaatttgg ttcacctaat gcaccaaaca caaatcccct caaaacaaaa attggccatg  37200
gcctagaatt tgattcaaac aaggctatgg ttcctaaact aggaactggc cttagttttg  37260
acagcacagg tgccattaca gtaggaaaca aaaataatga taagctaact ttatggactg  37320
gaataaaccc tccacctaac tgtcaaattg tggaaaacac taatacaaat gatggcaaac  37380
ttactttagt attagtaaaa aacggagggc ttgttaatgg ctacgtgtct ctagttggtg  37440
tatcagacac tgtgaaccaa atgttcacac aaaagacagc aaacatccaa ttaagattat  37500
attttgactc ttctggaaat ctattaactg atgaatcaga cttaaaaatt ccacttaaaa  37560
ataaatcttc tacagcgacc agtgaaactg tagccagcag caaagccttt atgccaagta  37620
ctacagctta tcccttcaac accactacta gggatagtga aaactacatt catggaatat  37680
gttactacat gactagttat gatagaagtc tatttccctt gaacatttct ataatgctaa  37740
acagccgtat gatttcttcc aatgttgcct atgccataca atttgaatgg aatctaaatg  37800
caagtgaatc tccagaaagc aacatagcta cgctgaccac atcccccttt ttcttttctt  37860
acattacaga agacgacaac taataaagaa tcgtttgtgt tatgtttcaa cgtgtttatt  37920
tttcaattgc agaaaatttc aagtcatttt tcattcagta gtatagcccc accaccacat  37980
agcttataca gatcaccgta cctcaacttt gtataataaa gttgtaatca aactcacaga  38040
accctagtat tcaacctgcc acctccctcc caacacacag agtacacagt cctttctccc  38100
cggctggcct taaaaagcat catatcatgg gtaacagaca tattcttagg tgttatattc  38160
cacacggttt cctgtcgagc caaacgctca tcagtgatat taataaactc cccgggcagc  38220
tcacttaagt tcatgtcgct gtccagctgc tgagccacag gctgctgtcc aacttgcggt  38280
tgcttaacgg gcggcgaagg agaagtccac gcctacatgg gggtagagtc ataatcgtgc  38340
atcaggatag ggcggtggtg ctgcagcagc gcgcgaataa actgctgccg ccgccgctcc  38400
gtcctgcagg aatacaacat ggcagtggtc tcctcagcga tgattcgcac cgcccgcagc  38460
ataaggcgcc ttgtcctccg ggcacagcag cgcaccctga tctcacttaa atcagcacag  38520
taactgcagc acagcaccac aatattgttc aaaatcccac agtgcaaggc gctgtatcca  38580
aagctcatgg cggggaccac agaacccacg tggccatcat accacaagcg caggtagatt  38640
aagtggcgac ccctcataaa cacgctggac ataaacatta cctcttttgg catgttgtaa  38700
ttcaccacct cccggtacca tataaacctc tgattaaaca tggcgccatc caccaccatc  38760
ctaaaccagc tggccaaaac ctgcccgccg gctatacact gcagggaacc gggactggaa  38820
caatgacagt ggagagccca ggactcgtaa ccatggatca tcatgctcgt catgatatca  38880
atgttggcac aacacaggca cacgtgcata cacttcctca ggattacaag ctcctcccgc  38940
gttagaacca tatcccaggg aacaacccat tcctgaatca gcgtaaatcc cacactgcag  39000
ggaagacctc gcacgtaact cacgttgtgc attgtcaaag tgttacattc gggcagcagc  39060
ggatgatcct ccagtatggt agcgcgggtt tctgtctcaa aaggaggtag acgatcccta  39120
ctgtacggag tgcgccgaga caaccgagat cgtgttggtc gtagtgtcat gccaaatgga  39180
acgccggacg tagtcatatt tcctgaagca aaaccaggtg cgggcgtgac aaacagatct  39240
gcgtctccgg tctcgccgct tagatcgctc tgtgtagtag ttgtagtata tccactctct  39300
caaagcatcc aggcgccccc tggcttcggg ttctatgtaa actccttcat gcgccgctgc  39360
cctgataaca tccaccaccg cagaataagc cacacccagc caacctacac attcgttctg  39420
```

```
cgagtcacac acgggaggag cgggaagagc tggaagaacc atgttttttt ttttattcca  39480

aaagattatc caaaacctca aaatgaagat ctattaagtg aacgcgctcc cctccggtgg  39540

cgtggtcaaa ctctacagcc aaagaacaga taatggcatt tgtaagatgt tgcacaatgg  39600

cttccaaaag gcaaacggcc ctcacgtcca agtggacgta aaggctaaac ccttcagggt  39660

gaatctcctc tataaacatt ccagcacctt caaccatgcc caaataattc tcatctcgcc  39720

accttctcaa tatatctcta agcaaatccc gaatattaag tccggccatt gtaaaaatct  39780

gctccagagc gccctccacc ttcagcctca agcagcgaat catgattgca aaaattcagg  39840

ttcctcacag acctgtataa gattcaaaag cggaacatta acaaaaatac cgcgatcccg  39900

taggtccctt cgcagggcca gctgaacata atcgtgcagg tctgcacgga ccagcgcggc  39960

cacttccccg ccaggaacca tgacaaaaga acccacactg attatgacac gcatactcgg  40020

agctatgcta accagcgtag ccccgatgta agcttgttgc atgggcggcg atataaaatg  40080

caaggtgctg ctcaaaaaat caggcaaagc ctcgcgcaaa aaagaaagca catcgtagtc  40140

atgctcatgc agataaaggc aggtaagctc cggaaccacc acagaaaaag acaccatttt  40200

tctctcaaac atgtctgcgg gtttctgcat aaacacaaaa taaaataaca aaaaaacatt  40260

taaacattag aagcctgtct tacaacagga aaaacaaccc ttataagcat aagacggact  40320

acggccatgc cggcgtgacc gtaaaaaaac tggtcaccgt gattaaaaag caccaccgac  40380

agctcctcgg tcatgtccgg agtcataatg taagactcgg taaacacatc aggttgattc  40440

acatcggtca gtgctaaaaa gcgaccgaaa tagcccgggg gaatacatac ccgcaggcgt  40500

agagacaaca ttacagcccc cataggaggt ataacaaaat taataggaga gaaaaacaca  40560

taaacacctg aaaaaccctc ctgcctaggc aaaatagcac cctcccgctc cagaacaaca  40620

tacagcgctt ccacagcggc agccataaca gtcagcctta ccagtaaaaa agaaaaccta  40680

ttaaaaaaac accactcgac acggcaccag ctcaatcagt cacagtgtaa aaaagggcca  40740

agtgcagagc gagtatatat aggactaaaa aatgacgtaa cggttaaagt ccacaaaaaa  40800

cacccagaaa accgcacgcg aacctacgcc cagaaacgaa agccaaaaaa cccacaactt  40860

cctcaaatcg tcacttccgt tttcccacgt tacgtcactt cccattttaa gaaaactaca  40920

attcccaaca catacaagtt actccgccct aaaacctacg tcacccgccc cgttcccacg  40980

ccccgcgcca cgtcacaaac tccaccccct cattatcata ttggcttcaa tccaaaataa  41040

ggtatattat tgatgatgta gggataacag ggtaatcagc tttcttgtac aaagttgaaa  41100

tccggggatc ctctagagtc gacctgcagg catgcaagct tggcgtaatc atggtcatag  41160

ctgtttcctg tgtgaaattg ttatccgctc acaattccac acaacatacg agccggaagc  41220

ataaagtgta aagcctgggg tgcctaatga gtgagcta                          41258
```

<210> SEQ ID NO 6
<211> LENGTH: 41228
<212> TYPE: DNA
<213> ORGANISM: Artificial Sequence
<220> FEATURE:
<223> OTHER INFORMATION: Synthetic adenovirus genome (AdSyn-CO989)

<400> SEQUENCE: 6

```
gttccactga gcgtcagacc ccttaataag atgatcttct tgagatcgtt ttggtctgcg     60

cgtaatctct tgctctgaaa acgaaaaaac cgccttgcag ggcggttttt cgaaggttct    120

ctgagctacc aactctttga accgaggtaa ctggcttgga ggagcgcagt caccaaaact    180
```

-continued

```
tgtcctttca gtttagcctt aaccggcgca tgacttcaag actaactcct ctaaatcaat    240
taccagtggc tgctgccagt ggtgcttttg catgtctttc cgggttggac tcaagacgat    300
agttaccgga taaggcgcag cggtcggact gaacgggggg ttcgtgcata cagtccagct    360
tggagcgaac tgcctacccg gaactgagtg tcaggcgtgg aatgagacaa acgcggccat    420
aacagcggaa tgacaccggt aaaccgaaag gcaggaacag gagagcgcac gagggagccg    480
ccaggggaaa cgcctggtat ctttatagtc ctgtcgggtt tcgccaccac tgatttgagc    540
gtcagatttc gtgatgcttg tcaggggggc ggagcctatg gaaaaacggc tttgccgcgg    600
ccctctcact tccctgttaa gtatcttcct ggcatcttcc aggaaatctc cgccccgttc    660
gtaagccatt tccgctcgcc gcagtcgaac gaccgagcgt agcgagtcag tgagcgagga    720
agcggaatat atcctgtatc acatattctg ctgacgcacc ggtgcagcct tttttctcct    780
gccacatgaa gcacttcact gacaccctca tcagtgccaa catagtaagc cagtatacac    840
tccgctagcg ctgaggtctg cctcgtgaag aaggtgttgc tgactcatac caggcctgaa    900
tcgccccatc atccagccag aaagtgaggg agccacggtt gatgagagct ttgttgtagg    960
tggaccagtt ggtgattttg aacttttgct ttgccacgga acggtctgcg ttgtcgggaa   1020
gatgcgtgat ctgatccttc aactcagcaa aagttcgatt tattcaacaa agccacgttg   1080
tgtctcaaaa tctctgatgt tacattgcac aagataaaaa tatatcatca tgaacaataa   1140
aactgtctgc ttacataaac agtaatacaa ggggtgttga tactctcagt acaatctgct   1200
ctgatgccgc atagttaagc cagtatctgc tccctgcttg tgtgttggag gtcgctgagt   1260
agtgcgcgag caaaatttaa gctacaacaa ggcaaggctt gaccgacaat tgcatgaaga   1320
atctgcttag ggttaggcgt tttgcgctgc ttcgcgatgt acgggccaga tatacgcgta   1380
tctgagggga ctagggtgtg tttaggcgaa aagcggggct tcggttgtac gcggttagga   1440
gtcccctcag gatatagtag tttcgctttt gcatagggag ggggaaatgt agtcttatgc   1500
aatactcttg tagtcttgca acatggtaac gatgagttag caacatgcct tacaaggaga   1560
gaaaaagcac cgtgcatgcc gattggtgga agtaaggtgg tacgatcgtg ccttattagg   1620
aaggcaacag acgggtctga catggattgg acgaaccact gaattccgca ttgcagagat   1680
attgtattta agtgcctagc tcgatacaat aaacgccatt tgaccattca ccacattggt   1740
gtgcacctcc aagctgggta cggatccggc cttgccggcc tcgagcggcc gctagcgccg   1800
ccactatggg atcaagatcg ccaaaaaaga agagaaaggt gccgaagaag catgcagcac   1860
caccaaaaaa aaaacgaaaa gtagaagacc cacgatttat gtacccatac gatgttcctg   1920
actatgcggg tatgaaaaac atcaaaaaaa accaggtaat gaacctgggt ccgaactcta   1980
aactgctgaa agaatacaaa tcccagctga tcgaactgaa catcgaacag ttcgaagcag   2040
gtatcggtct gatcctgggt gatgcttaca tccgttctcg tgatgaaggt aaaacctact   2100
gtatgcagtt cgagtggaaa aacaaagcat acatggacca cgtatgtctg ctgtacgatc   2160
agtgggtact gtccccgccg cacaaaaaag aacgtgttaa ccacctgggt aacctggtaa   2220
tcacctgggg cgcccagact ttcaaacacc aagctttcaa caaactggct aacctgttca   2280
tcgttaacaa caaaaaaacc atcccgaaca acctggttga aaactacctg accccgatgt   2340
ctctggcata ctggttcatg gatgatggtg gtaaatggga ttacaacaaa aactctacca   2400
acaaatcgat cgtactgaac acccagtctt tcactttcga agaagtagaa tacctggtta   2460
agggtctgcg taacaaattc caactgaact gttacgtaaa aatcaacaaa aacaaaccga   2520
tcatctacat cgattctatg tcttacctga tcttctacaa cctgatcaaa ccgtacctga   2580
```

tcccgcagat gatgtacaaa ctgccgaaca ctatctcctc cgaaactttc ctgaaataag 2640
gtaccgatcc agacatgata agatacattg atgagtttgg acaaaccaca actagaatgc 2700
agtgaaaaaa atgctttatt tgtgaaattt gtgatgctat tgctttattt gtaaccatta 2760
taagctgcaa taaacaagtt aacaacaaca attgcattca ttttatgttt caggttcagg 2820
gggaggtgtg ggaggttttt taaagcaagt aaaacctcta caaatgtggt atggctgatt 2880
atgatcatcg taaacttggt ctgacagtta ccaatgctta atcagtgagg cacctatctc 2940
agcgatctgt ctatttcgtt catccatagt tgcctgactc cccgtcgtgt agataactac 3000
gatacgggag ggcttaccat ctggccccag tgctgcaatg ataccgcgag acccacgctc 3060
accggctcca gatttatcag caataaacca gccagccgga agggccgagc gcagaagtgg 3120
tcctgcaact ttatccgcct ccatccagtc tattaattgt tgccgggaag ctagagtaag 3180
tagttcgcca gttaatagtt tgcgcaacgt tgttgccatt gctacaggca tcgtggtgtc 3240
acgctcgtcg tttggtatgg cttcattcag ctccggttcc caacgatcaa ggcgagttac 3300
atgatccccc atgttgtgca aaaaagcggt tagctccttc ggtcctccga tcgttgtcag 3360
aagtaagttg gccgcagtgt tatcactcat ggttatggca gcactgcata attctcttac 3420
tgtcatgcca tccgtaagat gcttttctgt gactggtgag tactcaacca agtcattctg 3480
agaatagtgt atgcggcgac cgagttgctc ttgcccggcg tcaatacggg ataataccgc 3540
gccacatagc agaactttaa aagtgctcat cattggaaaa cgttcttcgg ggcgaaaact 3600
ctcaaggatc ttaccgctgt tgagatccag ttcgatgtaa cccactcgtg cacccaactg 3660
atcttcagca tcttttactt tcaccagcgt ttctgggtga gcaaaaacag gaaggcaaaa 3720
tgccgcaaaa aagggaataa gggcgacacg gaaatgttga atactcatac tcttcctttt 3780
tcaatattat tgaagcattt atcagggtta ttgtctcatg agcggataca tatttgaatg 3840
tatttagaaa aataaacaaa taggggttcc gcgcacattt ccccgaaaag tgccacctga 3900
cgtctaagaa accattatta tcatgacatt aacctataaa aataggcgta tcacgaggcc 3960
ctttcgtctc gcgcgtttcg gtgatgacgg tgaaaacctc tgacacatgc agctcccgga 4020
gacggtcaca gcttgtctgt aagcggatgc cgggagcaga caagcccgtc agggcgcgtc 4080
agcgggtgtt ggcgggtgtc ggggctggct taactatgcg gcatcagagc agattgtact 4140
gagagtgcac catatgcggt gtgaaatacc gcacagatgc gtaaggagaa aataccgcat 4200
caggcgccat tcgccattca ggctgcgcaa ctgttgggaa gggcgatcgg tgcgggcctc 4260
ttcgctatta cgccagctgg cgaaaggggg atgtgctgca aggcgattaa gttgggtaac 4320
gccagggttt tcccagtcac gacgttgtaa aacgacggcc agtgaattac aactttgtac 4380
aaaaaagcag attaccctgt tatccctaca tcatcaataa tataccttat tttggattga 4440
agccaatatg ataatgaggg ggtggagttt gtgacgtggc gcggggcgtg ggaacggggc 4500
gggtgacgta gtagtgtggc ggaagtgtga tgttgcaagt gtggcggaac acatgtaagc 4560
gacggatgtg gcaaaagtga cgtttttggt gtgcgccggt gtacacagga agtgacaatt 4620
ttcgcgcggt tttaggcgga tgttgtagta aatttgggcg taaccgagta agatttggcc 4680
attttcgcgg gaaaactgaa taagaggaag tgaaatctga ataattttgt gttactcata 4740
gcgcgtaata tttgtctagg gccgcgggga ctttgaccgt ttacgtggag actcgcccag 4800
gtgtttttct caggtgtttt ccgcgttccg ggtcaaagtt ggcgttttat tattaaaccg 4860
tattaccgcc atgcatttaa tggagtgcct cgtgaggctc cggtgcccgt cagtgggcag 4920

-continued

```
agcgcacatc gcccacagtc cccgagaagt tgggggggagg ggtcggcaat tgaaccggtg   4980
cctagagaag gtggcgcggg gtaaactggg aaagtgatgt cgtgtactgg ctccgccttt   5040
ttcccgaggg tgggggagaa ccgtatataa gtgcagtagt cgccgtgaac gttctttttc   5100
gcaacgggtt tgccgccaga acacaggtaa gtgccgtgtg tggttcccgc gggcctggcc   5160
tctttacggg ttatggccct tgcgtgcctt gaattacttc cacctggctg cagtacgtga   5220
ttcttgatcc cgagcttcgg gttggaagtg ggtgggagag ttcgaggcct tgcgcttaag   5280
gagccccttc gcctcgtgct tgagttgagg cctggcctgg gcgctggggc cgccgcgtgc   5340
gaatctggtg gcaccttcgc gcctgtctcg ctgctttcga taagtctcta gccatttaaa   5400
atttttgatg acctgctgcg acgctttttt tctggcaaga tagtcttgta aatgcgggcc   5460
aagatctgca cactggtatt tcggtttttg gggccgcggg cggcgacggg gcccgtgcgt   5520
cccagcgcac atgttcggcg aggcggggcc tgcgagcgcg gccaccgaga atcggacggg   5580
ggtagtctca agctggccgg cctgctctgg tgcctggcct cgcgccgccg tgtatcgccc   5640
cgccctgggc ggcaaggctg gcccggtcgg caccagttgc gtgagcggaa agatggccgc   5700
ttcccggccc tgctgcaggg agctcaaaat ggaggacgcg gcgctcggga gagcgggcgg   5760
gtgagtcacc cacacaaagg aaaagggcct ttccgtcctc agccgtcgct tcatgtgact   5820
ccacggagta ccgggcgccg tccaggcacc tcgattagtt ctcgagcttt tggagtacgt   5880
cgtctttagg ttggggggag gggttttatg cgatggagtt tccccacact gagtgggtgg   5940
agactgaagt taggccagct tggcacttga tgtaattctc cttggaattt gccctttttg   6000
agtttggatc ttggttcatt ctcaagcctc agacagtggt tcaaagtttt tttcttccat   6060
ttcaggtgtc gtgacgctag cgctaccgga ctcagatctc gagctcaagc ttcgaattct   6120
gcagcaccat ggactataaa gatgacgacg acaaggcttc gtaccccggc catcagcacg   6180
cgtctgcgtt cgaccaggct gcgcgttctc gcggccatag caaccgacgt acggcgttgc   6240
gccctcgccg gcagcaagaa gccacggaag tccgcccgga gcagaaaatg cccacgctac   6300
tgcgggttta tatagacggt ccccacggga tggggaaaac caccaccacg caactgctgg   6360
tggccctggg ttcgcgcgac gatatcgtct acgtacccga gccgatgact tactggcggg   6420
tgctgggggc ttccgagaca atcgcgaaca tctacaccac acaacaccgc cttgaccagg   6480
gtgagatatc ggccggggac gcggcggtgg taatgacaag cgcccagata acaatgggca   6540
tgccttatgc cgtgaccgac gccgttctgg ctcctcatat cggggggggag gctgggagct   6600
cacatgcccc gcccccggcc ctcaccctca tcttcgaccg ccatcccatc gccgccctcc   6660
tgtgctaccc ggccgcgcga taccttatgg gcagcatgac cccccaggcc gtgctggcgt   6720
tcgtggccct catcccgccg accttgcccg gcacaaacat cgtgttgggg gcccttccgg   6780
aggacagaca catcgaccgc ctggccaaac gccagcgccc cggcgagcgg cttgacctgg   6840
ctatgctggc cgcgattcgc cgcgtttacg ggctgcttgc caatacggtg cggtatctgc   6900
agggcggcgg gtcgtggcgg gaggattggg gacagctttc ggggacggcc gtgccgcccc   6960
agggtgccga gccccagagc aacgcgggcc cacgacccca tatcggggac acgttattta   7020
ccctgtttcg ggcccccgag ttgctggccc ccaacggcga cctgtacaac gtgtttgcct   7080
gggccttgga cgtcttggcc aaacgcctcc gtcccatgca cgtctttatc ctggattacg   7140
accaatcgcc cgccggctgc cgggacgccc tgctgcaact tacctccggg atgatccaga   7200
cccacgtcac caccccaggc tccataccga cgatctgcga cctggcgcgc acgtttgccc   7260
gggagatggg ggaggctaac ggaagcggag ctactaactt cagcctgctg aagcaggctg   7320
```

-continued

```
gtgacgtcga ggagaatcct ggcccaatga cttcgaaagt ttatgatcca gaacaaagga   7380
aacggatgat aactggtccg cagtggtggg ccagatgtaa acaaatgaat gttcttgatt   7440
catttattaa ttattatgat tcagaaaaac atgcagaaaa tgctgttatt tttttacatg   7500
gtaacgcggc ctcttcttat ttatggcgac atgttgtgcc acatattgag ccagtagcgc   7560
ggtgtattat accagacctt attggtatgg gcaaatcagg caaatctggt aatggttctt   7620
ataggttact tgatcattac aaatatctta ctgcatggtt tgaacttctt aatttaccaa   7680
agaagatcat ttttgtcggc catgattggg gtgcttgttt ggcatttcat tatagctatg   7740
agcatcaaga taagatcaaa gcaatagttc acgctgaaag tgtagtagat gtgattgaat   7800
catgggatga atggcctgat attgaagaag atattgcgtt gatcaaatct gaagaaggag   7860
aaaaaatggt tttggagaat aacttcttcg tggaaaccat gttgccatca aaaatcatga   7920
gaaagttaga accagaagaa tttgcagcat atcttgaacc attcaaagag aaaggtgaag   7980
ttcgtcgtcc aacattatca tggcctcgtg aaatcccgtt agtaaaaggt ggtaaacctg   8040
acgttgtaca aattgttagg aattataatg cttatctacg tgcaagtgat gatttaccaa   8100
aaatgtttat tgaatcggac ccaggattct tttccaatgc tattgttgaa ggtgccaaga   8160
agtttcctaa tactgaattt gtcaaagtaa aaggtcttca tttttcgcaa gaagatgcac   8220
ctgatgaaat gggaaaatat atcaaatcgt tcgttgagcg agttctcaaa aatgaacaat   8280
aaggagcgac tctagatcat aatcagccat accacatttg tagaggtttt acttgcttta   8340
aaaaacctcc cacacctccc cctgaacctg aaacataaaa tgaatgcaat tgttgttgtt   8400
aacttgttta ttgcagctta taatggttac aaataaagca atagcatcac aaatttcaca   8460
aataaagcat ttttttcact gcattctagt tgtggtttgt ccaaactcat caatgtaagt   8520
ttaaacggcg cgcctgaaat gtgtgggcgt ggcttaaggg tgggaaagaa tatataaggt   8580
gggggtctta tgtagttttg tatctgtttt gcagcagccg ccgccgccat gagcaccaac   8640
tcgtttgatg gaagcattgt gagctcatat ttgacaacgc gcatgccccc atgggccggg   8700
gtgcgtcaga atgtgatggg ctccagcatt gatggtcgcc ccgtcctgcc cgcaaactct   8760
actaccttga cctacgagac cgtgtctgga acgccgttgg agactgcagc ctccgccgcc   8820
gcttcagccg ctgcagccac cgcccgcggg attgtgactg actttgcttt cctgagcccg   8880
cttgcaagca gtgcagcttc ccgttcatcc gcccgcgatg acaagttgac ggctcttttg   8940
gcacaattgg attctttgac ccgggaactt aatgtcgttt ctcagcagct gttggatctg   9000
cgccagcagg tttctgccct gaaggcttcc tcccctccca atgcggttta aaacacaact   9060
tttctataca aagttgtaaa taaaaaacca gactctgttt ggatttggat caagctaagt   9120
gtcttgctgt ctttatttag gggttttgcg cgcgcggtag gcccgggacc agcggtctcg   9180
gtcgttgagg gtcctgtgta tttttttccag gacgtggtaa aggtgactct ggatgttcag   9240
atacatgggc ataagcccgt ctctggggtg gaggtagcac cactgcagag cttcatgctg   9300
cggggtggtg ttgtagatga tccagtcgta gcaggagcgc tgggcgtggt gcctaaaaat   9360
gtctttcagt agcaagctga ttgccagggg caggcccttg gtgtaagtgt ttacaaagcg   9420
gttaagctgg gatgggtgca tacgtgggga tatgagatgc atcttggact gtatttttag   9480
gttggctatg ttcccagcca tatccctccg ggattcatg ttgtgcagaa ccaccagcac   9540
agtgtatccg gtgcacttgg gaaatttgtc atgtagctta gaaggaaatg cgtggaagaa   9600
cttggagacg cccttgtgac ctccaagatt ttccatgcat tcgtccataa tgatggcaat   9660
```

-continued

```
gggcccacgg gcggcggcct gggcgaagat atttctggga tcactaacgt catagttgtg   9720
ttccaggatg agatcgtcat aggccatttt tacaaagcgc gggcggaggg tgccagactg   9780
cggtataatg gttccatccg gcccaggggc gtagttaccc tcacagattt gcatttccca   9840
cgctttgagt tcagatgggg ggatcatgtc tacctgcggg gcgatgaaga aaacggtttc   9900
cggggtaggg gagatcagct gggaagaaag caggttcctg agcagctgcg acttaccgca   9960
gccggtgggc ccgtaaatca cacctattac cggctgcaac tggtagttaa gagagctgca  10020
gctgccgtca tccctgagca ggggggccac ttcgttaagc atgtccctga ctcgcatgtt  10080
ttccctgacc aaatccgcca gaaggcgctc gccgcccagc gatagcagtt cttgcaagga  10140
agcaaagttt ttcaacggtt tgagaccgtc cgccgtaggc atgcttttga gcgtttgacc  10200
aagcagttcc aggcggtccc acagctcggt cacctgctct acggcatctc gatccagcat  10260
atctcctcgt ttcgcgggtt ggggcggctt tcgctgtacg gcagtagtcg gtgctcgtcc  10320
agacgggcca gggtcatgtc tttccacggg cgcagggtcc tcgtcagcgt agtctgggtc  10380
acggtgaagg ggtgcgctcc gggctgcgcg ctggccaggg tgcgcttgag gctggtcctg  10440
ctggtgctga agcgctgccg gtcttcgccc tgcgcgtcgg ccaggtagca tttgaccatg  10500
gtgtcatagt ccagcccctc cgcggcgtgg cccttggcgc gcagcttgcc cttggaggag  10560
gcgccgcacg aggggcagtg cagacttttg agggcgtaga gcttgggcgc gagaaatacc  10620
gattccgggg agtaggcatc cgcgccgcag gccccgcaga cggtctcgca ttccacgagc  10680
caggtgagct ctggccgttc ggggtcaaaa accaggtttc ccccatgctt tttgatgcgt  10740
ttcttacctc tggtttccat gagccggtgt ccacgctcgg tgacgaaaag gctgtccgtg  10800
tccccgtata cagacttgag aggcctgtcc tcgagcggtg ttccgcggtc ctcctcgtat  10860
agaaactcgg accactctga gacaaaggct cgcgtccagg ccagcacgaa ggaggctaag  10920
tgggaggggt agcggtcgtt gtccactagg gggtccactc gctccagggt gtgaagacac  10980
atgtcgccct cttcggcatc aaggaaggtg attggtttgt aggtgtaggc cacgtgaccg  11040
ggtgttcctg aaggggggct ataaaagggg gtgggggcgc gttcgtcctc actctcttcc  11100
gcatcgctgt ctgcgagggc cagctgttgg ggtgagtact ccctctgaaa agcgggcatg  11160
acttctgcgc taagattgtc agtttccaaa aacgaggagg atttgatatt cacctggccc  11220
gcggtgatgc ctttgagggt ggccgcatcc atctggtcag aaaagacaat ctttttgttg  11280
tcaagcttgg tggcaaacga cccgtagagg gcgttggaca gcaacttggc gatggagcgc  11340
agggtttggt ttttgtcgcg atcggcgcgc tccttggccg cgatgtttag ctgcacgtat  11400
tcgcgcgcaa cgcaccgcca ttcgggaaag acggtggtgc gctcgtcggg caccaggtgc  11460
acgcgccaac cgcggttgtg cagggtgaca aggtcaacgc tggtggctac ctctccgcgt  11520
aggcgctcgt tggtccagca gaggcggccg cccttgcgcg agcagaatgg cggtaggggg  11580
tctagctgcg tctcgtccgg ggggtctgcg tccacggtaa agaccccggg cagcaggcgc  11640
gcgtcgaagt agtctatctt gcatccttgc aagtctagcg cctgctgcca tgcgcgggcg  11700
gcaagcgcgc gctcgtatgg gttgagtggg ggaccccatg gcatggggtg ggtgagcgcg  11760
gaggcgtaca tgccgcaaat gtcgtaaacg tagaggggct ctctgagtat tccaagatat  11820
gtagggtagc atcttccacc gcggatgctg gcgcgcacgt aatcgtatag ttcgtgcgag  11880
ggagcgagga ggtcgggacc gaggttgcta cgggcgggct gctctgctcg gaagactatc  11940
tgcctgaaga tggcatgtga gttggatgat atggttggac gctggaagac gttgaagctg  12000
gcgtctgtga gacctaccgc gtcacgcacg aaggaggcgt aggagtcgcg cagcttgttg  12060
```

accagctcgg cggtgacctg cacgtctagg gcgcagtagt ccagggtttc cttgatgatg 12120
tcatacttat cctgtccctt ttttttccac agctcgcggt tgaggacaaa ctcttcgcgg 12180
tctttccagt actcttggat cggaaacccg tcggcctccg aacggtaaga gcctagcatg 12240
tagaactggt tgacggcctg gtaggcgcag catccctttt ctacgggtag cgcgtatgcc 12300
tgcgcggcct tccggagcga ggtgtgggtg agcgcaaagg tgtccctgac catgactttg 12360
aggtactggt atttgaagtc agtgtcgtcg catccgccct gctcccagag caaaaagtcc 12420
gtgcgctttt tggaacgcgg atttggcagg gcgaaggtga catcgttgaa gagtatcttt 12480
cccgcgcgag gcataaagtt gcgtgtgatg cggaagggtc ccggcacctc ggaacggttg 12540
ttaattacct gggcggcgag cacgatctcg tcaaagccgt tgatgttgtg gcccacaatg 12600
taaagttcca agaagcgcgg gatgcccttg atggaaggca atttttttaag ttcctcgtag 12660
gtgagctctt caggggagct gagcccgtgc tctgaaaggg cccagtctgc aagatgaggg 12720
ttggaagcga cgaatgagct ccacaggtca cgggccatta gcatttgcag gtggtcgcga 12780
aaggtcctaa actggcgacc tatggccatt ttttctgggg tgatgcagta gaaggtaagc 12840
gggtcttgtt cccagcggtc ccatccaagg ttcgcggcta ggtctcgcgc ggcagtcact 12900
agaggctcat ctccgccgaa cttcatgacc agcatgaagg gcacgagctg cttcccaaag 12960
gcccccatcc aagtataggt ctctacatcg taggtgacaa agagacgctc ggtgcgagga 13020
tgcgagccga tcgggaagaa ctggatctcc cgccaccaat tggaggagtg gctattgatg 13080
tggtgaaagt agaagtccct gcgacgggcc gaacactcgt gctggctttt gtaaaaacgt 13140
gcgcagtact ggcagcggtg cacgggctgt acatcctgca cgaggttgac ctgacgaccg 13200
cgcacaagga agcagagtgg gaatttgagc ccctcgcctg gcgggtttgg ctggtggtct 13260
tctacttcgg ctgcttgtcc ttgaccgtct ggctgctcga ggggagttac ggtggatcgg 13320
accaccacgc cgcgcgagcc caaagtccag atgtccgcgc gcggcggtcg gagcttgatg 13380
acaacatcgc gcagatggga gctgtccatg gtctggagct cccgcggcgt caggtcaggc 13440
gggagctcct gcaggtttac ctcgcataga cgggtcaggg cgcgggctag atccaggtga 13500
tacctaattt ccaggggctg gttggtggcg gcgtcgatgg cttgcaagag gccgcatccc 13560
cgcggcgcga ctacggtacc gcgcggcggg cggtgggccg cgggggtgtc cttggatgat 13620
gcatctaaaa gcggtgacgc gggcgagccc ccggaggtag ggggggctcc ggacccgccg 13680
ggagaggggg caggggcacg tcggcgccgc gcgcgggcag gagctggtgc tgcgcgcgta 13740
ggttgctggc gaacgcgacg acgcggcggt tgatctcctg aatctggcgc ctctgcgtga 13800
agacgacggg cccggtgagc ttgaacctga aagagagttc gacagaatca atttcggtgt 13860
cgttgacggc ggcctggcgc aaaatctcct gcacgtctcc tgagttgtct tgataggcga 13920
tctcggccat gaactgctcg atctcttcct cctggagatc tccgcgtccg gctcgctcca 13980
cggtggcggc gaggtcgttg gaaatgcggg ccatgagctg cgagaaggcg ttgaggcctc 14040
cctcgttcca gacgcggctg tagaccacgc cccttcggc atcgcgggcg cgcatgacca 14100
cctgcgcgag attgagctcc acgtgccggg cgaagacggc gtagtttcgc aggcgctgaa 14160
agaggtagtt gagggtggtg gcggtgtgtt ctgccacgaa gaagtacata acccagcgtc 14220
gcaacgtgga ttcgttgata tcccccaagg cctcaaggcg ctccatggcc tcgtagaagt 14280
ccacggcgaa gttgaaaaac tgggagttgc gcgccgacac ggttaactcc tcctccagaa 14340
gacggatgag ctcggcgaca gtgtcgcgca cctcgcgctc aaaggctaca ggggcctctt 14400

-continued

```
cttcttcttc aatctcctct tccataaggg cctccccttc ttcttcttct ggcggcggtg  14460
ggggaggggg gacacggcgg cgacgacggc gcaccgggag gcggtcgaca aagcgctcga  14520
tcatctcccc gcggcgacgg cgcatggtct cggtgacggc gcggccgttc tcgcgggggc  14580
gcagttggaa gacgccgccc gtcatgtccc ggttatgggt tggcgggggg ctgccatgcg  14640
gcagggatac ggcgctaacg atgcatctca acaattgttg tgtaggtact ccgccgccga  14700
gggacctgag cgagtccgca tcgaccggat cggaaaacct ctcgagaaag gcgtctaacc  14760
agtcacagtc gcaaggtagg ctgagcaccg tggcgggcgg cagcgggcgg cggtcggggt  14820
tgtttctggc ggaggtgctg ctgatgatgt aattaaagta ggcggtcttg agacggcgga  14880
tggtcgacag aagcaccatg tccttgggtc cggcctgctg aatgcgcagg cggtcggcca  14940
tgccccaggc ttcgttttga catcggcgca ggtctttgta gtagtcttgc atgagccttt  15000
ctaccggcac ttcttcttct ccttcctctt gtcctgcatc tcttgcatct atcgctgcgg  15060
cggcggcgga gtttggccgt aggtggcgcc ctcttcctcc catgcgtgtg accccgaagc  15120
ccctcatcgg ctgaagcagg gctaggtcgg cgacaacgcg ctcggctaat atggcctgct  15180
gcacctgcgt gagggtagac tggaagtcat ccatgtccac aaagcggtgg tatgcgcccg  15240
tgttgatggt gtaagtgcag ttggccataa cggaccagtt aacggtctgg tgacccggct  15300
gcgagagctc ggtgtacctg agacgcgagt aagccctcga gtcaaatacg tagtcgttgc  15360
aagtccgcac caggtactgg tatcccacca aaaagtgcgg cggcggctgg cggtagaggg  15420
gccagcgtag ggtggccggg gctccggggg cgagatcttc caacataagg cgatgatatc  15480
cgtagatgta cctggacatc caggtgatgc cggcggcggt ggtggaggcg cgcggaaagt  15540
cgcggacgcg gttccagatg ttgcgcagcg gcaaaaagtg ctccatggtc gggacgctct  15600
ggccggtcag gcgcgcgcaa tcgttgacgc tctagaccgt gcaaaaggag agcctgtaag  15660
cgggcactct tccgtggtct ggtggataaa ttcgcaaggg tatcatggcg gacgaccggg  15720
gttcgagccc cgtatccggc cgtccgccgt gatccatgcg gttaccgccc gcgtgtcgaa  15780
cccaggtgtg cgacgtcaga caacggggga gtgctccttt tggcttcctt ccaggcgcgg  15840
cggctgctgc gctagctttt ttggccactg gccgcgcgca gcgtaagcgg ttaggctgga  15900
aagcgaaagc attaagtggc tcgctccctg tagccggagg gttattttcc aagggttgag  15960
tcgcgggacc cccggttcga gtctcggacc ggccggactg cggcgaacgg gggtttgcct  16020
ccccgtcatg caagaccccg cttgcaaatt cctccggaaa cagggacgag ccccttttt  16080
gcttttccca gatgcatccg gtgctgcggc agatgcgccc ccctcctcag cagcggcaag  16140
agcaagagca gcggcagaca tgcagggcac cctcccctcc tcctaccgcg tcaggagggg  16200
cgacatccgc ggttgacgcg gcagcagatg gtgattacga acccccgcgg cgccgggccc  16260
ggcactacct ggacttggag gagggcgagg gcctggcgcg gctaggagcg ccctctcctg  16320
agcggcaccc aagggtgcag ctgaagcgtg atacgcgtga ggcgtacgtg ccgcggcaga  16380
acctgtttcg cgaccgcgag ggagaggagc ccgaggagat gcgggatcga aagttccacg  16440
cagggcgcga gctgcggcat ggcctgaatc gcgagcggtt gctgcgcgag gaggactttg  16500
agcccgacgc gcgaaccggg attagtcccg cgcgcgcaca cgtggcggcc gccgacctgg  16560
taaccgcata cgagcagacg gtgaaccagg agattaactt tcaaaaaagc tttaacaacc  16620
acgtgcgtac gcttgtggcg cgcgaggagg tggctatagg actgatgcat ctgtgggact  16680
ttgtaagcgc gctggagcaa aacccaaata gcaagccgct catggcgcag ctgttcctta  16740
tagtgcagca cagcagggac aacgaggcat tcagggatgc gctgctaaac atagtagagc  16800
```

ccgagggccg ctggctgctc gatttgataa acatcctgca gagcatagtg gtgcaggagc 16860
gcagcttgag cctggctgac aaggtggccg ccatcaacta ttccatgctt agcctgggca 16920
agttttacgc ccgcaagata taccataccc cttacgttcc catagacaag gaggtaaaga 16980
tcgaggggtt ctacatgcgc atggcgctga aggtgcttac cttgagcgac gacctgggcg 17040
tttatcgcaa cgagcgcatc cacaaggccg tgagcgtgag ccggcggcgc gagctcagcg 17100
accgcgagct gatgcacagc ctgcaaaggg ccctggctgg cacgggcagc ggcgatagag 17160
aggccgagtc ctactttgac gcgggcgctg acctgcgctg ggccccaagc cgacgcgccc 17220
tggaggcagc tggggccgga cctgggctgg cggtggcacc cgcgcgcgct ggcaacgtcg 17280
gcggcgtgga ggaatatgac gaggacgatg agtacgagcc agaggacggc gagtactaag 17340
cggtgatgtt tctgatcaga tgatgcaaga cgcaacggac ccggcggtgc gggcggcgct 17400
gcagagccag ccgtccggcc ttaactccac ggacgactgg cgccaggtca tggaccgcat 17460
catgtcgctg actgcgcgca atcctgacgc gttccggcag cagccgcagg ccaaccggct 17520
ctccgcaatt ctggaagcgg tggtcccggc gcgcgcaaac ccccacgcacg agaaggtgct 17580 ggcgatcgta aacgcgctgg ccgaaaacag ggccatccgg cccgacgagg ccggcctggt 17640
ctacgacgcg ctgcttcagc gcgtggctcg ttacaacagc ggcaacgtgc agaccaacct 17700
ggaccggctg gtgggggatg tgcgcgaggc cgtggcgcag cgtgagcgcg cgcagcagca 17760
gggcaacctg ggctccatgg ttgcactaaa cgccttcctg agtacacagc ccgccaacgt 17820
gccgcgggga caggaggact acaccaactt tgtgagcgca ctgcggctaa tggtgactga 17880
gacaccgcaa agtgaggtgt accagtctgg gccagactat tttttccaga ccagtagaca 17940
aggcctgcag accgtaaacc tgagccaggc tttcaaaaac ttgcaggggc tgtgggggt 18000 gcgggctccc acaggcgacc gcgcgaccgt gtctagcttg ctgacgccca actcgcgcct 18060
gttgctgctg ctaatagcgc ccttcacgga cagtggcagc gtgtcccggg acacatacct 18120
aggtcacttg ctgacactgt accgcgaggc cataggtcag gcgcatgtgg acgagcatac 18180
tttccaggag attacaagtg tcagccgcgc gctggggcag gaggacacgg gcagcctgga 18240
ggcaacccta aactacctgc tgaccaaccg gcggcagaag atcccctcgt tgcacagttt 18300
aaacagcgag gaggagcgca ttttgcgcta cgtgcagcag agcgtgagcc ttaacctgat 18360
gcgcgacggg gtaacgccca gcgtggcgct ggacatgacc gcgcgcaaca tggaaccggg 18420
catgtatgcc tcaaaccggc cgtttatcaa ccgcctaatg gactacttgc atcgcgcggc 18480
cgccgtgaac cccgagtatt tcaccaatgc catcttgaac ccgcactggc taccgccccc 18540
tggtttctac accgggggat tcgaggtgcc cgagggtaac gatggattcc tctgggacga 18600
catagacgac agcgtgtttt ccccgcaacc gcagaccctg ctagagttgc aacagcgcga 18660
gcaggcagag gcggcgctgc gaaaggaaag cttccgcagg ccaagcagct tgtccgatct 18720
aggcgctgcg gccccgcggt cagatgctag tagcccattt ccaagcttga tagggtctct 18780
taccagcact cgcaccaccc gcccgcgcct gctgggcgag gaggagtacc taaacaactc 18840
gctgctgcag ccgcagcgcg aaaaaaacct gcctccggca tttcccaaca acgggataga 18900
gagcctagtg gacaagatga gtagatggaa gacgtacgcg caggagcaca gggacgtgcc 18960
aggcccgcgc ccgcccaccc gtcgtcaaag gcacgaccgt cagcggggtc tggtgtggga 19020
ggacgatgac tcggcagacg acagcagcgt cctggatttg ggagggagtg gcaacccgtt 19080
tgcgcacctt cgccccaggc tggggagaat gttttaaaaa aaaaaaaaaa gcatgatgca 19140

```
aaataaaaaa ctcaccaagg ccatggcacc gagcgttggt tttcttgtat tccccttagt  19200
atgcggcgcg cggcgatgta tgaggaaggt cctcctccct cctacgagag tgtggtgagc  19260
gcggcgccag tggcggcggc gctgggttct cccttcgatg ctcccctgga cccgccgttt  19320
gtgcctccgc ggtacctgcg gcctaccggg gggagaaaca gcatccgtta ctctgagttg  19380
gcacccctat tcgacaccac ccgtgtgtac ctggtggaca acaagtcaac ggatgtggca  19440
tccctgaact accagaacga ccacagcaac tttctgacca cggtcattca aaacaatgac  19500
tacagcccgg gggaggcaag cacacagacc atcaatcttg acgaccggtc gcactggggc  19560
ggcgacctga aaaccatcct gcataccaac atgccaaatg tgaacgagtt catgtttacc  19620
aataagttta aggcgcgggt gatggtgtcg cgcttgccta ctaaggacaa tcaggtggag  19680
ctgaaatacg agtgggtgga gttcacgctg cccgagggca actactccga gaccatgacc  19740
atagacctta tgaacaacgc gatcgtggag cactacttga aagtgggcag acagaacggg  19800
gttctggaaa gcgacatcgg ggtaaagttt gacacccgca acttcagact ggggtttgac  19860
cccgtcactg gtcttgtcat gcctggggta tatacaaacg aagccttcca tccagacatc  19920
attttgctgc caggatgcgg ggtggacttc acccacagcc gcctgagcaa cttgttgggc  19980
atccgcaagc ggcaaccctt ccaggagggc tttaggatca cctacgatga tctggagggt  20040
ggtaacattc ccgcactgtt ggatgtggac gcctaccagg cgagcttgaa agatgacacc  20100
gaacagggcg ggggtggcgc aggcggcagc aacagcagtg gcagcggcgc ggaagagaac  20160
tccaacgcgg cagccgcggc aatgcagccg gtggaggaca tgaacgatca tgccattcgc  20220
ggcgacacct ttgccacacg ggctgaggag aagcgcgctg aggccgaagc agcggccgaa  20280
gctgccgccc ccgctgcgca acccgaggtc gagaagcctc agaagaaacc ggtgatcaaa  20340
cccctgacag aggacagcaa gaaacgcagt tacaacctaa taagcaatga cagcaccttc  20400
acccagtacc gcagctggta ccttgcatac aactacggcg accctcagac cggaatccgc  20460
tcatggaccc tgctttgcac tcctgacgta acctgcggct cggagcaggt ctactggtcg  20520
ttgccagaca tgatgcaaga ccccgtgacc ttccgctcca cgcgccagat cagcaacttt  20580
ccggtggtgg gcgccgagct gttgcccgtg cactccaaga gcttctacaa cgaccaggcc  20640
gtctactccc aactcatccg ccagtttacc tctctgaccc acgtgttcaa tcgctttccc  20700
gagaaccaga ttttggcgcg cccgccagcc cccaccatca ccaccgtcag tgaaaacgtt  20760
cctgctctca cagatcacgg gacgctaccg ctgcgcaaca gcatcggagg agtccagcga  20820
gtgaccatta ctgacgccag acgccgcacc tgcccctacg tttacaaggc cctgggcata  20880
gtctcgccgc gcgtcctatc gagccgcact ttttgagcaa gcatgtccat ccttatatcg  20940
cccagcaata acacaggctg gggcctgcgc ttcccaagca agatgtttgg cggggccaag  21000
aagcgctccg accaacaccc agtgcgcgtg cgcgggcact accgcgcgcc ctggggcgcg  21060
cacaaacgcg gccgcactgg gcgcaccacc gtcgatgacg ccatcgacgc ggtggtggag  21120
gaggcgcgca actacacgcc cacgccgcca ccagtgtcca cagtggacgc ggccattcag  21180
accgtggtgc gcggagcccg gcgctatgct aaaatgaaga gacggcggag gcgcgtagca  21240
cgtcgccacc gccgccgacc cggcactgcc gcccaacgcg cggcggcggc cctgcttaac  21300
cgcgcacgtc gcaccggccg acgggcggcc atgcgggccg ctcgaaggct ggccgcgggt  21360
attgtcactg tgcccccag gtccaggcga cgagcggccg ccgcagcagc cgcggccatt  21420
agtgctatga ctcagggtcg caggggcaac gtgtattggg tgcgcgactc ggttagcggc  21480
ctgcgcgtgc ccgtgcgcac ccgccccccg cgcaactaga ttgcaagaaa aaactactta  21540
```

gactcgtact gttgtatgta tccagcggcg gcggcgcgca acgaagctat gtccaagcgc 21600
aaaatcaaag aagagatgct ccaggtcatc gcgccggaga tctatggccc cccgaagaag 21660
gaagagcagg attacaagcc ccgaaagcta aagcgggtca aaaagaaaaa gaaagatgat 21720
gatgatgaac ttgacgacga ggtggaactg ctgcacgcta ccgcgcccag gcgacgggta 21780
cagtggaaag gtcgacgcgt aaaacgtgtt ttgcgacccg gcaccaccgt agtctttacg 21840
cccggtgagc gctccacccg cacctacaag cgcgtgtatg atgaggtgta cggcgacgag 21900
gacctgcttg agcaggccaa cgagcgcctc ggggagtttg cctacggaaa gcggcataag 21960
gacatgctgg cgttgccgct ggacgagggc aacccaacac ctagcctaaa gcccgtaaca 22020
ctgcagcagg tgctgcccgc gcttgcaccg tccgaagaaa agcgcggcct aaagcgcgag 22080
tctggtgact tggcacccac cgtgcagctg atggtaccca agcgccagcg actggaagat 22140
gtcttggaaa aaatgaccgt ggaacctggg ctggagcccg aggtccgcgt gcggccaatc 22200
aagcaggtgg cgccgggact gggcgtgcag accgtggacg ttcagatacc cactaccagt 22260
agcaccagta ttgccaccgc cacagagggc atggagacac aaacgtcccc ggttgcctca 22320
gcggtggcgg atgccgcggt gcaggcggtc gctgcggccg cgtccaagac ctctacggag 22380
gtgcaaacgg acccgtggat gtttcgcgtt tcagcccccc ggcgcccgcg ccgttcgagg 22440
aagtacggcg ccgccagcgc gctactgccc gaatatgccc tacatccttc cattgcgcct 22500
acccccggct atcgtggcta cacctaccgc cccagaagac gagcaactac ccgacgccga 22560
accaccactg gaacccgccg ccgccgtcgc cgtcgccagc ccgtgctggc cccgatttcc 22620
gtgcgcaggg tggctcgcga aggaggcagg accctggtgc tgccaacagc gcgctaccac 22680
cccagcatcg tttaaaagcc ggtctttgtg gttcttgcag atatggccct cacctgccgc 22740
ctccgtttcc cggtgccggg attccgagga agaatgcacc gtaggagggg catggccggc 22800
cacggcctga cgggcggcat gcgtcgtgcg caccaccggc ggcggcgcgc gtcgcaccgt 22860
cgcatgcgcg gcggtatcct gcccctcctt attccactga tcgccgcggc gattggcgcc 22920
gtgcccggaa ttgcatccgt ggccttgcag gcgcagagac actgattaaa aacaagttgc 22980
atgtggaaaa atcaaaataa aaagtctgga ctctcacgct cgcttggtcc tgtaactatt 23040
ttgtagaatg gaagacatca actttgcgtc tctggccccg cgacacggct cgcgcccgtt 23100
catgggaaac tggcaagata tcggcaccag caatatgagc ggtggcgcct tcagctgggg 23160
ctcgctgtgg agcggcatta aaaatttcgg ttccaccgtt aagaactatg gcagcaaggc 23220
ctggaacagc agcacaggcc agatgctgag ggataagttg aaagagcaaa atttccaaca 23280
aaaggtggta gatggcctgg cctctggcat tagcggggtg gtggacctgg ccaaccaggc 23340
agtgcaaaat aagattaaca gtaagcttga tccccgccct cccgtagagg agcctccacc 23400
ggccgtggag acagtgtctc cagaggggcg tggcgaaaag cgtccgcgcc ccgacaggga 23460
agaaactctg gtgacgcaaa tagacgagcc tccctcgtac gaggaggcac taaagcaagg 23520
cctgcccacc acccgtccca tcgcgcccat ggctaccgga gtgctgggcc agcacacacc 23580
cgtaacgctg gacctgcctc cccccgccga cacccagcag aaacctgtgc tgccaggccc 23640
gaccgccgtt gttgtaaccc gtcctagccg cgcgtccctg cgccgcgccg ccagcggtcc 23700
gcgatcgttg cggcccgtag ccagtggcaa ctggcaaagc acactgaaca gcatcgtggg 23760
tctgggggtg caatccctga agcgccgacg atgcttctga atagctaacg tgtcgtatgt 23820
gtgtcatgta tgcgtccatg tcgccgccag aggagctgct gagccgccgc gcgcccgctt 23880

```
tccaagatgg ctaccccttc gatgatgccg cagtggtctt acatgcacat ctcgggccag  23940
gacgcctcgg agtacctgag ccccgggctg gtgcagtttg cccgcgccac cgagacgtac  24000
ttcagcctga ataacaagtt tagaaacccc acggtggcgc ctacgcacga cgtgaccaca  24060
gaccggtccc agcgtttgac gctgcggttc atccctgtgg accgtgagga tactgcgtac  24120
tcgtacaagg cgcggttcac cctagctgtg ggtgataacc gtgtgctgga catggcttcc  24180
acgtactttg acatccgcgg cgtgctggac aggggcccta cttttaagcc ctactctggc  24240
actgcctaca acgccctggc tcccaagggt gccccaaatc cttgcgaatg ggatgaagct  24300
gctactgctc ttgaaataaa cctagaagaa gaggacgatg acaacgaaga cgaagtagac  24360
gagcaagctg agcagcaaaa aactcacgta tttgggcagg cgccttattc tggtataaat  24420
attacaaagg agggtattca aataggtgtc gaaggtcaaa cacctaaata tgccgataaa  24480
acatttcaac ctgaacctca aataggagaa tctcagtggt acgaaactga aattaatcat  24540
gcagctggga gagtccttaa aaagactacc ccaatgaaac catgttacgg ttcatatgca  24600
aaacccacaa atgaaaatgg agggcaaggc attcttgtaa agcaacaaaa tggaaagcta  24660
gaaagtcaag tggaaatgca atttttctca actactgagg cgaccgcagg caatggtgat  24720
aacttgactc ctaaagtggt attgtacagt gaagatgtag atatagaaac cccagacact  24780
catatttctt acatgcccac tattaaggaa ggtaactcac gagaactaat gggccaacaa  24840
tctatgccca acaggcctaa ttacattgct tttagggaca attttattgg tctaatgtat  24900
tacaacagca cgggtaatat gggtgttctg gcgggccaag catcgcagtt gaatgctgtt  24960
gtagatttgc aagacagaaa cacagagctt tcataccagc ttttgcttga ttccattggt  25020
gatagaacca ggtacttttc tatgtggaat caggctgttg acagctatga tccagatgtt  25080
agaattattg aaaatcatgg aactgaagat gaacttccaa attactgctt tccactggga  25140
ggtgtgatta atacagagac tcttaccaag gtaaaaccta aaacaggtca ggaaaatgga  25200
tgggaaaaag atgctacaga attttcagat aaaaatcaaa taagagttgg aaataatttt  25260
gccatggaaa tcaatctaaa tgccaacctg tggagaaatt tcctgtactc caacatagcg  25320
ctgtatttgc ccgacaagct aaagtacagt ccttccaacg taaaaatttc tgataaccca  25380
aacacctacg actacatgaa caagcgagtg gtggctcccg ggttagtgga ctgctacatt  25440
aaccttggag cacgctggtc ccttgactat atggacaacg tcaacccatt taaccaccac  25500
cgcaatgctg gcctgcgcta ccgctcaatg ttgctgggca atggtcgcta tgtgcccttc  25560
cacatccagg tgcctcagaa gttctttgcc attaaaaacc tccttctcct gccgggctca  25620
tacacctacg agtggaactt caggaaggat gttaacatgg ttctgcagag ctccctagga  25680
aatgacctaa gggttgacgg agccagcatt aagtttgata gcatttgcct ttacgccacc  25740
ttcttcccca tggcccacaa caccgcctcc acgcttgagg ccatgcttag aaacgacacc  25800
aacgaccagt cctttaacga ctatctctcc gccgccaaca tgctctaccc tatacccgcc  25860
aacgctacca acgtgcccat atccatcccc tcccgcaact gggcggcttt ccgcggctgg  25920
gccttcacgc gccttaagac taaggaaacc ccatcactgg gctcgggcta cgacccttat  25980
tacacctact ctggctctat accctaccta gatggaacct tttacctcaa ccacaccttt  26040
aagaaggtgg ccattacctt tgactcttct gtcagctggc ctggcaatga ccgcctgctt  26100
acccccaacg agtttgaaat taagcgctca gttgacgggg agggttacaa cgttgcccag  26160
tgtaacatga ccaaagactg gttcctggta caaatgctag ctaactacaa cattggctac  26220
cagggcttct atatcccaga gagctacaag gaccgcatgt actccttctt tagaaacttc  26280
```

cagcccatga gccgtcaggt ggtggatgat actaaataca aggactacca acaggtgggc 26340
atcctacacc aacacaacaa ctctggattt gttggctacc ttgcccccac catgcgcgaa 26400
ggacaggcct accctgctaa cttcccctat ccgcttatag gcaagaccgc agttgacagc 26460
attacccaga aaaagtttct ttgcgatcgc accctttggc gcatcccatt ctccagtaac 26520
tttatgtcca tgggcgcact cacagacctg ggccaaaacc ttctctacgc caactccgcc 26580
cacgcgctag acatgacttt tgaggtggat cccatggacg agcccaccct tctttatgtt 26640
ttgtttgaag tctttgacgt ggtccgtgtg caccggccgc accgcggcgt catcgaaacc 26700
gtgtacctgc gcacgccctt ctcggccggc aacgccacaa cataaagaag caagcaacat 26760
caacaacagc tgccgccatg ggctccagtg agcaggaact gaaagccatt gtcaaagatc 26820
ttggttgtgg gccatatttt ttgggcacct atgacaagcg ctttccaggc tttgtttctc 26880
cacacaagct cgcctgcgcc atagtcaata cggccggtcg cgagactggg ggcgtacact 26940
ggatggcctt tgcctggaac ccgcactcaa aaacatgcta cctctttgag ccctttggct 27000
tttctgacca gcgactcaag caggtttacc agtttgagta cgagtcactc ctgcgccgta 27060
gcgccattgc ttcttccccc gaccgctgta taacgctgga aaagtccacc caaagcgtac 27120
aggggcccaa ctcggccgcc tgtggactat tctgctgcat gtttctccac gcctttgcca 27180
actggcccca aactcccatg gatcacaacc ccaccatgaa ccttattacc ggggtaccca 27240
actccatgct caacagtccc caggtacagc ccaccctgcg tcgcaaccag gaacagctct 27300
acagcttcct ggagcgccac tcgccctact tccgcagcca cagtgcgcag attaggagcg 27360
ccacttcttt ttgtcacttg aaaaacatgt aaaaataatg tactagagac actttcaata 27420
aaggcaaatg cttttatttg tacactctcg ggtgattatt tacccccacc cttgccgtct 27480
gcgccgttta aaaatcaaag gggttctgcc gcgcatcgct atgcgccact ggcagggaca 27540
cgttgcgata ctggtgttta gtgctccact taaactcagg cacaaccatc cgcggcagct 27600
cggtgaagtt ttcactccac aggctgcgca ccatcaccaa cgcgtttagc aggtcgggcg 27660
ccgatatctt gaagtcgcag ttggggcctc cgccctgcgc gcgcgagttg cgatacacag 27720
ggttgcagca ctggaacact atcagcgccg ggtggtgcac gctggccagc acgctcttgt 27780
cggagatcag atccgcgtcc aggtcctccg cgttgctcag ggcgaacgga gtcaactttg 27840
gtagctgcct tcccaaaaag ggcgcgtgcc caggctttga gttgcactcg caccgtagtg 27900
gcatcaaaag gtgaccgtgc ccggtctggg cgttaggata cagcgcctgc ataaaagcct 27960
tgatctgctt aaaagccacc tgagcctttg cgccttcaga gaagaacatg ccgcaagact 28020
tgccggaaaa ctgattggcc ggacaggccg cgtcgtgcac gcagcacctt gcgtcggtgt 28080
tggagatctg caccacattt cggccccacc ggttcttcac gatcttggcc ttgctagact 28140
gctccttcag cgcgcgctgc ccgttttcgc tcgtcacatc catttcaatc acgtgctcct 28200
tatttatcat aatgcttccg tgtagacact taagctcgcc ttcgatctca gcgcagcggt 28260
gcagccacaa cgcgcagccc gtgggctcgt gatgcttgta ggtcacctct gcaaacgact 28320
gcaggtacgc ctgcaggaat cgccccatca tcgtcacaaa ggtcttgttg ctggtgaagg 28380
tcagctgcaa cccgcggtgc tcctcgttca gccaggtctt gcatacggcc gccagagctt 28440
ccacttggtc aggcagtagt ttgaagttcg cctttagatc gttatccacg tggtacttgt 28500
ccatcagcgc gcgcgcagcc tccatgccct tctcccacgc agacacgatc ggcacactca 28560
gcgggttcat caccgtaatt tcactttccg cttcgctggg ctcttcctct tcctcttgcg 28620

-continued tccgcatacc acgcgccact gggtcgtctt cattcagccg ccgcactgtg cgcttacctc 28680
ctttgccatg cttgattagc accggtgggt tgctgaaacc caccatttgt agcgccacat 28740
cttctctttc ttcctcgctg tccacgatta cctctggtga tggcgggcgc tcgggcttgg 28800
gagaagggcg cttctttttc ttcttgggcg caatggccaa atccgccgcc gaggtcgatg 28860
gccgcgggct gggtgtgcgc ggcaccagcg cgtcttgtga tgagtcttcc tcgtcctcgg 28920
actcgatacg ccgcctcatc cgcttttttg ggggcgcccg gggaggcggc ggcgacgggg 28980
acggggacga cacgtcctcc atggttgggg gacgtcgcgc cgcaccgcgt ccgcgctcgg 29040
gggtggtttc gcgctgctcc tcttcccgac tggccatttc cttctcctat aggcagaaaa 29100
agatcatgga gtcagtcgag aagaaggaca gcctaaccgc cccctctgag ttcgccacca 29160
ccgcctccac cgatgccgcc aacgcgccta ccaccttccc cgtcgaggca cccccgcttg 29220
aggaggagga agtgattatc gagcaggacc caggttttgt aagcgaagac gacgaggacc 29280
gctcagtacc aacagaggat aaaaagcaag accaggacaa cgcagaggca aacgaggaac 29340
aagtcgggcg gggggacgaa aggcatggcg actacctaga tgtgggagac gacgtgctgt 29400
tgaagcatct gcagcgccag tgcgccatta tctgcgacgc gttgcaagag cgcagcgatg 29460
tgcccctcgc catagcggat gtcagccttg cctacgaacg ccacctattc tcaccgcgcg 29520
tacccccaa acgccaagaa aacggcacat gcgagcccaa cccgcgcctc aacttctacc 29580
ccgtatttgc cgtgccagag gtgcttgcca cctatcacat ctttttccaa aactgcaaga 29640
tacccctatc ctgccgtgcc aaccgcagcc gagcggacaa gcagctggcc ttgcggcagg 29700
gcgctgtcat acctgatatc gcctcgctca acgaagtgcc aaaaatcttt gagggtcttg 29760
gacgcgacga gaagcgcgcg gcaaacgctc tgcaacagga aaacagcgaa aatgaaagtc 29820
actctggagt gttggtggaa ctcgagggtg acaacgcgcg cctagccgta ctaaaacgca 29880
gcatcgaggt cacccacttt gcctacccgg cacttaacct accccccaag gtcatgagca 29940
cagtcatgag tgagctgatc gtgcgccgtg cgcagcccct ggagagggat gcaaatttgc 30000
aagaacaaac agaggagggc ctacccgcag ttggcgacga gcagctagcg cgctggcttc 30060
aaacgcgcga gcctgccgac ttggaggagc gacgcaaact aatgatggcc gcagtgctcg 30120
ttaccgtgga gcttgagtgc atgcagcggt tctttgctga cccggagatg cagcgcaagc 30180
tagaggaaac attgcactac acctttcgac agggctacgt acgccaggcc tgcaagatct 30240
ccaacgtgga gctctgcaac ctggtctcct accttggaat tttgcacgaa aaccgccttg 30300
ggcaaaacgt gcttcattcc acgctcaagg gcgaggcgcg ccgcgactac gtccgcgact 30360
gcgtttactt atttctatgc tacacctggc agacggccat gggcgtttgg cagcagtgct 30420
tggaggagtg caacctcaag gagctgcaga aactgctaaa gcaaaacttg aaggacctat 30480
ggacggcctt caacgagcgc tccgtggccg cgcacctggc ggacatcatt ttccccgaac 30540
gcctgcttaa aaccctgcaa cagggtctgc cagacttcac cagtcaaagc atgttgcaga 30600
actttaggaa ctttatccta gagcgctcag gaatcttgcc cgccacctgc tgtgcacttc 30660
ctagcgactt tgtgcccatt aagtaccgcg aatgccctcc gccgctttgg ggccactgct 30720
accttctgca gctagccaac taccttgcct accactctga cataatggaa gacgtgagcg 30780
gtgacggtct actggagtgt cactgtcgct gcaacctatg caccccgcac cgctccctgg 30840
tttgcaattc gcagctgctt aacgaaagtc aaattatcgg tacctttgag ctgcagggtc 30900
cctcgcctga cgaaaagtcc gcggctccgg ggttgaaact cactccgggg ctgtggacgt 30960
cggcttacct tcgcaaattt gtacctgagg actaccacgc ccacgagatt aggttctacg 31020

-continued

```
aagaccaatc ccgcccgcca aatgcggagc ttaccgcctg cgtcattacc cagggccaca  31080
ttcttggcca attgcaagcc atcaacaaag cccgccaaga gtttctgcta cgaaagggac  31140
ggggggttta cttggacccc cagtccggcg aggagctcaa cccaatcccc ccgccgccgc  31200
agccctatca gcagcagccg cgggcccttg cttcccagga tggcacccaa aaagaagctg  31260
cagctgccgc cgccacccac ggacgaggag gaatactggg acagtcaggc agaggaggtt  31320
ttggacgagg aggaggagga catgatggaa gactgggaga gcctagacga ggaagcttcc  31380
gaggtcgaag aggtgtcaga cgaaacaccg tcaccctcgg tcgcattccc ctcgccggcg  31440
ccccagaaat cggcaaccgg ttccagcatg gctacaacct ccgctcctca ggcgccgccg  31500
gcactgcccg ttcgccgacc caaccgtaga tgggacacca ctggaaccag ggccggtaag  31560
tccaagcagc cgccgccgtt agcccaagag caacaacagc gccaaggcta ccgctcatgg  31620
cgcgggcaca agaacgccat agttgcttgc ttgcaagact gtgggggcaa catctccttc  31680
gcccgccgct ttcttctcta ccatcacggc gtggccttcc cccgtaacat cctgcattac  31740
taccgtcatc tctacagccc atactgcacc ggcggcagcg gcagcggcag caacagcagc  31800
ggccacacag aagcaaaggc gaccggatag caagactctg acaaagccca agaaatccac  31860
agcggcggca gcagcaggag gaggagcgct gcgtctggcg cccaacgaac ccgtatcgac  31920
ccgcgagctt agaaacagga tttttcccac tctgtatgct atatttcaac agagcagggg  31980
ccaagaacaa gagctgaaaa taaaaaacag gtctctgcga tccctcaccc gcagctgcct  32040
gtatcacaaa agcgaagatc agcttcggcg cacgctggaa gacgcggagg ctctcttcag  32100
taaatactgc gcgctgactc ttaaggacta gtttcgcgcc ctttctcaaa tttaagcgcg  32160
aaaactacgt catctccagc ggccacaccc ggcgccagca cctgtcgtca gcgccatttc  32220
aactttgtat acaaaagttg tgatgagcaa ggaaattccc acgccctaca tgtggagtta  32280
ccagccacaa atgggacttg cggctggagc tgcccaagac tactcaaccc gaataaacta  32340
catgagcgcg ggaccccaca tgatatcccg ggtcaacgga atacgcgccc accgaaaccg  32400
aattctcctg gaacaggcgg ctattaccac cacacctcgt aataacctta atccccgtag  32460
ttggcccgct gccctggtgt accaggaaag tcccgctccc accactgtgg tacttcccag  32520
agacgcccag gccgaagttc agatgactaa ctcaggggcg cagcttgcgg gcggctttcg  32580
tcacagggtg cggtcgcccg ggcagggtat aactcacctg acaatcagag ggcgaggtat  32640
tcagctcaac gacgagtcgg tgagctcctc gcttggtctc cgtccggacg ggacatttca  32700
gatcggcggc gccggccgct cttcattcac gcctcgtcag gcaatcctaa ctctgcagac  32760
ctcgtcctct gagccgcgct ctggaggcat tggaactctg caatttattg aggagtttgt  32820
gccatcggtc tactttaacc ccttctcggg acctcccggc cactatccgg atcaatttat  32880
tcctaacttt gacgcggtaa aggactcggc ggacggctac gactgaatgt taagtggaga  32940
ggcagagcaa ctgcgcctga aacacctggt ccactgtcgc cgccacaagt gctttgcccg  33000
cgactccggt gagttttgct actttgaatt gcccgaggat catatcgagg gcccggcgca  33060
cggcgtccgg cttaccgccc agggagagct tgcccgtagc ctgattcggg agtttaccca  33120
gcgcccccctg ctagttgagc gggacagggg accctgtgtt ctcactgtga tttgcaactg  33180
tcctaaccct ggattacatc aagatctttg ttgccatctc tgtgctgagt ataataaata  33240
cagaaattaa aatatactgg ggctcctatc gccatcctgt aaacgccacc gtcttcaccc  33300
gcccaagcaa accaaggcga accttacctg gtacttttaa catctctccc tctgtgattt  33360
```

-continued

```
acaacagttt caacccagac ggagtgagtc tacgagagaa cctctccgag ctcagctact  33420
ccatcagaaa aaacaccacc ctccttacct gccgggaacg tacgagtgcg tcaccggccg  33480
ctgcaccaca cctaccgcct gaccgtaaac cagacttttt ccggacagac ctcaataact  33540
ctgtttacca gaacaggagg tgagcttaga aaacccttag ggtattaggc caaaggcgca  33600
gctactgtgg ggtttatgaa caattcaagc aactctacgg gctattctaa ttcaggtttc  33660
tctagaatcg gggttggggt tattctctgt cttgtgattc tctttattct tatactaacg  33720
cttctctgcc taaggctcgc cgcctgctgt gtgcacattt gcatttattg tcagcttttt  33780
aaacgctggg gtcgccaccc aagatgatta ggtacataat cctaggttta ctcacccttg  33840
cgtcagccca cggtaccacc caaaaggtgg attttaagga gccagcctgt aatgttacat  33900
tcgcagctga agctaatgag tgcaccactc ttataaaatg caccacagaa catgaaaagc  33960
tgcttattcg ccacaaaaac aaaattggca agtatgctgt ttatgctatt tggcagccag  34020
gtgacactac agagtataat gttacagttt tccagggtaa aagtcataaa acttttatgt  34080
atacttttcc attttatgaa atgtgcgaca ttaccatgta catgagcaaa cagtataagt  34140
tgtggccccc acaaaattgt gtggaaaaca ctggcacttt ctgctgcact gctatgctaa  34200
ttacagtgct cgctttggtc tgtaccctac tctatattaa atacaaaagc agacgcagct  34260
ttattgagga aaagaaaatg ccttaattta ctaagttaca aagctaatgt caccactaac  34320
tgctttactc gctgcttgca aaacaaattc aaaaagttag cattataatt agaataggat  34380
ttaaaccccc cggtcatttc ctgctcaata ccattcccct gaacaattga ctctatgtgg  34440
gatatgctcc agcgctacaa ccttgaagtc aggcttcctg gatgtcagca tctgactttg  34500
gccagcacct gtcccgcgga tttgttccag tccaactaca gcgacccacc ctaacagaga  34560
tgaccaacac aaccaacgcg gccgccgcta ccggacttac atctaccaca aatacacccc  34620
aagtttctgc ctttgtcaat aactgggata acttgggcat gtggtggttc tccatagcgc  34680
ttatgtttgt atgccttatt attatgtggc tcatctgctg cctaaagcgc aaacgcgccc  34740
gaccacccat ctatagtccc atcattgtgc tacacccaaa caatgatgga atccatagat  34800
tggacggact gaaacacatg ttcttttctc ttacagtatg attaaatgag acatgattcc  34860
tcgagttttt atattactga cccttgttgc gctttttttgt gcgtgctcca cattggctgc  34920
ggtttctcac atcgaagtag actgcattcc agccttcaca gtctatttgc tttacggatt  34980
tgtcaccctc acgctcatct gcagcctcat cactgtggtc atcgccttta tccagtgcat  35040
tgactgggtc tgtgtgcgct ttgcatatct cagacaccat ccccagtaca gggacaggac  35100
tatagctgag cttcttagaa ttctttaatt atgaaattta ctgtgacttt tctgctgatt  35160
atttgcaccc tatctgcgtt ttgttccccg acctccaagc ctcaaagaca tatatcatgc  35220
agattcactc gtatatggaa tattccaagt tgctacaatg aaaaaagcga tctttccgaa  35280
gcctggttat atgcaatcat ctctgttatg gtgttctgca gtaccatctt agccctagct  35340
atatatccct accttgacat tggctggaac gcaatagatg ccatgaacca cccaactttc  35400
cccgcgcccg ctatgcttcc actgcaacaa gttgttgccg gcggctttgt cccagccaat  35460
cagcctcgcc caccttctcc cacccccact gaaatcagct actttaatct aacaggagga  35520
gatgactgac accctagatc tagaaatgga cggaattatt acagagcagc gcctgctaga  35580
aagacgcagg gcagcggccg agcaacagcg catgaatcaa gagctccaag acatggttaa  35640
cttgcaccag tgcaaaaggg gtatcttttg tctggtaaag caggccaaag tcacctacga  35700
cagtaatacc accggacacc gccttagcta caagttgcca accaagcgtc agaaattggt  35760
```

-continued ggtcatggtg ggagaaaagc ccattaccat aactcagcac tcggtagaaa ccgaaggctg 35820
cattcactca ccttgtcaag gacctgagga tctctgcacc cttattaaga ccctgtgcgg 35880
tctcaaagat cttattccct ttaactaata aaaaaaaata ataaagcatc acttacttaa 35940
aatcagttag caaatttctg tccagtttat tcagcagcac ctccttgccc tcctcccagc 36000
tctggtattg cagcttcctc ctggctgcaa actttctcca caatctaaat ggaatgtcag 36060
tttcctcctg ttcctgtcca tccgcaccca ctatcttcat gttgttgcag atgaagcgcg 36120
caagaccgtc tgaagatacc ttcaaccccg tgtatccata tgacacggaa accggtcctc 36180
caactgtgcc ttttcttact cctccctttg tatcccccaa tgggtttcaa gagagtcccc 36240
ctggggtact ctctttgcgc ctatccgaac ctctagttac ctccaatggc atgcttgcgc 36300
tcaaaatggg caacggcctc tctctggacg aggccggcaa ccttacctcc caaaatgtaa 36360
ccactgtgag cccacctctc aaaaaaacca agtcaaacat aaacctggaa atatctgcac 36420
ccctcacagt tacctcagaa gccctaactg tggctgccgc cgcacctcta atggtcgcgg 36480
gcaacacact caccatgcaa tcacaggccc cgctaaccgt gcacgactcc aaacttagca 36540
ttgccaccca aggacccctc acagtgtcag aaggaaagct agccctgcaa acatcaggcc 36600
ccctcaccac caccgatagc agtaccctta ctatcactgc ctcacccccct ctaactactg 36660
ccactggtag cttgggcatt gacttgaaag agcccattta tacacaaaat ggaaaactag 36720
gactaaagta cggggctcct ttgcatgtaa cagacgacct aaacactttg accgtagcaa 36780
ctggtccagg tgtgactatt aataatactt ccttgcaaac taaagttact ggagccttgg 36840
gttttgattc acaaggcaat atgcaactta atgtagcagg aggactaagg attgattctc 36900
aaaacagacg ccttatactt gatgttagtt atccgtttga tgctcaaaac caactaaatc 36960
taagactagg acagggccct ctttttataa actcagccca caacttggat attaactaca 37020
acaaaggcct ttacttgttt acagcttcaa acaattccaa aaagcttgag gttaacctaa 37080
gcactgccaa ggggttgatg tttgacgcta cagccatagc cattaatgca ggagatgggc 37140
ttgaatttgg ttcacctaat gcaccaaaca caaatcccct caaaacaaaa attggccatg 37200
gcctagaatt tgattcaaac aaggctatgg ttcctaaact aggaactggc cttagttttg 37260
acagcacagg tgccattaca gtaggaaaca aaaataatga taagctaact ttgtggacca 37320
caccagctcc atctcctaac tgtagactaa atgcagagaa agatgctaaa ctcactttgg 37380
tcttaacaaa atgtggcagt caaatacttg ctacagtttc agttttggct gttaaaggca 37440
gtttggctcc aatatctgga acagttcaaa gtgctcatct tattataaga tttgacgaaa 37500
atggagtgct actaaacaat tccttcctgg acccagaata ttggaacttt agaaatggag 37560
atcttactga aggcacagcc tatacaaacg ctgttggatt tatgcctaac ctatcagctt 37620
atccaaaatc tcacggtaaa actgccaaaa gtaacattgt cagtcaagtt tacttaaacg 37680
gagacaaaac taaacctgta acactaacca ttacactaaa cggtacacag gaaacaggag 37740
acacaactcc aagtgcatac tctatgtcat tttcatggga ctggtctggc cacaactaca 37800
ttaatgaaat atttgccaca tcctcttaca ctttttcata cattgcccaa gaataaagaa 37860
tcgtttgtgt tatgtttcaa cgtgtttatt tttcaattgc agaaaatttc gaatcatttt 37920
tcattcagta gtatagcccc accaccacat agcttataca gatcaccgta cctcaacttt 37980
gtataataaa gttgtaatca aactcacaga accctagtat tcaacctgcc acctccctcc 38040
caacacacag agtacacagt cctttctccc cggctggcct taaaaagcat catatcatgg 38100

-continued gtaacagaca tattcttagg tgttatattc cacacggttt cctgtcgagc caaacgctca 38160
tcagtgatat taataaactc cccgggcagc tcacttaagt tcatgtcgct gtccagctgc 38220
tgagccacag gctgctgtcc aacttgcggt tgcttaacgg gcggcgaagg agaagtccac 38280
gcctacatgg gggtagagtc ataatcgtgc atcaggatag ggcggtggtg ctgcagcagc 38340
gcgcgaataa actgctgccg ccgccgctcc gtcctgcagg aatacaacat ggcagtggtc 38400
tcctcagcga tgattcgcac cgcccgcagc ataaggcgcc ttgtcctccg ggcacagcag 38460
cgcaccctga tctcacttaa atcagcacag taactgcagc acagcaccac aatattgttc 38520
aaaatcccac agtgcaaggc gctgtatcca aagctcatgg cggggaccac agaacccacg 38580
tggccatcat accacaagcg caggtagatt aagtggcgac ccctcataaa cacgctggac 38640
ataaacatta cctcttttgg catgttgtaa ttcaccacct cccggtacca tataaacctc 38700
tgattaaaca tggcgccatc caccaccatc ctaaaccagc tggccaaaac ctgcccgccg 38760
gctatacact gcagggaacc gggactggaa caatgacagt ggagagccca ggactcgtaa 38820
ccatggatca tcatgctcgt catgatatca atgttggcac aacacaggca cacgtgcata 38880
cacttcctca ggattacaag ctcctcccgc gttagaacca tatcccaggg aacaacccat 38940
tcctgaatca gcgtaaatcc cacactgcag ggaagacctc gcacgtaact cacgttgtgc 39000
attgtcaaag tgttacattc gggcagcagc ggatgatcct ccagtatggt agcgcgggtt 39060
tctgtctcaa aaggaggtag acgatcccta ctgtacggag tgcgccgaga caaccgagat 39120
cgtgttggtc gtagtgtcat gccaaatgga acgccggacg tagtcatatt tcctgaagca 39180
aaaccaggtg cgggcgtgac aaacagatct gcgtctccgg tctcgccgct tagatcgctc 39240
tgtgtagtag ttgtagtata tccactctct caaagcatcc aggcgccccc tggcttcggg 39300
ttctatgtaa actccttcat gcgccgctgc cctgataaca tccaccaccg cagaataagc 39360
cacacccagc caacctacac attcgttctg cgagtcacac acgggaggag cgggaagagc 39420
tggaagaacc atgttttttt ttttattcca aaagattatc caaaacctca aaatgaagat 39480
ctattaagtg aacgcgctcc cctccggtgg cgtggtcaaa ctctacagcc aaagaacaga 39540
taatggcatt tgtaagatgt tgcacaatgg cttccaaaag gcaaacggcc ctcacgtcca 39600
agtggacgta aaggctaaac ccttcagggt gaatctcctc tataaacatt ccagcacctt 39660
caaccatgcc caaataattc tcatctcgcc accttctcaa tatatctcta agcaaatccc 39720
gaatattaag tccggccatt gtaaaaatct gctccagagc gccctccacc ttcagcctca 39780
agcagcgaat catgattgca aaaattcagg ttcctcacag acctgtataa gattcaaaag 39840
cggaacatta acaaaaatac cgcgatcccg taggtccctt cgcagggcca gctgaacata 39900
atcgtgcagg tctgcacgga ccagcgcggc cacttccccg ccaggaacca tgacaaaaga 39960
acccacactg attatgacac gcatactcgg agctatgcta accagcgtag ccccgatgta 40020
agcttgttgc atgggcggcg atataaaatg caaggtgctg ctcaaaaaat caggcaaagc 40080
ctcgcgcaaa aaagaaagca catcgtagtc atgctcatgc agataaaggc aggtaagctc 40140
cggaaccacc acagaaaaag acaccatttt tctctcaaac atgtctgcgg gtttctgcat 40200
aaacacaaaa taaaataaca aaaaaacatt taaacattag aagcctgtct tacaacagga 40260
aaaacaaccc ttataagcat aagacggact acggccatgc cggcgtgacc gtaaaaaaac 40320
tggtcaccgt gattaaaaag caccaccgac agctcctcgg tcatgtccgg agtcataatg 40380
taagactcgg taaacacatc aggttgattc acatcggtca gtgctaaaaa gcgaccgaaa 40440
tagcccgggg gaatacatac ccgcaggcgt agagacaaca ttacagcccc cataggaggt 40500

-continued

```
ataacaaaat taataggaga gaaaaacaca taaacacctg aaaaaccctc ctgcctaggc  40560
aaaatagcac cctcccgctc cagaacaaca tacagcgctt ccacagcggc agccataaca  40620
gtcagcctta ccagtaaaaa agaaaaccta ttaaaaaaac accactcgac acggcaccag  40680
ctcaatcagt cacagtgtaa aaaagggcca agtgcagagc gagtatatat aggactaaaa  40740
aatgacgtaa cggttaaagt ccacaaaaaa cacccagaaa accgcacgcg aacctacgcc  40800
cagaaacgaa agccaaaaaa cccacaactt cctcaaatcg tcacttccgt tttcccacgt  40860
tacgtcactt cccattttaa gaaaactaca attcccaaca catacaagtt actccgccct  40920
aaaacctacg tcacccgccc cgttcccacg ccccgcgcca cgtcacaaac tccacccccct 40980
cattatcata ttggcttcaa tccaaaataa ggtatattat tgatgatgta gggataacag  41040
ggtaatcagc tttcttgtac aaagttgaaa tccggggatc ctctagagtc gacctgcagg  41100
catgcaagct tggcgtaatc atggtcatag ctgtttcctg tgtgaaattg ttatccgctc  41160
acaattccac acaacatacg agccggaagc ataaagtgta aagcctgggg tgcctaatga  41220
gtgagcta                                                           41228
```